United States Patent
Huang et al.

(10) Patent No.: US 8,309,548 B2
(45) Date of Patent: *Nov. 13, 2012

(54) BENZENE, PYRIDINE, AND PYRIDAZINE DERIVATIVES

(75) Inventors: Kenneth He Huang, Northbrook, IL (US); Jeron Eaves, Durham, NC (US); Gunnar Hanson, Dallas, TX (US); James Veal, Apex, NC (US); Thomas Barta, Carrboro, NC (US); Lifeng Geng, Cary, NC (US); Lindsay Hinkley, Cary, NC (US)

(73) Assignee: Serenex, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/081,637

(22) Filed: Apr. 7, 2011

(65) Prior Publication Data

US 2011/0183977 A1     Jul. 28, 2011

Related U.S. Application Data

(63) Continuation of application No. 12/907,571, filed on Oct. 19, 2010, now Pat. No. 7,928,135, which is a continuation of application No. 11/959,784, filed on Dec. 19, 2007, now Pat. No. 7,906,529, which is a continuation of application No. 11/363,449, filed on Feb. 27, 2006, now Pat. No. 7,358,370.

(60) Provisional application No. 60/656,230, filed on Feb. 25, 2005, provisional application No. 60/705,715, filed on Aug. 4, 2005, provisional application No. 60/727,965, filed on Oct. 18, 2005.

(51) Int. Cl.
*A61K 31/5377* (2006.01)
*A61K 31/454* (2006.01)
*A61K 31/415* (2006.01)
*A61K 31/405* (2006.01)
*C07D 413/12* (2006.01)
*C07D 401/12* (2006.01)
*C07D 403/12* (2006.01)
*C07D 209/04* (2006.01)

(52) U.S. Cl. ............ 514/235.2; 514/323; 514/403; 514/415; 544/144; 546/201; 548/361.1; 548/469

(58) Field of Classification Search ............ 514/235.2, 514/323, 403, 415; 544/144; 546/201; 548/361.1, 548/469

See application file for complete search history.

(56) References Cited

U.S. PATENT DOCUMENTS

| | | | |
|---|---|---|---|
| 5,104,442 | A | 4/1992 | Schutze et al. |
| 6,395,766 | B1 | 5/2002 | Broughton et al. |
| 6,395,905 | B1 | 5/2002 | Bryant et al. |
| 6,716,856 | B1 | 4/2004 | Pevarello et al. |
| 7,358,370 | B2 | 4/2008 | Huang et al. |
| 7,906,529 | B2 * | 3/2011 | Huang et al. ............ 514/299 |
| 7,928,135 | B2 * | 4/2011 | Huang et al. ............ 514/403 |
| 2003/0212121 | A1 | 11/2003 | Kruger et al. |
| 2004/0180889 | A1 | 9/2004 | Suto et al. |
| 2004/0220169 | A1 | 11/2004 | Gillard et al. |
| 2006/0258728 | A1 | 11/2006 | Tani et al. |
| 2008/0269193 | A1 | 10/2008 | Huang et al. |

FOREIGN PATENT DOCUMENTS

| | | |
|---|---|---|
| EP | 1571146 A1 | 9/2005 |
| WO | WO 99/62899 | 12/1999 |
| WO | WO02/20480 | 3/2002 |
| WO | WO 2006/109846 | 10/2006 |

OTHER PUBLICATIONS

Brough, P., et al., "3-(5-Chioro-2,4-Dihydroxyphenyl)-Pyrazole-4-Carboxamides as Inhibitors of the HSP90 Molecular Chaperone," *Bioor. Med. Chem Letters*, 2005, 5197-5201, vol. 15.

Croce, P., et al., "A Convenient Systhesis of Indazoles," *Synthesis*, 1984, 982-983.

Database Caplus, Chemical Abstracts Service, XP-002386617, Database Accession No. 1968:486902; Abstract, "3-Methyl-6-Phenyl- and -6-alpha.-furyl-4, 5, 6, 7-Tetrahydroindazol-4-One and Their Derivatives," Latvijas PSR Zinatnu Akademijas Vestis, Kimijas Serija, vol. 2, 1968, 188-191.

Dymock, B., et al., "Inhibitors of HSP90 and Other Chaperones for the Treatment of Cancer," *Expert Opinion on Therapeutic Patents*, 2004, 837-847, vol. 14, No. 6.

Fukumoto, S., et al "Novel, Non-Acylguanidine-Type Na+/H+ Exchanger Inhibitors: Synthesis and Pharmacology of 5-Tetrahydroquinolinylidene Aminoguanidine Derivatives," *J. Med. Chem*, 2002, 3009-3021, vol. 45.

Gerhard, U., et al., "Accelerated Metabolite Identification By Extraction-NMR," *Journal of Pharmaceutical and Biomedical Analysis*, 2003, 531-538, vol. 32.

(Continued)

*Primary Examiner* — Kristin Bianchi
(74) *Attorney, Agent, or Firm* — McDonnell Boehnen Hulbert & Berghoff LLP

(57) ABSTRACT

Disclosed are compounds and pharmaceutically acceptable salts of Formula I

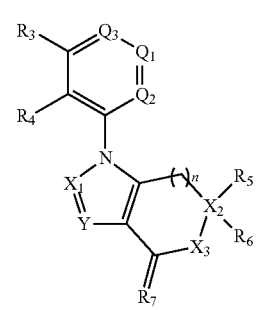

wherein $R_1$, $R_2$, $R_3$, $R_4$, $R_5$, $R_6$, $R_7$, n, $Q_1$, $Q_2$, $Q_3$, Y, and $X_1$-$X_4$ are as defined herein. Compounds of Formula I are useful in the treatment of diseases and/or conditions related to cell proliferation, such as cancer, inflammation, arthritis, angiogenesis, or the like. Also disclosed are pharmaceutical compositions comprising compounds of the invention and methods of treating the aforementioned conditions using such compounds.

19 Claims, No Drawings

OTHER PUBLICATIONS

International Search Report for PCT/US2006/006988, Jul. 10, 2006.
Kim, J., et al., "A Versatile Synthesis of Substituted Indazoles," *Heterocycles*, 1995, 1471-1478, vol. 41, No. 7.
Kubinyi, H. (3D QSAR in Drug Design: Ligand-Protein Interactions and Molecular Similarity, vol. 2-3, Springer 1998), vii, viii, ix, 243, 244.
Maloney, A., et al., "HSP90 as a New Therapeutic Target for Cancer Therapy: The Story Unfolds," *Expert Opinion on Biological Therapy*, 2002, 3-24, vol. 2, No. 1.
Parke, Caplus An 1969:491303.
Stetter, et al., Caplus An 1956:122272.
Strakova, I., et al., "1-(2Quinoxalyl)-, 1-[3, 5-DI-(Trifluoromethyl]-, 1-(2-Carboxyphenyl)-, and 1-Ethoxycarbonyl-4-Oxo-4,5,6,7-Tetrahydroindazoles," *Chemistry of Heterocyclic Compounds*, 2002, 429-433, vol. 38, No. 4.
Zhang, L., et al., "7'-Substituted Benzothiazolothio-And Pyridinothiazolothio-purines as Potent Heat Shock Protein 90 Inhibitors," *J. Med. Chem*. 2006, 5352-5362, vol. 49.

\* cited by examiner

BENZENE, PYRIDINE, AND PYRIDAZINE DERIVATIVES

CROSS-REFERENCE TO RELATED APPLICATIONS

This application is a continuation of U.S. patent application Ser. No. 12/907,571, filed Oct. 19, 2010, now U.S. Pat. No. 7,928,135, which is a continuation of U.S. patent application Ser. No. 11/959,784, filed Dec. 19, 2007, now U.S. Pat. No. 7,906,529, which is a continuation of U.S. patent application Ser. No. 11/363,449, filed Feb. 27, 2006, now U.S. Pat. No. 7,358,370, which claims the benefit of U.S. Provisional Application No. 60/656,230, filed Feb. 25, 2005, U.S. Provisional Application No. 60/705,715, filed Aug. 4, 2005, and U.S. Provisional Application No. 60/727,965, filed Oct. 18, 2005.

BACKGROUND OF THE INVENTION

1. Field of the Invention

The invention relates to benzene, pyridine, and pyridazine derivatives and more specifically to such compounds that are useful in the treatment and/or prevention of diseases and/or conditions related to cell proliferation, such as cancer, inflammation and inflammation-associated disorders, and conditions associated with angiogenesis. Compounds of the invention are also useful in the treatment and/or prevention of infectious diseases, in particular, fungal infections.

2. Description of the Related Art

Cancer is characterized by abnormal cellular proliferation. Cancer cells exhibit a number of properties that make them dangerous to the host, typically including an ability to invade other tissues and to induce capillary ingrowth, which assures that the proliferating cancer cells have an adequate supply of blood. A hallmark of cancerous cells is their abnormal response to control mechanisms that regulate cell division in normal cells and continue to divide until they ultimately kill the host.

Angiogenesis is a highly regulated process under normal conditions, however many diseases are driven by persistent unregulated angiogenesis. Unregulated angiogenesis may either cause a particular disease directly or exacerbate an existing pathological condition. For example, ocular neovascularization has not only been implicated as the most common cause of blindness, but also is believed the dominant cause of many eye diseases. Further, in certain existing conditions, for example arthritis, newly formed capillary blood vessels invade the joints and destroy cartilage, or in the case of diabetes, new capillaries formed in the retina invade the vitreous, bleed, and cause blindness. Growth and metastasis of solid tumors are also dependent on angiogenesis (Folkman, J., Cancer Research, 46, 467-473 (1986), Folkman, J., Journal of the National Cancer Institute, 82, 4-6 (1989). It has been shown, for example, that tumors which enlarge to greater than 2 mm must obtain their own blood supply and do so by inducing the growth of new capillary blood vessels. Once these new blood vessels become embedded in the tumor, they provide a means for tumor cells to enter the circulation and metastasize to distant sites such as liver, lung or bone (Weidner, N., et al., The New England Journal of Medicine, 324(1), 1-8 (1991). Under conditions of unregulated angiogenesis, therapeutic methods designed to control, repress, and/or inhibit angiogenesis could lead to the abrogation or mitigation of these conditions and diseases.

Inflammation is related to a variety of disorders such as pain, headaches, fever, arthritis, asthma, bronchitis, menstrual cramps, tendonitis, bursitis, psoriasis, eczema, burns, dermatitis, inflammatory bowel syndrome, Crohn's disease, gastritis, irritable bowel syndrome, ulcerative colitis, vascular diseases, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, post-injury swelling, myocardial ischemia, and the like.

Heat-shock protein 90 (HSP-90) is a cellular chaperone protein required for the activation of several eukaryotic protein kinases, including the cyclin-dependent kinase CDK4. Geldanamycin, an inhibitor of the protein-refolding activity of HSP-90, has been shown to have antiproliferative and antitumor activities.

HSP-90 is a molecular chaperone that guides the normal folding, intracellular disposition and proteolytic turnover of many key regulators of cell growth and survival. Its function is subverted during oncogenesis to make malignant transformation possible and to facilitate rapid somatic evolution, and to allow mutant proteins to retain or even gain function. Inhibition of HSP-90 will slow those process thus has potential therapeutic use (Whitesell L, Lindquist, S L, Nature Rev. Cancer, 2005, 10, 761-72).

Ansamycin antibiotics, e.g., herbimycin A (HA), geldanamycin (GM), and 17-allylaminogeldanamycin (17-AAG) are thought to exert their anticancerous effects by tight binding of the N-terminus pocket of HSP-90, thereby destabilizing substrates that normally interact with HSP-90 (Stebbins, C. et al. Cell 1997, 89, 239-250). This pocket is highly conserved and has weak homology to the ATP-binding site of DNA gyrase (Stebbins, C. et al., supra; Grenert, J. P. et al. J. Biol. Chem. 1997, 272, 23843-50).

In vitro and in vivo studies have demonstrated that occupancy of this N-terminal pocket by ansamycins and other HSP-90 inhibitors alters HSP-90 function and inhibits protein folding. At high concentrations, ansamycins and other HSP-90 inhibitors have been shown to prevent binding of protein substrates to HSP-90 (Scheibel, T. H. et al. Proc. Natl. Acad. Sci. USA 1999, 96, 1297-302; Schulte, T. W. et al. J. Biol. Chem. 1995, 270, 24585-8; Whitesell, L., et al. Proc. Natl. Acad. Sci. USA 1994, 91, 8324-8328). Ansamycins have also been demonstrated to inhibit the ATP-dependent release of chaperone-associated protein substrates (Schneider, C. L. et al. Proc. Natl. Acad. Sci., USA 1996, 93, 14536-41; Sepp-Lorenzino et al. J. Biol. Chem. 1995, 270, 16580-16587). In either event, the substrates are degraded by a ubiquitin-dependent process in the proteasome (Schneider, C. L., supra; Sepp-Lorenzino, L., et al. J. Biol. Claim. 1995, 270, 16580-16587; Whitesell, L. et al. Proc. Natl. Acad. Sci. USA 1994, 91, 8324-8328). HSP-90 substrate destabilization occurs in tumor and non-transformed cells alike and has been shown to be especially effective on a subset of signaling regulators, e.g., Raf (Schulte, T. W. et al., Biochem. Biophys. Res. Commun. 1997, 239, 655-9 Schulte, T. W., et al., J. Biol. Chem. 1995, 270, 24585-8), nuclear steroid receptors (Segnitz, B.; U. Gehring J. Biol. Chem. 1997, 272, 18694-18701; Smith, D. F. et al. Mol. Cell. Biol. 1995, 15, 6804-12), v-Src (Whitesell, L. et al. Proc. Natl. Acad. Sci. USA 1994, 91, 8324-8328) and certain transmembrane tyrosine kinases (Sepp-Lorenzino, L. et al. J. Biol. Chez. 1995, 270, 16580-16587) such as EGF receptor (EGFR) and HER2/Neu (Hartmann, F., et al. Int. J. Cancer 1997, 70, 221-9; Miller, P. et al. Cancer Res. 1994, 54, 2724-2730; Mimnaugh, E. G., et al. J. Biol. Chem. 1996, 271, 22796-801; Schnur, R. et al. J. Med. Chenu. 1995, 38, 3806-3812), CDK4, and mutant p53. Erlichman et al. Proc. AACR 2001, 42, abstract 4474. The ansamycin-induced loss of these proteins leads to the selective disruption of certain regulatory pathways and results in growth arrest at specific phases of the cell cycle (Muise-Heimericks, R. C. et al. J. Biol. Chez. 1998, 273, 29864-72), and apoptosis, and/or differentiation of cells so treated (Vasilevskaya, A. et al. Cancer Res., 1999, 59, 3935-40). Inhibitors of HSP-90 thus hold great promise for the treatment and/or prevention of many types of cancers and proliferative disorders, and also hold promise as traditional antibiotics.

Inhibition of HSP-90 is also known to result in up regulation of the expression of the chaperone HSP70. HSP70 up regulation is considered to be of therapeutic benefit for treatment of a wide range of neurodegenerative diseases including, but not limited to: Alzheimer's disease; Parkinson's disease; Dementia with Lewy bodies; Amyotropic lateral sclerosis (ALS); Polyglutamine disease; Huntington's disease; Spinal and bulbar muscular atrophy (SBMA); and Spinocerebellar ataxias (SCA1-3,7). Therefore, the compounds described in the invention are of potential therapeutic use for treatment of such neurodegenerative diseases (Muchowski, P. J., Wacker J. L., Nat. Rev. Neurosci. 2005, 6, 11-22.; Shen H. Y., et al. J. Biol. Chem. 2005, 280, 39962-9).

Inhibition of HSP-90 also has anti-fungal activity, both as a stand alone therapy and in combination with standard antifungal therapies such as the azole class of drugs. Therefore, the compounds described in the invention are of potential therapeutic use for treatment of fungal infections including, but not limited to, life threatening systemic fungal infections (Cowen, L. E., Lindquist, S., Science 2005, 309, 2185-9).

Inhibition of HSP-90 also has antimalarial activity; thus, inhibitors of this protein are useful as antimalarial drugs.

Therefore, there is a continuing need in the art for new methods of treating cancer, inflammation and inflammation-associated disorders, and conditions or diseases related to uncontrolled angiogenesis.

SUMMARY OF THE INVENTION

In a broad aspect, the invention encompasses the compounds of formula I shown below, pharmaceutical compositions containing those compounds and methods employing such compounds or compositions in the treatment of diseases and/or conditions related to cell proliferation, such as cancer, inflammation, arthritis, angiogenesis, or the like.

The invention provides compounds of formula I,

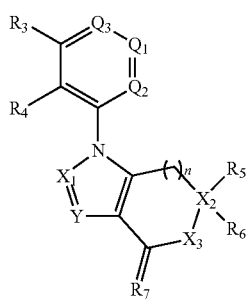

I or a pharmaceutically acceptable salt thereof, wherein
$R_3$ and $R_4$ are independently
(a) H,
(b) halo, or
(c) a $C_1$-$C_{15}$ alkyl group where up to six of the carbon atoms in said alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein
$R_{22}$ is
(i) heteroaryl,
(ii) aryl,
(iii) saturated or unsaturated $C_3$-$C_{10}$ cycloalkyl, or
(iv) saturated or unsaturated $C_2$-$C_{10}$ heterocycloalkyl, wherein
each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$) alkyl, —$SO_2$—($C_1$-$C_6$) alkyl, —$SO_2$-aryl, —SO—($C_1$-$C_6$)alkyl, —SO-aryl, —$SO_2NH_2$, —$SO_2NH$—($C_1$-$C_6$)alkyl, —$SO_2$NH-aryl, ($C_1$-$C_6$)alkoxy, or mono- or di-($C_1$-$C_{10}$)alkylamino; and
each $R_{22}$ is optionally fused to a $C_6$-$C_{10}$ aryl group, $C_5$-$C_8$ saturated cyclic group, or a $C_5$-$C_{10}$ heterocycloalkyl group;
wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$) alkyl, —$SO_2NH_2$, —$SO_2NH$—($C_1$-$C_6$) alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$, wherein
Z is $OR_0$ or —$N(R_{30})_2$, wherein
each $R_{30}$ is independently —H or $C_1$-$C_6$ alkyl, or $N(R_{30})_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen;
$R_O$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl;
$R_{23}$ is
(1) heteroaryl,
(2) aryl,
(3) saturated or unsaturated $C_5$-$C_{10}$ cycloalkyl, or
(4) saturated or unsaturated $C_5$-$C_{10}$ heterocycloalkyl, and
the $R_{23}$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NH_2$, —$SO_2NH$—($C_1$-$C_6$) alkyl, —$SO_2$NH-aryl, ($C_1$-$C_6$)alkoxy, or mono- or di-($C_1$-$C_{10}$)alkylamino;
or $R_3$ and $R_4$ together with the atoms to which they are attached form a 5-12 membered mono-, bi-, or tricyclic ring system fused to the ring containing $Q_1$ and $Q_2$, where the 5-12 membered ring is partially unsaturated or aromatic and optionally contains one or two of oxygen, $S(O)_m$ where m is 0, 1, or 2, nitrogen, or $NR_{33}$ where $R_{33}$ is hydrogen or $C_1$-$C_6$ alkyl;
$R_7$ is O, S, NH, N—OH, N—$NH_2$, N—$NHR_{22}$, N—NH—($C_1$-$C_6$ alkyl), N—O—($C_0$-$C_6$)alkyl-$R_{22}$, or N—($C_1$-$C_6$ alkoxy optionally substituted with carboxy);

Y is N or $CR_C$, wherein
  each $R_C$ independently is hydrogen, halogen, cyano, nitro, $-C(O)R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
    each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, cyano, nitro, halo($C_1$-$C_6$)alkyl, halo($C_1$-$C_6$)alkoxy, carboxamide, heterocycloalkyl, aryl, or heteroaryl, wherein
      the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, or carboxamide;
  $R_{C'}$ is $-C_1$-$C_6$ alkyl, $-OR_{C''}$, or $-N(R_{CN})_2$, wherein $R_{C''}$ is $-H$, $C_1$-$C_{10}$ alkyl, $C_1$-$C_{10}$ haloalkyl, $C_3$-$C_7$ cycloalkyl, heterocycloalkyl, aryl, or heteroaryl;
  each $R_{CN}$ is independently $-H$, $C_1$-$C_{10}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$)alkoxy, or carboxamide;
$X_1$ is N or $CR_C$;
$Q_1$, $Q_2$, and $Q_3$ are independently N or $CR_Q$, wherein one and only one of $Q_1$, $Q_2$, and $Q_3$ is $C-R_{21}$, and wherein each $R_Q$ is independently hydrogen, halogen, $-N(R_{CN})_2$, $C_1$-$C_6$ alkyl, $C_1$-$C_6$ haloalkyl, $C_3$-$C_7$ cycloalkyl, aryl, or heteroaryl, or $R_{21}$, wherein
  each alkyl, cycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, halo($C_1$-$C_6$)alkyl, halo($C_1$-$C_6$)alkoxy, or carboxamide;
$R_{21}$ is cyano, $-C(O)OH$, $-C(O)-O(C_1$-$C_6$alkyl), or a group of the formula

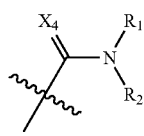

$R_1$ and $R_2$ are independently H, hydroxy, $C_1$-$C_6$ alkyl, $C_2$-$C_6$ alkenyl, $C_2$-$C_6$ alkynyl, heteroaryl, aryl, $C_3$-$C_8$ cycloalkyl, heterocycloalkyl, wherein
  each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$)alkylamino, nitro, halo($C_1$-$C_6$)alkyl, halo($C_1$-$C_6$) alkoxy, or carboxamide;
or $R_1$ and $R_2$ together with the nitrogen to which they are both attached, form a heterocycloalkyl which optionally contains one or more additional heteroatoms which are, independently, O, N, S, or $N(R_{CN})$ and
$X_4$ is O, S, NH, NOH, N—$NH_2$, N—NHaryl, N—NH—($C_1$-$C_6$ alkyl), or N—($C_1$-$C_6$ alkoxy);
$X_2$ and $X_3$ are independently C, O, N, or $S(O)_p$ wherein p is 0, 1, or 2; and
n is 0, 1, 2, 3, or 4;
provided that when
(i) $X_2$ is C, then
  $R_5$ and $R_6$ are independently H, $C_1$-$C_6$ alkyl, or aryl, wherein the aryl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$) alkoxy, or carboxamide,
  or wherein any two adjacent substituted aryl positions, together with the carbon atoms to which they are attached, form an unsaturated cycloalkyl or heterocycloalkyl; or
  $R_5$ and $R_6$ together with the carbon to which they are attached form a 3-8 membered ring;
(ii) $X_2$ is N, then
  $R_6$ is absent and $R_5$ is H or $C_1$-$C_6$ alkyl;
(iii) $X_3$ is C, then
  it is substituted with two groups that are independently H or $C_1$-$C_6$ alkyl, or mono- or di-($C_1$-$C_6$)alkylamino($C_1$-$C_6$) alkyl; and
(iv) $X_2$ is O or $S(O)_p$, then $R_6$ and $R_5$ are absent.

The invention also includes intermediates that are useful in making the compounds of the invention.

The invention also provides pharmaceutical compositions comprising a compound or pharmaceutically acceptable salt of Formula I and at least one pharmaceutically acceptable carrier, solvent, adjuvant or diluent.

The invention further provides methods of treating disease such as cancer, inflammation, arthritis, angiogenesis, and infection in a patient in need of such treatment, comprising administering to the patient a compound or pharmaceutically acceptable salt of Formula I, or a pharmaceutical composition comprising a compound or salt of Formula I.

The invention also provides the use of a compound or salt according to Formula I for the manufacture of a medicament for use in treating cancer, inflammation, arthritis, angiogenesis, or infection.

The invention also provides methods of preparing the compounds of the invention and the intermediates used in those methods.

The invention also provides methods of treating a disease or condition related to cell proliferation comprising administering a therapeutically effective amount of a compound or salt of Formula I to a patient in need of such treatment.

The invention also provides methods of treating a disease or condition related to cell proliferation comprising administering a therapeutically effective amount of a compound or salt of Formula I to a patient in need of such treatment, where the disease of condition is cancer, inflammation, or arthritis.

The invention further provides methods of treating a subject suffering from a disease or disorder of proteins that are either client proteins for HSP-90 or indirectly affect its client proteins, comprising administering to a subject in need of such treatment a therapeutically effective amount of a compound or salt of Formula I.

The invention further provides methods of treating a subject suffering from a disease or disorder of proteins that are either client proteins for HSP-90 or indirectly affect its client proteins, comprising administering to a subject in need of such treatment a therapeutically effective amount of a compound or salt of Formula I, wherein the HSP-90 mediated disorder is selected from the group of inflammatory diseases, infections, autoimmune disorders, stroke, ischemia, cardiac disorders, neurological disorders, fibrogenetic disorders, proliferative disorders, tumors, leukemias, neoplasms, cancers, carcinomas, metabolic diseases and malignant disease.

The invention further provides methods of treating a subject suffering from a fibrogenetic disorder of proteins that are either client proteins for HSP-90 or indirectly affect its client proteins, comprising administering to a subject in need of such treatment a therapeutically effective amount of a compound or salt of Formula I, wherein the fibrogenetic disorder is selected from the group of scleroderma, polymyositis, systemic lupus, rheumatoid arthritis, liver cirrhosis, keloid formation, interstitial nephritis and pulmonary fibrosis.

The invention provides methods of protecting a subject from infection caused by an organism selected from *Plasmodium* species, preferably *Plasmodium falciparum*. These methods comprising administering a compound or salt of Formula I, preferably in an effective amount, to a subject at risk of infection due to exposure to such organism.

The invention additionally provides methods of reducing the level of infection in a subject where the infection is caused by an organism selected from *Plasmodium* species, again preferably *Plasmodium falciparum*. These methods comprise administering to an infected subject an effective amount of a compound or salt of Formula I.

The invention further provides methods for treating a patient infected with a metazoan parasite. These methods involve administering an amount of a compound of the invention effective to kill the parasite.

The invention further provides methods for treating a patient infected with a metazoan parasite wherein the parasite is *Plasmodium falciparum*. These methods involve administering an amount of a compound or salt of the invention effective to kill the parasite.

The invention further provides a compound or pharmaceutical composition thereof in a kit with instructions for using the compound or composition.

The invention further provides compounds that may be administered alone or in combination with other drugs or therapies known to be effective to treat the disease to enhance overall effectiveness of therapy.

The invention further provides methods for treating a fungal infection in a patient in need of such treatment, comprising administering an effective amount of a compound or salt of Formula I and an optional anti-fungal agent or drug.

DETAILED DESCRIPTION OF THE INVENTION

In Formula I, $R_3$ and $R_4$ are, as noted above, independently (a) hydrogen, (b) halo, or (c) an alkyl group having from 1-15 carbon atoms. All, but no more than about six, of the carbon atoms in the alkyl group may be replaced independently by the various groups listed above in connection with Formula I.

Thus, when the alkyl group is methyl, i.e., a one carbon atom alkyl group, replacement of that carbon atom with, for example, nitrogen or sulfur, the resulting group will not be an alkyl group but instead will be an amino or thio group, respectively. Similarly, when the carbon atom being replaced terminates the alkyl group, the terminal group will become another moiety such as pyrimidinyl, amino, phenyl, or hydroxy.

Replacement of a carbon atom with a group such as, for example, oxygen, nitrogen, or sulfur will require appropriate adjustment of the number of hydrogens or other atoms required to satisfy the replacing atom's valency. Thus, when the replacement is N or O, the number of groups attached to the atom being replaced will be reduced by one or two to satisfy the valency of the nitrogen or oxygen respectively. Similar considerations will be readily apparent to those skilled in the art with respect to replacement by ethenyl and ethynyl.

Thus, replacement as permitted herein results in the term "$C_1$-$C_{15}$ alkyl" as defined in connection with Formula I encompassing groups such as, but not limited to:

amino, hydroxy, phenyl, benzyl, propylaminoethoxy, butoxyethylamino, pyrid-2-ylpropyl, diethylaminomethyl, pentylsulfonyl, methylsulfonamidoethyl, 3-[4-(butylpyrimidin-2-yl)ethyl]phenyl, butoxy, dimethylamino, 4-(2-(benzylamino)ethyl)pyridyl, but-2-enylamino, 4-(1-(methylamino)pent-3-en-2-ylthio)phenyl, 2-(N-methyl-hexanamido)ethoxy)methyl, and 4-(((3-methoxy-4-(4-methyl-1H-imidazol-2-yl)but-1-enyl)(methyl)amino)-methyl)phenyl.

Preferred compounds of Formula I include those where $R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$-haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Even more preferred compounds of Formula I include those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Additional preferred compounds of Formula I include those where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-

$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Most preferred compounds of Formula I include those where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
wherein $R_{Z1}$ is optionally substituted at any available position with $C_1$-$C_{10}$ alkyl, $C_1$-$C_{10}$ haloalkyl, hydroxy, carboxy, carboxamido, oxo, halo, amino, $C_1$-$C_6$ alkoxy, mono- or di-($C_1$-$C_{10}$)alkylamino, —$OC_1$-$C_{10}$ alkyl-Z, or $R_{23}$.

Additional preferred compounds of Formula I include those where $R_3$ and $R_4$ are independently hydrogen, halo, or —$OR_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Most preferred compounds of Formula I include those where $R_3$ and $R_4$ are independently hydrogen, halo, or —$OR_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
wherein $R_{Z1}$ is optionally substituted at any available position with $C_1$-$C_{10}$ alkyl, $C_1$-$C_{10}$ haloalkyl, hydroxy, carboxy, carboxamido, oxo, halo, amino, $C_1$-$C_6$ alkoxy, mono- or di-($C_1$-$C_{10}$)alkylamino, —$OC_1$-$C_{10}$ alkyl-Z, or $R_{23}$.

Preferred compounds of Formula I include those where $X_1$ is carbon optionally substituted with $C_1$-$C_6$ alkyl, more preferably $C_1$-$C_3$ alkyl. Other preferred compounds of Formula I are those where $X_1$ is carbon optionally substituted with $C_1$-$C_6$ alkyl and Y is $CR_C$ wherein $R_C$ is —H, $C_1$-$C_6$ alkyl, $C_1$-$C_3$ haloalkyl, $C_3$-$C_7$ cycloalkyl, or $C_3$-$C_7$ cycloalkyl($C_1$-$C_6$)alkyl. More preferably, in compounds of Formula I, $X_1$ is carbon optionally substituted with $C_1$-$C_2$ alkyl and Y is $CR_C$ wherein $R_C$ is —H, $C_1$-$C_4$ alkyl, $C_1$-$C_3$ haloalkyl, cyclopropyl, or cyclopropyl($C_1$-$C_2$)alkyl.

Still more preferred compounds of Formula I are those where $X_1$ is CH. Other more preferred compounds of Formula I are those where $X_1$ is CH and Y is $CR_C$ wherein $R_C$ is —H, $C_1$-$C_3$ alkyl, $C_1$-$C_3$ haloalkyl, $C_3$-$C_5$ cycloalkyl, or $C_3$-$C_5$ cycloalkyl($C_1$-$C_2$)alkyl. Even more preferred compounds of Formula I are those where $X_1$ is CH and Y is $CR_C$ wherein $R_C$ is —H, methyl, ethyl, trifluoromethyl, cyclopropyl, or cyclopropylmethyl. Particularly preferred compounds of Formula I are those where $X_1$ is CH and, Y is $CR_C$ wherein $R_C$ is methyl, ethyl, or cyclopropyl. Other particularly preferred compounds of Formula I are those where $X_1$ is CH and Y is $CR_C$ wherein $R_C$ is trifluoromethyl. Other particularly preferred compounds of Formula I are those where $X_1$ is CH and Y is $CR_C$ wherein $R_C$ is methyl. Other particularly preferred compounds of Formula I are those where $X_1$ is CH and Y is $CR_C$ wherein $R_C$ is ethyl. Other particularly preferred compounds of Formula I are those where $X_1$ is CH and Y is $CR_C$ wherein $R_C$ is cyclopropyl.

Still other preferred compounds of formula I are those where $X_1$ is CH, Y is $CR_C$ wherein $R_C$ is —H, $C_1$-$C_3$ alkyl, $C_1$-$C_3$ haloalkyl, or $C_3$-$C_7$ cycloalkyl, and $R_3$ is amino or $C_1$-$C_3$ alkylamino substituted on the amino or the alkyl with an optionally substituted aryl, optionally substituted heterocycloalkyl, or optionally substituted cycloalkyl group. Preferred substituents on these cyclic groups are hydroxy, $C_1$-$C_3$ alkoxy, oxo, halo, $C_1$-$C_3$ alkyl, amino, mono- or di-$C_1$-$C_3$alkylamino, and nitro. More preferably the optional substituents on these cyclic groups are hydroxy, $C_1$-$C_3$alkoxy, and oxo. These cyclic groups are optionally substituted with from 1-4, preferably 1-3 of these substituents.

Still more preferred compounds of Formula I are those where $X_1$ is N. Other more preferred compounds of Formula I are those where $X_1$ is N and Y is $CR_C$ wherein $R_C$ is —H, $C_1$-$C_3$ alkyl, $C_1$-$C_3$ haloalkyl, $C_3$-$C_5$ cycloalkyl, or $C_3$-$C_5$ cycloalkyl($C_1$-$C_2$)alkyl. Even more preferred compounds of Formula I are those where $X_1$ is N and Y is $CR_C$ wherein $R_C$ is —H, methyl, ethyl, trifluoromethyl, cyclopropyl, or cyclopropylmethyl. Particularly preferred compounds of Formula I are those where $X_1$ is N and Y is $CR_C$ wherein $R_C$ is methyl, ethyl, or cyclopropyl. Other particularly preferred compounds of Formula I are those where $X_1$ is N and Y is $CR_C$ wherein $R_C$ is trifluoromethyl. Other particularly preferred compounds of Formula I are those where $X_1$ is N and Y is $CR_C$ wherein $R_C$ is methyl. Other particularly preferred compounds of Formula I are those where $X_1$ is N and Y is $CR_C$ wherein $R_C$ is ethyl. Other particularly preferred compounds of Formula I are those where $X_1$ is N and Y is $CR_C$ wherein $R_C$ is cyclopropyl.

Still other preferred compounds of formula I are those where $X_1$ is N, Y is $CR_C$ wherein $R_C$ is —H, $C_1$-$C_3$ alkyl, $C_1$-$C_3$ haloalkyl, or $C_3$-$C_7$ cycloalkyl and $R_3$ is amino or $C_1$-$C_3$ alkylamino substituted on the amino or the alkyl with an optionally substituted aryl, optionally substituted heterocycloalkyl, or optionally substituted cycloalkyl group. Preferred substituents on these cyclic groups are hydroxy, $C_1$-$C_3$alkoxy, oxo, halo, $C_1$-$C_3$alkyl, amino, mono- or di-$C_1$-$C_3$alkylamino, and nitro. More preferably the optional substituents on these cyclic groups are hydroxy, $C_1$-$C_3$alkoxy, and oxo. These cyclic groups are optionally substituted with from 1-4, preferably 1-3 of these substituents.

Other preferred compounds of Formula I are those where $Q_3$ is $CR_{21}$, wherein
$R_{21}$ is a group of the formula,

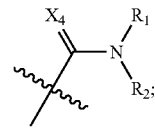

$R_7$ is O; and
Y is $CR_C$, wherein $R_C$ is hydrogen, $C_1$-$C_3$ alkyl, $C_3$-$C_5$ cycloalkyl, trifluoromethyl, or $C_3$-$C_5$ cycloalkyl($C_1$-$C_2$) alkyl. Such compounds are compounds of Formula II herein.

Other preferred compounds of Formula II are those where, $R_3$ and $R_4$ are, as noted above, independently (a) hydrogen, (b) halo, or (c) an alkyl group having from 1-15 carbon atoms. All, but no more than about six, of the carbon atoms in the alkyl group may be replaced independently by the various groups listed above in connection with Formula I.

Other preferred compounds of Formula I are those where $Q_3$ is $CR_{21}$, wherein
$R_{21}$ is a group of the formula,

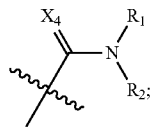

$X_3$ is C substituted with $R_{9a}$ and $R_{9b}$, wherein $R_{9a}$ and $R_{9b}$ are independently H or $C_1$-$C_6$ alkyl.
Such compounds are hereinafter compounds of Formula III.

Other preferred compounds of Formula I are those where $Q_3$ is $CR_{21}$, wherein
$R_{21}$ is a group of the formula,

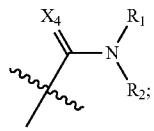

$Q_1$ and $Q_2$ are independently C substituted with $R_{10a}$ and $R_{10b}$ respectively, wherein $R_{10a}$ and $R_{10b}$ are independently H or $C_1$-$C_6$ alkyl. Such compounds are hereinafter compounds of Formula IV.

Other preferred compounds of Formula I are those where $Q_3$ is $CR_{21}$, wherein
$R_{21}$ is a group of the formula,

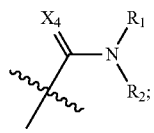

$X_1$ is C substituted with $R_{11}$ where $R_{11}$ hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
$R_{C'}$ is —$C_1$-$C_6$ alkyl, —$OR_{C''}$, or —N($R_{CN}$)$_2$, wherein
$R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;
each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl. Such compounds are hereinafter compounds of Formula V.

Preferred compounds of Formula V are those where $R_{11}$ is hydrogen, halogen, $C_1$-$C_{10}$ alkyl, $C_1$-$C_{10}$ haloalkyl, $C_3$-$C_7$ cycloalkyl, $C_3$-$C_7$ cycloalkyl($C_1$-$C_{10}$)alkyl, aryl, or heteroaryl.

More preferred compounds of Formula V are those where $R_{11}$ is H or $C_1$-$C_6$ alkyl.

Other preferred compounds of Formula I are those where $Q_3$ is $CR_{21}$, wherein
$R_{21}$ is a group of the formula,

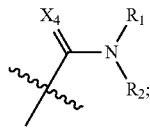

$X_1$ is N. Such compounds are hereinafter compounds of Formula Va.

Other preferred compounds of Formula I are those where $Q_3$ is $CR_{21}$, wherein
$R_{21}$ is a group of the formula,

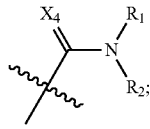

$X_2$ is C substituted with $R_5$ and $R_6$, wherein $R_5$ and $R_6$ are independently H or $C_1$-$C_4$ alkyl. Such compounds are hereinafter compounds of Formula VI.

Preferred compounds of any of Formulas I-VI include compounds where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

More preferred compounds of the invention are those of Formulas I-VI where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

More preferred compounds of the invention are those of Formulas I-VI where $R_4$ is H, $C_1$-$C_4$ alkyl or halogen.

Preferred compounds of Formulas II-VI include those where $X_1$ is carbon optionally substituted with $C_1$-$C_3$ alkyl (preferably methyl) and Y is $CR_C$ wherein $R_C$ is $C_1$-$C_2$ alkyl, trifluoromethyl, cyclopropyl, or cyclopropyl($C_1$-$C_2$)alkyl. More preferably in compounds of Formulas II-VI, $X_1$ is CH and Y is $CR_C$ wherein $R_C$ is $C_1$-$C_2$ alkyl (preferably methyl).

More preferred compounds of the invention are those of Formula I wherein $Q_3$ is $CR_{21}$, wherein
$R_{21}$ is a group of the formula,

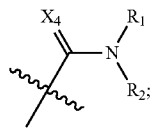

$X_2$ is C substituted with two groups that are independently H or $C_1$-$C_4$ alkyl;
$X_1$ is C substituted with H or $C_1$-$C_6$ alkyl;
$Q_1$ and $Q_2$ are independently C substituted with H or $C_1$-$C_6$ alkyl;
$R_7$ is O;
Y is $CR_C$, wherein
$R_C$ is —H, methyl, ethyl, trifluoromethyl, or cyclopropyl;
$R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other,
    wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and
n is 1 or 2.

More preferred compounds of the invention are those of Formula I wherein
$R_1$ and $R_2$ are independently H or $C_1$-$C_4$ alkyl;
$Q_1$ and $Q_2$ are both CH;
$X_2$ is C substituted with two independently selected $C_1$-$C_4$ alkyl groups; and
n is 1.

Other preferred compounds of the invention include those having the formula VII,

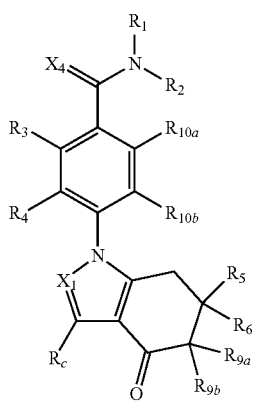

VII wherein $X_1$ and $R_C$ are as defined in Formula I;
$R_5$ and $R_6$ are independently H or $C_1$-$C_4$ alkyl;
$R_{11}$ is H or $C_1$-$C_6$ alkyl;
$R_{10a}$ and $R_{10b}$ are independently H or $C_1$-$C_6$ alkyl;
$R_{9a}$ and $R_{9b}$ are independently H or $C_1$-$C_6$ alkyl;
$R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally-replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other,
    wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and
n is 1 or 2.

Preferred compounds of Formula VII include those where
$R_1$ and $R_2$ are independently H or $C_1$-$C_4$ alkyl;
$R_{10a}$ and $R_{10b}$ are both H; and
$R_5$ and $R_6$ are independently $C_1$-$C_4$ alkyl.

Other preferred compounds of Formula VII include those where
$X_1$ is N.

Other preferred compounds of Formula VII include those where $X_1$ is $CR_C$, wherein $R_C$ is hydrogen, methyl, ethyl, cyclopropyl, cyclopropylmethyl, fluoromethyl, difluoromethyl, or trifluoromethyl. In a preferred embodiment of this aspect, the $R_C$ group derived from $X_1$ is hydrogen, methyl, or trifluoromethyl, and the $R_C$ group derived from Y carries the definition given in connection with Formula I.

Other preferred compounds of Formula I include those of formula VIII,

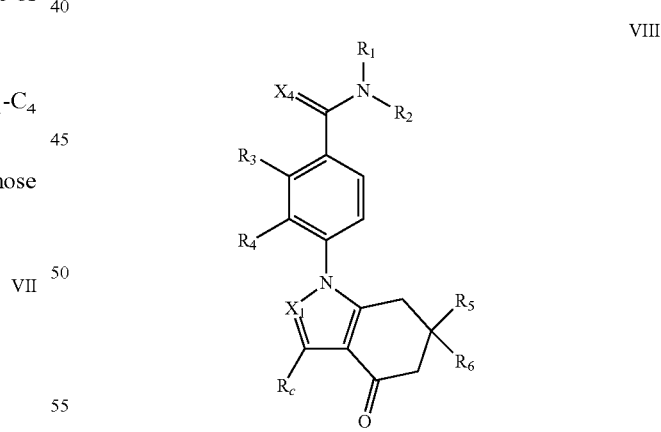

VIII wherein $R_C$ is H, $C_1$-$C_6$ alkyl, trifluoromethyl, or cyclopropyl; and
$R_1$-$R_6$, $X_1$, and $X_4$ carry the same definitions as for Formula I.

Preferred compounds of Formula VIII include those where $X_1$ is N.

Preferred compounds of Formula VIII include those where $X_1$ is $CR_C$, wherein $R_C$ is hydrogen, methyl, ethyl, cyclopropyl, cyclopropylmethyl, fluoromethyl, difluoromethyl, or trifluoromethyl. In a preferred embodiment of this aspect, the $R_C$ group derived from $X_1$ is hydrogen, methyl, or trifluoromethyl, and the $R_C$ group derived from Y carries the definition given in connection with Formula I.

Preferred compounds of Formula VIII include those where $R_3$ and $R_4$ are independently hydrogen, halo, or $—Z_1R_{Z1}$, wherein $Z_1$ is $—O—$, $—NH—$, $—S(O)_p—$, or $—S(O)_2NH—$, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $—SH$, $—S—(C_1$-$C_6)$alkyl, $—SO_2—(C_1$-$C_6)$alkyl, $—SO_2NH_2$, $—SO_2NH—(C_1$-$C_6)$alkyl, $—SO_2NH$-aryl, $—SO_2$-aryl, $—SO—(C_1$-$C_6)$alkyl, $—SO_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $—OC_1$-$C_{10}$ alkyl-Z, or $R_{23}$.

Preferred compounds of Formula VIII include those where $R_3$ and $R_4$ are independently hydrogen, halo, or $—Z_1R_{Z1}$, wherein $Z_1$ is $—O—$, $—NH—$, $—S(O)_p—$, or $—S(O)_2NH—$, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $—SH$, $—S—(C_1$-$C_6)$alkyl, $—SO_2—(C_1$-$C_6)$alkyl, $—SO_2NH_2$, $—SO_2NH—(C_1$-$C_6)$alkyl, $—SO_2NH$-aryl, $—SO_2$-aryl, $—SO—(C_1$-$C_6)$alkyl, $—SO_2$-aryl, $C_1$-$C_6$ alkoxy, $C_2$-$C_{10}$alkenyloxy, $C_2$-$C_{10}$ alkynyloxy, mono- or di-$(C_1$-$C_{10})$alkylamino, $—OC_1$-$C_{10}$ alkyl-Z, or $R_{23}$; and $X_4$ is O.

Preferred compounds of Formula VIII include those where $R_3$ and $R_4$ are independently hydrogen, halo, or $—Z_1R_{Z1}$, wherein $Z_1$ is $—O—$, $—NH—$, $—S(O)_p—$, or $—S(O)_2NH—$, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $—SH$, $—S—(C_1$-$C_6)$alkyl, $—SO_2—(C_1$-$C_6)$alkyl, $—SO_2NH_2$, $—SO_2NH—(C_1$-$C_6)$alkyl, $—SO_2NH$-aryl, $—SO_2$-aryl, $—SO—(C_1$-$C_6)$alkyl, $—SO_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $—OC_1$-$C_{10}$ alkyl-Z, or $R_{23}$; and $X_4$ is N—OH.

Other preferred compounds of Formula VIII include those where $R_3$ and $R_4$ are independently hydrogen, halo, or $—Z_1R_{Z1}$, wherein $Z_1$ is $—O—$ or $—NH—$; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $—SH$, $—S—(C_1$-$C_6)$alkyl, $—SO_2—(C_1$-$C_6)$alkyl, $—SO_2NH_2$, $—SO_2NH—(C_1$-$C_6)$alkyl, $—SO_2NH$-aryl, $—SO_2$-aryl, $—SO—(C_1$-$C_6)$alkyl, $—SO_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $—OC_1$-$C_{10}$ alkyl-Z, or $R_{23}$.

Other preferred compounds of Formula VIII include those where $R_3$ and $R_4$ are independently hydrogen, halo, or $—Z_1R_{Z1}$, wherein $Z_1$ is $—O—$ or $—NH—$; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $—SH$, $—S—(C_1$-$C_6)$alkyl, $—SO_2—(C_1$-$C_6)$alkyl, $—SO_2NH_2$, $—SO_2NH—(C_1$-$C_6)$alkyl, $—SO_2NH$-aryl, $—SO_2$-aryl, $—SO—(C_1$-$C_6)$alkyl, $—SO_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $—OC_1$-$C_{10}$ alkyl-Z, or $R_{23}$; and $X_4$ is O.

Other preferred compounds of Formula VIII include those where $R_3$ and $R_4$ are independently hydrogen, halo, or $—Z_1R_{Z1}$, wherein $Z_1$ is $—O—$ or $—NH—$; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $—SH$, $—S—(C_1$-$C_6)$alkyl, $—SO_2—(C_1$-$C_6)$alkyl, $—SO_2NH_2$, $—SO_2NH—(C_1$-$C_6)$alkyl, $—SO_2NH$-aryl, $—SO_2$-aryl, $—SO—(C_1$-$C_6)$alkyl, $—SO_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $—OC_1$-$C_{10}$ alkyl-Z, or $R_{23}$; and $X_4$ is N—OH.

Still other preferred compounds of Formula VIII are those wherein $R_3$ and $R_4$ are independently hydrogen, halo, or $—N(H)R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $—SH$, $—S—(C_1$-$C_6)$alkyl, $—SO_2—(C_1$-$C_6)$alkyl, $—SO_2NH_2$, $—SO_2NH—(C_1$-$C_6)$alkyl, $—SO_2NH$-aryl, $—SO_2$-aryl, $—SO—(C_1$-$C_6)$alkyl, $—SO_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $—OC_1$-$C_{10}$ alkyl-Z, or $R_{23}$.

Still other preferred compounds of Formula VIII are those wherein $R_3$ and $R_4$ are independently hydrogen, halo, or $—N(H)R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein R$_{Z1}$ is optionally substituted at any available position with C$_1$-C$_{10}$ alkyl, C$_1$-C$_{10}$ haloalkyl, C$_2$-C$_{10}$ alkenyl, C$_2$-C$_{10}$ alkynyl, hydroxy, carboxy, carboxamido, oxo, halo, amino, cyano, nitro, —SH, —S—(C$_1$-C$_6$) alkyl, —SO$_2$—(C$_1$-C$_6$)alkyl, —SO$_2$NH$_2$, —SO$_2$NH—(C$_1$-C$_6$)alkyl, —SO$_2$NH-aryl, —SO$_2$-aryl, —SO—(C$_1$-C$_6$)alkyl, —SO$_2$-aryl, C$_1$-C$_6$ alkoxy, C$_2$-C$_{10}$ alkenyloxy, C$_2$-C$_{10}$ alkynyloxy, mono- or di-(C$_1$-C$_{10}$)alkylamino, —OC$_1$-C$_{10}$ alkyl-Z, or R$_{23}$; and X$_4$ is O.

Still other preferred compounds of Formula VIII are those where R$_3$ and R$_4$ are independently hydrogen, halo, or —N(H)R$_{Z1}$, wherein R$_{Z1}$ is a C$_1$-C$_{14}$ alkyl group where up to five of the carbon atoms in the alkyl group are optionally replaced independently by R$_{22}$, carbonyl, ethenyl, ethynyl or a moiety selected from N, O, S, SO$_2$, or SO, with the proviso that two O atoms, two S atoms, or an O and S atom are not immediately adjacent each other, wherein R$_{Z1}$ is optionally substituted at any available position with C$_1$-C$_{10}$ alkyl, C$_1$-C$_{10}$ haloalkyl, C$_2$-C$_{10}$ alkenyl, C$_2$-C$_{10}$ alkynyl, hydroxy, carboxy, carboxamido, oxo, halo, amino, cyano, nitro, —SH, —S—(C$_1$-C$_6$) alkyl, —SO$_2$—(C$_1$-C$_6$)alkyl, —SO$_2$NH$_2$, —SO$_2$NH—(C$_1$-C$_6$)alkyl, —SO$_2$NH-aryl, —SO$_2$-aryl, —SO—(C$_1$-C$_6$)alkyl, —SO$_2$-aryl, C$_1$-C$_6$ alkoxy, C$_2$-C$_{10}$ alkenyloxy, C$_2$-C$_{10}$ alkynyloxy, mono- or di-(C$_1$-C$_{10}$)alkylamino, —OC$_1$-C$_{10}$ alkyl-Z, or R$_{23}$; and X$_4$ is N—OH.

Yet other preferred compounds of Formula VIII are those where R$_3$, R$_4$ and the carbons to which they are attached form a 6-membered ring.

Yet other preferred compounds of Formula VIII are those where R$_3$, R$_4$ and the carbons to which they are attached form a 6-membered ring; and X$_4$ is O.

Yet other preferred compounds of Formula VIII are those where R$_3$, R$_4$ and the carbons to which they are attached form a 6-membered ring; and X$_4$ is N—OH.

Other preferred compounds of Formula I are those of Formula IX:

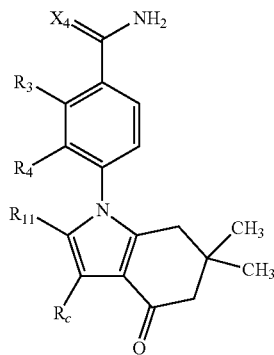

IX where R$_{11}$ is hydrogen or methyl, preferably hydrogen;
R$_C$ is H, C$_1$-C$_2$ alkyl, trifluoromethyl, or cyclopropyl; and
R$_3$, R$_4$, and X$_4$ carry the same definitions as for Formula I.
Preferred compounds of Formula IX include those where R$_C$ is C$_1$-C$_2$ alkyl, trifluoromethyl, or cyclopropyl.

Preferred compounds of Formula IX include those where R$_3$ and R$_4$ are independently hydrogen, halo, or —Z$_1$R$_{Z1}$, wherein Z$_1$ is —O—, —NH—, —S(O)$_p$—, or —S(O)$_2$NH—, wherein p is 0, 1 or 2; and R$_{Z1}$ is a C$_1$-C$_{14}$ alkyl group where up to five of the carbon atoms in the alkyl group are optionally replaced independently by R$_{22}$, carbonyl, ethenyl, ethynyl or a moiety selected from N, O, S, SO$_2$, or SO, with the proviso that two O atoms, two S atoms, or an O and S atom are not immediately adjacent each other, wherein R$_{Z1}$ is optionally substituted at any available position with C$_1$-C$_{10}$ alkyl, C$_1$-C$_{10}$ haloalkyl, C$_2$-C$_{10}$ alkenyl, C$_2$-C$_{10}$ alkynyl, hydroxy, carboxy, carboxamido, oxo, halo, amino, cyano, nitro, —SH, —S—(C$_1$-C$_6$) alkyl, —SO$_2$—(C$_1$-C$_6$)alkyl, —SO$_2$NH$_2$, —SO$_2$NH—(C$_1$-C$_6$)alkyl, —SO$_2$NH-aryl, —SO$_2$-aryl, —SO—(C$_1$-C$_6$)alkyl, —SO$_2$-aryl, C$_1$-C$_6$ alkoxy, C$_2$-C$_{10}$ alkenyloxy, C$_2$-C$_{10}$ alkynyloxy, mono- or di-(C$_1$-C$_{10}$)alkylamino, —OC$_1$-C$_{10}$ alkyl-Z, or R$_{23}$.

Preferred compounds of Formula IX include those where R$_C$ is methyl, ethyl, trifluoromethyl, or cyclopropyl; R$_3$ and R$_4$ are independently hydrogen, halo, or —Z$_1$R$_{Z1}$, wherein Z$_1$ is —O—, —NH—, —S(O)$_p$—, or —S(O)$_2$NH—, wherein p is 0, 1 or 2; and R$_{Z1}$ is a C$_1$-C$_{14}$ alkyl group where up to five of the carbon atoms in the alkyl group are optionally replaced independently by R$_{22}$, carbonyl, ethenyl, ethynyl or a moiety selected from N, O, S, SO$_2$, or SO, with the proviso that two O atoms, two S atoms, or an O and S atom are not immediately adjacent each other, wherein R$_{Z1}$ is optionally substituted at any available position with C$_1$-C$_{10}$ alkyl, C$_1$-C$_{10}$ haloalkyl, C$_2$-C$_{10}$ alkenyl, C$_2$-C$_{10}$ alkynyl, hydroxy, carboxy, carboxamido, oxo, halo, amino, cyano, nitro, —SH, —S—(C$_1$-C$_6$) alkyl, —SO$_2$—(C$_1$-C$_6$)alkyl, —SO$_2$NH$_2$, —SO$_2$NH—(C$_1$-C$_6$)alkyl, —SO$_2$NH-aryl, —SO$_2$-aryl, —SO—(C$_1$-C$_6$)alkyl, —SO$_2$-aryl, C$_1$-C$_6$ alkoxy, C$_2$-C$_{10}$ alkenyloxy, C$_2$-C$_{10}$ alkynyloxy, mono- or di-(C$_1$-C$_{10}$)alkylamino, —OC$_1$-C$_{10}$ alkyl-Z, or R$_{23}$; and X$_4$ is O.

Preferred compounds of Formula IX include those where R$_C$ is methyl, ethyl, trifluoromethyl, or cyclopropyl; R$_3$ and R$_4$ are independently hydrogen, halo, or —Z$_1$R$_{Z1}$, wherein Z$_1$ is —O—, —NH—, —S(O)$_p$—, or —S(O)$_2$NH—, wherein p is 0, 1 or 2; and R$_{Z1}$ is a C$_1$-C$_{14}$ alkyl group where up to five of the carbon atoms in the alkyl group are optionally replaced independently by R$_{22}$, carbonyl, ethenyl, ethynyl or a moiety selected from N, O, S, SO$_2$, or SO, with the proviso that two O atoms, two S atoms, or an O and S atom are not immediately adjacent each other, wherein R$_{Z1}$ is optionally substituted at any available position with C$_1$-C$_{10}$ alkyl, C$_1$-C$_{10}$ haloalkyl, C$_2$-C$_{10}$ alkenyl, C$_2$-C$_{10}$ alkynyl, hydroxy, carboxy, carboxamido, oxo, halo, amino, cyano, nitro, —SH, —S—(C$_1$-C$_6$) alkyl, —SO$_2$—(C$_1$-C$_6$)alkyl, —SO$_2$NH$_2$, —SO$_2$NH—(C$_1$-C$_6$)alkyl, —SO$_2$NH-aryl, —SO$_2$-aryl, —SO—(C$_1$-C$_6$)alkyl, —SO$_2$-aryl, C$_1$-C$_6$ alkoxy, C$_2$-C$_{10}$ alkenyloxy, C$_2$-C$_{10}$ alkynyloxy, mono- or di-(C$_1$-C$_{10}$)alkylamino, —OC$_1$-C$_{10}$ alkyl-Z, or R$_{23}$; and X$_4$ is N—OH.

Still other preferred compounds of Formula IX include those where R$_3$ and R$_4$ are independently hydrogen, halo, or —Z$_1$R$_{Z1}$, wherein Z$_1$ is —O— or —NH—; and R$_{Z1}$ is a C$_1$-C$_{14}$ alkyl group where up to five of the carbon atoms in the alkyl group are optionally replaced independently by R$_{22}$, carbonyl, ethenyl, ethynyl or a moiety selected from N, O, S, SO$_2$, or SO, with the proviso that two O atoms, two S atoms, or an O and S atom are not immediately adjacent each other, wherein R$_{Z1}$ is optionally substituted at any available position with C$_1$-C$_{10}$ alkyl, C$_1$-C$_{10}$ haloalkyl, C$_2$-C$_{10}$ alkenyl, C$_2$-C$_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Still other preferred compounds of Formula IX include those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$; and $X_4$ is O.

Still other preferred compounds of Formula IX include those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$; and $X_4$ is N—OH.

Yet other preferred compounds of Formula IX include those where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Yet other preferred compounds of Formula IX include those where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$; and $X_4$ is O.

Yet other preferred compounds of Formula IX include those where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$; and $X_4$ is N—OH.

Still other preferred compounds of Formula IX include those where $R_3$, $R_4$ and the carbons to which they are attached form a 6-membered ring.

Still other preferred compounds of Formula IX include those where $R_3$, $R_4$ and the carbons to which they are attached form a 6-membered ring; and $X_4$ is O.

Still other preferred compounds of Formula IX include those where $R_3$, $R_4$ and the carbons to which they are attached form a 6-membered ring; and $X_4$ is N—OH.

Preferred compounds of Formulas I-IX include compounds where $X_4$ is O.

Still other preferred compounds of Formulas I-IX are those where $X_4$ is N—OH.

Other preferred compounds of Formula I are those where $R_{21}$ is cyano, $R_7$ is O, and Y is $CR_C$, wherein $R_C$ is H, methyl, ethyl, trifluoromethyl, or cyclopropyl.

Other preferred compounds of Formula I are those where, $R_{21}$ is cyano; $R_7$ is O; and Y is $CR_C$, wherein $R_C$ is H, methyl, trifluoromethyl, or cyclopropyl.

Yet other preferred compounds of Formula I are those where $R_{21}$ is cyano, and $X_3$ is C substituted with two groups that are independently H or $C_1$-$C_6$ alkyl.

More preferred compounds of Formula I are those where $R_{21}$ is cyano, and $Q_1$ and $Q_2$ are independently C substituted with H or $C_1$-$C_6$ alkyl.

Yet other preferred compounds of Formula I are those where $R_{21}$ is cyano, and $X_1$ is C substituted with H or $C_1$-$C_6$ alkyl.

Still other preferred compounds of Formula I are those where $R_{21}$ is cyano, and $X_2$ is C substituted with two groups that are independently H or $C_1$-$C_4$ alkyl.

In other preferred compounds of Formula I, $R_{21}$ is cyano, and $R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In still other preferred compounds of Formula I, $R_{21}$ is cyano, and $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In still other preferred compounds of Formula I, $R_{21}$ is cyano, and $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Other more preferred compounds of Formula I are those where $R_{21}$ is cyano, and $R_4$ is H, $C_1$-$C_4$ alkyl or halogen.

Particularly preferred compounds of Formula I include those where
$R_{21}$ is cyano, and
$X_2$ is C substituted with two groups that are independently H or $C_1$-$C_4$ alkyl;
$X_1$ is C substituted with H or $C_1$-$C_6$ alkyl;
$Q_1$ and $Q_2$ are independently C substituted with H or $C_1$-$C_6$ alkyl;
$X_3$ is C substituted with two groups that are independently H or $C_1$-$C_6$ alkyl;
$R_7$ is O;
Y is CR$_C$ wherein R$_C$ is H or CH$_3$; and
$R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and
n is 1 or 2.

Such compounds are referred to herein as compounds of Formula X.

Preferred compounds of Formula X include those where
$R_1$ and $R_2$ are independently H or $C_1$-$C_4$ alkyl;
$Q_1$ and $Q_2$ are both CH;
$X_2$ is C substituted with two independently selected $C_1$-$C_4$ alkyl groups; and
n is 1.

Particularly preferred compounds of Formula I include those where $R_{21}$ is cyano. Such compounds are referred to hereinafter as compounds of Formula XI.

Preferred compounds of Formula XI are those where $R_3$ and $R_4$ are independently halogen or hydrogen.

Preferred compounds of Formula XI are those where $R_3$ is halogen.

Preferred compounds of Formula XI are those where $R_3$ is hydrogen and $R_4$ is halogen.

Preferred compounds of Formula XI are those where $R_4$ is halogen.

Other preferred compounds of Formula I include those of Formula XII:

XII

[Structure: bicyclic compound with CN, R3, R4 substituents on benzene ring, fused to pyrazole ring with X1, N, and cyclohexanone with R5, R6, Rc substituents]

$R_3$ and $R_4$ are independently halogen or hydrogen, provided that at least one of $R_3$ and $R_4$ is halogen, and $X_1$, $R_C$, $R_5$ and $R_6$ are as defined for Formula I.

Preferred compounds of Formula XII include those where $X_1$ is N.

Preferred compounds of Formula XII include those where $X_1$ is CR$_C$, wherein R$_C$ is hydrogen, methyl, ethyl, cyclopropyl, cyclopropylmethyl, fluoromethyl, difluoromethyl, or trifluoromethyl.

Preferred compounds of Formula XII are those where $R_3$ is halogen.

Other preferred compounds of Formula XII are those where $R_4$ is halogen.

Still other preferred compounds of Formula XII are those where $R_3$ is fluoro and $R_4$ is hydrogen or fluoro.

Particularly preferred compounds of Formula XII are those where $R_4$ is fluoro and $R_3$ is hydrogen, bromo, or fluoro.

Other particularly preferred compounds of Formula XII are those where $R_4$ is hydrogen.

Still other preferred compounds of Formula XII are those where $R_3$ is hydrogen.

Particularly preferred compounds of Formula XII include those where $R_3$ and $R_4$ are fluoro.

Preferred compounds of Formula XII are those where $R_3$ and $R_4$ are bromo and fluoro respectively.

Yet other preferred compounds of Formula I include those of Formula XIII,

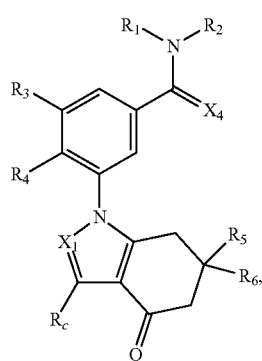

XIII wherein $R_1$-$R_6$, $X_4$, $X_1$, and $R_C$ are as defined in Formula I.

Preferred compounds of Formula XIII include those where $R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Other preferred compounds of Formula XIII are those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Other preferred compounds of Formula XIII are those where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In still other preferred compounds of Formula XIII $R_3$, $R_4$ and the carbons to which they are attached form a 6-membered ring.

In more preferred aspects, the previously described preferred embodiments of Formula XIII include compounds wherein $X_1$ is N or $CR_C$, wherein $R_C$ is hydrogen, methyl, ethyl, cyclopropyl, cyclopropylmethyl, fluoromethyl, difluoromethyl, or trifluoromethyl.

In more preferred aspects, the previously described preferred embodiments of Formula XIII include compounds wherein $X_1$ is N.

In more preferred aspects, the previously described preferred embodiments of Formula XIII include compounds wherein $X_1$ is $CR_C$, wherein $R_C$ is hydrogen, methyl, ethyl, cyclopropyl, cyclopropylmethyl, fluoromethyl, difluoromethyl, or trifluoromethyl.

Other preferred compounds of Formula I include those of Formula XIV,

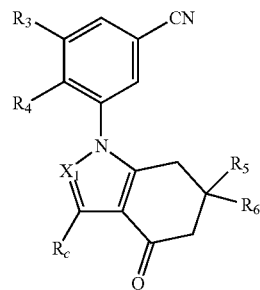

XIV wherein $R_C$ is —H, —CH$_3$, —CF$_3$, or cyclopropyl; and $R_3$ and $R_4$ are independently halogen or hydrogen, provided that at least one of $R_3$ and $R_4$ is halogen, and $R_5$ and $R_6$ are as defined for Formula I.

Yet other preferred compounds of Formula II through XIV are those where $R_{21}$ is cyano; $R_7$ is O; and Y is CH or C(CH$_3$).

Yet other preferred compounds of Formula II through XIV are those where $R_{21}$ is cyano; and $R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Yet other preferred compounds of Formula II through XIV are those where $R_{21}$ is cyano; and $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Yet other preferred compounds of Formula II through XIV are those where $R_{21}$ is cyano; and $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

In another aspect, the invention encompasses compounds of Formula I, wherein Y is $CR_C$, wherein $R_C$ is —H, $C_1$-$C_{10}$ alkyl, $C_1$-$C_{10}$ haloalkyl, or $C_3$-$C_7$ cycloalkyl.

In another aspect, the invention encompasses compounds of Formula I, wherein Y is CH.

In another aspect, the invention encompasses compounds of Formula I, wherein Y is $CR_C$, wherein $R_C$ is $C_1$-$C_{10}$ alkyl, $C_1$-$C_{10}$ haloalkyl, or $C_3$-$C_7$ cycloalkyl.

In another aspect, the invention encompasses compounds of Formula I, wherein Y is $CR_C$, wherein $R_C$ is methyl, ethyl, trifluoromethyl, or cyclopropyl.

In another aspect, the invention encompasses compounds of Formula I, wherein Y is $CR_C$, wherein $R_C$ is methyl.

In another aspect, the invention encompasses compounds of Formula I, wherein Y is $CR_C$, wherein $R_C$ is cyclopropyl.

Yet other preferred compounds of Formula I include those of Formula XV,

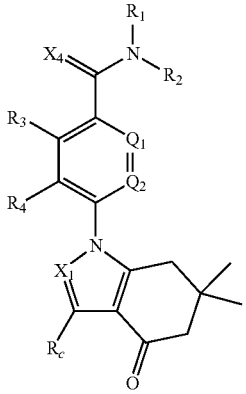

XV wherein $X_1$-$X_4$, $Q_1$, $Q_2$, $R_C$, and $R_1$-$R_4$ are as defined in Formula I.

Preferred compounds of formula XV are those where $Q_1$ and $Q_2$ are each independently hydrogen or $C_1$-$C_6$ alkyl.

Other preferred compounds of formula XV are those where $R_C$ is $C_1$-$C_6$alkyl, $C_3$-$C_7$cycloalkyl, $C_1$-$C_6$ haloalkyl, $C_3$-$C_7$cycloalkyl($C_1$-$C_6$)alkyl, or heterocycloalkyl.

More preferred compounds of Formula XV include those where $R_C$ is $C_3$-$C_7$cycloalkyl, $C_1$-$C_6$ haloalkyl, heterocycloalkyl, or $C_3$-$C_7$cycloalkyl($C_1$-$C_6$)alkyl.

Particularly preferred compounds of Formula XV include those where $R_C$ is $C_1$-$C_3$alkyl, $C_3$-$C_5$cycloalkyl, $C_3$-$C_5$cycloalkyl($C_1$-$C_3$)alkyl, or $C_1$-$C_2$ haloalkyl.

Additional preferred compounds of Formula XV include those where $R_3$ and $R_4$ are independently hydrogen, halo, or —$Z_1R_{Z1}$, wherein $Z_1$ is —O—, —NH—, —$S(O)_p$—, or —$S(O)_2NH$—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Other preferred compounds of Formula XV include those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

Still other preferred compounds of Formula XV are those wherein $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

More preferred compounds of Formula XV are those wherein $R_3$ and $R_4$ are independently hydrogen, —N(H)—$R_{22}$—$R_{Z2}$, wherein $R_{Z2}$ is a $C_1$-$C_{13}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z2}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$) alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Such compounds are referred to herein as compounds of Formula XVa.

Preferred compounds of Formula XVa are those where $X_1$ is N.

Preferred compounds of Formula XVa are those where $R_{22}$ is heteroaryl, aryl, saturated $C_3$-$C_{10}$ cycloalkyl, or saturated $C_2$-$C_{10}$ heterocycloalkyl.

More preferred compounds of Formula XVa are those where $R_{22}$ is heteroaryl, aryl, saturated $C_3$-$C_{10}$ cycloalkyl, or saturated $C_2$-$C_{10}$ heterocycloalkyl; and $X_1$ is N.

Particularly preferred compounds of Formula XVa are those where $R_{22}$ is saturated $C_3$-$C_7$ cycloalkyl, or saturated $C_2$-$C_6$ heterocycloalkyl.

Particularly preferred compounds of Formula XVa are those where $R_{22}$ is saturated $C_3$-$C_7$ cycloalkyl, or saturated $C_2$-$C_6$ heterocycloalkyl and $X_1$ is N.

Preferred compounds of Formula XV are those where $X_1$ is N. Such compounds are referred to herein as compounds of Formula XVI.

Preferred compounds of Formula XVI include those where $R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Preferred compounds of Formula XVI include those where $R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and $X_4$ is O.

Preferred compounds of Formula XVI include those where $R_3$ and $R_4$ are independently hydrogen, halo, or —$Z_1R_{Z1}$, wherein $Z_1$ is —O—, —NH—, —S(O)$_p$—, or —S(O)$_2$NH—, wherein p is 0, 1 or 2; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and $X_4$ is N—OH.

Other preferred compounds of Formula XVI include those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$-alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Other preferred compounds of Formula XVI include those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and $X_4$ is O.

Other preferred compounds of Formula XVI include those where $R_3$ and $R_4$ are independently hydrogen, halo, or —$Z_1R_{Z1}$, wherein $Z_1$ is —O— or —NH—; and $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and $X_4$ is N—OH.

Still other preferred compounds of Formula XVI are those wherein $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$) alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

Still other preferred compounds of Formula XVI are those wherein $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and $X_4$ is O.

Still other preferred compounds of Formula XVI are those where $R_3$ and $R_4$ are independently hydrogen, halo, or —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$) alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and $X_4$ is N—OH.

Yet other preferred compounds of Formula XVI are those where $R_3$, $R_4$ and the carbons to which they are attached form a 6-membered ring.

Yet other preferred compounds of Formula XVI are those where $R_3$, $R_4$ and the carbons to which they are attached form a 6-membered ring; and $X_4$ is O.

Yet other preferred compounds of Formula XVI are those where $R_3$, $R_4$ and the carbons to which they are attached form a 6-membered ring; and $X_4$ is N—OH.

Yet other preferred compounds of Formula XVI are those where $R_3$ and $R_4$ are both —H.

Yet other preferred compounds of Formula XVI are those where $R_3$ and $R_4$ are both —H; and $X_4$ is O.

Yet other preferred compounds of Formula XVIII are those where $R_3$ and $R_4$ are both —H; and $X_4$ is N—OH.

In another aspect, the invention provides compounds of Formula XXII

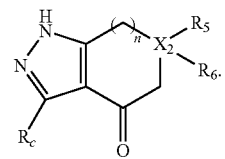

XXII

Preferred compounds of Formula XXII include those where $R_C$ is $C_1$-$C_6$alkyl, $C_3$-$C_7$cycloalkyl, $C_1$-$C_6$ haloalkyl, $C_3$-$C_7$cycloalkyl($C_1$-$C_6$)alkyl, or heterocycloalkyl.

More preferred compounds of Formula XXII include those where $R_C$ is $C_3$-$C_7$cycloalkyl, $C_1$-$C_6$ haloalkyl, heterocycloalkyl, or $C_3$-$C_7$cycloalkyl($C_1$-$C_6$)alkyl, and $X_2$ is carbon and $R_5$ and $R_6$ are $C_1$-$C_6$alkyl.

Particularly preferred compounds of Formula XXII include those where $R_C$ is $C_1$-$C_3$alkyl, $C_3$-$C_5$cycloalkyl, $C_3$-$C_5$cycloalkyl($C_1$-$C_3$)alkyl, or $C_1$-$C_2$ haloalkyl.

Other particularly preferred compounds of Formula XXII include those where $R_C$ is methyl, ethyl, cyclopropyl, cyclopropylmethyl, perfluoropropyl, 2,2,2-trifluoroethyl, fluoromethyl, difluoromethyl, perfluoroethyl, or trifluoromethyl.

In a preferred aspect, the invention provides compounds formula I, wherein $Q_3$ is C—$R_{21}$.

In a more preferred aspect, the invention provides compounds formula I, wherein $Q_3$ is C—$R_{21}$, wherein $R_{21}$ is cyano.

In more preferred aspect, the invention provides compounds Formula XXIV,

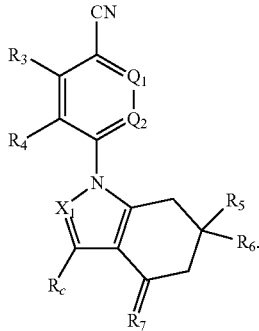

XXIV

In another preferred aspect, the invention provides compounds formula I, wherein $X_1$ is N.

In a more preferred aspect, the invention provides compounds formula I, wherein $Q_3$ is C—$R_{21}$, wherein $R_{21}$ is —C(O)OH, —C(O)—O($C_1$-$C_6$ alkyl), or a group of the formula,

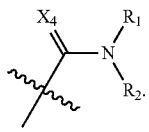

In a another more preferred aspect, the invention provides compounds formula I, wherein $Q_3$ is C—$R_{21}$, wherein $R_{21}$ is a group of the formula,

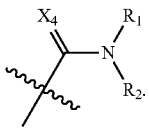

In a preferred aspect, the invention provides compounds formula XXV,

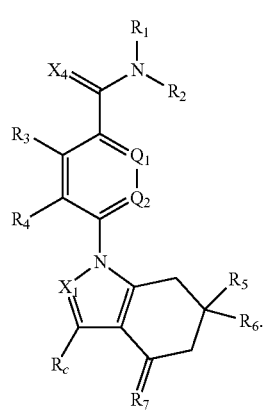

XXV

In a preferred aspect, the invention provides compounds formula XXV, wherein $X_1$ is N.

In a preferred aspect, the invention provides compounds formula XXV, wherein $X_1$ is N; and $R_3$ and $R_4$ are independently hydrogen, halo, or —$Z_1R_{Z1}$, wherein $Z_1$ is —O— or —NH—;

$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In a preferred aspect, the invention provides compounds formula XXV, wherein $X_1$ is N; and $R_4$ is H; and $R_3$ hydrogen, halo, or —$Z_1R_{Z1}$, wherein $Z_1$ is —O— or —NH—;

$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In a preferred aspect, the invention provides compounds formula XXV, wherein $X_1$ is N; and $R_4$ is H; and $R_3$ is —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In a preferred aspect, the invention provides compounds formula XXV, wherein $X_1$ is N;
$R_4$ is H;
$R_3$ is —N(H)$R_{Z1}$, wherein
   $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
      wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$; and
$R_C$ is methyl, ethyl, cyclopropyl, cyclopropylmethyl, fluoromethyl, difluoromethyl, or trifluoromethyl.

In a preferred aspect, the invention provides compounds formula XXV, wherein $X_1$ is N; and
$R_3$ is H; and
$R_4$ is hydrogen, halo, or —$Z_1R_{Z1}$, wherein
   $Z_1$ is —O— or —NH—;
   $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
      wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In a preferred aspect, the invention provides compounds formula XXV, wherein $X_1$ is N;
$R_3$ is H;
$R_4$ is hydrogen, halo, or —$Z_1R_{Z1}$, wherein
   $Z_1$ is —O— or —NH—;
   $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
      wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$;
   and
$R_C$ is methyl, ethyl, cyclopropyl, cyclopropylmethyl, fluoromethyl, difluoromethyl, or trifluoromethyl.

In a preferred aspect, the invention provides compounds formula XXV, wherein
$X_1$ is $CR_{11}$, wherein
   $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
      $R_{C'}$ is —$C_1$-$C_6$ alkyl, —O$R_{C''}$, or —N($R_{CN}$)$_2$, wherein
         $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;
         each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl.

In a more preferred aspect, the invention provides compounds formula XXV, wherein
$X_1$ is $CR_{11}$, wherein
   $R_{11}$ is hydrogen, halogen, $C_1$-$C_{10}$ alkyl, $C_1$-$C_{10}$ haloalkyl, $C_3$-$C_7$ cycloalkyl, $C_3$-$C_7$ cycloalkyl($C_1$-$C_{10}$)alkyl, aryl, or heteroaryl.

In a preferred aspect, the invention provides compounds formula XXV, wherein
$X_1$ is $CR_{11}$, wherein
   $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
      $R_{C'}$ is —$C_1$-$C_6$ alkyl, —O$R_{C''}$, or —N($R_{CN}$)$_2$, wherein
         $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;
         each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl; and
$R_3$ and $R_4$ are independently hydrogen, halo, or —$Z_1R_{Z1}$, wherein
   $Z_1$ is —O— or —NH—;
   $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
      wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

In a preferred aspect, the invention provides compounds formula XXV, wherein
$X_1$ is $CR_{11}$, wherein
   $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
      $R_{C'}$ is —$C_1$-$C_6$ alkyl, —O$R_{C''}$, or —N($R_{CN}$)$_2$, wherein
         $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;
         each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl;

$R_4$ is H; and $R_3$ hydrogen, halo, or —$Z_1R_{Z1}$, wherein $Z_1$ is —O— or —NH—;

$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

In a preferred aspect, the invention provides compounds formula XXV, wherein $X_1$ is $CR_{11}$, wherein $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein $R_{C'}$ is —$C_1$-$C_6$ alkyl, —$OR_{C''}$, or —N($R_{CN}$)$_2$, wherein $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;

each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl;

$R_4$ is H; and $R_3$ is —N(H)$R_{Z1}$, wherein $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

In a preferred aspect, the invention provides compounds formula XXV, wherein $X_1$ is $CR_{11}$, wherein $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein $R_{C'}$ is —$C_1$-$C_6$ alkyl, —$OR_{C''}$, or —N($R_{CN}$)$_2$, wherein $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;

each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl;

$R_4$ is H;

$R_3$ is —N(H)$R_{Z1}$, wherein $R_{Z1}$ is a $C_1$-$C_{14}$ alkyl group where up to five of the carbon atoms in the alkyl group are optionally replaced inde- $R_C$ is hydrogen, methyl, ethyl, cyclopropyl, cyclopropylmethyl, fluoromethyl, difluoromethyl, or trifluoromethyl.

In a preferred aspect, the invention provides compounds formula XXV, wherein $X_1$ is $CR_{11}$, wherein $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein $R_{C'}$ is —$C_1$-$C_6$ alkyl, —$OR_{C''}$, or —N($R_{CN}$)$_2$, wherein $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;

each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl;

$R_3$ is H; and $R_4$ is hydrogen, halo, or —$Z_1R_{Z1}$, wherein $Z_1$ is —O— or —NH—;

$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

In a preferred aspect, the invention provides compounds formula XXV, wherein $X_1$ is $CR_{11}$, wherein $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein $R_{C'}$ is —$C_1$-$C_6$ alkyl, —$OR_{C''}$, or —N($R_{CN}$)$_2$, wherein $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;

each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl;

$R_3$ is H;

$R_4$ is hydrogen, halo, or —$Z_1R_{Z1}$, wherein $Z_1$ is —O— or —NH—;

$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$; and $R_C$ is hydrogen, methyl, ethyl, cyclopropyl, cyclopropylmethyl, fluoromethyl, difluoromethyl, or trifluoromethyl.

In another aspect, the invention encompasses a method of treating cancer comprising administering to a patient in need thereof, a pharmaceutically acceptable amount of a compound or salt of Formula I or a pharmaceutical composition comprising a compound or salt of Formula I.

In another aspect, the invention encompasses the use of a therapeutically effective amount of a compound or salt of Formula I for the preparation of a medicament for the treatment of cancer, inflammation, or arthritis in a patient in need of such treatment.

In another aspect, the invention encompasses a package comprising a compound or salt of Formula I in a container with instructions on how to use the compound.

In another aspect, the invention encompasses the use of a therapeutically effective amount of a compound or salt according of Formula I for the preparation of a medicament for the treatment of a disease or condition related to cell proliferation in a patient in need of such treatment.

In another aspect, the invention encompasses the use of a therapeutically effective amount of a compound or salt according of Formula I for the preparation of a medicament for the treatment of a disease or condition related to cell proliferation in a patient in need of such treatment, wherein the disease or condition is cancer, inflammation, or arthritis.

In another aspect, the invention encompasses the use of therapeutically effective amount of a compound or salt of Formula I for the preparation of a medicament for the treatment of a disease or disorder related to the activity of heat shock protein 90, in a subject in need of such.

In another aspect, the invention encompasses the use of therapeutically effective amount of a compound or salt of Formula I, alone or in combination with another therapeutic agent, for the preparation of a medicament for the treatment of a disease or disorder related to the activity of heat shock protein 90 and/or its client proteins, in a subject in need of such, wherein the HSP-90 mediated disorder is selected from the group of inflammatory diseases, infections, autoimmune disorders, stroke, ischemia, cardiac disorders, neurological disorders, fibrogenetic disorders, proliferative disorders, tumors, leukemias, neoplasms, cancers, carcinomas, metabolic diseases and malignant disease.

In a preferred aspect, the invention encompasses methods for the treatment of cancer in a subject in need of such treatment comprising administration of therapeutically effective amount of a compound or salt of Formula I, in combination with at least one other therapeutic agent.

In a more preferred aspect, the invention encompasses methods for treating cancer in a subject in need of such treatment, the methods comprising administration of therapeutically effective amount of a compound or salt of Formula I, in combination with at least one other anti-cancer agent.

In another preferred aspect, the invention encompasses methods for treating cancer, the methods comprising administration, to a subject in need of such treatment, of a therapeutically effective amount of a compound or salt of Formula I, in combination with radiation therapy.

In another aspect, the invention encompasses the use of therapeutically effective amount of a compound or salt of Formula I for the preparation of a medicament for the treatment of a fibrogenetic disorder related to the activity of heat shock protein 90, in a subject in need of such, wherein the fibrogenetic disorder is selected from the group of scleroderma, polymyositis, systemic lupus, rheumatoid arthritis, liver cirrhosis, keloid formation, interstitial nephritis and pulmonary fibrosis.

In another aspect, the invention encompasses the use of a therapeutically effective amount of a compound or salt of Formula I for the preparation of a medicament for protecting a subject from infection caused by an organism selected from *Plasmodium* species.

In a preferred aspect, the invention encompasses the use of a therapeutically effective amount of a compound or salt of Formula I for the preparation of a medicament for protecting a subject from infection caused by *Plasmodium falciparum*.

In another aspect, the invention encompasses the use of a therapeutically effective amount of a compound or salt of Formula I for the preparation of a medicament for reducing the level of infection caused by an organism selected from *Plasmodium* species in a subject in need of such treatment.

In a preferred aspect, the invention encompasses the use of a therapeutically effective amount of a compound or salt of Formula I for the preparation of a medicament for reducing the level of infection caused by *Plasmodium falciparum* in a subject in need of such treatment.

In another aspect, the invention encompasses the use of a therapeutically effective amount of a compound or salt of Formula I for the preparation of a medicament for treating a patient infected with a metazoan parasite.

In a preferred aspect, the invention encompasses the use of a therapeutically effective amount of a compound or salt of Formula I for the preparation of a medicament for treating a patient infected by a metazoan parasite which is *Plasmodium falciparum*.

In another aspect, the invention encompasses the use of a therapeutically effective amount of a compound or salt of Formula I in combination with one or more known antifungal drugs for the preparation of a medicament for treating a patient infected with a fungal infection.

Definitions

The term "alkoxy" represents an alkyl group of indicated number of carbon atoms attached to the parent molecular moiety through an oxygen bridge. Examples of alkoxy groups include, for example, methoxy, ethoxy, propoxy and isopropoxy.

As used herein, the term "alkyl" includes those alkyl groups of a designated number of carbon atoms. Alkyl groups may be straight, or branched. Examples of "alkyl" include methyl, ethyl, propyl, isopropyl, butyl, iso-, sec- and tert-butyl, pentyl, hexyl, heptyl, 3-ethylbutyl, and the like.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenoxy" refers to an alkenyl group attached to the parent group through an oxygen atom.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl, naphthyl, and anthracenyl. More preferred aryl groups are phenyl and naphthyl. Most preferred is phenyl. The aryl groups of the invention may be substituted with various groups as provided herein. Thus, any carbon atom present within an aryl ring system and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_9$heterocycloalkyl, $C_1$-$C_8$alkenyl, $C_1$-$C_8$alkynyl, halo($C_1$-$C_8$)alkyl, halo($C_1$-$C_8$)alkoxy, oxo, amino($C_1$-$C_8$)alkyl, mono- and di($C_1$-$C_8$alkyl)amino($C_1$-$C_8$)alkyl, $C_1$-$C_8$acyl, $C_1$-$C_8$acyloxy, $C_1$-$C_8$sulfonyl, $C_1$-$C_8$thio, $C_1$-$C_8$sulfonamido, $C_1$-$C_8$-aminosulfonyl.

The term "carboxy" as used herein, means a —$CO_2H$ group.

The term "cycloalkyl" refers to a $C_3$-$C_8$ cyclic hydrocarbon. Examples of cycloalkyl include cyclopropyl, cyclobutyl, cyclopentyl, cyclohexyl, cycloheptyl and cyclooctyl. More preferred are $C_3$-$C_6$ cycloalkyl groups. The cycloalkyl groups of the invention may be substituted with various groups as provided herein. Thus, any carbon atom present within a cycloalkyl ring system and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_9$heterocycloalkyl, $C_1$-$C_8$alkenyl, $C_1$-$C_8$alkynyl, halo($C_1$-$C_8$)alkyl, halo($C_1$-$C_8$) alkoxy, oxo, amino($C_1$-$C_8$)alkyl and mono- and di($C_1$-$C_8$alkyl)amino($C_1$-$C_8$)alkyl.

The terms "halogen" or "halo" indicate fluorine, chlorine, bromine, and iodine.

The term "haloalkoxy" refers to an alkoxy group substituted with one or more halogen atoms, where each halogen is independently F, Cl, Br or I. Preferred halogens are F and Cl. Preferred haloalkoxy groups contain 1-6 carbons, more preferably 1-4 carbons, and still more preferably 1-2 carbons. "Haloalkoxy" includes perhaloalkoxy groups, such as $OCF_3$ or $OCF_2CF_3$. A preferred haloalkoxy group is trifluoromethoxy.

The term "haloalkyl" refers to an alkyl group substituted with one or more halogen atoms, where each halogen is independently F, Cl, Br or I. Preferred halogens are F and Cl. Preferred haloalkyl groups contain 1-6 carbons, more preferably 1-4 carbons, and still more preferably 1-2 carbons. "Haloalkyl" includes perhaloalkyl groups, such as $CF_3$ or $CF_2CF_3$. A preferred haloalkyl group is trifluoromethyl.

The term "heterocycloalkyl" refers to a ring or ring system containing at least one heteroatom selected from nitrogen, oxygen, and sulfur, wherein said heteroatom is in a non-aromatic ring. The heterocycloalkyl ring is optionally fused to or otherwise attached to other heterocycloalkyl rings and/or non-aromatic hydrocarbon rings and/or phenyl rings. Preferred heterocycloalkyl groups have from 3 to 7 members. More preferred heterocycloalkyl groups have 5 or 6 members. Examples of heterocycloalkyl groups include, for example, 1,2,3,4-tetrahydroisoquinolinyl, piperazinyl, morpholinyl, piperidinyl, tetrahydrofuranyl, pyrrolidinyl, pyridinonyl, and pyrazolidinyl. Preferred heterocycloalkyl groups include piperidinyl, piperazinyl, morpholinyl, pyrrolidinyl, pyridinonyl, dihydropyrrolidinyl, and pyrrolidinonyl. The heterocycloalkyl groups of the invention may be substituted with various groups as provided herein. Thus, any atom present within a heterocycloalkyl ring and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl)alkyl, ($C_3$-$C_{10}$cycloalkyl)alkoxy, $C_2$-$C_9$heterocycloalkyl, $C_1$-$C_8$alkenyl, $C_1$-$C_8$alkynyl, halo($C_1$-$C_8$)alkyl, halo($C_1$-$C_8$) alkoxy, oxo, amino($C_1$-$C_8$)alkyl and mono- and di($C_1$-$C_8$alkyl)amino($C_1$-$C_8$)alkyl.

The term "heteroaryl" refers to an aromatic ring system containing at least one heteroatom selected from nitrogen, oxygen, and sulfur. The heteroaryl ring may be fused or otherwise attached to one or more heteroaryl rings, aromatic or non-aromatic hydrocarbon rings or heterocycloalkyl rings. Examples of heteroaryl groups include, for example, pyridine, furan, thienyl, 5,6,7,8-tetrahydroisoquinoline and pyrimidines. The heteroaryl groups of the invention may be substituted with various groups as provided herein. Thus, any carbon atom present within an heteroaryl ring system and available for substitution may be further bonded to a variety of ring substituents, such as, for example, halogen, hydroxy, nitro, cyano, amino, $C_1$-$C_8$alkyl, $C_1$-$C_8$alkoxy, mono- and di($C_1$-$C_8$alkyl)amino, $C_3$-$C_{10}$cycloalkyl, ($C_3$-$C_{10}$cycloalkyl) alkyl, ($C_3$-$C_{10}$cycloalkyl)alkoxy, $C_2$-$C_9$heterocycloalkyl, $C_1$-$C_8$alkenyl, $C_1$-$C_8$alkynyl, halo($C_1$-$C_8$)alkyl, halo($C_1$-$C_8$) alkoxy, oxo, amino($C_1$-$C_8$)alkyl and mono- and di($C_1$-$C_8$alkyl)amino($C_1$-$C_8$)alkyl.

Preferred examples of heteroaryl groups include thienyl, benzothienyl, pyridyl, quinolyl, pyrazolyl, pyrimidyl, imidazolyl, benzimidazolyl, furanyl, benzofuranyl, dibenzofuranyl, thiazolyl, benzothiazolyl, isoxazolyl, oxadiazolyl, isothiazolyl, benzisothiazolyl, triazolyl, pyrrolyl, indolyl, pyrazolyl, and benzopyrazolyl.

The compounds of this invention may contain one or more asymmetric carbon atoms, so that the compounds can exist in different stereoisomeric forms. These compounds can be, for example, racemates, chiral non-racemic or diastereomers. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound.

When the compounds described herein contain olefinic double bonds or other centers of geometric asymmetry, and unless otherwise specified, it is intended that the compounds include the cis, trans, Z- and E-configurations. Likewise, all tautomeric forms are also intended to be included.

Pharmaceutical Compositions

The compounds of general Formula I may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants, and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula I may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of general Formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For disorders of the eye or other external tissues, e.g., mouth and skin, the formulations are preferably applied as a topical gel, spray, ointment or cream, or as a suppository, containing the active ingredients in a total amount of, for example, 0.075 to 30% w/w, preferably 0.2 to 20% w/w and most preferably 0.4 to 15% w/w. When formulated in an ointment, the active ingredients may be employed with either a paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w. For therapeutic purposes, the active compounds of this combination invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may be preferable to apply a topical preparation of compounds of this invention to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water. Preferred non-human animals include domesticated animals.

The compounds of the present invention may be administered alone or in combination with at least one additional therapeutic agent or therapy, e.g., radiation therapy, to a patient in need of such treatment. The additional therapeutic agent or therapy may be administered at the same time, separately, or sequentially with respect to the administration of a compound of the invention. Such additional therapeutic agents included, but are not limited to, anti-cancer agents, anti-inflammatory agents, and the like.

The compounds of the present invention may be prepared by use of known chemical reactions and procedures. Representative methods for synthesizing compounds of the invention are presented below. It is understood that the nature of the substituents required for the desired target compound often determines the preferred method of synthesis. All variable groups of these methods are as described in the generic description if they are not specifically defined below.

Methods of Preparation
General Procedure

Representative synthetic procedures for the preparation of compounds of the invention are outlined below in following schemes. Unless otherwise indicated, $X_1$, $X_2$, $X_3$, n, $R_5$, $R_6$, $R_7$, $R_C$, $R_{11}$, and Y carry the definitions given in connection with Formula I. The definition of R is as set forth above in connection with Formula XVII.

Scheme 1

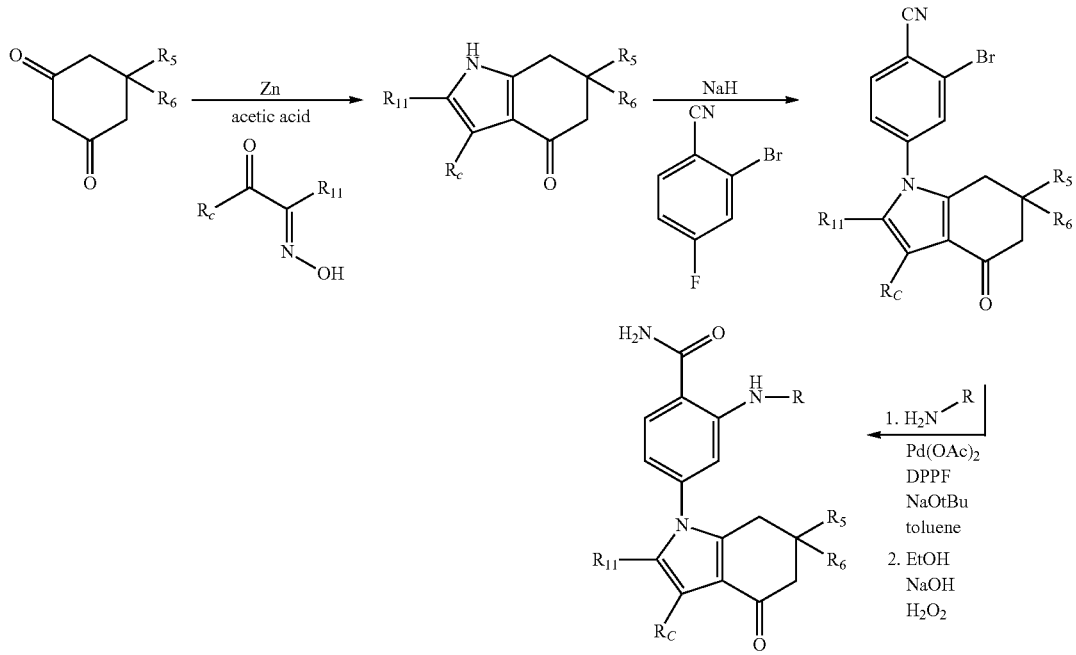

Scheme 2

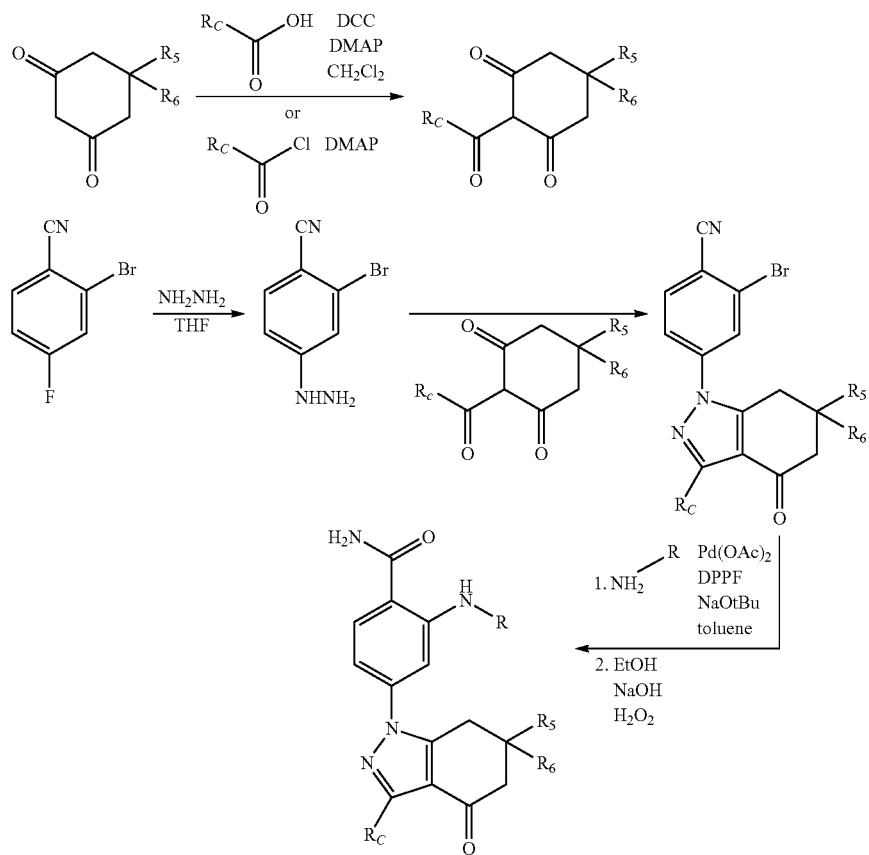

Scheme 3
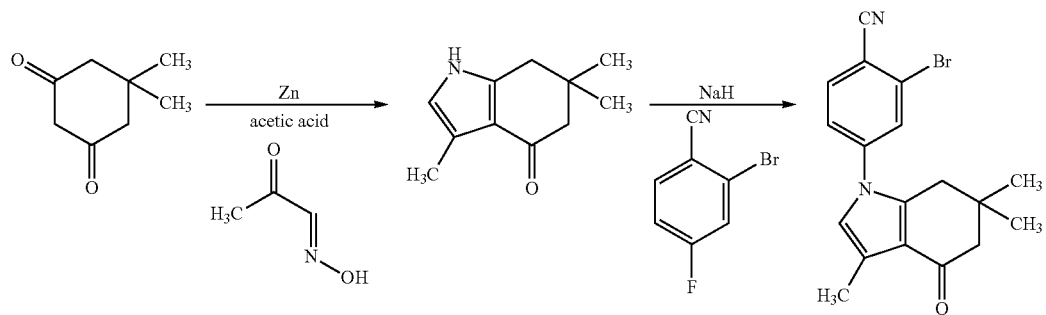
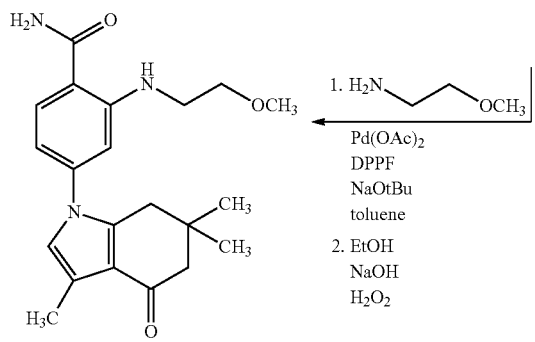
Scheme 4
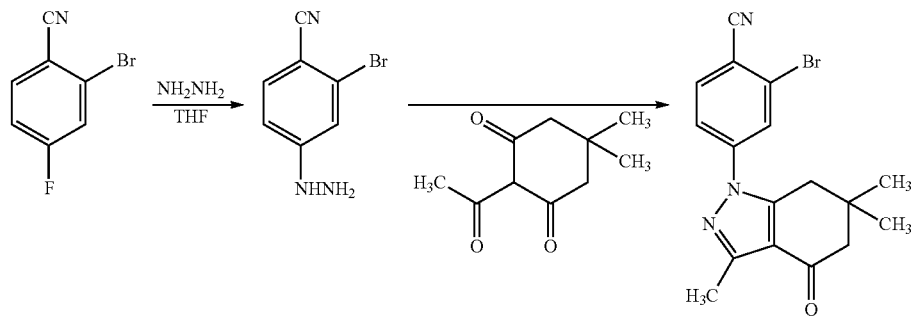
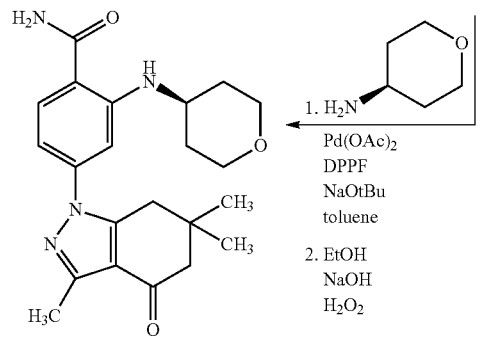

Scheme 5
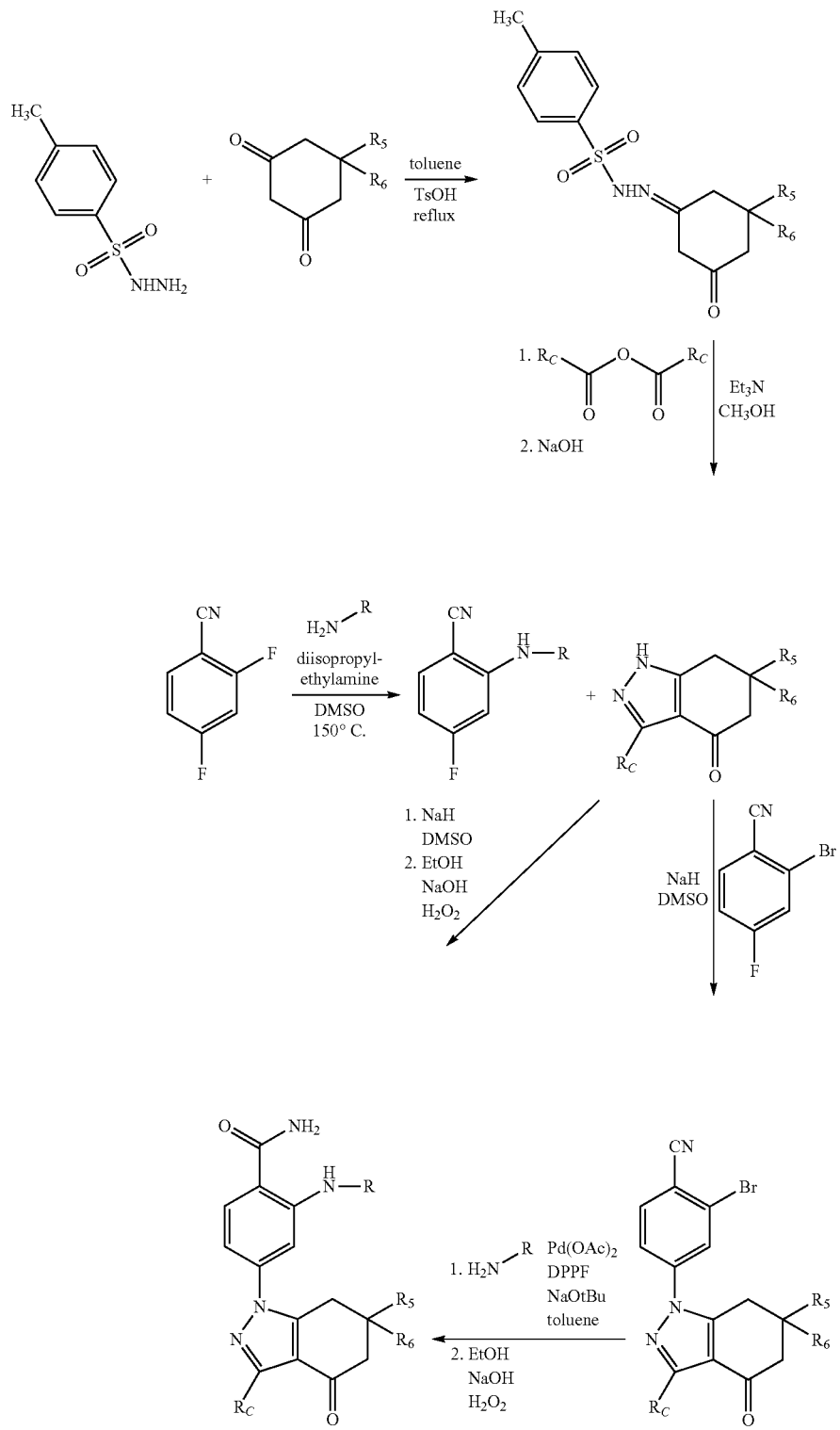

Scheme 6
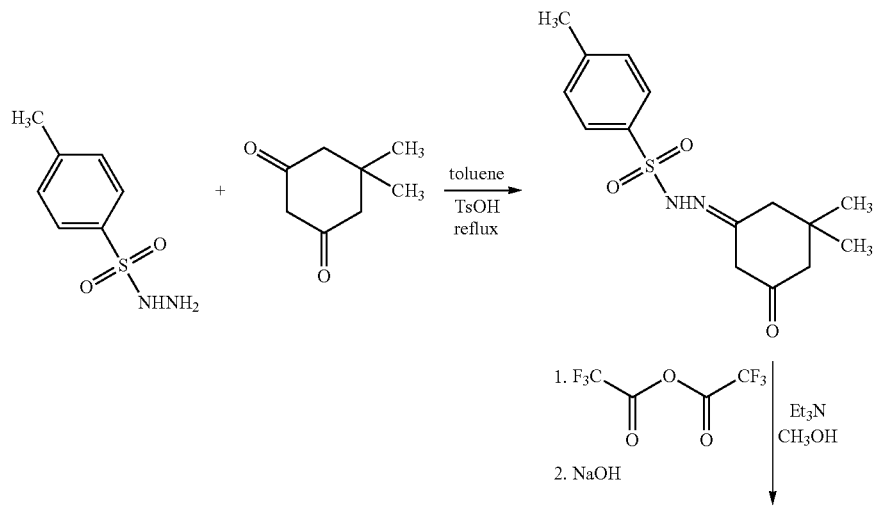
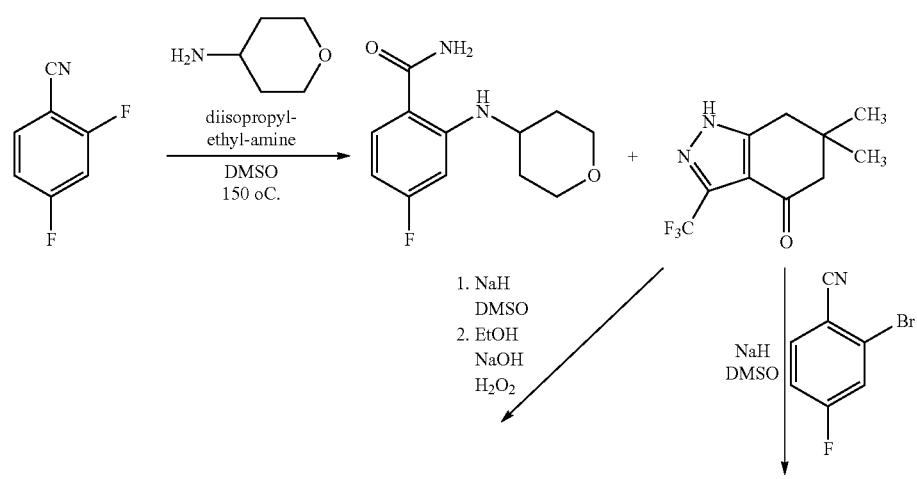
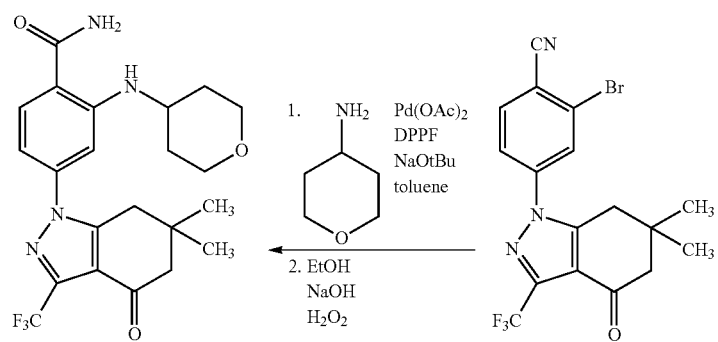

Scheme 7
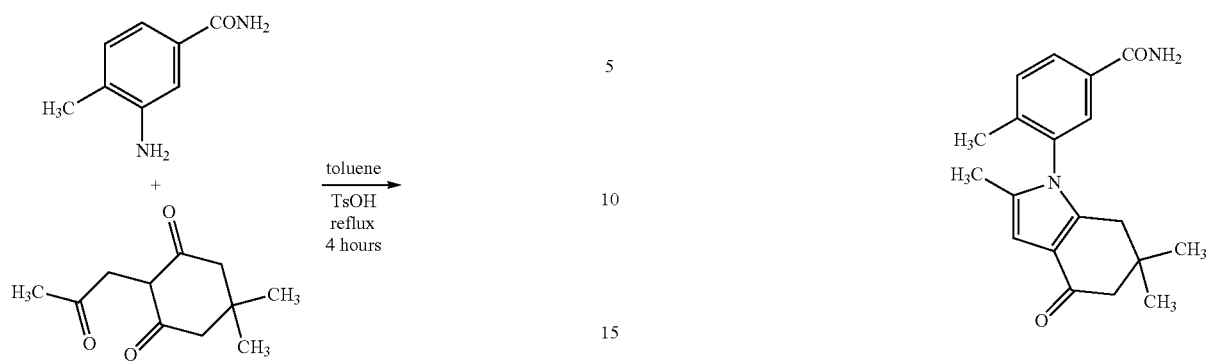
Scheme 8
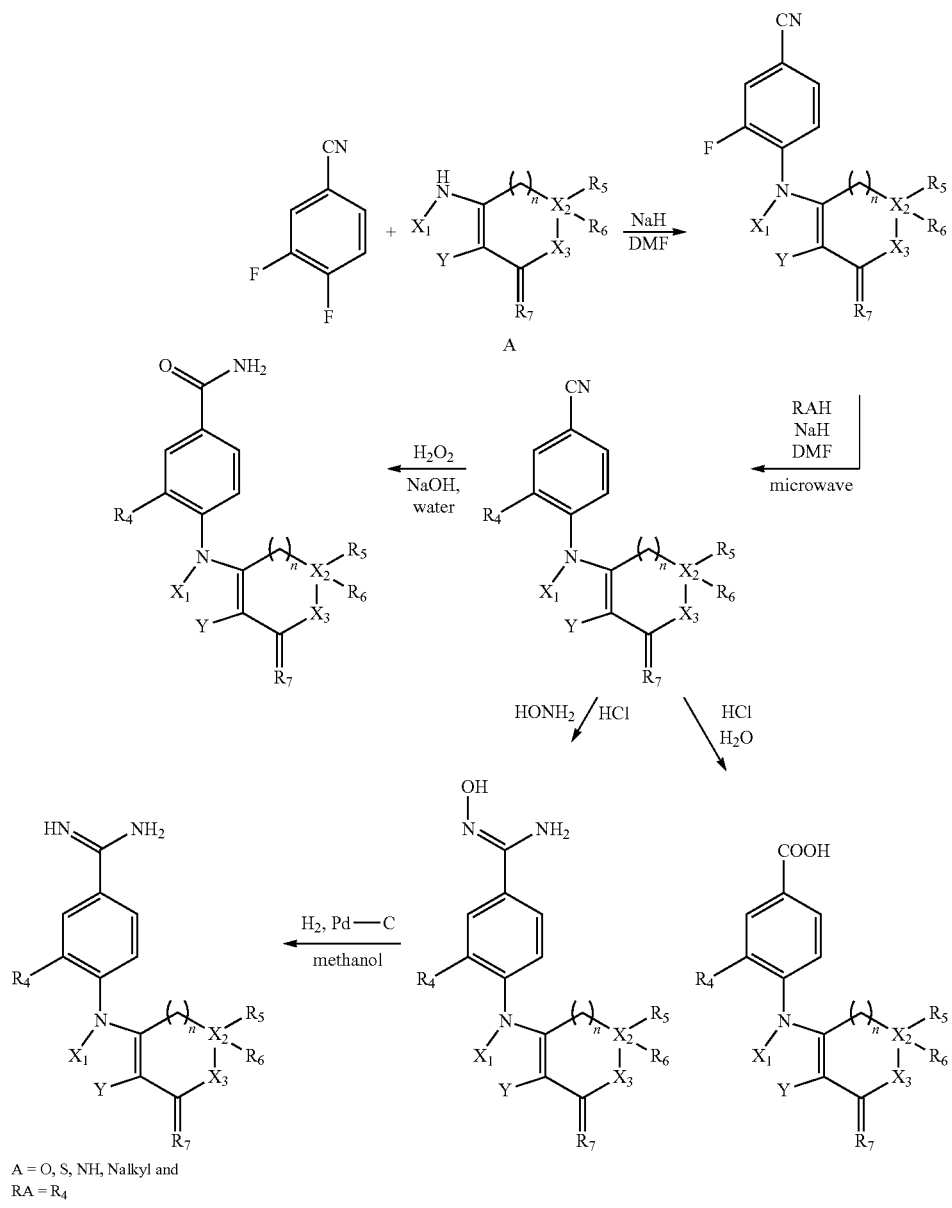
A = O, S, NH, Nalkyl and
RA = R4

Scheme 9

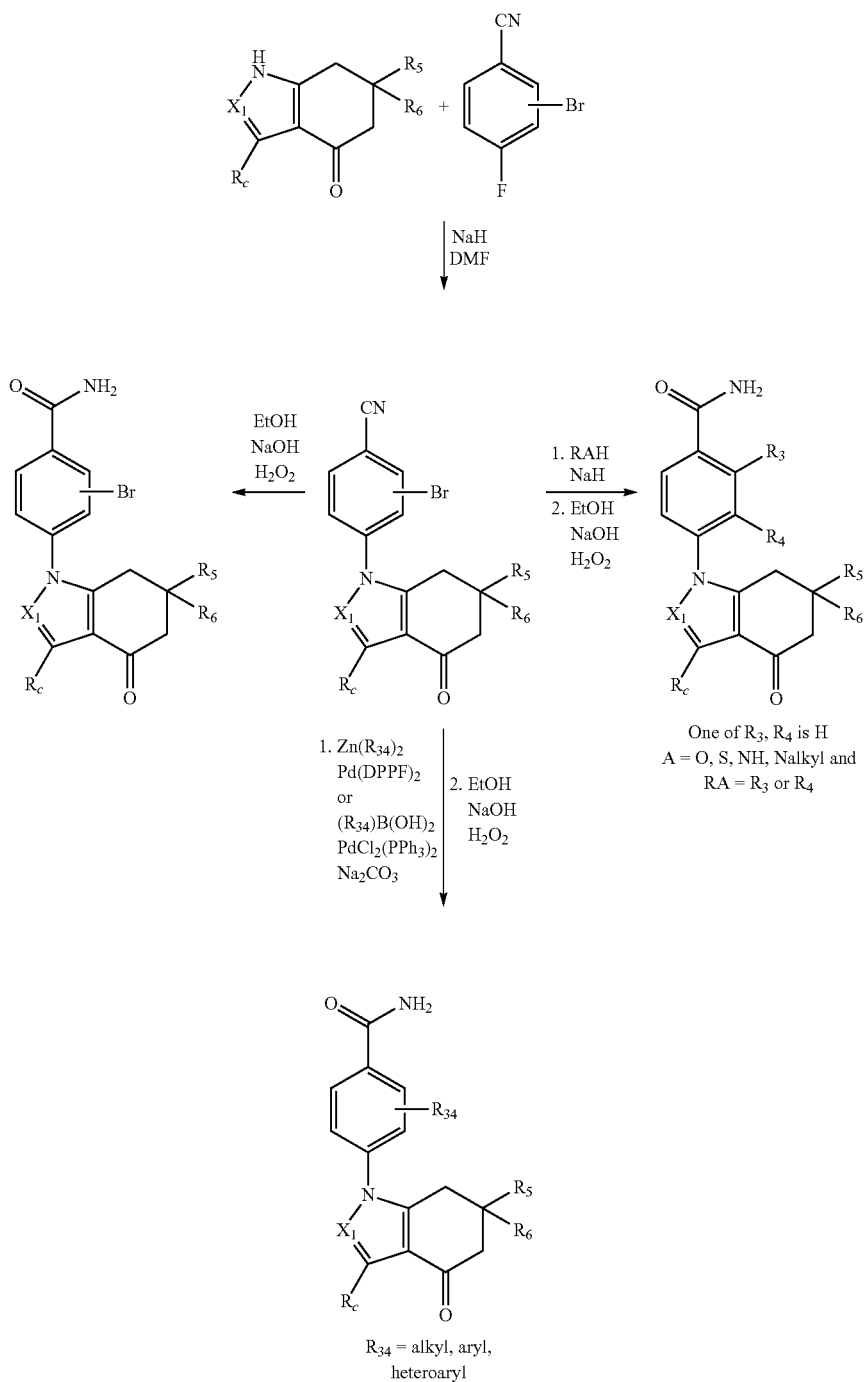

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference in their entirety.

EXAMPLES

The preparation of the compounds of the invention is illustrated further by the following examples, which are not to be construed as limiting the invention in scope or spirit to the specific procedures and compounds described in them. In all cases, unless otherwise specified, the column chromatography is performed using a silica gel solid phase.

Example 1

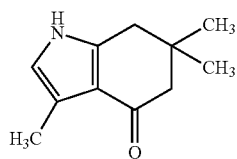

3,6,6-Trimethyl-1,5,6,7-tetrahydro-indol-4-one
(Compound 1)

To a solution of anti-pyruvic aldehyde-1-oxime (10 g, 1 eq) and 5,5-dimethyl-1,3-cyclohexanedione (16.1 g, 1 eq) in HOAc-$H_2O$ (7:3, 200 mL) was added zinc powder (14.95 g, 2 eq) slowly with cooling by a water bath at room temperature. The mixture then was refluxed overnight, concentrated to dryness, partitioned between brine (300 mL) and dichloromethane (300 mL). The pH was adjusted to ca. 6 with saturated aqueous $NaHCO_3$, then the mixture was extracted with dichloromethane (3×200 mL). The organic layers were combined, dried over $Na_2SO_4$, filtered, concentrated. The crude product was purified by flash chromatography eluting with 5% ethyl acetate in dichloromethane. The combined organic fractions were concentrated, triturated in ether-hexane (2:1) for 1 hour, then filtered, washed with hexane to give the pure title compound (9 g, 45% yield) as a solid. LCMS m/z: (M+H)=178.1.

Example 2

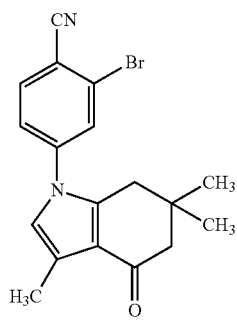

2-Bromo-4-(3,6,6-trimethyl-4-oxo-4,5,6,7-tetrahydro-indol-1-yl)-benzonitrile (Compound 2)

The title compound of Example 1 (9.8 g, 55.3 mmol) and 2-bromo-4-fluorobenzonitrile (13.27 g, 66.4 mmol) were dissolved in anhydrous dimethylformamide (DMF, 300 mL). To this was added sodium hydride (95%, 2.79 g, 111 mmol) and the reaction was stirred at 55° C. for 1 hour. The reaction mixture was cooled to room temperature and water was added. A tan solid precipitated which was filtered, washed with water and ether and then dried in vacuo (16.5 g, 84%). LCMS m/z: (M+H)=358.1.

Example 3

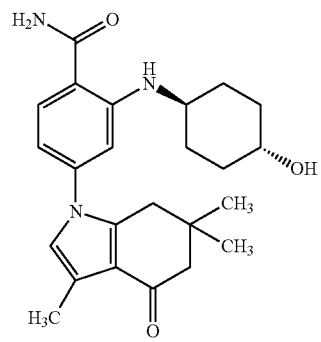

2-(trans-4-Hydroxy-cyclohexylamino)-4-(3,6,6-trimethyl-4-oxo-4,5,6,7-tetrahydro-indol-1-yl)-benzamide (Compound 3)

A "Personal Chemistry" microwave vial was charged with the title compound of Example 2 [2-Bromo-4-(3,6,6-trimethyl-4-oxo-4,5,6,7-tetrahydro-indol-1-yl)-benzonitrile (1.072 g, 3.0 mmol)], trans-4-aminocyclohexanol (1.382 g, 12.0 mmol), palladium (II) acetate (33.7 mg, 5 mol %), 1,1'-bis(diphenylphosphino)ferrocene (DPPF) (166.3 mg, 10 mol %), and sodium tert-butoxide (576.7 mg, 6.0 mmol). To this was added toluene (20 mL) and the reaction was heated with microwave irradiation to 115° C. for 15 min. After allowing the reaction vessel to cool, a suspension formed and was filtered and the filtrate evaporated. The residue was purified by flash chromatography. The intermediate product was hydrolyzed by dissolution in 25% dimethylsulfoxide/ethanol, adding 0.5 mL of 1 N sodium hydroxide and 0.5 mL of 30% aqueous hydrogen peroxide, followed by stirring at room temperature for 4 hours. After judging the reaction to be complete by TLC, the DMSO/ethanol mixture was diluted with water and extracted with ethyl acetate (3×). The combined organics were washed with brine (2×), dried over $Na_2SO_4$, and evaporated. The compound was purified by column chromatography eluting with EtOAc-MeOH to yield 575 mg (47% yield) of the title compound as a white powder. LCMS m/z: (M+H)=410.3

Example 4

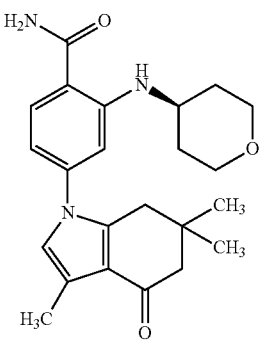

2-(Tetrahydro-pyran-4-ylamino)-4-(3,6,6-trimethyl-4-oxo-4,5,6,7-tetrahydro-indol-1-yl)-benzamide (Compound 4)

A "Personal Chemistry" microwave vial was charged with the title compound of Example 2 (2.858 g, 8.0 mmol), 4-aminotetrahydropyran (3.236 g, 32.0 mmol), palladium (II) acetate (89.8 mg, 5 mol %), 1,1'-bis(diphenylphosphino)ferrocene (443.6 mg, 10 mol %), and sodium tert-butoxide (1.538 g, 16.0 mmol). The reagents were suspended in toluene (40 mL) and were heated with microwave radiation to a temperature of 115° C. for fifteen minutes. After allowing the reaction vessel to cool, the suspension was filtered and the filtrate concentrated. After purifying the crude intermediate nitrile by flash chromatography, the nitrile was dissolved in 25% dimethylsulfoxide/ethanol, and 2 mL of 1 N sodium hydroxide and 2 mL of 30% aqueous hydrogen peroxide were added, followed by stirring at room temperature for 16 hours. The DMSO/ethanol mixture was then diluted with water and extracted with ethyl acetate (3×). The combined organics were washed with brine (2×), dried over $Na_2SO_4$, and evaporated. The residue was purified by column chromatography (EtOAc/MeOH) to yield 1.132 g (36%) of the title compound as an off-white powder. LCMS m/z: (M+H)=396.7.

Example 5

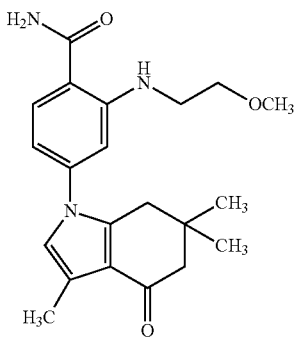

2-(2-Methoxy-ethylamino)-4-(3,6,6-trimethyl-4-oxo-4,5,6,7-tetrahydro-indol-1-yl)-benzamide (Compound 5)

A "Personal Chemistry" microwave vial was charged with the title compound of Example 2 (107.1 mg, 0.3 mmol), 2-methoxyethylamine (91.3 mg, 1.2 mmol), palladium (II) acetate (3.4 mg, 5 mol %), 1,1'-bis(diphenylphosphino)ferrocene (16.6 mg, 10 mol %), and sodium tert-butoxide (57.7 mg, 0.6 mmol). The reagents were suspended in toluene (2 mL) and were heated with microwave radiation to a temperature of 115° C. for fifteen minutes. After allowing the reaction vessel to cool, the suspension was filtered and the filtrate evaporated. After purifying the crude intermediate nitrile by flash chromatography, hydrolysis was performed by dissolving the residue in 25% dimethylsulfoxide/ethanol, adding 5 drops of 1 N sodium hydroxide and 5 drops of 30% aqueous hydrogen peroxide, followed by stirring at room temperature for 3 hours. The DMSO/ethanol mixture was then diluted with water and extracted with $CH_2Cl_2$ (3×). The combined organics were washed with brine (2×), dried over $Na_2SO_4$, and concentrated. The compound was purified by column chromatography (hexane/EtOAc) to yield the title compound (94.4 mg, 85% yield) of an off-white powder. LCMS m/z: (M+H) 370.2.

Example 6

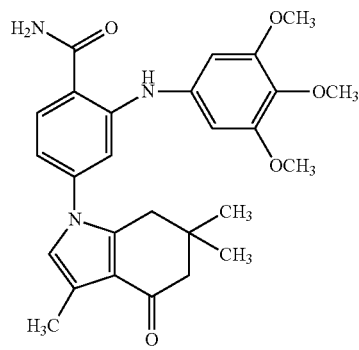

2-(3,4,5-Trimethoxy-phenylamino)-4-(3,6,6-trimethyl-4-oxo-4,5,6,7-tetrahydro-indol-1-yl)-benzamide (Compound 6)

A "Personal Chemistry" microwave vial was charged with the title compound of Example 2 (107.1 mg, 0.3 mmol), 3,4,5-trimethoxyaniline (219.9 mg, 1.2 mmol), palladium (II) acetate (3.4 mg, 5 mol %), 1,1'-bis(diphenylphosphino)ferrocene (16.6 mg, 10 mol %), and sodium tert-butoxide (57.7 mg, 0.6 mmol). The reagents were suspended in toluene (2 mL) and were heated with microwave radiation to a temperature of 115° C. for fifteen minutes. After allowing the reaction vessel to cool, the suspension was filtered and the filtrate evaporated. The residue was purified by flash chromatography, and hydrolysis was performed by dissolving the product in 25% dimethylsulfoxide/ethanol, adding 5 drops of 1 N sodium hydroxide and 5 drops of 30% aqueous hydrogen peroxide, followed by stirring at room temperature for 3 hours. The DMSO/ethanol mixture was then diluted with water and extracted into EtOAc (3×). The combined organics were washed with brine (2×), dried over $Na_2SO_4$, and concentrated. The compound was purified by column chromatography (hexane/EtOAc) to yield 28.4 mg (20%) of the title compound as a yellow powder. LCMS m/z: (M+H) 478.3

Example 7

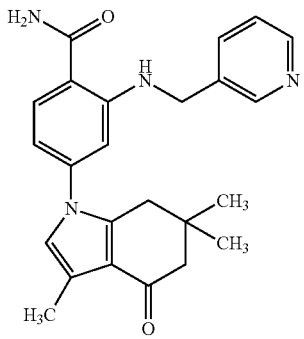

2-[(Pyridin-3-ylmethyl)-amino]-4-(3,6,6-trimethyl-4-ox-4,5,6,7-tetrahydro-indol-1-yl)-benzamide (Compound 7)

A "Personal Chemistry" microwave vial was charged with the title compound of Example 2 (107.1 mg, 0.3 mmol), 3-(aminomethyl)pyridine (129.8 mg, 1.2 mmol), palladium (II) acetate (3.4 mg, 5 mol %), 1,1'-bis(diphenylphosphino) ferrocene (16.6 mg, 10 mol %), and sodium tert-butoxide (57.7 mg, 0.6 mmol). The reagents were suspended in toluene (2 mL) and were heated with microwave radiation to a temperature of 125° C. for fifteen minutes. The crude intermediate nitrile was purified by flash chromatography (hexane/EtOAc) chromatography. Hydrolysis was performed by dissolving the residue in 25% dimethyl sulfoxide/ethanol, adding 4 drops of 1 N sodium hydroxide and 4 drops of 30% aqueous hydrogen peroxide, and stirring at room temperature for 15 minutes. The DMSO/ethanol mixture was then diluted with water and extracted into EtOAc (3×). The combined organics were washed with brine (2×), dried over $Na_2SO_4$, and concentrated. The compound was purified by column chromatography (hexane/EtOAc) to yield 50 mg (41%) of the title compound as a yellow powder. LCMS m/z: (M+H) 403.

Example 8

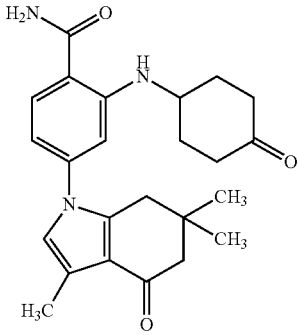

2-(4-oxo-cyclohexylamino)-4-(3,6,6-trimethyl-4-oxo-4,5,6,7-tetrahydro-indol-1-yl)-benzamide (Compound 8)

The title compound of Example 3 [2-(4-Hydroxy-cyclohexylamino)-4-(3,6,6-trimethyl-4-oxo-4,5,6,7-tetrahydro-indol-1-yl)-benzamide] (150 mg, 0.366 mmol) and Dess-Martin periodinane (0.366 mmol) were dissolved in anhydrous $CH_2Cl_2$ and stirred at room temperature for one hour. The reaction mixture was concentrated and the title compound was isolated as a white solid (36.2 mg, 24% yield) after purification by column chromatography eluting with EtOAc-MeOH. LCMS m/z: (M+H)=408.3.

Example 9

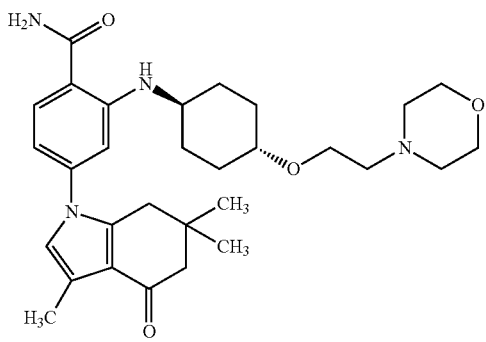

2-[trans-4-(2-Morpholin-4-yl-ethoxy)-cyclohexylamino]-4-(3,6,6-trimethyl-4-oxo-4,5,6,7-tetrahydroindol-1-yl)-benzamide (Compound 9)

A microwave reaction vial was charged with the title compound of Example 3 [2-(trans-4-Hydroxy-cyclohexylamino)-4-(3,6,6-trimethyl-4-oxo-4,5,6,7-tetrahydro-indazol-1-yl)-benzamide] (100 mg, 0.244 mmol), 4-(2-chloroethyl)morpholine hydrochloride (45.4 mg, 0.244 mmol), sodium hydride (17.3 mg, 0.732 mmol), and a catalytic amount of potassium iodide. After suspending in DMF, the reaction mixture was heated to 180° C. in the "Personal Chemistry" microwave for eight minutes. The solution was then diluted with water and extracted into EtOAc (2×). The organic layers were extracted with 2N HCl (2×). The aqueous extracts basified with aqueous sodium hydroxide, and were extracted with EtOAc (3×). The combined organics were dried over $Na_2SO_4$, concentrated, and purified by column chromatography (EtOAc/MeOH) to yield the title compounds as a white solid. LCMS m/z: (M+H) 523.9.

Example 10

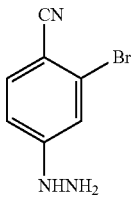

3-bromo-4-cyanophenylhydrazine (Compound 10)

In a clean, dry 250-mL round-bottom flask, 2-bromo-4-fluorobenzonitrile (25.34 g) was dissolved in tetrahydrofuran (50 mL) under $N_2$. To this was slowly added anhydrous hydrazine (50 mL). The solution color changed from yellow to red-orange. The reaction was allowed to stir at room temperature for 16 hours. A yellow-white crystalline solid precipitated from the solution. The mixture was then diluted with THF (50 mL) to dissolve the solids. The organic layer was then washed with saturated sodium bicarbonate solution until the pH of the organic layer was approximately 8.5. The organic layer was isolated and the solvent was removed under reduced pressure to give a white solid. This was place in a fritted glass funnel and washed with 1.5 L of water, followed by of diethyl ether (ca. 200 mL). The ether wash was then combined with the white solid and dried under reduced pressure. The title compound was isolated as a fluffy, white or off-white solid (23.43 g, 87.2% yield). LCMS m/z: calculated=212.05; observed=252.98 (M+H+ acetonitrile).

Example 11

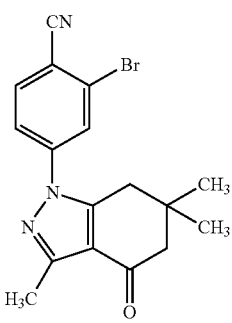

2-Bromo-4-(3,6,6-trimethyl-4-oxo-4,5,6,7-tetrahydro-indazol-1-yl)-benzonitrile (Compound 11)

In a clean, dry 20 mL microwave reaction vial, the title compound of Example 10 (2.49 g) was combined with 2-acetyl-5,5-dimethyl-1,3-cyclohexanedione (2.14 g). The contents of the vial were dissolved in ethanol-acetic acid (12 mL, 3:1). The vial was sealed and agitated on a vortex. The vial was then placed in the microwave reactor and heated to 150° C. for 15 min. The vial was then cooled then placed in the refrigerator for 1 hour. The cooled solution was then diluted with water (8 mL) and poured onto a fritted glass funnel. The orange solid was washed with $H_2O$ (100 mL) followed by ethanol (25 mL). The solid was then dried under reduced pressure. The title compound was obtained as of a light-orange crystalline solid (3.7463 g, 88.85% yield). LCMS m/z M+H=358.1.

Example 12

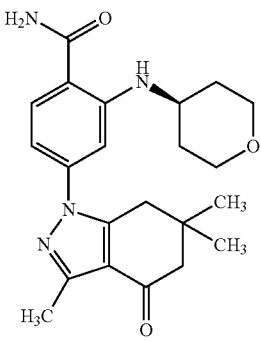

2-(Tetrahydro-pyran-4-ylamino)-4-(3,6,6-trimethyl-4-oxo-4,5,6,7-tetrahydro-indazol-1-yl)-benzamide (Compound 12)

The title compound of Example 11 (100 mg, 0.28 mmol), Pd(OAc)$_2$ (3.2 mg, 5 mol %), DPPF (15.5 mg, 10 mol %) and NaO$^t$Bu (54 mg, 0.56 mmol) were added to a 2 mL microwave vial. Toluene (0.5 mL) and 4-aminotetrahydropyran (56 µL, 0.56 mmol) were added and the vial was evacuated and back-filled with N$_2$. The reaction mixture was heated at 120° C. for 15 min (microwave). The reaction mixture was filtered and the solids washed with methylene chloride. The product was purified using flash chromatography eluting with hexanes and ethyl acetate. Product was recovered as an off-white solid (88 mg, 83%), LCMS m/z: (M+H)=379.3. Ethanol (0.8 mL), DMSO (0.2 mL), NaOH (5 N, 93 µL, 2 mol eq) and H$_2$O$_2$ (0.1 mL, 30% solution in H$_2$O) were added to the pyrazole (88 mg, 0.23 mmol) in a 2 mL microwave vial. The reaction mixture was heated at 100° C. for 10 min. Product was recovered by washing with H$_2$O and ethyl acetate. Solvent was removed in vacuo to yield the title compound as a yellow solid (88 mg, 100%), LCMS m/z: (M+H)=397.3.

Example 13

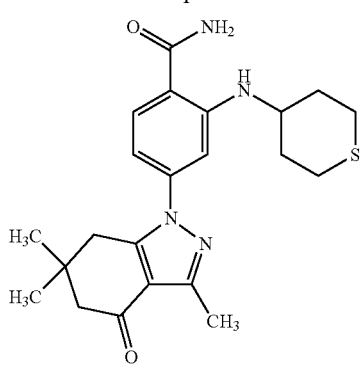

2-(Tetrahydrothiopyran-4-ylamino)-4-(3,6,6-trimethyl-4-oxo-4,5,6,7-tetrahydroindazol-1-yl)benzamide (Compound 13)

Tetrahydro-thiopyran-4-one (10.0 g, 86.0 mmol) and NH$_4$OAc (60 g, 10 mole eq) were dissolved in 200 mL of MeOH/H$_2$O (1:1). To this was added NaCNBH$_3$ (10.8 g, 172.0 mmol) and the reaction mixture was allowed to stir at room temperature overnight. Methanol was removed under vacuum and the product was extracted from the aqueous layer with ethyl acetate (3×100 mL) and washed with brine. The organic layer was washed with 10% aqueous HCl (150 mL) that was then basified with 10% NaOH solution (to pH 11). The basic solution was then washed with ethyl acetate and dried over MgSO$_4$, to give 4-aminotetrahydrothiopyran which was used without further purification, LCMS m/z: (M+H)$^+$=118.2. Compound 11 (1.4 g, 3.9 mmol), Pd(OAc)$_2$ (44.7 mg, 5 mol %), DPPF (229 mg, 10 mol %) and NaO$^t$Bu (790 mg, 7.8 mmol) were added to a 20 mL microwave vial. Toluene (12 mL) and 4-aminotetrahydrothiopyran (550 mg, 1.2 mol eq) were added and the vial was evacuated and back-filled with N$_2$. The reaction mixture was heated at 130° C. for 20 min (microwave). The reaction mixture was filtered and the solids washed with CH$_2$Cl$_2$. The product was purified using flash chromatography eluting with Hexanes and Ethyl acetate. The product, 2-(tetrahydro-thiopyran-4-ylamino)-4-(3,6,6-trimethyl-4-oxo-4,5,6,7-tetrahydro-indazol-1-yl)-benzonitrile, was recovered as a off-white solid (350 mg), LCMS m/z (M+H)$^+$=395.3.

The preceeding product (830 mg, 2.1 mmol) was dissolved in ethanol (12 mL) and DMSO (3 mL) to which NaOH (5 N, 841 µL, 2 mol eq) was added. The reaction mixture was heated at 70° C. overnight. The reaction mixture was washed with H$_2$O and EtOAc. The product was purified by flash chromatography eluting with Hexanes and Ethyl acetate. The title compound was obtained as an off-white solid (490 mg), LCMS m/z (M+H)$^+$ 413.2

Example 14

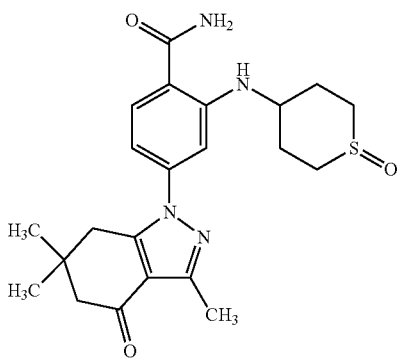

2-(1-Oxo-hexahydro-1-Tetrahydrothiopyran-4-ylamino)-4-(3,6,6-trimethyl-4-oxo-4,5,6,7-tetrahydroindazol-1-yl)benzamide (Compound 14)

2-(Tetrahydrothiopyran-4-ylamino)-4-(3,6,6-trimethyl-4-oxo-4,5,6,7-tetrahydroindazol-1-yl)benzamide was dissolved in ethanol to which $H_2O_2$ (a few drops of 30% solution in $H_2O$) was added. The reaction mixture was allowed to stir at rt for 30 min. Product was isolated via extraction with EtOAc and $H_2O$. The title compound was obtained as an off-white solid (20 mg), LCMS m/z $(M+H)^+=429.2$

Example 15

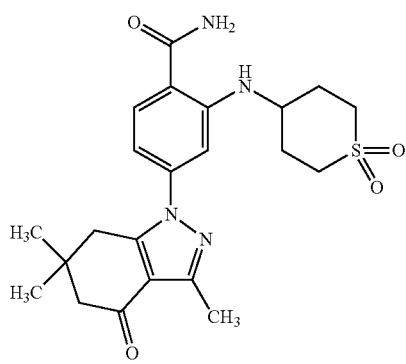

2-(1,1-Dioxo-hexahydro-1-Tetrahydrothiopyran-4-ylamino)-4-(3,6,6-trimethyl-4-oxo-4,5,6,7-tetrahydroindazol-1-yl)benzamide (Compound 15)

2-(Tetrahydrothiopyran-4-ylamino)-4-(3,6,6-trimethyl-4-oxo-4,5,6,7-tetrahydroindazol-1-yl)benzamide (25 mg, 0.063 mmol) was dissolved in a mixture of ethanol (1 mL) and DMSO (0.25 mL) to which NaOH (5 N, 25 μL, 2 mol eq) and $H_2O_2$ (excess, 30% solution in $H_2O$) was added. The reaction mixture was heated at 70° C. overnight. The reaction mixture was washed with $H_2O$ and EtOAc. The product was purified using flash chromatography eluting with dichloromethane and methanol. The title compound was obtained as an off-white solid (20 mg), LCMS m/z $(M+H)^+=445.2$

Example 16

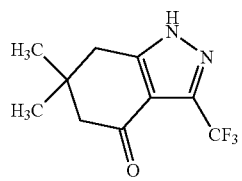

6,6-Dimethyl-3-trifluoromethyl-1,5,6,7-tetrahydro-indazol-4-one (Compound 16)

A mixture of 5,5-dimethyl-1,3-cyclohexandione (7.0 g, 49.9 mmol, 1.0 equiv), p-toluenesulfonylhydrazide (9.3 g, 49.9 mmol, 1.0 eq.), and p-toluenesulfonic acid (100 mg, 0.53 mmol, 0.01 eq.) in 300 mL of toluene was heated at reflux. After 30 minutes the reaction mixture was cooled, and 50 mL of toluene was added to the reaction mixture. The reaction was returned to heating at reflux. After 1 hour the reaction mixture was cooled to ambient temperature. The solids were collected by filtration, washed three times with ether, and dried under vacuum to afford 3,3-dimethyl-5-(p-tolylsulfonylhydrazono)-cyclohexanone (14.26 g, 93%) as a light yellow solid: LC/MS (m/z) $[M+H]^+=309.1$.

To a solution/suspension of 3,3-dimethyl-5-(p-tolylsulfonylhydrazono)-cyclohexanone (4.0 g, 12.97 mmol, 1.0 eq.) in 72 ml of tetrahydrofuran and 24 mL of triethylamine was added trifluoroacetic anhydride (1.8 mL, 12.97 mmol, 1.0 eq.). The dark red reaction mixture was heated at 55° C. After 15 min the reaction mixture was homogeneous. After 2 h the reaction mixture was cooled to ambient temperature. Methanol (16 mL) and a 1:1 solution of water-1 M aqueous sodium hydroxide (16 mL) were added. After stirring for 3 h, the reaction mixture was diluted with 50 mL of saturated aqueous ammonium chloride and extracted with ethyl acetate (3×50 mL). The combined organic layers were washed with brine, dried over sodium sulfate, filtered, and concentrated in vacuo. The residue was filtered through a plug of silica gel, eluting with ethyl acetate. The filtrate was concentrated in vacuo, and the residue was treated with ether. The solids were collected by filtration and washed with ether. The filtrate was concentrated in vacuo, and the resulting residue was treated with ether. The solids were collected by filtration, washed with ether, and combined with the initial solids to provide 6,6-dimethyl-3-trifluoromethyl-1,5,6,7-tetrahydro-indazol-4-one (1.24 g, 41%) as a reddish orange solid: LC/MS (m/z): $[M+H]^+$ 233.1.

Example 17

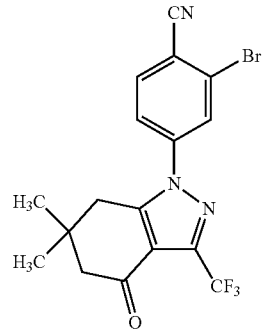

2-bromo-4-(6,6-dimethyl-4-oxo-3-trifluoromethyl-4,5,6,7-tetrahydro-indazol-1-yl)-benzonitrile (Compound 17)

Sodium hydride (168 mg, 7.02 mmol, 1.0 eq.) was added to a solution of 6,6-dimethyl-3-trifluoromethyl-1,5,6,7-tetrahydro-indazol-4-one (1.63 g, 7.02 mmol, 1.0 eq.) in 35 mL of anhydrous dimethyl sulfoxide. After 15 min 2-bromo-4-fluorobenzonitrile (2.25 g, 11.23 mmol, 1.6 eq.) was added as a solid. The reaction mixture was heated at 45° C. After 23 h the reaction mixture was cooled to ambient temperature and quenched with 10 mL of saturated aqueous ammonium chloride. The mixture was diluted with water and extracted with ethyl acetate (4×). The combined organic layers were washed with brine, dried over sodium sulfate, filtered, and concentrated in vacuo. The residue was purified on a Biotage ($SiO_2$, hexanes-ethyl acetate) to afford 2-bromo-4-(6,6-dimethyl-4-oxo-3-trifluoromethyl-4,5,6,7-tetrahydro-indazol-1-yl)-benzonitrile (1.83 g, 63%) as an off-white powder, LC/MS: (M+H)=412.0.

Example 18

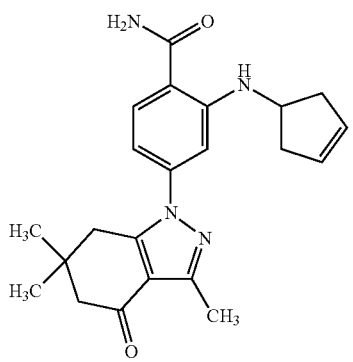

2-(Cyclopent-3-enylamino)-4-(3,6,6-trimethyl-4-oxo-4,5,6,7-tetrahydro-indazol-1-yl)benzamide (Compound 18)

1-(2-Bromo-4-cyanophen-4-yl)-3,6,6-trimethyltetrahydroindazal-4-one (2.0 g, 5.6 mmol), Pd(OAc)$_2$ (64 mg, 5 mol %), DPPF (328 mg, 10 mol %) and NaO$^t$Bu (1.13 mg, 11.2 mmol) were added to a 20 mL microwave vial. Toluene (15 mL) and 1-amino-3-cyclopentene (11.2 mmol) were added and the vial was evacuated and back-filled with N$_2$. The reaction mixture was heated at 120° C. for 15 minutes. The reaction mixture was filtered and the solids washed with CH$_2$Cl$_2$. The product was purified using flash chromatography eluting with hexanes and ethyl acetate. Product was obtained as an off-white solid (1.35 g), LCMS m/z (M+H)$^+$=361.2.

The preceeding product (2.71 g, 7.5 mmol) was dissolved in ethanol (20 mL) and DMSO (5 mL), and NaOH (5 N, 2.51 mL, 2 mol eq) and H$_2$O$_2$ (3.0 mL, 30% solution in H$_2$O) were added. The reaction mixture was stirred at room temperature for 2 hours. The reaction mixture was washed with H$_2$O and extracted with EtOAc. The product was purified using flash chromatography eluting with hexanes and ethyl acetate. The title compound was obtained as an off-white solid (490 mg), LCMS m/z: (M+H)$^+$=379.2

Example 19

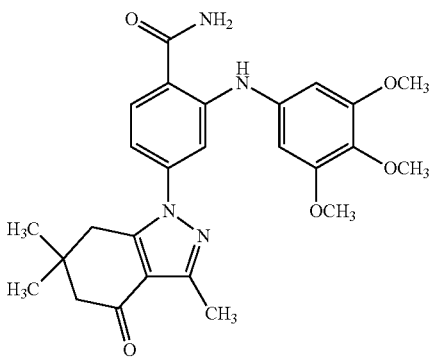

4-(6,6-Dimethyl-4-oxo-3-methyl-4,5,6,7-tetrahydro-indazol-1-yl)-2-(3,4,5-trimethoxyanilino)-benzamide (Compound 19)

Sodium tert-butoxide (269 mg, 2.80 mmol, 2.0 equiv) was added to a stirred solution/suspension of 2-bromo-4-(6,6-dimethyl-4-oxo-3-methyl-4,5,6,7-tetrahydro-indazol-1-yl)-benzonitrile (500 mg, 1.40 mmol, 1.0 eq.), 3,4,5-trimethoxyaniline (513 mg, 2.80 mmol, 2.0 eq.), palladium (II) acetate (16 mg, 0.07 mmol, 0.05 eq.), and 1,1'-bis(diphenylphosphino)ferrocene (78 mg, 0.14 mmol, 0.10 eq.) in 3.75 mL of toluene. The reaction vial was capped, and the reaction mixture was heated 20 minutes at 120° C. under microwave irradiation. The individual reaction mixtures were diluted with ethyl acetate, combined, and partitioned with water. The layers were separated, and the aqueous layer was extracted with ethyl acetate. The combined organic layers were washed with brine, dried over sodium sulfate, filtered, and concentrated in vacuo. The residue was purified on a Biotage System (SiO$_2$, hexanes-ethyl acetate) to afford 4-(6,6-dimethyl-4-oxo-3-methyl-4,5,6,7-tetrahydro-indazol-1-yl)-2-(3,4,5-trimethoxyanilino)-benzonitrile (1.59 g, 82%) as a tan solid: LC/MS (m/z): [M+H]$^+$ 461.9.

To a mixture of 4-(6,6-dimethyl-4-oxo-3-methyl-4,5,6,7-tetrahydro-indazol-1-yl)-2-(3,4,5-trimethoxyanilino)-benzonitrile (1.56 g, 3.39 mmol, 1.0 eq.) in 17 mL of a mixture of 4:1 ethanol-dimethyl sulfoxide was added 2 mL of 1 M aqueous sodium hydroxide and 2 mL of 30% hydrogen peroxide. After 3 hours the reaction mixture was diluted with water and extracted with ethyl acetate (3×). The combined organic layers were washed with brine, dried over sodium sulfate, filtered, and concentrated in vacuo to afford the title compound, 4-(6,6-dimethyl-4-oxo-3-methyl-4,5,6,7-tetrahydro-indazol-1-yl)-2-(3,4,5-trimethoxyanilino)-benzamide, (1.61 g, 99%) as a tan solid: LC/MS (m/z): [M+H]$^+$ 479.3.

Example 20

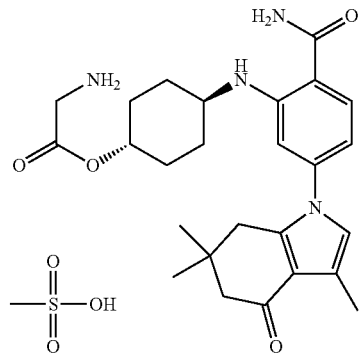

Amino-acetic acid trans-4-[2-carbamoyl-5-(3,6,6-trimethyl-4-oxo-4,5,6,7-tetrahydro-indol-1-yl)-phenylamino]-cyclohexyl ester; methanesulfonic acid salt (Compound 20)

2-(trans-4-Hydroxy-cyclohexylamino)-4-(3,6,6-trimethyl-4-oxo-4,5,6,7-tetrahydro-indol-1-yl)-benzamide (750.0 mg, 1.832 mmol), N-(tert-butoxycarbonyl)glycine (641.8 mg, 3.664 mmol, 2.0 eq.), 1-(3-dimethylaminopropyl)-3-ethylcarbodiimide hydrochloride (702.4 mg, 3.664 mmol, 2.0 eq.) and a catalytic amount of 4-dimethylaminopyridine were dissolved in 20 mL of CH$_2$Cl$_2$ and stirred at room temperature for sixteen hours. The solvent was removed in vacuo, and the residue purified by column chromatography (eluting with EtOAc), yielding 780.5 mg (75.2% yield) of a Boc protected pale yellow foam.

The preceeding product was dissolved in 15 mL of CH$_2$Cl$_2$ and cooled to 0° C. in an ice bath. 15 mL of trifluoroacetic acid was then added and the reaction mixture stirred at 0° C. for 5 minutes and 30 minutes at room temperature. The trifluoroacetic acid and CH$_2$Cl$_2$ were removed in vacuo, and the residue dissolved in water. The aqueous solution was basified by addition of saturated aqueous sodium bicarbonate. The aqueous suspension was extracted with EtOAc (3×), and the combined organics washed with water and dried over Na$_2$SO$_4$. Removal of the solvent in vacuo yielded 569.7 mg (66.6% yield through coupling and deprotection) of an off-white foam, which by LC/MS showed pure product (m/z: (M+H)=467.3). This free base was then converted to the mesylate salt by dissolution in CH$_2$Cl$_2$, and adding one equivalent dropwise of methanesulfonic acid, followed by stirring at room temperature for 1 hour. Removal of the solvent in vacuo yielded 680.7 mg of the title compound as an off-white powder.

Example 21

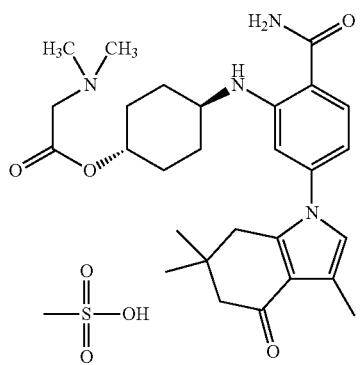

Dimethylamino-acetic acid trans-4-[2-carbamoyl-5-(3,6,6-trimethyl-4-oxo-4,5,6,7-tetrahydro-indol-1-yl)-phenylamino]-cyclohexyl ester; methanesulfonic acid salt (Compound 21)

The procedure of Example 20 was used, substituting dimethylamino-acetic acid for N-(tert-butoxycarbonyl)glycine to give the title compound. LCMS m/z: (M+H)=495.2.

Example 22

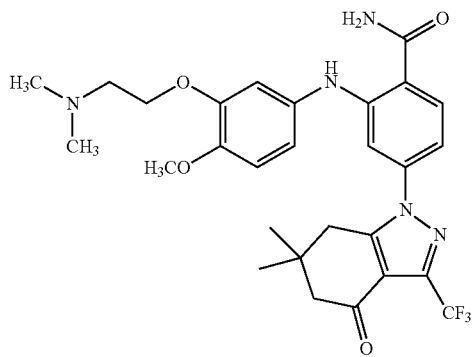

2-[3-(2-Dimethylamino-ethoxy)-4-methoxy-phenylamino]-4-(6,6-dimethyl-4-oxo-3-trifluoromethyl-4,5,6,7-tetrahydro-indazol-1-yl)-benzamide (Compound 22)

To a solution of 2-methoxy-5-nitro-phenol (10 g), (2-chloro-ethyl)-dimethyl-amine hydrochloride (9.37 g) in dimethylformamide (150 mL) was added NaH (2.98 g) slowly under N$_2$ and at room temperature. The mixture was then stirred at 140° C. heating with an oil bath for 5 hours. The reaction was concentrated to dryness, dissolved in 2 M HCl (200 mL) and washed with ethyl acetate (2×100 mL). The aqueous layer was basified with K$_2$CO$_3$, extracted with dichloromethane (3×200 mL) and ethyl acetate (2×100 mL), dried over Na$_2$SO$_4$, filtered, concentrated to give [2-(2-Methoxy-5-nitro-phenoxy)-ethyl]-dimethylamine (9.17 g, 65% yield). LCMS (m/z) M+H: 241.1.

The preceding product (10.53 g) and 10% Pd/C (1 g) were mixed with EtOH (200 mL) and hydrogenated at 50 psi overnight. The reaction mixture was filtered through a Celite plug, and the filter cake was washed with MeOH. The filtrate was concentrated to dryness to give 3-(2-dimethylamino-ethoxy)-4-methoxy-phenylamine (9.05 g, 98% yield). LCMS (m/z) M+H: 211.2.

2-bromo-4-(6,6-dimethyl-4-oxo-3-trifluoromethyl-4,5,6,7-tetrahydro-indazol-1-yl)-benzonitrile (500 mg, 1 eq), 3-(2-dimethylamino-ethoxy)-4-methoxy-phenylamine (306 mg, 1.2 eq), Pd(OAc)$_2$ (14 mg), DPPF (66 mg), and NaOtBu (214 mg, 2 eq) were mixed in toluene (5 mL) and microwaved at 140° C. for 25 minutes. Then 10 mL of EtOH(4)/H$_2$O(1) were added, followed by NaOH (700 mg, 2 eq) and H$_2$O$_2$ (1 mL). The mixture was microwaved at 100° C. for 15 min, then concentrated to dryness, and purified by flash chromatography, eluting with 20% EtOH in dichloromethane to give the title compound (480 mg, 71% two-step yield). LCMS (m/z): M+H=560.3.

Example 23

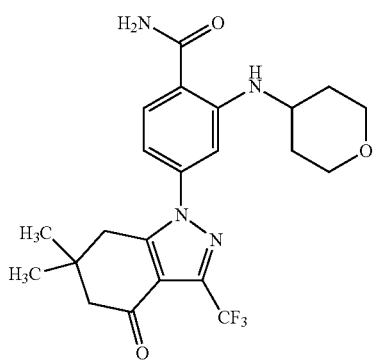

4-(6,6-Dimethyl-4-oxo-3-trifluoromethyl-4,5,6,7-tetrahydro-indazol-1-yl)-2-(tetrahydro-pyran-4-ylamino)-benzamide (Compound 23)

4-Aminotetrahydropyran (245 mg, 2.42 mmol, 2.0 eq) and sodium tert-butoxide (233 mg, 2.42 mmol, 2.0 eq) were added to a stirred solution/suspension of 2-bromo-4-(6,6-dimethyl-4-oxo-3-trifluoromethyl-4,5,6,7-tetrahydro-indazol-1-yl)-benzonitrile (500 mg, 1.21 mmol, 1.0 eq), palladium (II) acetate (14 mg, 0.06 mmol, 0.05 eq), and DPPF (67 mg, 0.12 mmol, 0.10 eq) in 3.75 mL of toluene. The reaction vial was capped, and the reaction mixture was heated 20 minutes at 120° C. under microwave irradiation. The reaction mixture was diluted with water and ethyl acetate and combined. The layers were separated, and the aqueous layer was extracted with ethyl acetate (3×). The combined organic layers were washed with brine, dried over sodium sulfate, filtered, and concentrated in vacuo. The residue was purified on a Biotage system (SiO$_2$, hexanes-ethyl acetate) to afford 4-(6,6-dimethyl-4-oxo-3-trifluoromethyl-4,5,6,7-tetrahydro-indazol-1-yl)-2-(tetrahydro-pyran-4-ylamino)-benzonitrile (772 mg, 49%) as a tan solid: LC/MS (m/z): [M+H]$^+$ 433.7. Further elution with ethyl acetate afforded 4-(6,6-dimethyl-4-oxo-3-trifluoromethyl-4,5,6,7-tetrahydro-indazol-1-yl)-2-(tetrahydro-pyran-4-ylamino)-benzamide (713 mg, 44%) as a yellow solid: LC/MS (m/z): [M+H]$^+$ 451.2.

To a solution/suspension of 4-(6,6-dimethyl-4-oxo-3-trifluoromethyl-4,5,6,7-tetrahydro-indazol-1-yl)-2-(tetrahydro-pyran-4-ylamino)-benzonitrile (772 mg, 1.79 mmol, 1.0 eq) in 10 mL of 4:1 ethanol-dimethyl sulfoxide was added 1 mL of 1 M aqueous sodium hydroxide and 1 mL of 30% hydrogen peroxide. After 30 minutes the reaction mixture was diluted with water and extracted with ethyl acetate (4×). The combined organic layers were washed with brine, dried over sodium sulfate, filtered, and concentrated in vacuo to afford the title compound, 4-(6,6-dimethyl-4-oxo-3-trifluoromethyl-4,5,6,7-tetrahydro-indazol-1-yl)-2-(tetrahydro-pyran-4-ylamino)-benzamide (788 mg, 98%) as a tan solid: LC/MS (m/z): [M+H]$^+$ 451.2.

Example 24

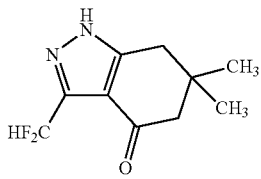

3-Difluoromethyl-6,6-dimethyl-1,5,6,7-tetrahydro-indazol-4-one (Compound 24)

A mixture of 5,5-Dimethyl-cyclohexane-1,3-dione (10 g), p-toluenesulfonylhydrazide (13.3 g) p-toluesulfonic acid (140 mg) in toluene (450 mL) was refluxed for 0.5 h. Then 100 mL of toluene was added and the mixture was refluxed for another 1 h. The mixture was cooled to room temperature, filtered, the solids were washed by ether (3×200 mL), and dried completely to give the hydrazone as a solid (20.4 g, 92.7%). LCMS M+H, 309.1 (MW: 308). It was used in the next step without further purification.

The preceeding product (8.86 g) was dissolved in a mixture of tetrahydrofuran (100 mL) and triethylamine (30 mL), placed under N$_2$, and difluoroacetic anhydride (5 g) was added slowly while swirling, then the mixture was heated to 55° C. overnight. The mixture was cooled to room temperature, and MeOH (35.5 mL) was added, followed by 35.5 mL of a 1:1 mixture of H$_2$O and 1 N NaOH. This mixture was stirred at room temperature for 3 h. The reaction mixture was diluted with saturated aqueous NH$_4$Cl (120 mL), extracted with ethyl acetate (4×150 mL), dried over Na$_2$SO$_4$, filtered, concentrated, purified by column chromatography eluting with a 1:1 mixture of ethyl acetate and hexanes to give 3-difluoromethyl-6,6-dimethyl-1,5,6,7-tetrahydro-indazol-4-one (3.12 g, 50.6%). LCMS (M+H): 215.1 (MW: 214).

Example 25

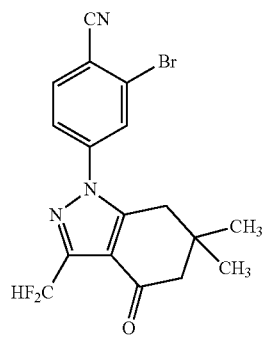

2-Bromo-4-(3-difluoromethyl-6,6-dimethyl-4-oxo-4,5,6,7-tetrahydro-indazol-1-yl)-benzonitrile (Compound 25)

NaH (350 mg) was added to a solution of 3-difluoromethyl-6,6-dimethyl-1,5,6,7-tetrahydro-indazol-4-one (3.12 g) in DMSO (75 mL) at room temperature. After 20 minutes of stirring, 2-bromo-4-fluorobenzonitrile (4.67 g) was added and stirred at 45° C. overnight. The reaction was diluted with saturated aqueous NH$_4$Cl (100 mL), H$_2$O (100 mL). The mixture was extracted with ethyl acetate (4×150 mL), dried over Na$_2$SO$_4$, filtered, concentrated, purified by column chromatography eluting with a 1:2 mixture of ethyl acetate/hexanes. The concentrate of desired fractions was made into a slurry in ether, stirred for 2 h, filtered, washed by hexane to give pure solid 2-bromo-4-(6,6-dimethyl-4-oxo-3-difluoromethyl-4,5,6,7-tetrahydro-indazol-1-yl)-benzonitrile (2.82 g, 49.2%). LCMS m/z: (M+H)=395.65, (MW: 394).

Example 26

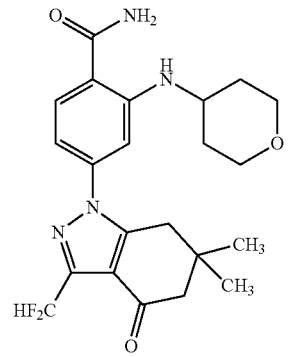

4-(6,6-Dimethyl-4-oxo-3-difluoromethyl-4,5,6,7-tetrahydro-indazol-1-yl)-2-(tetrahydro-pyran-4-ylamino)-benzamide (Compound 26)

The following reaction was conducted at the 300 mg scale and in duplicate at the 500 mg scale: 4-Aminotetrahydropyran (154 mg, 1.52 mmol, 2.0 eq.) and sodium tert-butoxide (146 mg, 1.52 mmol, 2.0 eq.) were added to a stirred solution/suspension of 2-bromo-4-(6,6-dimethyl-4-oxo-3-difluoromethyl-4,5,6,7-tetrahydro-indazol-1-yl)-benzonitrile (300 mg, 0.76 mmol, 1.0 eq.), palladium (II) acetate (8.5 mg, 0.04 mmol, 0.05 eq.), and 1,1'-bis(diphenylphosphino)ferrocene (42 mg, 0.08 mmol, 0.1 eq.) in toluene (2.25 mL). The reaction vial was capped, and the reaction mixture was heated for 20 min at 120° C. under microwave irradiation. The reaction mixture was diluted with water and ethyl acetate and combined. The layers were separated, and the aqueous layer was extracted with ethyl acetate (3×). The combined organic layers were washed with brine, dried over sodium sulfate, filtered, and concentrated in vacuo. The residue was purified on a Biotage system (SiO$_2$, hexanes-ethyl acetate) to afford 4-(6,6-dimethyl-4-oxo-3-difluoromethyl-4,5,6,7-tetrahydro-indazol-1-yl)-2-(tetrahydro-pyran-4-ylamino)-benzonitrile (897 mg, 65% yield) as a tan solid: LC/MS (m/z): [M+H]$^+$ 415.2. Further elution with ethyl acetate afforded the title compound, 4-(6,6-dimethyl-4-oxo-3-difluoromethyl-4,5,6,7-tetrahydro-indazol-1-yl)-2-(tetrahydro-pyran-4-ylamino)-benzamide, (131 mg, 9%) as a yellow solid: LC/MS (m/z): [M+H]$^+$ 433.3.

To a solution/suspension of 4-(6,6-dimethyl-4-oxo-3-difluoromethyl-4,5,6,7-tetrahydro-indazol-1-yl)-2-(tetrahydro-pyran-4-ylamino)-benzonitrile (897 mg, 2.16 mmol, 1.0 eq) in 10.8 mL of 4:1 mixture of ethanol-dimethyl sulfoxide was added 1 mL of 1 M aqueous sodium hydroxide and 1 mL of 30% hydrogen peroxide. After 30 minutes the reaction mixture was diluted with water and extracted with ethyl acetate. The combined organic layers were washed with brine, dried over sodium sulfate, filtered, and concentrated in vacuo to afford the title compound, 4-(6,6-dimethyl-4-oxo-3-difluoromethyl-4,5,6,7-tetrahydro-indazol-1-yl)-2-(tetrahydro-pyran-4-ylamino)-benzamide, (869 mg, 93%) as a tan solid: LC/MS (m/z): [M+H]$^+$ 433.3.

Example 27

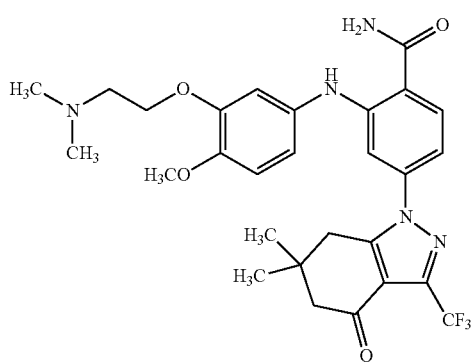

2-[3-(2-Dimethylamino-ethoxy)-4-methoxy-phenylamino]-4-(3,6,6-trimethyl-4-oxo-4,5,6,7-tetrahydro-indazol-1-yl)-benzamide (Compound 27)

2-Bromo-4-(6,6-dimethyl-4-oxo-3-methyl-4,5,6,7-tetrahydro-indazol-1-yl)-benzonitrile (100 mg, 0.28 mmol), Pd(OAc)$_2$ (3.1 mg, 5 mol %), DPPF (15.5 mg, 10 mol %) and NaO$^t$Bu (52 mg, 0.56 mmol) were added to a microwave vial. Toluene (0.5 mL) and 3-(2-dimethylamino-ethoxy)-4-methoxy-phenylamine (118 mg, 2 mol eq) were added and the vial was evacuated and back-filled with N$_2$. The reaction mixture was heated at 130° C. for 30 min (microwave). The reaction mixture was filtered and the solids washed with CH$_2$Cl$_2$. The product nitrile was purified using flash chromatography eluting with CH$_2$Cl$_2$ and methanol. This nitrile (32 mg, 0.66 mmol) was dissolved in ethanol (0.8 mL) and DMSO (0.2 mL) to which NaOH (5 N, 26 μL, 2 eq) and H$_2$O$_2$ (excess, 30% solution in H$_2$O) was added. The reaction mixture was stirred at room temperature for 1 hour. The reaction mixture was washed with H$_2$O and extracted with EtOAc. The product was purified using flash chromatography eluting with CH$_2$Cl$_2$ and methanol. The title compound was obtained as a yellow solid (10 mg, 30%); LC/MS (m/z): M+H=506.5.

Example 28

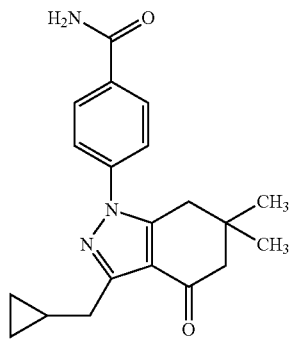

4-(3-Cyclopropylmethyl-6,6-dimethyl-4-oxo-4,5,6,7-tetrahydro-indazol-1-yl)-benzamide (Compound 28)

5,5-Dimethyl-1,3-cyclohexanedione (1.051 g, 7.5 mmol, 1.5 eq), cyclopropylacetic acid (500.6 mg, 5.0 mmol), and 4-dimethylaminopyridine (916.3 mg, 7.5 mmol, 1.5 eq) were dissolved in 10 mL of CH$_2$Cl$_2$, cooled to 0° C. in an ice bath. A solution of N,N'-dicyclohexylcarbodiimide (1.238 g, 16.0 mmol, 1.2 eq) in 5 mL of CH$_2$Cl$_2$ was added dropwise over two minutes to the cyclohexanedione solution. The reaction mixture was then stirred at 0° C. for 10 minutes and at room temperature for 16 hours. The reaction mixture was then filtered and the filtrate purified by column chromatography (hexane to 30% EtOAc/hexane) to yield 1.022 g (92% yield) 2-(2-Cyclopropyl-acetyl)-5,5-dimethyl-cyclohexane-1,3-dione as a pale yellow oil.

2-(2-Cyclopropyl-acetyl)-5,5-dimethyl-cyclohexane-1,3-dione (111.1 mg, 0.5 mmol) and 4-cyanophenylhydrazine hydrochloride (84.8 mg, 0.5 mmol, 1.0 eq) were suspended in 4 mL of 3:1 EtOH:AcOH and microwaved at 100° C. for 10 minutes. The solvent was removed in vacuo and the resultant residue purified by column chromatography to yield 81.8 mg (51% yield) of 4-(3-Cyclopropylmethyl-6,6-dimethyl-4-oxo-4,5,6,7-tetrahydro-indazol-1-yl)-benzonitrile as an off-white powder.

After dissolving the nitrile in 10 mL of 4:1 EtOH-DMSO, approximately 0.1 mL of 1 N NaOH (aq.) and 0.1 mL of 30% H$_2$O$_2$ (aq.) were added and the solution stirred for 1.5 hours. The reaction mixture was poured into brine, extracted with EtOAc (×3), and the combined organics washed with brine (×2). The organic extracts were dried over Na$_2$SO$_4$ and concentrated in vacuo to afford 73.2 mg (43% yield) of 4-(3-

Cyclopropylmethyl-6,6-dimethyl-4-oxo-4,5,6,7-tetrahydro-indazol-1-yl)-benzamide as an off-white solid. LCMS (m/z): M+H=339.4.

Example 29

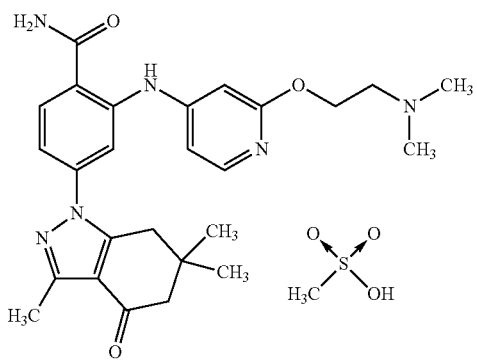

2-[2-(2-Dimethylamino-ethoxy)-pyridin-4-ylamino]-4-(3,6,6-trimethyl-4-oxo-4,5,6,7-tetrahydro-indazol-1-yl)-benzamide, methansulfonic acid salt (Compound 29)

2-Chloro-4-nitropyridine (5.3 g, 33.43 mmol) and N,N-dimethylethanolamine (8 mL) were sealed in a pressure tube and stirred at 110° C. for 24 hours. The reaction mixture was then concentrated and dried under reduced pressure to remove excess N,N-dimethylethanolamine. The resulting yellow residue diluted with 1 N HCl, and a yellow solid, which was identified as 2-chloro-4-nitropyridine, was collected by filtration. The acidic aqueous solution was washed with EtOAc (×2), made basic by the addition of 3 N NaOH, and extracted into EtOAc (x 4). The combined organics were dried-over $Na_2SO_4$ and the solvent removed in vacuo, yielding 3.55 g (50.3% yield) of N,N-dimethyl-N'-(4-nitro-pyridin-2-yl)-ethane-1,2-diamine as an orange solid.

This product (3.55 g, 16.807 mmol) was dissolved in 60 mL ethanol. About five drops of conc. HCl was added, followed by addition of a spatula tip of Pd/C (10% wt). The reaction vessel was purged with $N_2$ filled with $H_2$ and evacuated three times, and filled with $H_2$ to a pressure of 60 psi. After shaking at room temperature for three hours, complete reduction of the nitro group was verified by LC/MS. The reaction mixture was filtered through Celite and the solvent removed in vacuo. The residue was then dissolved in EtOAc, washed with saturated aqueous $NaHCO_3$, water, and brine, and dried over $Na_2SO_4$. After removing the solvent in vacuo, 2.95 g (48.7% yield over two steps) of 2-(2-dimethylamino-ethoxy)-pyridin-4-ylamine as a waxy red solid was obtained.

2-Bromo-4-(3,6,6-trimethyl-4-oxo-4,5,6,7-tetrahydro-indazol-1-yl)-benzonitrile (358.2 mg, 1.0 mmol), 2-(2-dimethylamino-ethoxy)-pyridin-4-ylamine (362.5 mg, 2.0 mmol, 2.0 eq.), palladium (II) acetate (11.2 mg, 5 mol %), 1,1'-bis(diphenylphosphino)ferrocene (55.4 mg, 10 mol %), and sodium tert-butixide (192.2 mg, 2.0 mmol, 2.0 eq.) were suspended in 4 mL of toluene. The reaction mixture was microwaved at 120° C. for 20 minutes. After cooling the reaction mixture, the solvent was removed in vacuo, and the residue diluted with water. The aqueous suspension was extracted with EtOAc×3 and the combined organics washed with brine, dried over $Na_2SO_4$, and concentrated under reduced pressure. The intermediate nitrile and the desired amide were collected and combined after purifying by column chromatography (EtOAc/MeOH), and were dissolved in 20 mL of 4:1 EtOH/DMSO. Five drops of 1 N NaOH and five drops of 30% $H_2O_2$ were added, and the reaction mixture stirred at room temperature for 2 hours. The solution was diluted with water, extracted into EtOAc (×3), and the combined organics washed with brine (×2), dried over $Na_2SO_4$, and concentrated under reduced pressure. The resultant residue was purified by column chromatography (EtOAc/MeOH), yielding 347.3 mg (72.9% yield) of a pink foam. This was dissolved in $CH_2Cl_2$ and treated with of one equivalent of methanesulfonic acid, stirring at room temperature for 1 hour. The mixture was evaporated under reduced pressure to yield the title compound. LCMS m/z (M+H)=477.3.

Example 30

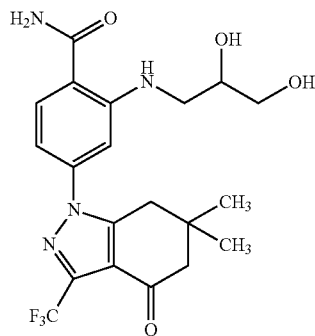

2-(2,3-Dihydroxy-propylamino)-4-(6,6-dimethyl-4-oxo-3-trifluoromethyl-4,5,6,7-tetrahydro-indazol-1-yl)-benzamide (Compound 30)

A mixture of 2,4-Difluoro-benzonitrile (1.39 g, 10 mmol), 3-amino-propane-1,2-diol (0.911 g, 10 mmol), and ethyl-diisopropyl-amine (1.74 mL) in DMSO (10 mL) was microwaved at 200° C. for 7 min. Then the reaction mixture was poured into a saturated $NH_4Cl$ aq. solution (100 mL), extracted with EtOAc (3×100 mL), dried over $Na_2SO_4$, filtered, concentrated. The crude mixture was purified by flash silica gel chromatography (EtOAc-Hexane 1:1) to give 2-(2,3-Dihydroxy-propylamino)-4-fluoro-benzonitrile (0.87 g, 41.4% yield). LCMS (m/z): M+H=211.

To a mixture of 6,6-Dimethyl-3-trifluoromethyl-1,5,6,7-tetrahydro-indazol-4-one (0.961 g, 4.14 mmol, 1 eq) and NaH (99 mg, 4.14 mmol, 1 eq) in dimethyl acetamide (20 mL) was added slowly 2-(2,3-Dihydroxy-propylamino)-4-fluoro-benzonitrile (0.87 g, 4.14 mmol, 1 eq). Then the reaction mixture was stirred at 150° C. overnight, cooled, poured into saturated $NH_4Cl$ aq. solution (100 mL), extracted by EtOAc (3×150 mL), dried over $Na_2SO_4$, filtered, concentrated. The crude product was purified by flash silica gel chromatography, eluted by EtOAc to give 2-(2,3-Dihydroxy-propylamino)-4-(6,6-dimethyl-4-oxo-3-trifluoromethyl-4,5,6,7-tetrahydro-indazol-1-yl)-benzonitrile (1.7 g, 97% yield). LCMS (m/z): M+H=423.

2-(2,3-Dihydroxy-propylamino)-4-(6,6-dimethyl-4-oxo-3-trifluoromethyl-4,5,6,7-tetrahydro-indazol-1-yl)-benzonitrile (1.7 g, 4 mmol, 1 eq), NaOH (806 mg, 20 mmol, 5 eq), and $H_2O_2$ (3 mL) were dissolved in EtOH-water (4:1) (40 mL). The mixture was microwaved at 120° C. for 15 min, then concentrated to dryness, and purified by flash chromatography, eluted by 10% MeOH in EtOAc to give pure 2-(2,3-Dihydroxy-propylamino)-4-(6,6-dimethyl-4-oxo-3-trifluoromethyl-4,5,6,7-tetrahydro-indazol-1-yl)-benzamide (0.52 g, 29% yield). LCMS (m/z): M+H=441.

Example 31

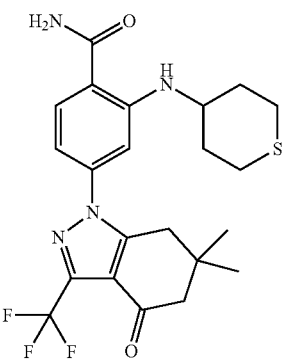

4-(6,6-Dimethyl-4-oxo-3-trifluoromethyl-4,5,6,7-tetrahydro-indazol-1-yl)-2-(tetrahydro-thiopyran-4-ylamino)-benzamide (Compound 31)

1-(2-Bromo-4-cyanophen-4-yl)-3-trifluoromethyl-6,6-dimethyltetrahydroindazal-4-one (313 mg, 0.76 mmol), Pd(OAc)$_2$ (8.7 mg, 5 mol %), DPPF (44.5 mg, 10 mol %) and NaO$^t$Bu (153 mg, 1.52 mmol) were added to a microwave vial. Toluene (1 mL) and 4-aminotetrahydrothiopyran (116 mg, 1.3 mol eq) were added and the vial was evacuated and back-filled with N$_2$. The reaction mixture was heated at 130° C. for 20 min (microwave). The reaction mixture was filtered and the solids washed with CH$_2$Cl$_2$. The product was purified using flash chromatography eluting with hexanes and EtOAc. Product was recovered as a off-white solid (23 mg, 7%), LCMS (M+H)$^+$=449.4

This pyrazole (23 mg, 0.05 mmol) was dissolved in ethanol (0.8 mL) and DMSO (0.2 mL) to which NaOH (5 N, 21 μL, 2 mol eq) was added and the reaction mixture was heated at 70° C. for 12 hours. The reaction mixture was washed with water and EtOAc. The product was purified using flash chromatography eluting with hexanes and EtOAc. The title compound was obtained as an off-white solid (16 mg, 67%); LC/MS (m/z): M+H=467.2.

Example 32

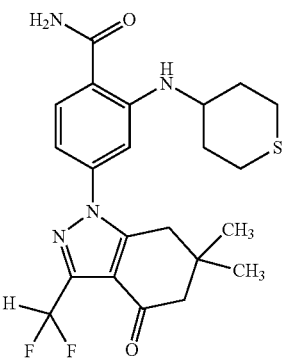

4-(3-Difluoromethyl-6,6-dimethyl-4-oxo-4,5,6,7-tetrahydro-indazol-1-yl)-2-(tetrahydro-thiopyran-4-ylamino)-benzamide (Compound 32)

2-Bromo-4-(3-difluoromethyl-6,6-dimethyl-4-oxo-4,5,6,7-tetrahydro-indazol-1-yl)-benzamide (300 mg, 0.76 mmol), Pd(OAc)$_2$ (8.7 mg, 5 mol %), DPPF (44.5 mg, 10 mol %) and NaO$^t$Bu (153 mg, 1.52 mmol) were added to a microwave vial. Toluene (1 mL) and 4-aminotetrahydrothiopyran (116 mg, 1.3 mol eq) were added and the vial was evacuated and back-filled with N$_2$. The reaction mixture was heated at 120° C. for 15 min (microwave). The reaction mixture was filtered and the solids washed with CH$_2$Cl$_2$. The product was purified using flash chromatography eluting with hexanes and EtOAc. Product was recovered as an off-white solid (70 mg, 21%).

The preceding product pyrazole (70 mg, 0.16 mmol) was dissolved in ethanol (0.8 mL) and DMSO (0.2 mL) to which NaOH (5 N, 65 mL, 2 eq) was added and the reaction mixture was heated at 70° C. for 12 hours. The reaction mixture was washed with H$_2$O and EtOAc. The product was purified using flash chromatography eluting with hexanes and EtOAc. The title compound was obtained as an off-white solid (40 mg, 56% yield), LC/MS (m/z): M+H=449.2.

Example 33

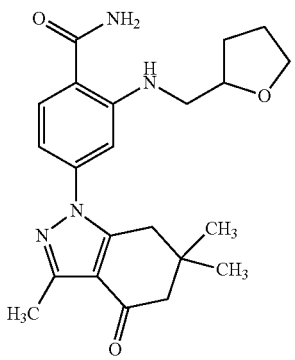

2-[(Tetrahydro-furan-2-ylmethyl)-amino]-4-(3,6,6-trimethyl-4-oxo-4,5,6,7-tetrahydro-indazol-1-yl)-benzamide (Compound 33)

2-Bromo-4-(3,6,6-trimethyl-4-oxo-4,5,6,7-tetrahydro-indazol-1-yl)-benzonitrile (1.0 mmol, 358 mg), palladium acetate (0.13 mmol, 30 mg), 1,1'-bis(diphenylphosphino)ferrocene (0.1 mmol, 56 mg), sodium t-butoxide (2 mmol, 192 mg), toluene (2 mL), and 2-(aminomethyl)tetrahydrofuran (3 mmol, 0.31 mL) were combined in a microwave tube, stirred briefly, and heated in a Personal Chemistry microwave set at high absorbance to 110° C. for 900 seconds. After cooling, the reaction mixture was taken up in ethyl acetate (200 mL) and washed with water (50 mL). The organic phase was dried over magnesium sulfate, filtered, and concentrated. The residue was subjected to chromatography, affording the desired nitrile intermediate as a tan solid (305 mg, 81% yield).

DMSO (6 drops) and ethanol (4 mL) were added to the above nitrile (0.79 mmol, 300 mg). The flask was lowered into a 50° C. oil bath and KOH (5.8 mmol, 325 mg) was added, followed by 30% hydrogen peroxide (ca. 10 mmol, 1 mL). After 45 minutes, the reaction was taken up in ethyl acetate (100 mL) and washed with water (50 mL). The organic layer was dried over magnesium sulfate, filtered, and concentrated. Chromatography of the residue afforded the title compound as a white solid (313 mg, 100% yield). LCMS (m/z): M+H=397.3.

Example 34

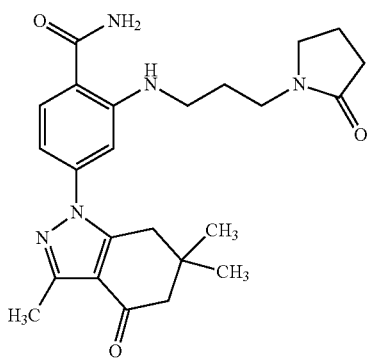

2-[3-(2-Oxo-pyrrolidin-1-yl)-propylamino]-4-(3,6,6-trimethyl-4-oxo-4,5,6,7-tetrahydro-indazol-1-yl)-benzamide (Compound 34)

2-Bromo-4-(3,6,6-trimethyl-4-oxo-4,5,6,7-tetrahydro-indazol-1-yl)-benzonitrile (1.0 mmol, 358 mg), palladium acetate (0.13 mmol, 30 mg), 1,1'bis(diphenylphosphino)ferrocene (0.1 mmol, 56 mg), sodium t-butoxide (2 mmol, 192 mg), toluene (2 mL), and N-(3-aminopropyl)-2-pyrrolidinone (2 mmol, 0.28 mL) were combined in a 2-5 mL microwave tube, stirred briefly, and heated in a Personal Chemistry microwave set at high absorbance to 110° C. for 900 seconds. After cooling, the reaction mixture was taken up in ethyl acetate (200 mL) and washed with water (25 mL). The aqueous layer was extracted with additional ethyl acetate (200 mL), and the combined organic phase was dried over magnesium sulfate, filtered, and concentrated. The residue was subjected to chromatography, affording the desired nitrile as a tan solid (258 mg, 61%).

DMSO (0.1 mL) and ethanol (4 mL) were added to the above nitrile (0.60 mmol, 250 mg). The flask was lowered into a 50° C. oil bath and KOH (4.5 mmol, 255 mg) was added, followed by 30% hydrogen peroxide (ca 10 mmol, 1 mL). After 30 minutes, the reaction was taken up in ethyl acetate (100 mL) and washed with water (50 mL). The aqueous layer was extracted with additional ethyl acetate (100 mL). The combined organic layer was dried over magnesium sulfate, filtered, and concentrated. Chromatography of the residue afforded the title benzamide as a white solid (187 mg, 71%). LCMS (m/z): M+H=438.2.

Example 35

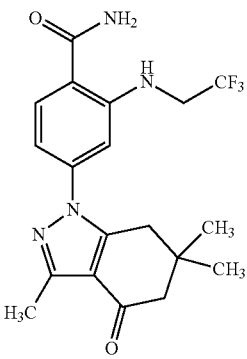

2-(2,2,2-Trifluoro-ethylamino)-4-(3,6,6-trimethyl-4-oxo-4,5,6,7-tetrahydro-indazol-1-yl)-benzamide (Compound 35)

2-Bromo-4-(3,6,6-trimethyl-4-oxo-4,5,6,7-tetrahydro-indazol-1-yl)-benzonitrile (2.0 mmol, 714 mg), palladium acetate (0.13 mmol, 60 mg), 1,1'-bis(diphenylphosphino)ferrocene (0.2 mmol, 112 mg), sodium t-butoxide (4 mmol, 384 mg), toluene (4 mL), and 2,2,2-trifluoroethylamine (8 mmol, 0.63 mL) were combined in a 2-5 mL microwave tube, stirred briefly, and heated in a Personal Chemistry microwave set at high absorbance to 110° C. for 900 seconds. After cooling, the reaction mixture was taken up in ethyl acetate (200 mL) and washed with water (25 mL). The organic phase was dried over magnesium sulfate, filtered, and concentrated. The residue was subjected to chromatography, affording a mixture of the anticipated 2-(2,2,2-trifluoro-ethylamino)-4-(3,6,6-trimethyl-4-oxo-4,5,6,7-tetrahydro-indazol-1-yl)-benzonitrile (346 mg, 50%) as a tan solid, and the desired ultimate product, 2-(2,2,2-trifluoro-ethylamino)-4-(3,6,6-trimethyl-4-oxo-4,5,6,7-tetrahydro-indazol-1-yl)-benzamide, as a tan solid (77 mg, 10%). LCMS (m/z): M+H=395.1.

Example 36

The following compounds are prepared essentially according to the procedures set forth in Schemes 1-4 above and described in the above examples.

| Compound No. | Structure | Name |
| --- | --- | --- |
| 36 | ![structure] | 2(allyamino)-4-(3-methyl-4-oxo-4,5,6,7-tetrahydroindol-1-yl)benzamide; M + H = 324.1 |

-continued
| Compound No. | Structure | Name |
|---|---|---|
| 37 | 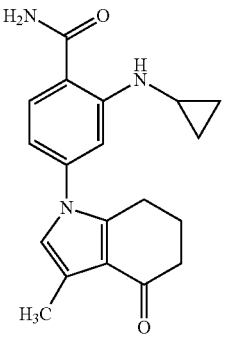 | 2-(cyclopropylamino)-4-(3-methyl-4-oxo-4,5,6,7-tetrahydroindol-1-yl)benzamide; M + H = 324.1 |
| 38 | 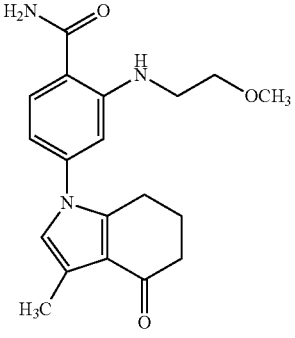 | 2-(2-methoxyethylamino)-4-(3-methyl-4-oxo-4,5,6,7-tetrahydroindol-1-yl)benzamide; M + H = 342.1 |
| 39 | 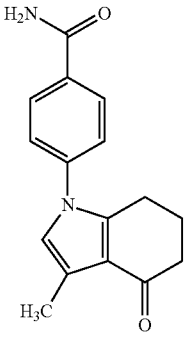 | 4-(3-methyl-4-oxo-4,5,6,7-tetrahydroindol-1-yl)benzamide; M + H = 269.1 |
| 40 | 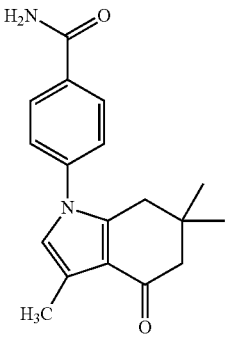 | 4-(3,6,6-trimethyl-4-oxo-4,5,6,7-tetrahydroindol-1-yl)benzamide; M + H = 297.1 |

-continued
| Compound No. | Structure | Name |
|---|---|---|
| 41 | 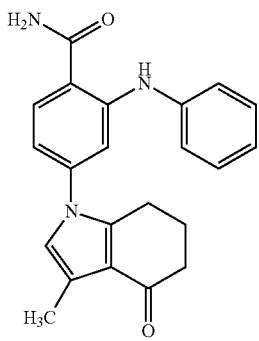 | 4-(3-methyl-4-oxo-4,5,6,7-tetrahydroindol-1-yl)-2-(phenylamino)benzamide; M + H = 360.1 |
| 42 | 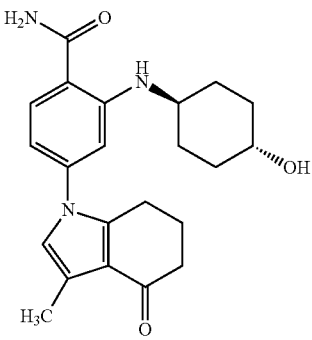 | 2-(trans-4-hydroxycyclohexylamino)-4-(3-methyl-4-oxo-4,5,6,7-tetrahydroindol-1-yl)benzamide; M + H = 382.2 |
| 43 | 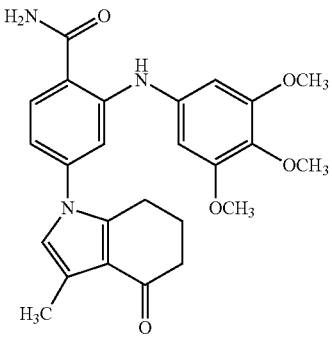 | 4-(3-methyl-4-oxo-4,5,6,7-tetrahydroindol-1-yl)-2-(3,4,5-trimethoxyphenylamino)benzamide; M + H = 450.2 |
| 44 | 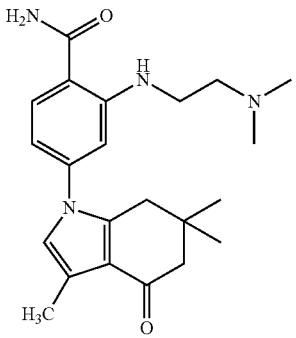 | 2-(2-(dimethylamino)ethylamino)-4-(3,6,6-trimethyl-4-oxo-4,5,6,7-tetrahydroindol-1-yl)benzamide; M + H = 383.2 |

-continued
| Compound No. | Structure | Name |
|---|---|---|
| 45 | 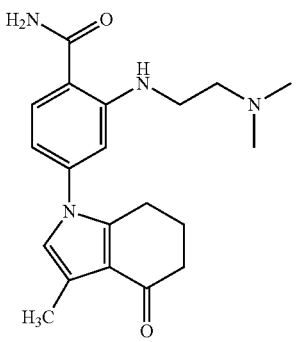 | 2-(2-(dimethylamino)ethylamino)-4-(3-methyl-4-oxo-4,5,6,7-tetrahydroindol-1-yl)benzamide; M + H = 355.2 |
| 46 | 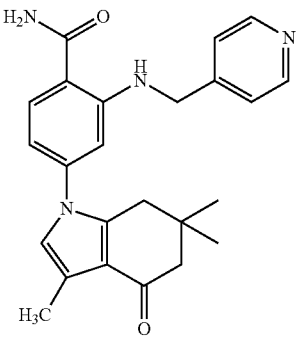 | 2-(pyridin-4-ylmethylamino)-4-(3,6,6-trimethyl-4-oxo-4,5,6,7-tetrahydroindol-1-yl)benzamide; M + H = 403.2 |
| 47 | 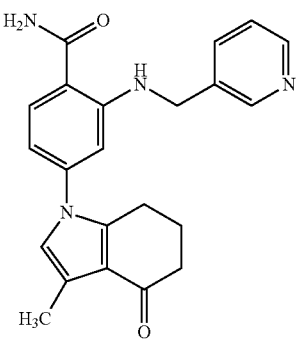 | 4-(3-methyl-4-oxo-4,5,6,7-tetrahydroindol-1-yl)-2-(pyridin-3-ylmethylamino)benzamide; M + H = 375.1 |
| 48 | 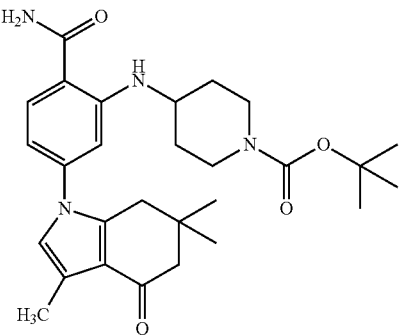 | tert-butyl 4-(2-carbamoyl-5-(3,6,6-trimethyl-4-oxo-4,5,6,7-tetrahydroindol-1-yl)phenylamino)piperidine-1-carboxylate; M + H = 495.2 |

-continued

| Compound No. | Structure | Name |
|---|---|---|
| 49 | 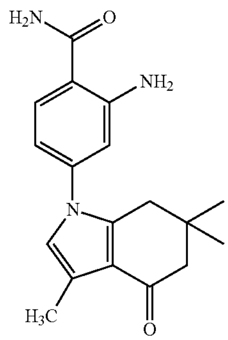 | 2-amino-4-(3,6,6-trimethyl-4-oxo-4,5,6,7-tetrahydroindol-1-yl)benzamide; M + H = 312.1 |
| 50 | 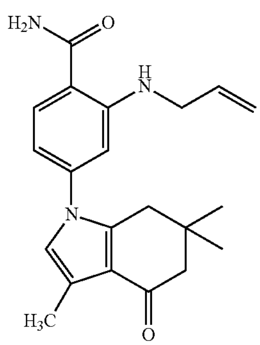 | 2-(allylamino)-4-(3,6,6-trimethyl-4-oxo-4,5,6,7-tetrahydroindol-1-yl)benzamide; M + H = 352.2 |
| 51 | 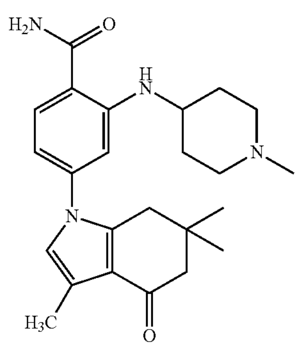 | 2-(1-methylpiperidin-4-ylamino)-4-(3,6,6-trimethyl-4-oxo-4,5,6,7-tetrahydroindol-1-yl)benzamide; M + H = 409.2 |
| 52 | 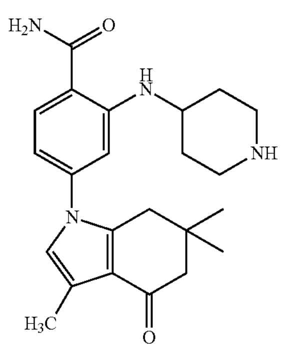 | 2-(piperidin-4-ylamino)-4-(3,6,6-trimethyl-4-oxo-4,5,6,7-tetrahydroindol-1-yl)benzamide; M + H = 395.2 |

-continued

| Compound No. | Structure | Name |
|---|---|---|
| 53 | 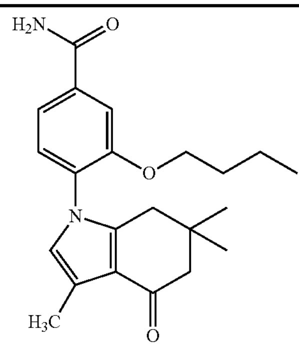 | 3-butoxy-4-(3,6,6-trimethyl-4-oxo-4,5,6,7-tetrahydroindol-1-yl)benzamide; M + H = 369.2 |
| 54 | 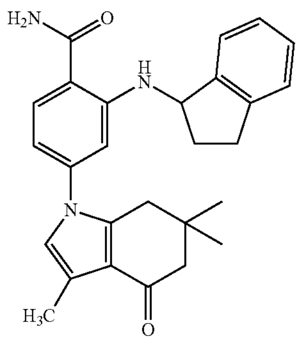 | 2-(2,3-dihydro-1H-inden-1-ylamino)-4-(3,6,6-trimethyl-4-oxo-4,5,6,7-tetrahydroindol-1-yl)benzamide; M + H = 428.2 |
| 55 | 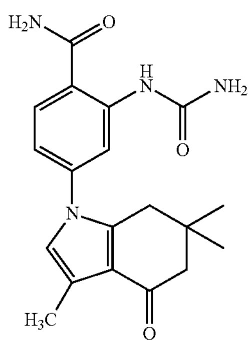 | 1-(2-carbamoyl-5-(3,6,6-trimethyl-4-oxo-4,5,6,7-tetrahydroindol-1-yl)phenyl)urea M + H = 355.1 |

Example 37

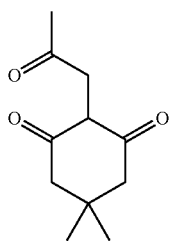

5,5-dimethyl-2-(2-oxopropyl)cyclohexane-1,3-dione (Compound 56)

An oven dried flask was charged with sodium hydride (3.61 g, 142.7 mmol) to which 200 mL of anhydrous DMF was added. The flask was cooled in an ice bath before adding 5,5-dimethyl-1,3-cyclohexanedione (20.0 g, 142.7 mmol) and chloroacetone (11.36 mL, 142.7 mmol) in 100 mL DMF in a controlled manner. The reaction was allowed to warm to RT and stirred for 3 h. Saturated NH$_4$Cl was added and the mixture was washed several times with EtOAc. The combined organic layer was dried over MgSO$_4$, filtered, the solvent removed in vacuo (below 40° C.). LCMS m/z M+H=197.1.

Example 38

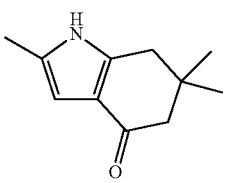

2,6,6-trimethyl-6,7-dihydro-1H-indol-4(5H)-one (Compound 57)

The crude tri-ketone from Example 37 was dissolved in 300 mL of acetic acid to which ammonium acetate (55 g, 0.714 mmol) was added. The reaction mixture was heated at 65° C. until all starting material had disappeared (2-3 h), cooled to RT, added to H₂O, and washed with EtOAc. The organic layer was washed with saturated NaHCO₃ (×3), brine (×1) and dried over MgSO₄. Solvent was removed in vacuo and the oily residue was passed through a plug of silica. The appropriate fractions were collected and solvent was removed. The resulting solid was washed with EtOAc and hexanes (if too much hexanes is added the material crashing back out of solution after the addition of EtOAc will be gummy. To remedy this simply add a little EtOAc). The solid was filtered and washed with hexanes. More solid can be recovered by removing the solvent and repeating this procedure. LCMS m/z M+H=178.1. Approximately 5 g of a tan solid was collected and identified as 2,6,6-trimethyltetrahydroindol-4-one.

Example 39

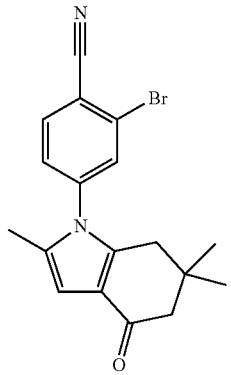

2-bromo-4-(2,6,6-trimethyl-4-oxo-4,5,6,7-tetrahydro-1H-indol-1-yl)benzonitrile (Compound 58)

Pyrrole (2,6,6-trimethyltetrahydroindol-4-one) (1.5 g, 8.5 mmol) and 2-bromo-4-fluorobenzonitrile (1.69 g, 8.5 mmol) were dissolved in anhydrous DMF (50 mL). To this NaH (95%, 408 mg, 17.0 mmol) was added and stirred at 50° C. for 1 h. The reaction mixture was cooled to RT and H₂O was added. Product crashed out of solution and was filtered and dried under vacuo (2.4 g, 79%). (100% clean by LCMS, product M+H=357).

Example 40

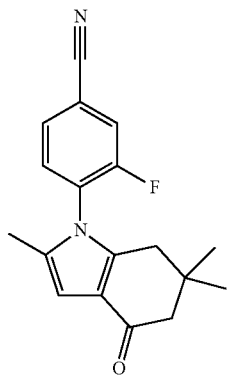

3-fluoro-4-(2,6,6-trimethyl-4-oxo-4,5,6,7-tetrahydro-1H-indol-1-yl)benzonitrile (Compound 59)

Pyrrole (2,6,6-trimethyltetrahydroindol-4-one) (1.0 g, 5.6 mmol) and 3,4-difluorobenzonitrile (785 mg, 5.6 mmol) were dissolved in anhydrous DMF (20 mL). To this NaH (95%, 270 mg, 11.2 mmol) was added and stirred at 50° C. for 30 min. The reaction mixture was cooled to RT and washed with H₂O and EtOAc. The organic layer was dried over MgSO₄. Column chromatography on silica eluting with EtOAc-hexanes (1:1) gave the product as a yellow solid (100% clean by LCMS, product M+H=397.1).

Example 41

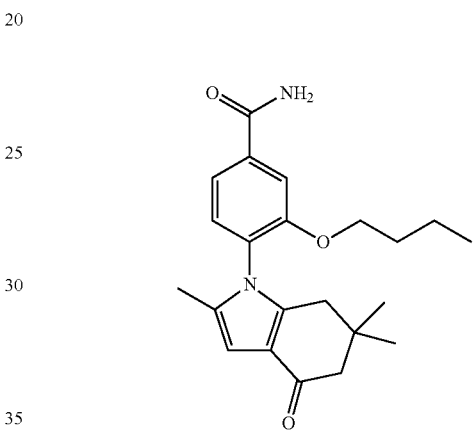

3-butoxy-4-(2,6,6-trimethyl-4-oxo-4,5,6,7-tetrahydro-1H-indol-1-yl)benzamide (Compound 60)

3-Fluoro-4-(2,6,6-trimethyl-4-oxo-4,5,6,7-tetrahydro-indol-1-yl)-benzonitrile (148 mg, 0.5 mmol) and 1-butanol (185.3 mg, 2.5 mmol) were dissolved in anhydrous DMF (1.5 mL). To this solution was added NaH (24.0 mg, 1 mmol). After purging the reaction vessel (Personal Chemistry Microwave Vial) with nitrogen, the reaction vessel was sealed and heated to 100° C. for 300 seconds in an Emyrs Optimizer Microwave. After cooling, the reaction mixture was diluted with H₂O and extracted into EtOAc (×2). The combined organics were washed with brine (×2), dried over Na₂SO₄, and concentrated to dryness. The yellow residue (3-Butoxy-4-(2,6,6-trimethyl-4-oxo-4,5,6,7-tetrahydro-indol-1-yl)-benzonitrile) was then dissolved in EtOH (3 mL) and treated with 1 mL of 1 N NaOH (aq) and a catalytic amount of H₂O₂. Quantitative conversion of the nitrile to the amide occurred after heating this solution at 65° C. for 3 hours. Column chromatography on silica eluting with EtOAc gave the product as a white solid (119.9 mg, 65%). (100% clean by LC/MS, product M+H=369.2).

Example 42

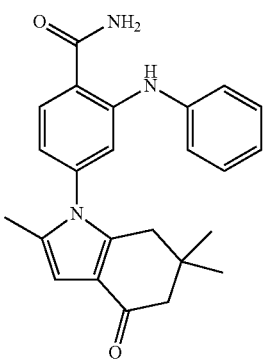

2-(phenylamino)-4-(2,6,6-trimethyl-4-oxo-4,5,6,7-tetrahydro-1H-indol-1-yl)benzamide (Compound 61)

2-Bromo-4-(2,6,6-trimethyl-4-oxo-4,5,6,7-tetrahydro-indol-1-yl)-benzonitrile (107.2 mg, 0.3 mmol), aniline (111.8 mg, 1.2 mmol), Pd(OAc)$_2$ (10.1 mmol, 5 mol %), DPPF (16.6 mg, 10 mol %), and NaOtBu (57.7 mg, 0.6 mmol) were placed in a Personal Chemistry Microwave Vial. The reagents were suspended in 2.5 mL of anhydrous toluene and the vessel purged with nitrogen. The reaction vessel was sealed and heated to 110° C. for 480 seconds. Upon cooling, the reaction mixture was filtered through SiO$_2$ (eluted with 2:1 EtOAc/hexanes) and the eluent concentrated in vacuo. The residue was then dissolved in 2 mL EtOH and treated with 0.6 mL of 1 N NaOH and a catalytic amount of H$_2$O$_2$. After stirring this solution at 50° C. for 2 hours, the mixture of nitrile and amide was purified by column chromatography (silica, EtOAc/hexanes). The product 2-(phenylamino)-4-(2,6,6-trimethyl-4-oxo-4,5,6,7-tetrahydroindol-1-yl)benzamide was isolated as a yellow powder (55.6 mg, 47%). (100% clean by LC/MS, product M+H=388.1). The corresponding nitrile was also isolated (46.9 mg, 42%). (100% clean by LC/MS).

Example 43

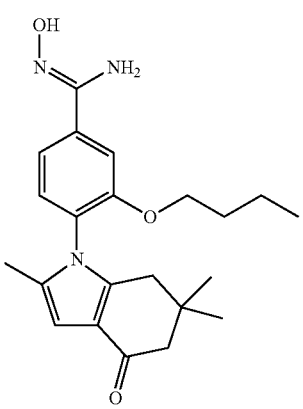

(Z)-3-butoxy-N'-hydroxy-4-(2,6,6-trimethyl-4-oxo-4,5,6,7-tetrahydro-1H-indol-1-yl)benzimidamide (Compound 62)

Treatment of 3-Butoxy-4-(2,6,6-trimethyl-4-oxo-4,5,6,7-tetrahydro-indol-1-yl)-benzonitrile with hydroxylamine hydrochloride affords the title compound, LCMS m/z M+H=384.2.

Example 44

The following compounds are prepared essentially according to the procedures forth in Scheme 7-9 and described in the preceding examples.

| Compound No. | Structure | Name |
|---|---|---|
| 63 | 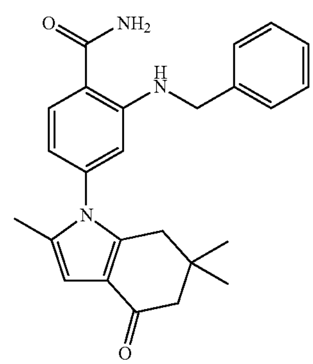 | 2-Benzylamino-4-(2,6,6-trimethyl-4-oxo-4,5,6,7-tetrahydro-indol-1-yl)-benzamide; M + H = 402.2 |

-continued

| Compound No. | Structure | Name |
|---|---|---|
| 64 | 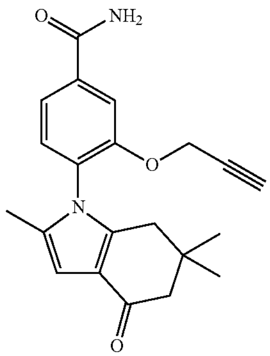 | 3-Prop-2-ynyloxy-4-(2,6,6-trimethyl-4-oxo-4,5,6,7-tetrahydro-indol-1-yl)-benzamide; M + H = 351.1 |
| 65 | 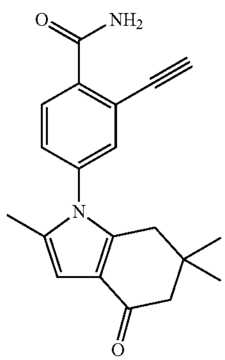 | 2-Ethynyl-4-(2,6,6-trimethyl-4-oxo-4,5,6,7-tetrahydro-indol-1-yl)-benzamide; M + H = 321.1 |
| 66 | 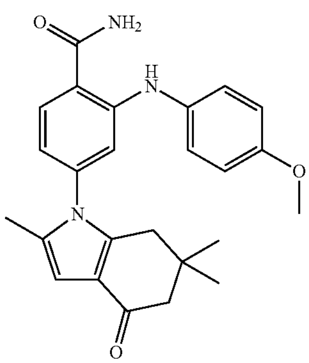 | 2-(4-Methoxy-phenylamino)-4-(2,6,6-trimethyl-4-oxo-4,5,6,7-tetrahydro-indol-1-yl)-benzamide; M + H = 418.2 |
| 67 | 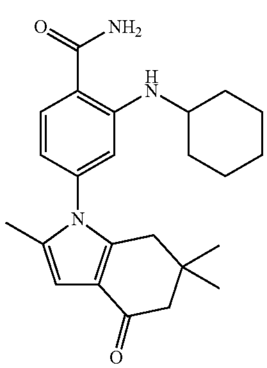 | 2-Cyclohexylamino-4-(2,6,6-trimethyl-4-oxo-4,5,6,7-tetrahydro-indol-1-yl)-benzamide; M + H = 394.1 |

-continued

| Compound No. | Structure | Name |
|---|---|---|
| 68 | 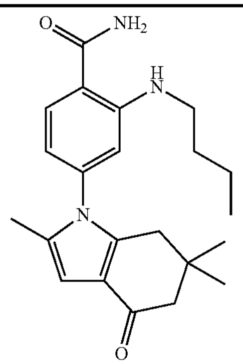 | 2-(butylamino)-4-(2,6,6-trimethyl-4-oxo-4,5,6,7-tetrahydroindol-1-yl)benzamide; M + H = 368.2 |
| 69 | 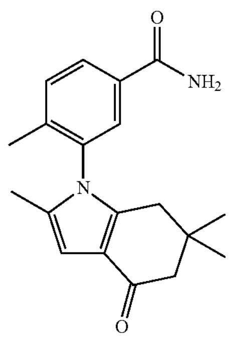 | 4-Methyl-3-(2,6,6-trimethyl-4-oxo-4,5,6,7-tetrahydro-indol-1-yl)-benzamide M + H = 311.1 |

Example 45

The following compounds are prepared essentially according to the procedures forth in Scheme 1-9 and described in the preceding examples.

| Compound No. | M + H | Name |
|---|---|---|
| 70 | 379.1 | 3-(3-thienyl)-4-(2,6,6-trimethyl-4-oxo-4,5,6,7-tetrahydro-1H-indol-1-yl)benzamide |
| 71 | 311.1 | 2-methyl-4-(2,6,6-trimethyl-4-oxo-4,5,6,7-tetrahydro-1H-indol-1-yl)benzamide |
| 72 | 412.1 | 2-[(3-ethynylphenyl)amino]-4-(2,6,6-trimethyl-4-oxo-4,5,6,7-tetrahydro-1H-indol-1-yl)benzamide |
| 73 | 422.1 | 2-[(4-chlorophenyl)amino]-4-(2,6,6-trimethyl-4-oxo-4,5,6,7-tetrahydro-1H-indol-1-yl)benzamide |
| 74 | 360.1 | 2-anilino-4-(2-methyl-4-oxo-4,5,6,7-tetrahydro-1H-indol-1-yl)benzamide |
| 75 | 389.1 | 3-anilino-5-(2,6,6-trimethyl-4-oxo-4,5,6,7-tetrahydro-1H-indol-1-yl)pyridine-2-carboxamide |
| 76 | 478.2 | 2-[(3,4,5-trimethoxyphenyl)amino]-4-(2,6,6-trimethyl-4-oxo-4,5,6,7-tetrahydro-1H-indol-1-yl)benzamide |
| 77 | 374.1 | 2-pyridin-4-yl-4-(2,6,6-trimethyl-4-oxo-4,5,6,7-tetrahydro-1H-indol-1-yl)benzamide |
| 78 | 412.2 | N-[2-(aminocarbonyl)-5-(2,6,6-trimethyl-4-oxo-4,5,6,7-tetrahydro-1H-indol-1-yl)phenyl]-L-valine |
| 79 | 382.2 | 2-morpholin-4-yl-4-(2,6,6-trimethyl-4-oxo-4,5,6,7-tetrahydro-1H-indol-1-yl)benzamide |
| 80 | 363.1 | 2-(1H-imidazol-1-yl)-4-(2,6,6-trimethyl-4-oxo-4,5,6,7-tetrahydro-1H-indol-1-yl)benzamide |
| 81 | 513.2 | 4-(3-chloro-2,6,6-trimethyl-4-oxo-4,5,6,7-tetrahydro-1H-indol-1-yl)-2-[(3,4,5-trimethoxyphenyl)amino]benzamide |
| 82 | 404.1 | 2-[(4-hydroxyphenyl)amino]-4-(2,6,6-trimethyl-4-oxo-4,5,6,7-tetrahydro-1H-indol-1-yl)benzamide |
| 83 | 406.2 | 2-[(1-ethyl-1H-pyrazol-5-yl)amino]-4-(2,6,6-trimethyl-4-oxo-4,5,6,7-tetrahydro-1H-indol-1-yl)benzamide |
| 84 | 393.1 | 2-[(5-methylisoxazol-3-yl)amino]-4-(2,6,6-trimethyl-4-oxo-4,5,6,7-tetrahydro-1H-indol-1-yl)benzamide |
| 85 | 403.2 | 2-{[4-(aminocarbonyl)phenyl]amino}-4-(2-methyl-4-oxo-4,5,6,7-tetrahydro-1H-indol-1-yl)benzamide |
| 86 | 436.1 | 4-(4-oxo-4,5,6,7-tetrahydro-1H-indol-1-yl)-2-[(3,4,5-trimethoxyphenyl)amino]benzamide |
| 87 | 419.2 | 2-[(6-methoxypyridin-3-yl)amino]-4-(2,6,6-trimethyl-4-oxo-4,5,6,7-tetrahydro-1H-indol-1-yl)benzamide |
| 88 | 310.1 | 2-(allylamino)-4-(4-oxo-4,5,6,7-tetrahydro-1H-indol-1-yl)benzamide |
| 89 | 283.1 | 4-(2,3-dimethyl-4-oxo-4,5,6,7-tetrahydro-1H-indol-1-yl)benzamide |
| 90 | 361 | 3-bromo-4-(2,3-dimethyl-4-oxo-4,5,6,7-tetrahydro-1H-indol-1-yl)benzamide |
| 91 | 338.1 | 2-(allylamino)-4-(2,3-dimethyl-4-oxo-4,5,6,7-tetrahydro-1H-indol-1-yl)benzamide |
| 92 | 356.2 | 4-(2,3-dimethyl-4-oxo-4,5,6,7-tetrahydro-1H-indol-1-yl)-2-[(2-methoxyethyl)amino]benzamide |
| 93 | 519.2 | 2-({3-[3-(dimethylamino)propoxy]-4-methoxyphenyl}amino)-4-(2,6,6-trimethyl-4-oxo-4,5,6,7-tetrahydro-1H-indol-1-yl)benzamide |

-continued

| Compound No. | M + H | Name |
|---|---|---|
| 94 | 397.2 | 2-(morpholin-4-ylamino)-4-(2,6,6-trimethyl-4-oxo-4,5,6,7-tetrahydro-1H-indol-1-yl)benzamide |
| 95 | 371.2 | 2-[(2-methoxyethyl)amino]-4-(3,6,6-trimethyl-4-oxo-4,5,6,7-tetrahydro-1H-indazol-1-yl)benzamide |
| 96 | 425.2 | 2-[(2-morpholin-4-ylethyl)amino]-4-(3,6,6-trimethyl-4-oxo-4,5,6,7-tetrahydro-1H-indol-1-yl)benzamide |
| 97 | 389.1 | 2-(pyridin-4-ylamino)-4-(3,6,6-trimethyl-4-oxo-4,5,6,7-tetrahydro-1H-indol-1-yl)benzamide |
| 98 | 354.1 | 2-(acetylamino)-4-(3,6,6-trimethyl-4-oxo-4,5,6,7-tetrahydro-1H-indol-1-yl)benzamide |
| 99 | 395.2 | 2-(4-methylpiperazin-1-yl)-4-(3,6,6-trimethyl-4-oxo-4,5,6,7-tetrahydro-1H-indol-1-yl)benzamide |
| 100 | 367.2 | 2-[(cyclopropylmethyl)amino]-4-(3,6,6-trimethyl-4-oxo-4,5,6,7-tetrahydro-1H-indazol-1-yl)benzamide |
| 101 | 384.1 | 2-[(methoxyacetyl)amino]-4-(3,6,6-trimethyl-4-oxo-4,5,6,7-tetrahydro-1H-indol-1-yl)benzamide |
| 102 | 326.1 | 2-ethyl-4-(3,6,6-trimethyl-4-oxo-4,5,6,7-tetrahydro-1H-indazol-1-yl)benzamide |
| 103 | 386.1 | 2-(butylthio)-4-(3,6,6-trimethyl-4-oxo-4,5,6,7-tetrahydro-1H-indazol-1-yl)benzamide |
| 104 | 505.2 | 2-({3-[2-(dimethylamino)ethoxy]-4-methoxyphenyl}amino)-4-(3,6,6-trimethyl-4-oxo-4,5,6,7-tetrahydro-1H-indol-1-yl)benzamide |
| 105 | 406.1 | 2-(pyridin-4-ylthio)-4-(3,6,6-trimethyl-4-oxo-4,5,6,7-tetrahydro-1H-indol-1-yl)benzamide |
| 106 | 417.2 | 2-{[(1R)-1-phenylethyl]amino}-4-(3,6,6-trimethyl-4-oxo-4,5,6,7-tetrahydro-1H-indazol-1-yl)benzamide |
| 107 | 533.1 | 4-[6,6-dimethyl-4-oxo-3-(trifluoromethyl)-4,5,6,7-tetrahydro-1H-indazol-1-yl]-2-[(3,4,5-trimethoxyphenyl)amino]benzamide |
| 108 | 476.2 | 2-({2-[2-(dimethylamino)ethoxy]pyridin-4-yl}amino)-4-(3,6,6-trimethyl-4-oxo-4,5,6,7-tetrahydro-1H-indol-1-yl)benzamide |
| 109 | 480.2 | 2-{[1-(N,N-dimethylglycyl)piperidin-4-yl]amino}-4-(3,6,6-trimethyl-4-oxo-4,5,6,7-tetrahydro-1H-indol-1-yl)benzamide |
| 110 | 359.1 | 4-(6,6-dimethyl-4-oxo-3-phenyl-4,5,6,7-tetrahydro-1H-indol-1-yl)benzamide |
| 111 | 455.2 | 2-[(2-{[2-(aminocarbonyl)-5-(3,6,6-trimethyl-4-oxo-4,5,6,7-tetrahydro-1H-indol-1-yl)phenyl]amino}ethyl)amino]-2-oxoethyl acetate |
| 112 | 413.2 | 2-{[2-(glycoloylamino)ethyl]amino}-4-(3,6,6-trimethyl-4-oxo-4,5,6,7-tetrahydro-1H-indol-1-yl)benzamide |
| 113 | 419.1 | 2-{[2-(methylsulfonyl)ethyl]amino}-4-(3,6,6-trimethyl-4-oxo-4,5,6,7-tetrahydro-1H-indazol-1-yl)benzamide |
| 114 | 419.2 | 2-[(4-methoxyphenyl)amino]-4-(3,6,6-trimethyl-4-oxo-4,5,6,7-tetrahydro-1H-indazol-1-yl)benzamide |
| 115 | 406.1 | 2-[(6-oxo-1,6-dihydropyridin-3-yl)amino]-4-(3,6,6-trimethyl-4-oxo-4,5,6,7-tetrahydro-1H-indazol-1-yl)benzamide |
| 116 | 415.2 | 2-(cyclopent-3-en-1-ylamino)-4-[3-(difluoromethyl)-6,6-dimethyl-4-oxo-4,5,6,7-tetrahydro-1H-indazol-1-yl]benzamide |
| 117 | 367.2 | 2-(cyclobutylamino)-4-(3,6,6-trimethyl-4-oxo-4,5,6,7-tetrahydro-1H-indol-1-yl)benzamide |
| 118 | 455.2 | 2-[trans-4-(2-Hydroxy-ethoxy)-cyclohexylamino]-4-(3,6,6-trimethyl-4-oxo-4,5,6,7-tetrahydro-indazol-1-yl)-benzamide |
| 119 | 411.2 | 2-(trans-4-Hydroxy-cyclohexylamino)-4-(3,6,6-trimethyl-4-oxo-4,5,6,7-tetrahydro-indazol-1-yl)-benzamide |
| 120 | 415.2 | 2-(2-Methoxy-1-methoxymethyl-ethylamino)-4-(3,6,6-trimethyl-4-oxo-4,5,6,7-tetrahydro-indazol-1-yl)-benzamide; |
| 121 | 415.2 | 2-{[3-hydroxy-1-(2-hydroxyethyl)propyl]amino}-4-(3,6,6-trimethyl-4-oxo-4,5,6,7-tetrahydro-1H-indazol-1-yl)benzamide |
| 122 | 469.2 | 4-[6,6-dimethyl-4-oxo-3-(trifluoromethyl)-4,5,6,7-tetrahydro-1H-indazol-1-yl]-2-{[2-methoxy-1-(methoxymethyl)ethyl]amino}benzamide |
| 123 | 451.1 | 2-{[3-(methylsulfinyl)phenyl]amino}-4-(3,6,6-trimethyl-4-oxo-4,5,6,7-tetrahydro-1H-indazol-1-yl)benzamide |
| 124 | 528.1 | 4-[6,6-dimethyl-4-oxo-3-(trifluoromethyl)-4,5,6,7-tetrahydro-1H-indazol-1-yl]-2-{[1-(methylsulfonyl)piperidin-4-yl]amino}benzamide |
| 125 | 465.2 | 4-(6,6-Dimethyl-4-oxo-3-trifluoromethyl-4,5,6,7-tetrahydro-indazol-1-yl)-2-(trans-4-hydroxy-cyclohexylamino)-benzamide |
| 126 | 509.2 | 4-(6,6-Dimethyl-4-oxo-3-trifluoromethyl-4,5,6,7-tetrahydro-indazol-1-yl)-2-[trans-4-(2-hydroxy-ethoxy)-cyclohexylamino]-benzamide |
| 127 | 537.3 | 2-{[1-(3-morpholin-4-ylpropanoyl)piperidin-4-yl]amino}-4-(3,6,6-trimethyl-4-oxo-4,5,6,7-tetrahydro-1H-indazol-1-yl)benzamide |
| 128 | 508.2 | 2-[trans-4-(2-Amino-ethoxy)-cyclohexylamino]-4-(6,6-dimethyl-4-oxo-3-trifluoromethyl-4,5,6,7-tetrahydro-indazol-1-yl)-benzamide |
| 129 | 453.2 | 2-[(1-glycylpiperidin-4-yl)amino]-4-(3,6,6-trimethyl-4-oxo-4,5,6,7-tetrahydro-1H-indazol-1-yl)benzamide |
| 130 | 454.2 | 2-[trans-4-(2-Amino-ethoxy)-cyclohexylamino]-4-(3,6,6-trimethyl-4-oxo-4,5,6,7-tetrahydro-indazol-1-yl)-benzamide |
| 131 | 446.1 | 2-{[1-(methylsulfonyl)azetidin-3-yl]amino}-4-(3,6,6-trimethyl-4-oxo-4,5,6,7-tetrahydro-1H-indazol-1-yl)benzamide |
| 132 | 433.1 | 2-{[3-(methylsulfonyl)propyl]amino}-4-(3,6,6-trimethyl-4-oxo-4,5,6,7-tetrahydro-1H-indazol-1-yl)benzamide |
| 133 | 488.1 | 4-[6,6-dimethyl-4-oxo-3-(trifluoromethyl)-4,5,6,7-tetrahydro-1H-indazol-1-yl]-2-({2-[(methylsulfonyl)amino]ethyl}amino)benzamide |
| 134 | 338.1 | 4-(3-but-3-en-1-yl-6,6-dimethyl-4-oxo-4,5,6,7-tetrahydro-1H-indazol-1-yl)benzamide |
| 135 | 460.1 | 2-{[(3S)-1-(methylsulfonyl)pyrrolidin-3-yl]amino}-4-(3,6,6-trimethyl-4-oxo-4,5,6,7-tetrahydro-1H-indazol-1-yl)benzamide |
| 136 | 502.1 | 2-({2-[(dimethylamino)sulfonyl]ethyl}amino)-4-[6,6-dimethyl-4-oxo-3-(trifluoromethyl)-4,5,6,7-tetrahydro-1H-indazol-1-yl]benzamide |
| 137 | 327.1 | 4-[3-(2-Amino-ethyl)-6,6-dimethyl-4-oxo-4,5,6,7-tetrahydro-indazol-1-yl]-benzamide |

Example 46

The following compounds have been prepared essentially according to the procedures set forth in Schemes 1-9 above and described in the above examples.

| Compound No. | M + H | Name |
|---|---|---|
| 138 | 285.1 | 4-(6,6-dimethyl-4-oxo-4,5,6,7-tetrahydro-1H-indazol-1-yl)benzoic acid; |
| 139 | 284.1 | 4-(6,6-dimethyl-4-oxo-4,5,6,7-tetrahydro-1H-indazol-1-yl)benzamide; |

| Compound No. | M+H | Name |
|---|---|---|
| 140 | 297.1 | 4-(2,6,6-trimethyl-4-oxo-4,5,6,7-tetrahydro-1H-indol-1-yl)benzamide; |
| 141 | 313.1 | 4-[(4Z)-4-(methoxyimino)-6,6-dimethyl-4,5,6,7-tetrahydro-1H-indazol-1-yl]benzamide; |
| 142 | 299.1 | 4-[(4Z)-4-(hydroxyimino)-6,6-dimethyl-4,5,6,7-tetrahydro-1H-indazol-1-yl]benzamide; |
| 143 | 311.1 | 4-methyl-3-(2,6,6-trimethyl-4-oxo-4,5,6,7-tetrahydro-1H-indol-1-yl)benzamide; |
| 144 | 297.1 | 3-(2,6,6-trimethyl-4-oxo-4,5,6,7-tetrahydro-1H-indol-1-yl)benzamide; |
| 145 | 332.1 | 2-chloro-4-(2,6,6-trimethyl-4-oxo-4,5,6,7-tetrahydro-1H-indol-1-yl)benzoic acid; |
| 146 | 327.1 | 4-[(4Z)-4-(ethoxyimino)-6,6-dimethyl-4,5,6,7-tetrahydro-1H-indazol-1-yl]benzamide; |
| 147 | 375.1 | 4-[(4Z)-6,6-dimethyl-4-(phenoxyimino)-4,5,6,7-tetrahydro-1H-indazol-1-yl]benzamide; |
| 148 | 355.2 | 4-[(4Z)-4-(isobutoxyimino)-6,6-dimethyl-4,5,6,7-tetrahydro-1H-indazol-1-yl]benzamide; |
| 149 | 339.1 | 4-{(4Z)-4-[(allyloxy)imino]-6,6-dimethyl-4,5,6,7-tetrahydro-1H-indazol-1-yl}benzamide; |
| 150 | 383.2 | 4-{(4Z)-6,6-dimethyl-4-[(tetrahydro-2H-pyran-2-yloxy)imino]-4,5,6,7-tetrahydro-1H-indazol-1-yl}benzamide; |
| 151 | 389.1 | 4-{(4Z)-4-[(benzyloxy)imino]-6,6-dimethyl-4,5,6,7-tetrahydro-1H-indazol-1-yl}benzamide; |
| 152 | 312.1 | 4-[(4E)-4-(hydroxyimino)-2,6,6-trimethyl-4,5,6,7-tetrahydro-1H-indol-1-yl]benzamide; |
| 153 | 326.1 | 4-[(4E)-4-(methoxyimino)-2,6,6-trimethyl-4,5,6,7-tetrahydro-1H-indol-1-yl]benzamide; |
| 154 | 352.1 | 4-{(4E)-4-[(allyloxy)imino]-2,6,6-trimethyl-4,5,6,7-tetrahydro-1H-indol-1-yl}benzamide; |
| 155 | 368.2 | 4-[(4E)-4-(isobutoxyimino)-2,6,6-trimethyl-4,5,6,7-tetrahydro-1H-indol-1-yl]benzamide; |
| 156 | 402.2 | 4-{(4E)-4-[(benzyloxy)imino]-2,6,6-trimethyl-4,5,6,7-tetrahydro-1H-indol-1-yl}benzamide; |
| 157 | 340.1 | 3-[(4Z)-4-(methoxyimino)-2,6,6-trimethyl-4,5,6,7-tetrahydro-1H-indol-1-yl]-4-methylbenzamide; |
| 158 | 326.1 | 3-[(4Z)-4-(hydroxyimino)-2,6,6-trimethyl-4,5,6,7-tetrahydro-1H-indol-1-yl]-4-methylbenzamide; |
| 159 | 377.1 | 4-[6-(1,3-benzodioxol-5-yl)-4-oxo-4,5,6,7-tetrahydro-1H-indazol-1-yl]benzoic acid; |
| 160 | 376.1 | 4-[6-(1,3-benzodioxol-5-yl)-4-oxo-4,5,6,7-tetrahydro-1H-indazol-1-yl]benzamide; |
| 161 | 391.1 | 4-[(4Z)-6-(1,3-benzodioxol-5-yl)-4-(hydroxyimino)-4,5,6,7-tetrahydro-1H-indazol-1-yl]benzamide; |
| 162 | 365.1 | 2-(trifluoromethyl)-4-(2,6,6-trimethyl-4-oxo-4,5,6,7-tetrahydro-1H-indol-1-yl)benzamide; |
| 163 | 327.1 | 2-methoxy-4-(2,6,6-trimethyl-4-oxo-4,5,6,7-tetrahydro-1H-indol-1-yl)benzamide; |
| 164 | 369.2 | 2-butoxy-4-(2,6,6-trimethyl-4-oxo-4,5,6,7-tetrahydro-1H-indol-1-yl)benzamide; |
| 165 | 368.2 | 2-(butylamino)-4-(2,6,6-trimethyl-4-oxo-4,5,6,7-tetrahydro-1H-indol-1-yl)benzamide; |
| 166 | 385.2 | 3-(2-ethoxyethoxy)-4-(2,6,6-trimethyl-4-oxo-4,5,6,7-tetrahydro-1H-indol-1-yl)benzamide; |
| 167 | 371.1 | 3-(2-methoxyethoxy)-4-(2,6,6-trimethyl-4-oxo-4,5,6,7-tetrahydro-1H-indol-1-yl)benzamide; |
| 168 | 341.1 | 2-ethoxy-4-(2,6,6-trimethyl-4-oxo-4,5,6,7-tetrahydro-1H-indol-1-yl)benzamide; |
| 169 | 357.1 | 2-(2-hydroxyethoxy)-4-(2,6,6-trimethyl-4-oxo-4,5,6,7-tetrahydro-1H-indol-1-yl)benzamide; |
| 170 | 370.2 | 2-[(2-methoxyethyl)amino]-4-(2,6,6-trimethyl-4-oxo-4,5,6,7-tetrahydro-1H-indol-1-yl)benzamide; |
| 171 | 385.2 | 2-(2-ethoxyethoxy)-4-(2,6,6-trimethyl-4-oxo-4,5,6,7-tetrahydro-1H-indol-1-yl)benzamide; |
| 172 | 255.1 | 4-(4-oxo-4,5,6,7-tetrahydro-1H-indol-1-yl)benzamide; |
| 173 | 384.2 | 3-[2-(dimethylamino)ethoxy]-4-(2,6,6-trimethyl-4-oxo-4,5,6,7-tetrahydro-1H-indol-1-yl)benzamide; |
| 174 | 397.2 | 3-(tetrahydrofuran-3-ylmethoxy)-4-(2,6,6-trimethyl-4-oxo-4,5,6,7-tetrahydro-1H-indol-1-yl)benzamide; |
| 175 | 407.1 | 3-(4-fluorophenoxy)-4-(2,6,6-trimethyl-4-oxo-4,5,6,7-tetrahydro-1H-indol-1-yl)benzamide; |
| 176 | 383.2 | 2-{[2-(dimethylamino)ethyl]amino}-4-(2,6,6-trimethyl-4-oxo-4,5,6,7-tetrahydro-1H-indol-1-yl)benzamide; |
| 177 | 388.1 | 2-anilino-4-(2,6,6-trimethyl-4-oxo-4,5,6,7-tetrahydro-1H-indol-1-yl)benzamide; |
| 178 | 315.1 | 3-fluoro-4-(2,6,6-trimethyl-4-oxo-4,5,6,7-tetrahydro-1H-indol-1-yl)benzamide; |
| 179 | 359.1 | 4-(6,6-dimethyl-4-oxo-2-phenyl-4,5,6,7-tetrahydro-1H-indol-1-yl)benzamide; |
| 180 | 331.1 | 2-chloro-4-(2,6,6-trimethyl-4-oxo-4,5,6,7-tetrahydro-1H-indol-1-yl)benzamide; |
| 181 | 402.2 | 2-(benzylamino)-4-(2,6,6-trimethyl-4-oxo-4,5,6,7-tetrahydro-1H-indol-1-yl)benzamide; |
| 182 | 375 | 2-bromo-4-(2,6,6-trimethyl-4-oxo-4,5,6,7-tetrahydro-1H-indol-1-yl)benzamide; |
| 183 | 357.1 | 3-(2-hydroxyethoxy)-4-(2,6,6-trimethyl-4-oxo-4,5,6,7-tetrahydro-1H-indol-1-yl)benzamide; |
| 184 | 312.1 | 2-amino-4-(2,6,6-trimethyl-4-oxo-4,5,6,7-tetrahydro-1H-indol-1-yl)benzamide; |
| 185 | 385.1 | 3-(tert-butylthio)-4-(2,6,6-trimethyl-4-oxo-4,5,6,7-tetrahydro-1H-indol-1-yl)benzamide; |
| 186 | 405.1 | 3-(phenylthio)-4-(2,6,6-trimethyl-4-oxo-4,5,6,7-tetrahydro-1H-indol-1-yl)benzamide; |
| 187 | 385.1 | 3-(butylthio)-4-(2,6,6-trimethyl-4-oxo-4,5,6,7-tetrahydro-1H-indol-1-yl)benzamide; |
| 188 | 340.1 | 2-(dimethylamino)-4-(2,6,6-trimethyl-4-oxo-4,5,6,7-tetrahydro-1H-indol-1-yl)benzamide; |
| 189 | 327.1 | 3-methoxy-4-(2,6,6-trimethyl-4-oxo-4,5,6,7-tetrahydro-1H-indol-1-yl)benzamide; |
| 190 | 341.1 | 3-ethoxy-4-(2,6,6-trimethyl-4-oxo-4,5,6,7-tetrahydro-1H-indol-1-yl)benzamide; |
| 191 | 355.1 | 3-propoxy-4-(2,6,6-trimethyl-4-oxo-4,5,6,7-tetrahydro-1H-indol-1-yl)benzamide; |
| 192 | 403.1 | 3-(benzyloxy)-4-(2,6,6-trimethyl-4-oxo-4,5,6,7-tetrahydro-1H-indol-1-yl)benzamide; |
| 193 | 426.2 | 3-(2-morpholin-4-ylethoxy)-4-(2,6,6-trimethyl-4-oxo-4,5,6,7-tetrahydro-1H-indol-1-yl)benzamide; |
| 194 | 404.1 | 3-(pyridin-2-ylmethoxy)-4-(2,6,6-trimethyl-4-oxo-4,5,6,7-tetrahydro-1H-indol-1-yl)benzamide; |
| 195 | 404.1 | 3-(pyridin-4-ylmethoxy)-4-(2,6,6-trimethyl-4-oxo-4,5,6,7-tetrahydro-1H-indol-1-yl)benzamide; |
| 196 | 399.2 | 3-(2-isopropoxyethoxy)-4-(2,6,6-trimethyl-4-oxo-4,5,6,7-tetrahydro-1H-indol-1-yl)benzamide; |
| 197 | 410.2 | 3-(2-pyrrolidin-2-ylethoxy)-4-(2,6,6-trimethyl-4-oxo-4,5,6,7-tetrahydro-1H-indol-1-yl)benzamide; |
| 198 | 411.2 | 3-(tetrahydro-2H-pyran-2-ylmethoxy)-4-(2,6,6-trimethyl-4-oxo-4,5,6,7-tetrahydro-1H-indol-1-yl)benzamide; |
| 199 | 397.2 | 3-(tetrahydro-2H-pyran-4-yloxy)-4-(2,6,6-trimethyl-4-oxo-4,5,6,7-tetrahydro-1H-indol-1-yl)benzamide; |
| 200 | 368.2 | 3-(butylamino)-4-(2,6,6-trimethyl-4-oxo-4,5,6,7-tetrahydro-1H-indol-1-yl)benzamide; |
| 201 | 331.1 | 3-chloro-4-(2,6,6-trimethyl-4-oxo-4,5,6,7-tetrahydro-1H-indol-1-yl)benzamide; |
| 202 | 393.1 | 3-(1H-imidazol-4-ylmethoxy)-4-(2,6,6-trimethyl-4-oxo-4,5,6,7-tetrahydro-1H-indol-1-yl)benzamide; |
| 203 | 418.2 | 2-[(4-methoxyphenyl)amino]-4-(2,6,6-trimethyl-4-oxo-4,5,6,7-tetrahydro-1H-indol-1-yl)benzamide; |
| 204 | 370.1 | 3-butoxy-4-(2,6,6-trimethyl-4-oxo-4,5,6,7-tetrahydro-1H-indol-1-yl)benzoic acid; |
| 205 | 388.1 | 3-anilino-4-(2,6,6-trimethyl-4-oxo-4,5,6,7-tetrahydro-1H-indol-1-yl)benzamide; |
| 206 | 402.2 | 3-(benzylamino)-4-(2,6,6-trimethyl-4-oxo-4,5,6,7-tetrahydro-1H-indol-1-yl)benzamide; |
| 207 | 371.1 | 3-(3-hydroxypropoxy)-4-(2,6,6-trimethyl-4-oxo-4,5,6,7-tetrahydro-1H-indol-1-yl)benzamide; |
| 208 | 385.2 | 3-(3-hydroxybutoxy)-4-(2,6,6-trimethyl-4-oxo-4,5,6,7-tetrahydro-1H-indol-1-yl)benzamide; |

| Compound No. | M + H | Name |
|---|---|---|
| 209 | 387.1 | 3-(2,3-dihydroxypropoxy)-4-(2,6,6-trimethyl-4-oxo-4,5,6,7-tetrahydro-1H-indol-1-yl)benzamide; |
| 210 | 340.1 | N-butyl-4-(6,6-dimethyl-4-oxo-4,5,6,7-tetrahydro-1H-indazol-1-yl)benzamide; |
| 211 | 383.2 | 3-(2-methylbutoxy)-4-(2,6,6-trimethyl-4-oxo-4,5,6,7-tetrahydro-1H-indol-1-yl)benzamide; |
| 212 | 383.2 | 3-(pentyloxy)-4-(2,6,6-trimethyl-4-oxo-4,5,6,7-tetrahydro-1H-indol-1-yl)benzamide; |
| 213 | 383.2 | 3-(3-methylbutoxy)-4-(2,6,6-trimethyl-4-oxo-4,5,6,7-tetrahydro-1H-indol-1-yl)benzamide; |
| 214 | 313.1 | 3-hydroxy-4-(2,6,6-trimethyl-4-oxo-4,5,6,7-tetrahydro-1H-indol-1-yl)benzamide; |
| 215 | 360.1 | 4-(6,6-dimethyl-4-oxo-4,5,6,7-tetrahydro-1H-indazol-1-yl)-N-phenylbenzamide; |
| 216 | 394.2 | 2-(cyclohexylamino)-4-(2,6,6-trimethyl-4-oxo-4,5,6,7-tetrahydro-1H-indol-1-yl)benzamide; |
| 217 | 395.2 | 3-(cyclohexyloxy)-4-(2,6,6-trimethyl-4-oxo-4,5,6,7-tetrahydro-1H-indol-1-yl)benzamide; |
| 218 | 381.2 | 3-(pent-4-en-1-yloxy)-4-(2,6,6-trimethyl-4-oxo-4,5,6,7-tetrahydro-1H-indol-1-yl)benzamide; |
| 219 | 432.1 | 2-(1,3-benzodioxol-5-ylamino)-4-(2,6,6-trimethyl-4-oxo-4,5,6,7-tetrahydro-1H-indol-1-yl)benzamide; |
| 220 | 396.2 | 2-(hexylamino)-4-(2,6,6-trimethyl-4-oxo-4,5,6,7-tetrahydro-1H-indol-1-yl)benzamide; |
| 221 | 341.1 | 3-butoxy-4-(2-methyl-4-oxo-4,5,6,7-tetrahydro-1H-indol-1-yl)benzamide; |
| 222 | 385.2 | 3-(4-hydroxybutoxy)-4-(2,6,6-trimethyl-4-oxo-4,5,6,7-tetrahydro-1H-indol-1-yl)benzamide; |
| 223 | 397.2 | 3-[(3-methyloxetan-3-yl)methoxy]-4-(2,6,6-trimethyl-4-oxo-4,5,6,7-tetrahydro-1H-indol-1-yl)benzamide; |
| 224 | 384.2 | 3-(4-aminobutoxy)-4-(2,6,6-trimethyl-4-oxo-4,5,6,7-tetrahydro-1H-indol-1-yl)benzamide; |
| 225 | 383.1 | 3-(tetrahydrofuran-3-yloxy)-4-(2,6,6-trimethyl-4-oxo-4,5,6,7-tetrahydro-1H-indol-1-yl)benzamide; |
| 226 | 397.2 | 3-(tetrahydrofuran-2-ylmethoxy)-4-(2,6,6-trimethyl-4-oxo-4,5,6,7-tetrahydro-1H-indol-1-yl)benzamide; |
| 227 | 381.2 | 3-[(1-ethylprop-2-en-1-yl)oxy]-4-(2,6,6-trimethyl-4-oxo-4,5,6,7-tetrahydro-1H-indol-1-yl)benzamide; |
| 228 | 362 | 2-bromo-4-(6,6-dimethyl-4-oxo-4,5,6,7-tetrahydro-1H-indazol-1-yl)benzamide; |
| 229 | 409.1 | 3-(2-thienylmethoxy)-4-(2,6,6-trimethyl-4-oxo-4,5,6,7-tetrahydro-1H-indol-1-yl)benzamide; |
| 230 | 283.1 | 4-(6,6-dimethyl-4-oxo-4,5,6,7-tetrahydro-1H-indol-1-yl)benzamide; |
| 231 | 390.1 | 2-[(methylsulfonyl)amino]-4-(2,6,6-trimethyl-4-oxo-4,5,6,7-tetrahydro-1H-indol-1-yl)benzamide; |
| 232 | 354.1 | 2-(acetylamino)-4-(2,6,6-trimethyl-4-oxo-4,5,6,7-tetrahydro-1H-indol-1-yl)benzamide; |
| 233 | 355.1 | 2-[(aminocarbonyl)amino]-4-(2,6,6-trimethyl-4-oxo-4,5,6,7-tetrahydro-1H-indol-1-yl)benzamide; |
| 234 | 416.1 | 2-(benzoylamino)-4-(2,6,6-trimethyl-4-oxo-4,5,6,7-tetrahydro-1H-indol-1-yl)benzamide; |
| 235 | 382.2 | 2-(butyrylamino)-4-(2,6,6-trimethyl-4-oxo-4,5,6,7-tetrahydro-1H-indol-1-yl)benzamide; |
| 236 | 342.1 | 3-ethoxy-5-(2,6,6-trimethyl-4-oxo-4,5,6,7-tetrahydro-1H-indol-1-yl)pyridine-2-carboxamide; |
| 237 | 389.1 | 2-(pyridin-3-ylamino)-4-(2,6,6-trimethyl-4-oxo-4,5,6,7-tetrahydro-1H-indol-1-yl)benzamide; |
| 238 | 390.1 | 2-(pyridin-2-ylamino)-4-(2,6,6-trimethyl-4-oxo-4,5,6,7-tetrahydro-1H-indol-1-yl)benzoic acid; |
| 239 | 432.2 | 2-[(3-ethoxyphenyl)amino]-4-(2,6,6-trimethyl-4-oxo-4,5,6,7-tetrahydro-1H-indol-1-yl)benzamide; |
| 240 | 418.2 | 2-[(3-methoxyphenyl)amino]-4-(2,6,6-trimethyl-4-oxo-4,5,6,7-tetrahydro-1H-indol-1-yl)benzamide; |
| 241 | 356.1 | 3-butoxy-4-(6,6-dimethyl-4-oxo-4,5,6,7-tetrahydro-1H-indazol-1-yl)benzamide; |
| 242 | 371.2 | 3-butoxy-4-(6,6-dimethyl-4-oxo-4,5,6,7-tetrahydro-1H-indazol-1-yl)-N'-hydroxybenzenecarboximidamide; |
| 243 | 326.1 | N'-hydroxy-3-methyl-4-(2,6,6-trimethyl-4-oxo-4,5,6,7-tetrahydro-1H-indol-1-yl)benzenecarboximidamide; |
| 244 | 311.1 | 3-methyl-4-(2,6,6-trimethyl-4-oxo-4,5,6,7-tetrahydro-1H-indol-1-yl)benzamide; |
| 245 | 346.1 | 2-chloro-N-hydroxy-4-(2,6,6-trimethyl-4-oxo-4,5,6,7-tetrahydro-1H-indol-1-yl)benzenecarboximidamide; |
| 246 | 348.1 | 2,3-difluoro-N-hydroxy-4-(2,6,6-trimethyl-4-oxo-4,5,6,7-tetrahydro-1H-indol-1-yl)benzenecarboximidamide; |
| 247 | 355.1 | 8-(2,6,6-trimethyl-4-oxo-4,5,6,7-tetrahydro-1H-indol-1-yl)-2,3-dihydro-1,4-benzodioxine-5-carboxamide; |
| 248 | 367.2 | 2-pentyl-4-(2,6,6-trimethyl-4-oxo-4,5,6,7-tetrahydro-1H-indol-1-yl)benzamide; |
| 249 | 367.2 | 3-pentyl-4-(2,6,6-trimethyl-4-oxo-4,5,6,7-tetrahydro-1H-indol-1-yl)benzamide; |
| 250 | 460.2 | 2-[(4-butoxyphenyl)amino]-4-(2,6,6-trimethyl-4-oxo-4,5,6,7-tetrahydro-1H-indol-1-yl)benzamide; |
| 251 | 403.2 | 2-anilino-N'-hydroxy-4-(2,6,6-trimethyl-4-oxo-4,5,6,7-tetrahydro-1H-indol-1-yl)benzenecarboximidamide; |
| 252 | 472.1 | 2-{[4-(trifluoromethoxy)phenyl]amino}-4-(2,6,6-trimethyl-4-oxo-4,5,6,7-tetrahydro-1H-indol-1-yl)benzamide; |
| 253 | 440.1 | 2-[(2-chloro-4-fluorophenyl)amino]-4-(2,6,6-trimethyl-4-oxo-4,5,6,7-tetrahydro-1H-indol-1-yl)benzamide; |
| 254 | 436.1 | 2-[(2-chloro-4-methylphenyl)amino]-4-(2,6,6-trimethyl-4-oxo-4,5,6,7-tetrahydro-1H-indol-1-yl)benzamide; |
| 255 | 452.1 | 2-[(2-chloro-4-methoxyphenyl)amino]-4-(2,6,6-trimethyl-4-oxo-4,5,6,7-tetrahydro-1H-indol-1-yl)benzamide; |
| 256 | 448.2 | 2-[(3,4-dimethoxyphenyl)amino]-4-(2,6,6-trimethyl-4-oxo-4,5,6,7-tetrahydro-1H-indol-1-yl)benzamide; |
| 257 | 436.2 | 2-[(3-fluoro-4-methoxyphenyl)amino]-4-(2,6,6-trimethyl-4-oxo-4,5,6,7-tetrahydro-1H-indol-1-yl)benzamide; |
| 258 | 448.2 | 2-[(3,5-dimethoxyphenyl)amino]-4-(2,6,6-trimethyl-4-oxo-4,5,6,7-tetrahydro-1H-indol-1-yl)benzamide; |
| 259 | 448.2 | 2-[(2,5-dimethoxyphenyl)amino]-4-(2,6,6-trimethyl-4-oxo-4,5,6,7-tetrahydro-1H-indol-1-yl)benzamide; |
| 260 | 432.2 | 2-[(4-ethoxyphenyl)amino]-4-(2,6,6-trimethyl-4-oxo-4,5,6,7-tetrahydro-1H-indol-1-yl)benzamide; |
| 261 | 406.1 | 2-[(4-fluorophenyl)amino]-4-(2,6,6-trimethyl-4-oxo-4,5,6,7-tetrahydro-1H-indol-1-yl)benzamide; |
| 262 | 389.1 | 2-phenoxy-4-(2,6,6-trimethyl-4-oxo-4,5,6,7-tetrahydro-1H-indol-1-yl)benzamide; |
| 263 | 405.1 | 2-(phenylthio)-4-(2,6,6-trimethyl-4-oxo-4,5,6,7-tetrahydro-1H-indol-1-yl)benzamide; |
| 264 | 352.1 | 2-(cyclopropylamino)-4-(2,6,6-trimethyl-4-oxo-4,5,6,7-tetrahydro-1H-indol-1-yl)benzamide; |
| 265 | 350.1 | 2-(prop-2-yn-1-ylamino)-4-(2,6,6-trimethyl-4-oxo-4,5,6,7-tetrahydro-1H-indol-1-yl)benzamide; |
| 266 | 371.1 | 3-(propylthio)-4-(2,6,6-trimethyl-4-oxo-4,5,6,7-tetrahydro-1H-indol-1-yl)benzamide; |
| 267 | 386.1 | N-hydroxy-3-(propylthio)-4-(2,6,6-trimethyl-4-oxo-4,5,6,7-tetrahydro-1H-indol-1-yl)benzenecarboximidamide; |
| 268 | 460.2 | N-[2-(aminocarbonyl)-5-(2,6,6-trimethyl-4-oxo-4,5,6,7-tetrahydro-1H-indol-1-yl)phenyl]-L-phenylalanine; |
| 269 | 371.2 | 3-butoxy-4-[(4Z)-4-(hydroxyimino)-6,6-dimethyl-4,5,6,7-tetrahydro-1H-indazol-1-yl]benzamide; |
| 270 | 469.3 | 2-(diethylamino)ethyl 3-butoxy-4-(2,6,6-trimethyl-4-oxo-4,5,6,7-tetrahydro-1H-indol-1-yl)benzoate; |
| 271 | 546.1 | 2-[(2-chloro-3,4,5-trimethoxyphenyl)amino]-4-(3-chloro-2,6,6-trimethyl-4-oxo-4,5,6,7-tetrahydro-1H-indol-1-yl)benzamide; |

| Compound No. | M+H | Name |
|---|---|---|
| 272 | 464.2 | 4-(6,6-dimethyl-4-oxo-4,5,6,7-tetrahydro-1H-indol-1-yl)-2-[(3,4,5-trimethoxyphenyl)amino]benzamide; |
| 273 | 450.2 | 4-(2-methyl-4-oxo-4,5,6,7-tetrahydro-1H-indol-1-yl)-2-[(3,4,5-trimethoxyphenyl)amino]benzamide; |
| 274 | 442.1 | 2-[(3,4,5-trifluorophenyl)amino]-4-(2,6,6-trimethyl-4-oxo-4,5,6,7-tetrahydro-1H-indol-1-yl)benzamide; |
| 275 | 410.2 | 2-[(trans-4-hydroxycyclohexyl)amino]-4-(2,6,6-trimethyl-4-oxo-4,5,6,7-tetrahydro-1H-indol-1-yl)benzamide; |
| 276 | 408.2 | 2-[(4-oxocyclohexyl)amino]-4-(2,6,6-trimethyl-4-oxo-4,5,6,7-tetrahydro-1H-indol-1-yl)benzamide; |
| 277 | 402.2 | 2-[(4-methylphenyl)amino]-4-(2,6,6-trimethyl-4-oxo-4,5,6,7-tetrahydro-1H-indol-1-yl)benzamide; |
| 278 | 428.2 | 2-(2,3-dihydro-1H-inden-4-ylamino)-4-(2,6,6-trimethyl-4-oxo-4,5,6,7-tetrahydro-1H-indol-1-yl)benzamide; |
| 279 | 430.2 | 2-[(2-propylphenyl)amino]-4-(2,6,6-trimethyl-4-oxo-4,5,6,7-tetrahydro-1H-indol-1-yl)benzamide; |
| 280 | 430.2 | 2-[(2-isopropylphenyl)amino]-4-(2,6,6-trimethyl-4-oxo-4,5,6,7-tetrahydro-1H-indol-1-yl)benzamide; |
| 281 | 351.1 | 2-(3-hydroxyprop-1-yn-1-yl)-4-(2,6,6-trimethyl-4-oxo-4,5,6,7-tetrahydro-1H-indol-1-yl)benzamide; |
| 282 | 512.1 | 2-[(2-chloro-3,4,5-trimethoxyphenyl)amino]-4-(2,6,6-trimethyl-4-oxo-4,5,6,7-tetrahydro-1H-indol-1-yl)benzamide; |
| 283 | 331.1 | 4-(4-oxo-2-phenyl-4,5,6,7-tetrahydro-1H-indol-1-yl)benzamide; |
| 284 | 442.1 | 2-[(2,4,5-trifluorophenyl)amino]-4-(2,6,6-trimethyl-4-oxo-4,5,6,7-tetrahydro-1H-indol-1-yl)benzamide; |
| 285 | 492.2 | 2-[(3,4,5-trimethoxybenzyl)amino]-4-(2,6,6-trimethyl-4-oxo-4,5,6,7-tetrahydro-1H-indol-1-yl)benzamide; |
| 286 | 406.1 | 2-[(2-fluorophenyl)amino]-4-(2,6,6-trimethyl-4-oxo-4,5,6,7-tetrahydro-1H-indol-1-yl)benzamide; |
| 287 | 406.2 | 2-[(3-fluorophenyl)amino]-4-(2,6,6-trimethyl-4-oxo-4,5,6,7-tetrahydro-1H-indol-1-yl)benzamide; |
| 288 | 420.2 | 2-[(4-fluoro-3-methylphenyl)amino]-4-(2,6,6-trimethyl-4-oxo-4,5,6,7-tetrahydro-1H-indol-1-yl)benzamide; |
| 289 | 434.2 | 2-[(3-hydroxy-4-methoxyphenyl)amino]-4-(2,6,6-trimethyl-4-oxo-4,5,6,7-tetrahydro-1H-indol-1-yl)benzamide; |
| 290 | 436.2 | 2-[(2-fluoro-4-methoxyphenyl)amino]-4-(2,6,6-trimethyl-4-oxo-4,5,6,7-tetrahydro-1H-indol-1-yl)benzamide; |
| 291 | 396.2 | 2-(tetrahydro-2H-pyran-4-ylamino)-4-(2,6,6-trimethyl-4-oxo-4,5,6,7-tetrahydro-1H-indol-1-yl)benzamide; |
| 292 | 424.1 | 2-[(2,4-difluorophenyl)amino]-4-(2,6,6-trimethyl-4-oxo-4,5,6,7-tetrahydro-1H-indol-1-yl)benzamide; |
| 293 | 424.1 | 2-[(3,4-difluorophenyl)amino]-4-(2,6,6-trimethyl-4-oxo-4,5,6,7-tetrahydro-1H-indol-1-yl)benzamide; |
| 294 | 445.2 | 2-anilino-4-{5-[(dimethylamino)methyl]-2,6,6-trimethyl-4-oxo-4,5,6,7-tetrahydro-1H-indol-1-yl}benzamide; |
| 295 | 346.1 | 4-[(4E)-4-(hydroxyimino)-2-phenyl-4,5,6,7-tetrahydro-1H-indol-1-yl]benzamide; |
| 296 | 494.2 | 2-{[4-(benzyloxy)phenyl]amino}-4-(2,6,6-trimethyl-4-oxo-4,5,6,7-tetrahydro-1H-indol-1-yl)benzamide; |
| 297 | 396.2 | 2-[(tetrahydrofuran-2-ylmethyl)amino]-4-(2,6,6-trimethyl-4-oxo-4,5,6,7-tetrahydro-1H-indol-1-yl)benzamide; |
| 298 | 398.2 | 2-[(1,3-dioxolan-2-ylmethyl)amino]-4-(2,6,6-trimethyl-4-oxo-4,5,6,7-tetrahydro-1H-indol-1-yl)benzamide; |
| 299 | 384.2 | 2-[(2-methoxy-1-methylethyl)amino]-4-(2,6,6-trimethyl-4-oxo-4,5,6,7-tetrahydro-1H-indol-1-yl)benzamide; |
| 300 | 400.2 | 2-{[2-(2-hydroxyethoxy)ethyl]amino}-4-(2,6,6-trimethyl-4-oxo-4,5,6,7-tetrahydro-1H-indol-1-yl)benzamide; |
| 301 | 356.1 | 2-[(4-hydroxybutyl)amino]-4-(2-methyl-4-oxo-4,5,6,7-tetrahydro-1H-indol-1-yl)benzamide; |
| 302 | 411.2 | 4-(2-methyl-4-oxo-4,5,6,7-tetrahydro-1H-indol-1-yl)-2-[(3-morpholin-4-ylpropyl)amino]benzamide; |
| 303 | 403.2 | 2-[(pyridin-2-ylmethyl)amino]-4-(2,6,6-trimethyl-4-oxo-4,5,6,7-tetrahydro-1H-indol-1-yl)benzamide; |
| 304 | 503.2 | 2-{[2-(diethylamino)-4-ethoxyphenyl]amino}-4-(2,6,6-trimethyl-4-oxo-4,5,6,7-tetrahydro-1H-indol-1-yl)benzamide; |
| 305 | 454.1 | 2-{[4-(difluoromethoxy)phenyl]amino}-4-(2,6,6-trimethyl-4-oxo-4,5,6,7-tetrahydro-1H-indol-1-yl)benzamide; |
| 306 | 462.2 | 2-[(3,4-dimethoxybenzyl)amino]-4-(2,6,6-trimethyl-4-oxo-4,5,6,7-tetrahydro-1H-indol-1-yl)benzamide; |
| 307 | 370.2 | 2-[(3-hydroxypropyl)amino]-4-(2,6,6-trimethyl-4-oxo-4,5,6,7-tetrahydro-1H-indol-1-yl)benzamide; |
| 308 | 352.1 | 2-(allylamino)-4-(2,6,6-trimethyl-4-oxo-4,5,6,7-tetrahydro-1H-indol-1-yl)benzamide; |
| 309 | 493.2 | 4-[(4E)-4-(hydroxyimino)-2,6,6-trimethyl-4,5,6,7-tetrahydro-1H-indol-1-yl]-2-[(3,4,5-trimethoxyphenyl)amino]benzamide; |
| 310 | 384.2 | 2-[(3-methoxypropyl)amino]-4-(2,6,6-trimethyl-4-oxo-4,5,6,7-tetrahydro-1H-indol-1-yl)benzamide; |
| 311 | 389.1 | 2-(pyridin-4-ylamino)-4-(2,6,6-trimethyl-4-oxo-4,5,6,7-tetrahydro-1H-indol-1-yl)benzamide; |
| 312 | 420.2 | 2-{[3-(1H-imidazol-1-yl)propyl]amino}-4-(2,6,6-trimethyl-4-oxo-4,5,6,7-tetrahydro-1H-indol-1-yl)benzamide; |
| 313 | 406.2 | 2-{[2-(1H-imidazol-1-yl)ethyl]amino}-4-(2,6,6-trimethyl-4-oxo-4,5,6,7-tetrahydro-1H-indol-1-yl)benzamide; |
| 314 | 379.1 | 2-(isoxazol-3-ylamino)-4-(2,6,6-trimethyl-4-oxo-4,5,6,7-tetrahydro-1H-indol-1-yl)benzamide; |
| 315 | 403.2 | 2-[(pyridin-3-ylmethyl)amino]-4-(2,6,6-trimethyl-4-oxo-4,5,6,7-tetrahydro-1H-indol-1-yl)benzamide; |
| 316 | 340.1 | 4-(2,6,6-trimethyl-4-oxo-4,5,6,7-tetrahydro-1H-indol-1-yl)phthalamide; |
| 317 | 348 | 3-bromo-N'-hydroxy-4-(4-oxo-4,5,6,7-tetrahydro-1H-indol-1-yl)benzenecarboximidamide; |
| 318 | 342.1 | 4-(2,6,6-trimethyl-4-oxo-4,5,6,7-tetrahydro-1H-indol-1-yl)phthalic acid; |
| 319 | 467.3 | 2-[(10-aminodecyl)amino]-4-(2,6,6-trimethyl-4-oxo-4,5,6,7-tetrahydro-1H-indol-1-yl)benzamide; |
| 320 | 324.1 | 2-(allylamino)-4-(2-methyl-4-oxo-4,5,6,7-tetrahydro-1H-indol-1-yl)benzamide; |
| 321 | 386.1 | 2-(2,3-dihydro-1H-inden-1-ylamino)-4-(4-oxo-4,5,6,7-tetrahydro-1H-indol-1-yl)benzamide; |
| 322 | 338.1 | 2-cyclopropylamino)-4-(2,3-dimethyl-4-oxo-4,5,6,7-tetrahydro-1H-indol-1-yl)benzamide; |
| 323 | 342.1 | 2-[(2-methoxyethyl)amino]-4-(2-methyl-4-oxo-4,5,6,7-tetrahydro-1H-indol-1-yl)benzamide; |
| 324 | 324.1 | 3-[(cyclopropylmethyl)amino]-4-(4-oxo-4,5,6,7-tetrahydro-1H-indol-1-yl)benzamide; |
| 325 | 492.2 | 2-{[3-(3-hydroxypropoxy)-4-methoxyphenyl]amino}-4-(2,6,6-trimethyl-4-oxo-4,5,6,7-tetrahydro-1H-indol-1-yl)benzamide; |
| 326 | 324.1 | 2-(allylamino)-4-(3-methyl-4-oxo-4,5,6,7-tetrahydro-1H-indol-1-yl)benzamide; |
| 327 | 324.1 | 2-(cyclopropylamino)-4-(3-methyl-4-oxo-4,5,6,7-tetrahydro-1H-indol-1-yl)benzamide; |
| 328 | 342.1 | 2-[(2-methoxyethyl)amino]-4-(3-methyl-4-oxo-4,5,6,7-tetrahydro-1H-indol-1-yl)benzamide; |
| 329 | 269.1 | 4-(2-methyl-4-oxo-4,5,6,7-tetrahydro-1H-indol-1-yl)benzamide; |

| Compound No. | M + H | Name |
|---|---|---|
| 330 | 297.1 | 4-(3-ethyl-2-methyl-4-oxo-4,5,6,7-tetrahydro-1H-indol-1-yl)benzamide; |
| 331 | 269.1 | 4-(3-methyl-4-oxo-4,5,6,7-tetrahydro-1H-indol-1-yl)benzamide; |
| 332 | 487.2 | 2-[(2-{2-[2-(2-aminoethoxy)ethoxy]ethoxy}ethyl)amino]-4-(2,6,6-trimethyl-4-oxo-4,5,6,7-tetrahydro-1H-indol-1-yl)benzamide; |
| 333 | 382.2 | 2-[(trans-4-hydroxycyclohexyl)amino]-4-(2-methyl-4-oxo-4,5,6,7-tetrahydro-1H-indol-1-yl)benzamide; |
| 334 | 297.1 | 4-(3,6,6-trimethyl-4-oxo-4,5,6,7-tetrahydro-1H-indol-1-yl)benzamide; |
| 335 | 360.1 | 2-anilino-4-(3-methyl-4-oxo-4,5,6,7-tetrahydro-1H-indol-1-yl)benzamide; |
| 336 | 382.2 | 2-[(trans-4-hydroxycyclohexyl)amino]-4-(3-methyl-4-oxo-4,5,6,7-tetrahydro-1H-indol-1-yl)benzamide; |
| 337 | 396.2 | 4-(2,3-dimethyl-4-oxo-4,5,6,7-tetrahydro-1H-indol-1-yl)-2-[(trans-4-hydroxycyclohexyl)amino]benzamide; |
| 338 | 374.1 | 2-anilino-4-(2,3-dimethyl-4-oxo-4,5,6,7-tetrahydro-1H-indol-1-yl)benzamide; |
| 339 | 450.2 | 4-(3-methyl-4-oxo-4,5,6,7-tetrahydro-1H-indol-1-yl)-2-[(3,4,5-trimethoxyphenyl)amino]benzamide; |
| 340 | 383.2 | 2-{[2-(dimethylamino)ethyl]amino}-4-(3,6,6-trimethyl-4-oxo-4,5,6,7-tetrahydro-1H-indol-1-yl)benzamide; |
| 341 | 355.2 | 2-{[2-(dimethylamino)ethyl]amino}-4-(3-methyl-4-oxo-4,5,6,7-tetrahydro-1H-indol-1-yl)benzamide; |
| 342 | 395.2 | 2-(piperidin-4-ylamino)-4-(2,6,6-trimethyl-4-oxo-4,5,6,7-tetrahydro-1H-indol-1-yl)benzamide; |
| 343 | 298.1 | 4-(3,6,6-trimethyl-4-oxo-4,5,6,7-tetrahydro-1H-indazol-1-yl)benzamide; |
| 344 | 333 | 2-bromo-5-(4-oxo-4,5,6,7-tetrahydro-1H-indol-1-yl)benzamide; |
| 345 | 410.2 | 2-[(trans-4-hydroxycyclohexyl)amino]-4-(3,6,6-trimethyl-4-oxo-4,5,6,7-tetrahydro-1H-indol-1-yl)benzamide; |
| 346 | 409.2 | 2-[(1-methylpiperidin-4-yl)amino]-4-(2,6,6-trimethyl-4-oxo-4,5,6,7-tetrahydro-1H-indol-1-yl)benzamide; |
| 347 | 453.2 | (4-{[2-(aminocarbonyl)-5-(2,6,6-trimethyl-4-oxo-4,5,6,7-tetrahydro-1H-indol-1-yl)phenyl]amino}piperidin-1-yl)acetic acid; |
| 348 | 370.2 | 2-[(2-methoxyethyl)amino]-4-(3,6,6-trimethyl-4-oxo-4,5,6,7-tetrahydro-1H-indol-1-yl)benzamide; |
| 349 | 403.2 | 2-[(pyridin-4-ylmethyl)amino]-4-(3,6,6-trimethyl-4-oxo-4,5,6,7-tetrahydro-1H-indol-1-yl)benzamide; |
| 350 | 396.2 | 2-(tetrahydro-2H-pyran-4-ylamino)-4-(3,6,6-trimethyl-4-oxo-4,5,6,7-tetrahydro-1H-indol-1-yl)benzamide; |
| 351 | 478.2 | 2-[(3,4,5-trimethoxyphenyl)amino]-4-(3,6,6-trimethyl-4-oxo-4,5,6,7-tetrahydro-1H-indol-1-yl)benzamide; |
| 352 | 340.1 | 4-(3-isobutyl-6,6-dimethyl-4-oxo-4,5,6,7-tetrahydro-1H-indazol-1-yl)benzamide; |
| 353 | 312.1 | 2-amino-4-(3,6,6-trimethyl-4-oxo-4,5,6,7-tetrahydro-1H-indol-1-yl)benzamide; |
| 354 | 352.1 | 2-(allylamino)-4-(3,6,6-trimethyl-4-oxo-4,5,6,7-tetrahydro-1H-indol-1-yl)benzamide; |
| 355 | 409.2 | 2-[(1-methylpiperidin-4-yl)amino]-4-(3,6,6-trimethyl-4-oxo-4,5,6,7-tetrahydro-1H-indol-1-yl)benzamide; |
| 356 | 395.2 | 2-(piperidin-4-ylamino)-4-(3,6,6-trimethyl-4-oxo-4,5,6,7-tetrahydro-1H-indol-1-yl)benzamide; |
| 357 | 369.2 | 3-butoxy-4-(3,6,6-trimethyl-4-oxo-4,5,6,7-tetrahydro-1H-indol-1-yl)benzamide; |
| 358 | 428.2 | 2-(2,3-dihydro-1H-inden-1-ylamino)-4-(3,6,6-trimethyl-4-oxo-4,5,6,7-tetrahydro-1H-indol-1-yl)benzamide; |
| 359 | 408.2 | 2-[(4-oxocyclohexyl)amino]-4-(3,6,6-trimethyl-4-oxo-4,5,6,7-tetrahydro-1H-indol-1-yl)benzamide; |
| 360 | 355.1 | 2-[(aminocarbonyl)amino]-4-(3,6,6-trimethyl-4-oxo-4,5,6,7-tetrahydro-1H-indol-1-yl)benzamide; |
| 361 | 397.2 | 2-(tetrahydro-2H-pyran-4-ylamino)-4-(3,6,6-trimethyl-4-oxo-4,5,6,7-tetrahydro-1H-indazol-1-yl)benzamide; |
| 362 | 376 | 2-bromo-4-(3,6,6-trimethyl-4-oxo-4,5,6,7-tetrahydro-1H-indazol-1-yl)benzamide; |
| 363 | 440.2 | 2-[(3-morpholin-4-ylpropyl)amino]-4-(3,6,6-trimethyl-4-oxo-4,5,6,7-tetrahydro-1H-indazol-1-yl)benzamide; |
| 364 | 397.2 | 2-[(tetrahydrofuran-2-ylmethyl)amino]-4-(3,6,6-trimethyl-4-oxo-4,5,6,7-tetrahydro-1H-indazol-1-yl)benzamide; |
| 365 | 523.3 | 2-{[trans-4-(2-morpholin-4-ylethoxy)cyclohexyl]amino}-4-(3,6,6-trimethyl-4-oxo-4,5,6,7-tetrahydro-1H-indol-1-yl)benzamide; |
| 366 | 435.2 | 2-[(8-methyl-8-azabicyclo[3.2.1]oct-3-yl)amino]-4-(3,6,6-trimethyl-4-oxo-4,5,6,7-tetrahydro-1H-indol-1-yl)benzamide; |
| 367 | 312.1 | 4-(3-ethyl-6,6-dimethyl-4-oxo-4,5,6,7-tetrahydro-1H-indazol-1-yl)benzamide; |
| 368 | 394.2 | 2-cyclohexylamino)-4-(3,6,6-trimethyl-4-oxo-4,5,6,7-tetrahydro-1H-indol-1-yl)benzamide; |
| 369 | 410.2 | 2-[(1-methylpiperidin-4-yl)amino]-4-(3,6,6-trimethyl-4-oxo-4,5,6,7-tetrahydro-1H-indazol-1-yl)benzamide; |
| 370 | 353.1 | 2-(cyclopropylamino)-4-(3,6,6-trimethyl-4-oxo-4,5,6,7-tetrahydro-1H-indazol-1-yl)benzamide; |
| 371 | 352.1 | 2-(cyclopropylamino)-4-(3,6,6-trimethyl-4-oxo-4,5,6,7-tetrahydro-1H-indol-1-yl)benzamide; |
| 372 | 366.2 | 2-[(cyclopropylmethyl)amino]-4-(3,6,6-trimethyl-4-oxo-4,5,6,7-tetrahydro-1H-indol-1-yl)benzamide; |
| 373 | 448.2 | 2-[(3,4-dimethoxyphenyl)amino]-4-(3,6,6-trimethyl-4-oxo-4,5,6,7-tetrahydro-1H-indol-1-yl)benzamide; |
| 374 | 449.2 | 2-[(3,4-dimethoxyphenyl)amino]-4-(3,6,6-trimethyl-4-oxo-4,5,6,7-tetrahydro-1H-indazol-1-yl)benzamide; |
| 375 | 479.2 | 2-[(3,4,5-trimethoxyphenyl)amino]-4-(3,6,6-trimethyl-4-oxo-4,5,6,7-tetrahydro-1H-indazol-1-yl)benzamide; |
| 376 | 519.2 | 2-({3-[3-(dimethylamino)propoxy]-4-methoxyphenyl}amino)-4-(3,6,6-trimethyl-4-oxo-4,5,6,7-tetrahydro-1H-indol-1-yl)benzamide; |
| 377 | 411.2 | 2-[(trans-4-hydroxycyclohexyl)amino]-4-(3,6,6-trimethyl-4-oxo-4,5,6,7-tetrahydro-1H-indazol-1-yl)benzamide; |
| 378 | 409.2 | 2-[(4-oxocyclohexyl)amino]-4-(3,6,6-trimethyl-4-oxo-4,5,6,7-tetrahydro-1H-indazol-1-yl)benzamide; |
| 379 | 412.1 | 2-{[2-(aminocarbonyl)-5-(3,6,6-trimethyl-4-oxo-4,5,6,7-tetrahydro-1H-indol-1-yl)phenyl]amino}-2-oxoethyl acetate; |
| 380 | 385.2 | 2-[(3-methoxypropyl)amino]-4-(3,6,6-trimethyl-4-oxo-4,5,6,7-tetrahydro-1H-indazol-1-yl)benzamide; |
| 381 | 421.2 | 2-{[3-(1H-imidazol-1-yl)propyl]amino}-4-(3,6,6-trimethyl-4-oxo-4,5,6,7-tetrahydro-1H-indazol-1-yl)benzamide; |
| 382 | 467.2 | Trans-4-{[2-(aminocarbonyl)-5-(3,6,6-trimethyl-4-oxo-4,5,6,7-tetrahydro-1H-indol-1-yl)phenyl]amino}cyclohexyl glycinate; |
| 383 | 355.2 | 2-[(2-aminoethyl)amino]-4-(3,6,6-trimethyl-4-oxo-4,5,6,7-tetrahydro-1H-indol-1-yl)benzamide; |
| 384 | 452.2 | Trans-4-{[2-(aminocarbonyl)-5-(3,6,6-trimethyl-4-oxo-4,5,6,7-tetrahydro-1H-indol-1-yl)phenyl]amino}cyclohexyl acetate; |
| 385 | 383.2 | 4-(3-ethyl-4-oxo-4,5,6,7-tetrahydro-1H-indazol-1-yl)-2-[(tetrahydrofuran-2-ylmethyl)amino]benzamide; |

| Compound No. | M + H | Name |
|---|---|---|
| 386 | 413.2 | 2-[(1,4-dioxan-2-ylmethyl)amino]-4-(3,6,6-trimethyl-4-oxo-4,5,6,7-tetrahydro-1H-indazol-1-yl)benzamide; |
| 387 | 393.1 | 2-[(2-furylmethyl)amino]-4-(3,6,6-trimethyl-4-oxo-4,5,6,7-tetrahydro-1H-indazol-1-yl)benzamide; |
| 388 | 392.1 | 2-[(2-furylmethyl)amino]-4-(3,6,6-trimethyl-4-oxo-4,5,6,7-tetrahydro-1H-indol-1-yl)benzamide; |
| 389 | 425.2 | 2-[(2-piperazin-1-ylethyl)amino]-4-(3,6,6-trimethyl-4-oxo-4,5,6,7-tetrahydro-1H-indazol-1-yl)benzamide; |
| 390 | 424.2 | 2-[(2-piperazin-1-ylethyl)amino]-4-(3,6,6-trimethyl-4-oxo-4,5,6,7-tetrahydro-1H-indol-1-yl)benzamide; |
| 391 | 506.2 | 2-({3-[2-(dimethylamino)ethoxy]-4-methoxyphenyl}amino)-4-(3,6,6-trimethyl-4-oxo-4,5,6,7-tetrahydro-1H-indazol-1-yl)benzamide; |
| 392 | 352.1 | 4-[6,6-dimethyl-4-oxo-3-(trifluoromethyl)-4,5,6,7-tetrahydro-1H-indazol-1-yl]benzamide; |
| 393 | 353.1 | 2-(allylamino)-4-(3,6,6-trimethyl-4-oxo-4,5,6,7-tetrahydro-1H-indazol-1-yl)benzamide; |
| 394 | 468.2 | Trans-4-{[2-(aminocarbonyl)-5-(3,6,6-trimethyl-4-oxo-4,5,6,7-tetrahydro-1H-indazol-1-yl)phenyl]amino}cyclohexyl glycinate; |
| 395 | 411.2 | 2-[(cis-4-hydroxycyclohexyl)amino]-4-(3,6,6-trimethyl-4-oxo-4,5,6,7-tetrahydro-1H-indazol-1-yl)benzamide; |
| 396 | 324 | 4-[4-oxo-3-(trifluoromethyl)-4,5,6,7-tetrahydro-1H-indazol-1-yl]benzamide; |
| 397 | 398.2 | 4-(3-ethyl-4-oxo-4,5,6,7-tetrahydro-1H-indazol-1-yl)-N'-hydroxy-2-[(tetrahydrofuran-2-ylmethyl)amino]benzenecarboximidamide; |
| 398 | 424.2 | 2-{[2-(1-methylpyrrolidin-2-yl)ethyl]amino}-4-(3,6,6-trimethyl-4-oxo-4,5,6,7-tetrahydro-1H-indazol-1-yl)benzamide; |
| 399 | 423.2 | 2-{[2-(1-methylpyrrolidin-2-yl)ethyl]amino}-4-(3,6,6-trimethyl-4-oxo-4,5,6,7-tetrahydro-1H-indol-1-yl)benzamide; |
| 400 | 384.2 | 2-{[2-(dimethylamino)ethyl]amino}-4-(3,6,6-trimethyl-4-oxo-4,5,6,7-tetrahydro-1H-indazol-1-yl)benzamide; |
| 401 | 495.2 | Trans-4-{[2-(aminocarbonyl)-5-(3,6,6-trimethyl-4-oxo-4,5,6,7-tetrahydro-1H-indol-1-yl)phenyl]amino}cyclohexyl N,N-dimethylglycinate; |
| 402 | 332.1 | 3-chloro-4-(3,6,6-trimethyl-4-oxo-4,5,6,7-tetrahydro-1H-indazol-1-yl)benzamide; |
| 403 | 299.1 | 4-(3,6,6-trimethyl-4-oxo-4,5,6,7-tetrahydro-1H-indazol-1-yl)benzoic acid; |
| 404 | 390.1 | 2-(pyridin-3-ylamino)-4-(3,6,6-trimethyl-4-oxo-4,5,6,7-tetrahydro-1H-indazol-1-yl)benzamide; |
| 405 | 407.1 | 2-(pyridin-4-ylthio)-4-(3,6,6-trimethyl-4-oxo-4,5,6,7-tetrahydro-1H-indazol-1-yl)benzamide; |
| 406 | 452.2 | 2-[(1-glycylpiperidin-4-yl)amino]-4-(3,6,6-trimethyl-4-oxo-4,5,6,7-tetrahydro-1H-indol-1-yl)benzamide; |
| 407 | 314.1 | N-hydroxy-4-(3,6,6-trimethyl-4-oxo-4,5,6,7-tetrahydro-1H-indazol-1-yl)benzamide; |
| 408 | 356.1 | N-(2-methoxyethyl)-4-(3,6,6-trimethyl-4-oxo-4,5,6,7-tetrahydro-1H-indazol-1-yl)benzamide; |
| 409 | 416.2 | 2-{[(1R)-1-phenylethyl]amino}-4-(3,6,6-trimethyl-4-oxo-4,5,6,7-tetrahydro-1H-indol-1-yl)benzamide; |
| 410 | 423.2 | 2-[(1-ethylpiperidin-3-yl)amino]-4-(3,6,6-trimethyl-4-oxo-4,5,6,7-tetrahydro-1H-indazol-1-yl)benzamide; |
| 411 | 416.2 | 2-{[(1S)-1-phenylethyl]amino}-4-(3,6,6-trimethyl-4-oxo-4,5,6,7-tetrahydro-1H-indol-1-yl)benzamide; |
| 412 | 417.2 | 2-{[(1S)-1-phenylethyl]amino}-4-(3,6,6-trimethyl-4-oxo-4,5,6,7-tetrahydro-1H-indazol-1-yl)benzamide; |
| 413 | 424.2 | 2-[(trans-4-methoxycyclohexyl)amino]-4-(3,6,6-trimethyl-4-oxo-4,5,6,7-tetrahydro-1H-indol-1-yl)benzamide; |
| 414 | 438.2 | 2-{[3-(2-oxopyrrolidin-1-yl)propyl]amino}-4-(3,6,6-trimethyl-4-oxo-4,5,6,7-tetrahydro-1H-indazol-1-yl)benzamide; |
| 415 | 574.2 | 2-({3-[3-(dimethylamino)propoxy]-4-methoxyphenyl}amino)-4-[6,6-dimethyl-4-oxo-3-(trifluoromethyl)-4,5,6,7-tetrahydro-1H-indazol-1-yl]benzamide; |
| 416 | 447.1 | 2-(2,1,3-benzothiadiazol-4-ylamino)-4-(3,6,6-trimethyl-4-oxo-4,5,6,7-tetrahydro-1H-indazol-1-yl)benzamide; |
| 417 | 423.1 | 2-[(3-chlorophenyl)amino]-4-(3,6,6-trimethyl-4-oxo-4,5,6,7-tetrahydro-1H-indazol-1-yl)benzamide; |
| 418 | 419.2 | 2-[(3-methoxyphenyl)amino]-4-(3,6,6-trimethyl-4-oxo-4,5,6,7-tetrahydro-1H-indazol-1-yl)benzamide; |
| 419 | 477.2 | 2-({2-[2-(dimethylamino)ethoxy]pyridin-4-yl}amino)-4-(3,6,6-trimethyl-4-oxo-4,5,6,7-tetrahydro-1H-indazol-1-yl)benzamide; |
| 420 | 465.2 | 4-[6,6-dimethyl-4-oxo-3-(trifluoromethyl)-4,5,6,7-tetrahydro-1H-indazol-1-yl]-2-[(trans-4-hydroxycyclohexyl)amino]benzamide; |
| 421 | 451.1 | 4-[6,6-dimethyl-4-oxo-3-(trifluoromethyl)-4,5,6,7-tetrahydro-1H-indazol-1-yl]-2-(tetrahydro-2H-pyran-4-ylamino)benzamide; |
| 422 | 445.2 | 2-{[(1S,2R)-2-hydroxy-2,3-dihydro-1H-inden-1-yl]amino}-4-(3,6,6-trimethyl-4-oxo-4,5,6,7-tetrahydro-1H-indazol-1-yl)benzamide; |
| 423 | 445.2 | 2-{[(1R,2S)-2-hydroxy-2,3-dihydro-1H-inden-1-yl]amino}-4-(3,6,6-trimethyl-4-oxo-4,5,6,7-tetrahydro-1H-indazol-1-yl)benzamide; |
| 424 | 433.1 | 3-{[2-(aminocarbonyl)-5-(3,6,6-trimethyl-4-oxo-4,5,6,7-tetrahydro-1H-indazol-1-yl)phenyl]amino}benzoic acid; |
| 425 | 496.2 | Trans-4-{2-(aminocarbonyl)-5-(3,6,6-trimethyl-4-oxo-4,5,6,7-tetrahydro-1H-indazol-1-yl)phenyl]amino}cyclohexyl N,N-dimethylglycinate; |
| 426 | 430.1 | 2-[(1-oxidotetrahydro-2H-thiopyran-4-yl)oxy]-4-(3,6,6-trimethyl-4-oxo-4,5,6,7-tetrahydro-1H-indazol-1-yl)benzamide; |
| 427 | 446.1 | 2-[(1,1-dioxidotetrahydro-2H-thiopyran-4-yl)oxy]-4-(3,6,6-trimethyl-4-oxo-4,5,6,7-tetrahydro-1H-indazol-1-yl)benzamide; |
| 428 | 382.2 | 4-(3-methyl-4-oxo-5,6,7,8-tetrahydrocyclohepta[b]pyrrol-1(4H)-yl)-2-(tetrahydro-2H-pyran-4-ylamino)benzamide; |
| 429 | 387.1 | 2-{[2-(methylthio)ethyl]amino}-4-(3,6,6-trimethyl-4-oxo-4,5,6,7-tetrahydro-1H-indazol-1-yl)benzamide; |
| 430 | 560.2 | 2-({3-[2-(dimethylamino)ethoxy]-4-methoxyphenyl}amino)-4-[6,6-dimethyl-4-oxo-3-(trifluoromethyl)-4,5,6,7-tetrahydro-1H-indazol-1-yl]benzamide; |
| 431 | 531.2 | 2-({2-[2-(dimethylamino)ethoxy]pyridin-4-yl}amino)-4-[6,6-dimethyl-4-oxo-3-(trifluoromethyl)-4,5,6,7-tetrahydro-1H-indazol-1-yl]benzamide; |
| 432 | 511.2 | Trans-4-{[2-(aminocarbonyl)-5-(3,6,6-trimethyl-4-oxo-4,5,6,7-tetrahydro-1H-indazol-1-yl)phenyl]amino}cyclohexyl(acetyloxy)acetate; |
| 433 | 413.1 | 2-(tetrahydro-2H-thiopyran-4-ylamino)-4-(3,6,6-trimethyl-4-oxo-4,5,6,7-tetrahydro-1H-indazol-1-yl)benzamide; |
| 434 | 429.1 | 2-[(1-oxidotetrahydro-2H-thiopyran-4-yl)amino]-4-(3,6,6-trimethyl-4-oxo-4,5,6,7-tetrahydro-1H-indazol-1-yl)benzamide; |
| 435 | 445.2 | 2-[(1,1-dioxidotetrahydro-2H-thiopyran-4-yl)amino]-4-(3,6,6-trimethyl-4-oxo-4,5,6,7-tetrahydro-1H-indazol-1-yl)benzamide; |
| 436 | 432.2 | 2-{[3-(aminocarbonyl)phenyl]amino}-4-(3,6,6-trimethyl-4-oxo-4,5,6,7-tetrahydro-1H-indazol-1-yl)benzamide; |
| 437 | 379.2 | 2-(cyclopent-3-en-1-ylamino)-4-(3,6,6-trimethyl-4-oxo-4,5,6,7-tetrahydro-1H-indazol-1-yl)benzamide; |

| Compound No. | M + H | Name |
|---|---|---|
| 438 | 395.1 | 2-[(2,2,2-trifluoroethyl)amino]-4-(3,6,6-trimethyl-4-oxo-4,5,6,7-tetrahydro-1H-indazol-1-yl)benzamide; |
| 439 | 413.2 | 2-{[(3R,4S)-3,4-dihydroxycyclopentyl]amino}-4-(3,6,6-trimethyl-4-oxo-4,5,6,7-tetrahydro-1H-indazol-1-yl)benzamide; |
| 440 | 420.2 | 2-[(6-methoxypyridin-3-yl)amino]-4-(3,6,6-trimethyl-4-oxo-4,5,6,7-tetrahydro-1H-indazol-1-yl)benzamide; |
| 441 | 420.2 | 2-[(1-methyl-6-oxo-1,6-dihydropyridin-3-yl)amino]-4-(3,6,6-trimethyl-4-oxo-4,5,6,7-tetrahydro-1H-indazol-1-yl)benzamide; |
| 442 | 483.2 | Trans-4-{[2-(aminocarbonyl)-5-(3,6,6-trimethyl-4-oxo-4,5,6,7-tetrahydro-1H-indazol-1-yl)phenyl]amino}cyclohexyl methoxyacetate; |
| 443 | 491.2 | 2-({1-[3-(dimethylamino)propyl]-6-oxo-1,6-dihydropyridin-3-yl}amino)-4-(3,6,6-trimethyl-4-oxo-4,5,6,7-tetrahydro-1H-indazol-1-yl)benzamide; |
| 444 | 424.2 | 2-{[2-(2-oxopyrrolidin-1-yl)ethyl]amino}-4-(3,6,6-trimethyl-4-oxo-4,5,6,7-tetrahydro-1H-indazol-1-yl)benzamide; |
| 445 | 473.1 | 2-{[3-(trifluoromethoxy)phenyl]amino}-4-(3,6,6-trimethyl-4-oxo-4,5,6,7-tetrahydro-1H-indazol-1-yl)benzamide; |
| 446 | 433.2 | 4-[3-(difluoromethyl)-6,6-dimethyl-4-oxo-4,5,6,7-tetrahydro-1H-indazol-1-yl]-2-(tetrahydro-2H-pyran-4-ylamino)benzamide; |
| 447 | 447.2 | 4-[3-(difluoromethyl)-6,6-dimethyl-4-oxo-4,5,6,7-tetrahydro-1H-indazol-1-yl]-2-[(trans-4-hydroxycyclohexyl)amino]benzamide; |
| 448 | 467.1 | 4-[6,6-dimethyl-4-oxo-3-(trifluoromethyl)-4,5,6,7-tetrahydro-1H-indazol-1-yl]-2-(tetrahydro-2H-thiopyran-4-ylamino)benzamide; |
| 449 | 449.1 | 4-[3-(difluoromethyl)-6,6-dimethyl-4-oxo-4,5,6,7-tetrahydro-1H-indazol-1-yl]-2-(tetrahydro-2H-thiopyran-4-ylamino)benzamide; |
| 450 | 385.2 | 2-[(2-methoxy-1-methylethyl)amino]-4-(3,6,6-trimethyl-4-oxo-4,5,6,7-tetrahydro-1H-indazol-1-yl)benzamide; |
| 451 | 460.2 | N-(2-aminophenyl)-3-butoxy-4-(2,6,6-trimethyl-4-oxo-4,5,6,7-tetrahydro-1H-indol-1-yl)benzamide; |
| 452 | 410.2 | 2-{[(3S)-6-oxopiperidin-3-yl]amino}-4-(3,6,6-trimethyl-4-oxo-4,5,6,7-tetrahydro-1H-indazol-1-yl)benzamide; |
| 453 | 482.2 | Trans-4-{[2-(aminocarbonyl)-5-(3,6,6-trimethyl-4-oxo-4,5,6,7-tetrahydro-1H-indazol-1-yl)phenyl]amino}cyclohexyl L-alaninate; |
| 454 | 482.2 | Trans-4-{[2-(aminocarbonyl)-5-(3,6,6-trimethyl-4-oxo-4,5,6,7-tetrahydro-1H-indazol-1-yl)phenyl]amino}cyclohexyl D-alaninate; |
| 455 | 481.2 | Trans-4-{[2-(aminocarbonyl)-5-(3,6,6-trimethyl-4-oxo-4,5,6,7-tetrahydro-1H-indol-1-yl)phenyl]amino}cyclohexyl L-alaninate; |
| 456 | 481.2 | Trans-4-{[2-(aminocarbonyl)-5-(3,6,6-trimethyl-4-oxo-4,5,6,7-tetrahydro-1H-indol-1-yl)phenyl]amino}cyclohexyl D-alaninate; |
| 457 | 427.1 | 1-[4-(aminocarbonyl)-3-(tetrahydro-2H-pyran-4-ylamino)phenyl]-6,6-dimethyl-4-oxo-4,5,6,7-tetrahydro-1H-indazole-3-carboxylic acid; |
| 458 | 475.1 | 5-bromo-2-[(tetrahydrofuran-2-ylmethyl)amino]-4-(3,6,6-trimethyl-4-oxo-4,5,6,7-tetrahydro-1H-indazol-1-yl)benzamide; |
| 459 | 411.2 | 2-[(3-hydroxycyclohexyl)amino]-4-(3,6,6-trimethyl-4-oxo-4,5,6,7-tetrahydro-1H-indazol-1-yl)benzamide; |
| 460 | 439.2 | 4-{[2-(aminocarbonyl)-5-(3,6,6-trimethyl-4-oxo-4,5,6,7-tetrahydro-1H-indazol-1-yl)phenyl]amino}cyclohexanecarboxylic acid; |
| 461 | 522.2 | Trans-4-({2-(aminocarbonyl)-5-[6,6-dimethyl-4-oxo-3-(trifluoromethyl)-4,5,6,7-tetrahydro-1H-indazol-1-yl]phenyl}amino)cyclohexyl glycinate; |
| 462 | 509.3 | Trans-4-{[2-(aminocarbonyl)-5-(3,6,6-trimethyl-4-oxo-4,5,6,7-tetrahydro-1H-indol-1-yl)phenyl]amino}cyclohexyl L-valinate; |
| 463 | 429.2 | 2-[(2,6-dihydroxytetrahydro-2H-pyran-4-yl)amino]-4-(3,6,6-trimethyl-4-oxo-4,5,6,7-tetrahydro-1H-indazol-1-yl)benzamide; |
| 464 | 433.1 | 2-(cyclopent-3-en-1-ylamino)-4-[6,6-dimethyl-4-oxo-3-(trifluoromethyl)-4,5,6,7-tetrahydro-1H-indazol-1-yl]benzamide; |
| 465 | 445.2 | 4-[3-(difluoromethyl)-6,6-dimethyl-4-oxo-4,5,6,7-tetrahydro-1H-indazol-1-yl]-2-[(4-oxocyclohexyl)amino]benzamide; |
| 466 | 463.1 | 4-[6,6-dimethyl-4-oxo-3-(trifluoromethyl)-4,5,6,7-tetrahydro-1H-indazol-1-yl]-2-[(4-oxocyclohexyl)amino]benzamide; |
| 467 | 483.1 | 4-[6,6-dimethyl-4-oxo-3-(trifluoromethyl)-4,5,6,7-tetrahydro-1H-indazol-1-yl]-2-[(1-oxidotetrahydro-2H-thiopyran-4-yl)amino]benzamide; |
| 468 | 465.1 | 4-[3-(difluoromethyl)-6,6-dimethyl-4-oxo-4,5,6,7-tetrahydro-1H-indazol-1-yl]-2-[(1-oxidotetrahydro-2H-thiopyran-4-yl)amino]benzamide; |
| 469 | 393.2 | 2-(cyclohex-3-en-1-ylamino)-4-(3,6,6-trimethyl-4-oxo-4,5,6,7-tetrahydro-1H-indazol-1-yl)benzamide; |
| 470 | 427.2 | 2-{[(3S,4R)-3,4-dihydroxycyclohexyl]amino}-4-(3,6,6-trimethyl-4-oxo-4,5,6,7-tetrahydro-1H-indazol-1-yl)benzamide; |
| 471 | 473.1 | 2-{[4-(trifluoromethoxy)phenyl]amino}-4-(3,6,6-trimethyl-4-oxo-4,5,6,7-tetrahydro-1H-indazol-1-yl)benzamide; |
| 472 | 504.2 | trans-4-({2-(aminocarbonyl)-5-[3-(difluoromethyl)-6,6-dimethyl-4-oxo-4,5,6,7-tetrahydro-1H-indazol-1-yl]phenyl}amino)cyclohexyl glycinate; |
| 473 | 467.1 | 4-[6,6-dimethyl-4-oxo-3-(trifluoromethyl)-4,5,6,7-tetrahydro-1H-indazol-1-yl]-2-[(3-ethynylphenyl)amino]benzamide; |
| 474 | 383.2 | 4-(6,6-dimethyl-4-oxo-4,5,6,7-tetrahydro-1H-indazol-1-yl)-2-(tetrahydro-2H-pyran-4-ylamino)benzamide; |
| 475 | 492.2 | 4-[6,6-dimethyl-4-oxo-3-(trifluoromethyl)-4,5,6,7-tetrahydro-1H-indazol-1-yl]-2-{[3-(2-oxopyrrolidin-1-yl)propyl]amino}benzamide; |
| 476 | 365.1 | 4-(trifluoromethyl)-3-(2,6,6-trimethyl-4-oxo-4,5,6,7-tetrahydro-1H-indol-1-yl)benzamide; |
| 477 | 465.2 | 4-[6,6-dimethyl-4-oxo-3-(trifluoromethyl)-4,5,6,7-tetrahydro-1H-indazol-1-yl]-2-[(cis-4-hydroxycyclohexyl)amino]benzamide; |
| 478 | 435.1 | 2-{[3-(methylthio)phenyl]amino}-4-(3,6,6-trimethyl-4-oxo-4,5,6,7-tetrahydro-1H-indazol-1-yl)benzamide; |
| 479 | 366.1 | 4-(trifluoromethyl)-3-(3,6,6-trimethyl-4-oxo-4,5,6,7-tetrahydro-1H-indazol-1-yl)benzamide; |
| 480 | 338.1 | 3-(3-methyl-4-oxo-4,5,6,7-tetrahydro-1H-indazol-1-yl)-4-(trifluoromethyl)benzamide; |
| 481 | 465.2 | 2-[6,6-dimethyl-4-oxo-3-(trifluoromethyl)-4,5,6,7-tetrahydro-1H-indazol-1-yl]-4-[(trans-4-hydroxycyclohexyl)amino]benzamide; |
| 482 | 450.2 | 4-[6,6-dimethyl-4-oxo-3-(trifluoromethyl)-4,5,6,7-tetrahydro-1H-indazol-1-yl]-2-(piperidin-4-ylamino)benzamide; |
| 483 | 492.2 | 2-[(1-acetylpiperidin-4-yl)amino]-4-[6,6-dimethyl-4-oxo-3-(trifluoromethyl)-4,5,6,7-tetrahydro-1H-indazol-1-yl]benzamide; |
| 484 | 540.2 | 2-[(1-benzylpiperidin-4-yl)amino]-4-[6,6-dimethyl-4-oxo-3-(trifluoromethyl)-4,5,6,7-tetrahydro-1H-indazol-1-yl]benzamide; |
| 485 | 521.2 | 4-({2-(aminocarbonyl)-5-[6,6-dimethyl-4-oxo-3-(trifluoromethyl)-4,5,6,7-tetrahydro-1H-indazol-1-yl]phenyl}amino)-N,N-dimethylpiperidine-1-carboxamide; |
| 486 | 445 | 2-bromo-4-[6,6-dimethyl-4-oxo-3-(trifluoromethyl)-4,5,6,7-tetrahydro-1H-indazol-1-yl]-N'-hydroxybenzenecarboximidamide; |
| 487 | 526.2 | 2-[(1-benzylpyrrolidin-3-yl)amino]-4-[6,6-dimethyl-4-oxo-3-(trifluoromethyl)-4,5,6,7-tetrahydro-1H-indazol-1-yl]benzamide; |

| Compound No. | M + H | Name |
|---|---|---|
| 488 | 526.2 | 4-[6,6-dimethyl-4-oxo-3-(trifluoromethyl)-4,5,6,7-tetrahydro-1H-indazol-1-yl]-2-[(1-phenylpiperidin-4-yl)amino]benzamide; |
| 489 | 524.2 | ({[(4E)-1-[4-(aminocarbonyl)-3-(tetrahydro-2H-pyran-4-ylamino)phenyl]-6,6-dimethyl-3-(trifluoromethyl)-1,5,6,7-tetrahydro-4H-indazol-4-ylidene]amino}oxy)acetic acid; |
| 490 | 471.1 | 4-[6,6-dimethyl-4-oxo-3-(trifluoromethyl)-4,5,6,7-tetrahydro-1H-indazol-1-yl]-2-{[2-hydroxy-1,1-bis(hydroxymethyl)ethyl]amino}benzamide; |
| 491 | 437.1 | 4-[6,6-dimethyl-4-oxo-3-(trifluoromethyl)-4,5,6,7-tetrahydro-1H-indazol-1-yl]-2-[(3R)-tetrahydrofuran-3-ylamino]benzamide; |
| 492 | 536.2 | trans-4-({2-(aminocarbonyl)-5-[6,6-dimethyl-4-oxo-3-(trifluoromethyl)-4,5,6,7-tetrahydro-1H-indazol-1-yl]phenyl}amino)cyclohexyl L-alaninate; methanesulfonate |
| 493 | 564.2 | trans-4-({2-(aminocarbonyl)-5-[6,6-dimethyl-4-oxo-3-(trifluoromethyl)-4,5,6,7-tetrahydro-1H-indazol-1-yl]phenyl}amino)cyclohexyl L-valinate methanesulfonate; |
| 494 | 505.2 | 2-[allyl(trans-4-hydroxycyclohexyl)amino]-4-[6,6-dimethyl-4-oxo-3-(trifluoromethyl)-4,5,6,7-tetrahydro-1H-indazol-1-yl]benzamide; |
| 495 | 536.2 | 2-Amino-propionic acid trans-4-[2-carbamoyl-5-(6,6-dimethyl-4-oxo-3-trifluoromethyl-4,5,6,7-tetrahydro-indazol-1-yl)-phenylamino]-cyclohexyl ester; |
| 496 | 513.2 | 4-[6,6-dimethyl-4-oxo-3-(trifluoromethyl)-4,5,6,7-tetrahydro-1H-indazol-1-yl]-2-(4-pyridin-2-ylpiperazin-1-yl)benzamide; |
| 497 | 539.2 | 2-[(2,3-dihydroxypropyl)(trans-4-hydroxycyclohexyl)amino]-4-[6,6-dimethyl-4-oxo-3-(trifluoromethyl)-4,5,6,7-tetrahydro-1H-indazol-1-yl]benzamide; |
| 498 | 507.2 | 4-[6,6-dimethyl-4-oxo-3-(trifluoromethyl)-4,5,6,7-tetrahydro-1H-indazol-1-yl]-2-[(trans-4-hydroxycyclohexyl)(2-oxoethyl)amino]benzamide; |
| 499 | 441.1 | 2-[(2,3-dihydroxypropyl)amino]-4-[6,6-dimethyl-4-oxo-3-(trifluoromethyl)-4,5,6,7-tetrahydro-1H-indazol-1-yl]benzamide; |
| 500 | 442.1 | 2-[(2,3-dihydroxypropyl)amino]-4-[6,6-dimethyl-4-oxo-3-(trifluoromethyl)-4,5,6,7-tetrahydro-1H-indazol-1-yl]benzoic acid; |
| 501 | 597.2 | 2-(acetoxymethyl)-2-(2-carbamoyl-5-(6,6-dimethyl-4-oxo-3-(trifluoromethyl)-4,5,6,7-tetrahydro-1H-indazol-1-yl)phenylamino)propane-1,3-diyl diacetate; |
| 502 | 555.2 | 2-({2-(aminocarbonyl)-5-[6,6-dimethyl-4-oxo-3-(trifluoromethyl)-4,5,6,7-tetrahydro-1H-indazol-1-yl]phenyl}amino)-2-(hydroxymethyl)propane-1,3-diyl diacetate; |
| 503 | 513.1 | 2-({2-(aminocarbonyl)-5-[6,6-dimethyl-4-oxo-3-(trifluoromethyl)-4,5,6,7-tetrahydro-1H-indazol-1-yl]phenyl}amino)-3-hydroxy-2-(hydroxymethyl)propyl acetate; |
| 504 | 509.2 | 4-[6,6-dimethyl-4-oxo-3-(trifluoromethyl)-4,5,6,7-tetrahydro-1H-indazol-1-yl]-2-[(trans-4-hydroxycyclohexyl)(2-hydroxyethyl)amino]benzamide; |
| 505 | 555.1 | 2-({4-[2,2,2-trifluoro-1-hydroxy-1-(trifluoromethyl)ethyl]phenyl}amino)-4-(3,6,6-trimethyl-4-oxo-4,5,6,7-tetrahydro-1H-indazol-1-yl)benzamide; |
| 506 | 550.3 | 2-({1-[3-(4-methylpiperazin-1-yl)propanoyl]piperidin-4-yl}amino)-4-(3,6,6-trimethyl-4-oxo-4,5,6,7-tetrahydro-1H-indazol-1-yl)benzamide; |
| 507 | 501.2 | 2-[(1-isonicotinoylpiperidin-4-yl)amino]-4-(3,6,6-trimethyl-4-oxo-4,5,6,7-tetrahydro-1H-indazol-1-yl)benzamide; |
| 508 | 501.2 | 2-{[1-(pyridin-3-ylcarbonyl)piperidin-4-yl]amino}-4-(3,6,6-trimethyl-4-oxo-4,5,6,7-tetrahydro-1H-indazol-1-yl)benzamide; |
| 509 | 422.2 | 2-(1-azabicyclo[2.2.2]oct-3-ylamino)-4-(3,6,6-trimethyl-4-oxo-4,5,6,7-tetrahydro-1H-indazol-1-yl)benzamide; |
| 510 | 460.1 | 2-{[(3R)-1-(methylsulfonyl)pyrrolidin-3-yl]amino}-4-(3,6,6-trimethyl-4-oxo-4,5,6,7-tetrahydro-1H-indazol-1-yl)benzamide; |
| 511 | 467.2 | 2-[(1-beta-alanylpiperidin-4-yl)amino]-4-(3,6,6-trimethyl-4-oxo-4,5,6,7-tetrahydro-1H-indazol-1-yl)benzamide; |
| 512 | 493.2 | 2-[(1-prolylpiperidin-4-yl)amino]-4-(3,6,6-trimethyl-4-oxo-4,5,6,7-tetrahydro-1H-indazol-1-yl)benzamide; |
| 513 | 424.2 | 2-{[(3R)-1-acetylpyrrolidin-3-yl]amino}-4-(3,6,6-trimethyl-4-oxo-4,5,6,7-tetrahydro-1H-indazol-1-yl)benzamide; |
| 514 | 453.2 | (3R)-3-{[2-(aminocarbonyl)-5-(3,6,6-trimethyl-4-oxo-4,5,6,7-tetrahydro-1H-indazol-1-yl)phenyl]amino}-N,N-dimethylpyrrolidine-1-carboxamide; |
| 515 | 523.2 | [[2-Carbamoyl-5-(6,6-dimethyl-4-oxo-3-trifluoromethyl-4,5,6,7-tetrahydro-indazol-1-yl)-phenyl]-(trans-4-hydroxy-cyclohexyl)-amino]-acetic acid; |
| 516 | 419.2 | 2-{[4-(hydroxymethyl)phenyl]amino}-4-(3,6,6-trimethyl-4-oxo-4,5,6,7-tetrahydro-1H-indazol-1-yl)benzamide; |
| 517 | 451.1 | 4-[6,6-dimethyl-4-oxo-3-(trifluoromethyl)-4,5,6,7-tetrahydro-1H-indazol-1-yl]-2-{[(1R,3S)-3-hydroxycyclopentyl]amino}benzamide; |
| 518 | 451.1 | 4-[6,6-dimethyl-4-oxo-3-(trifluoromethyl)-4,5,6,7-tetrahydro-1H-indazol-1-yl]-2-{[(1R,3R)-3-hydroxycyclopentyl]amino}benzamide; |
| 519 | 397.2 | 2-{[(2R)-tetrahydrofuran-2-ylmethyl]amino}-4-(3,6,6-trimethyl-4-oxo-4,5,6,7-tetrahydro-1H-indazol-1-yl)benzamide; |
| 520 | 505.2 | 2-{[trans-4-(allyloxy)cyclohexyl]amino}-4-[6,6-dimethyl-4-oxo-3-(trifluoromethyl)-4,5,6,7-tetrahydro-1H-indazol-1-yl]benzamide; |
| 521 | 397.2 | 2-{[(2S)-tetrahydrofuran-2-ylmethyl]amino}-4-(3,6,6-trimethyl-4-oxo-4,5,6,7-tetrahydro-1H-indazol-1-yl)benzamide; |
| 522 | 473.2 | 2-[(1-isonicotinoylazetidin-3-yl)amino]-4-(3,6,6-trimethyl-4-oxo-4,5,6,7-tetrahydro-1H-indazol-1-yl)benzamide; |
| 523 | 473.2 | 2-{[1-(pyridin-3-ylcarbonyl)azetidin-3-yl]amino}-4-(3,6,6-trimethyl-4-oxo-4,5,6,7-tetrahydro-1H-indazol-1-yl)benzamide; |
| 524 | 509.2 | 2-{[1-(3-morpholin-4-ylpropanoyl)azetidin-3-yl]amino}-4-(3,6,6-trimethyl-4-oxo-4,5,6,7-tetrahydro-1H-indazol-1-yl)benzamide; |
| 525 | 522.3 | 2-({1-[3-(4-methylpiperazin-1-yl)propanoyl]azetidin-3-yl}amino)-4-(3,6,6-trimethyl-4-oxo-4,5,6,7-tetrahydro-1H-indazol-1-yl)benzamide; |
| 526 | 401.1 | 2-{[3-(methylthio)propyl]amino}-4-(3,6,6-trimethyl-4-oxo-4,5,6,7-tetrahydro-1H-indazol-1-yl)benzamide; |
| 527 | 437.1 | 2-[6,6-dimethyl-4-oxo-3-(trifluoromethyl)-4,5,6,7-tetrahydro-1H-indazol-1-yl]-4-[(3R)-tetrahydrofuran-3-ylamino]benzamide; |
| 528 | 385.2 | 2-{[(1S)-2-methoxy-1-methylethyl]amino}-4-(3,6,6-trimethyl-4-oxo-4,5,6,7-tetrahydro-1H-indazol-1-yl)benzamide; |
| 529 | 396.2 | 2-(tetrahydro-2H-pyran-2-ylamino)-4-(3,6,6-trimethyl-4-oxo-4,5,6,7-tetrahydro-1H-indol-1-yl)benzamide; |
| 530 | 655.3 | 2-[[trans-4-(allyloxy)cyclohexyl](3,5-dimethoxybenzyl)amino]-4-[6,6-dimethyl-4-oxo-3-(trifluoromethyl)-4,5,6,7-tetrahydro-1H-indazol-1-yl]benzamide; |
| 531 | 689.3 | 2-[[trans-4-(2,3-dihydroxypropoxy)cyclohexyl](3,5-dimethoxybenzyl)amino]-4-[6,6-dimethyl-4-oxo-3-(trifluoromethyl)-4,5,6,7-tetrahydro-1H-indazol-1-yl]benzamide; |

-continued

| Compound No. | M + H | Name |
|---|---|---|
| 532 | 404.1 | 4-{3-[(benzyloxy)methyl]-6,6-dimethyl-4-oxo-4,5,6,7-tetrahydro-1H-indazol-1-yl}benzamide; |
| 533 | 448.2 | 2-({2-[(dimethylamino)sulfonyl]ethyl}amino)-4-(3,6,6-trimethyl-4-oxo-4,5,6,7-tetrahydro-1H-indazol-1-yl)benzamide; |
| 534 | 382.2 | 2-[(3S)-pyrrolidin-3-ylamino]-4-(3,6,6-trimethyl-4-oxo-4,5,6,7-tetrahydro-1H-indazol-1-yl)benzamide hydrochloride; |
| 535 | 424.2 | 2-{[(3S)-1-acetylpyrrolidin-3-yl]amino}-4-(3,6,6-trimethyl-4-oxo-4,5,6,7-tetrahydro-1H-indazol-1-yl)benzamide; |
| 536 | 507.2 | 4-[6,6-dimethyl-4-oxo-3-(trifluoromethyl)-4,5,6,7-tetrahydro-1H-indazol-1-yl]-2-{[trans-4-(2-oxoethoxy)cyclohexyl]amino}benzamide; |
| 537 | 539.2 | 2-{[4-(2,3-dihydroxypropoxy)cyclohexyl]amino}-4-[6,6-dimethyl-4-oxo-3-(trifluoromethyl)-4,5,6,7-tetrahydro-1H-indazol-1-yl]benzamide; |
| 538 | 516.1 | 4-[6,6-dimethyl-4-oxo-3-(trifluoromethyl)-4,5,6,7-tetrahydro-1H-indazol-1-yl]-2-({2-[(isopropylsulfonyl)amino]ethyl}amino)benzamide; |
| 539 | 509.2 | 4-[6,6-dimethyl-4-oxo-3-(trifluoromethyl)-4,5,6,7-tetrahydro-1H-indazol-1-yl]-2-{[trans-4-(2-hydroxyethoxy)cyclohexyl]amino}benzamide; |
| 540 | 523.2 | {[trans-4-({2-(aminocarbonyl)-5-[6,6-dimethyl-4-oxo-3-(trifluoromethyl)-4,5,6,7-tetrahydro-1H-indazol-1-yl]phenyl}amino)cyclohexyl]oxy}acetic acid; |
| 541 | 550.1 | 4-[6,6-dimethyl-4-oxo-3-(trifluoromethyl)-4,5,6,7-tetrahydro-1H-indazol-1-yl]-2-({2-[(phenylsulfonyl)amino]ethyl}amino)benzamide; |
| 542 | 490.2 | 2-{[2-(morpholin-4-ylsulfonyl)ethyl]amino}-4-(3,6,6-trimethyl-4-oxo-4,5,6,7-tetrahydro-1H-indazol-1-yl)benzamide; |
| 543 | 327.1 | 4-[3-(2-aminoethyl)-6,6-dimethyl-4-oxo-4,5,6,7-tetrahydro-1H-indazol-1-yl]benzamide; |
| 544 | 451.1 | 2-[6,6-dimethyl-4-oxo-3-(trifluoromethyl)-4,5,6,7-tetrahydro-1H-indazol-1-yl]-4-{methyl[(3R)-tetrahydrofuran-3-yl]amino}benzamide; |
| 545 | 439.1 | 2-[6,6-dimethyl-4-oxo-3-(trifluoromethyl)-4,5,6,7-tetrahydro-1H-indazol-1-yl]-4-[(2-methoxy-1-methylethyl)amino]benzamide; |
| 546 | 430 | 4-bromo-2-[6,6-dimethyl-4-oxo-3-(trifluoromethyl)-4,5,6,7-tetrahydro-1H-indazol-1-yl]benzamide; |
| 547 | 425.2 | 4-(3-ethyl-6,6-dimethyl-4-oxo-4,5,6,7-tetrahydro-1H-indazol-1-yl)-2-[(trans-4-hydroxycyclohexyl)amino]benzamide; |
| 548 | 522.2 | 4-[6,6-dimethyl-4-oxo-3-(trifluoromethyl)-4,5,6,7-tetrahydro-1H-indazol-1-yl]-2-[(trans-4-{[(2E)-2-(hydroxyimino)ethyl]oxy}cyclohexyl)amino]benzamide; |
| 549 | 453.2 | 2-[(trans-4-hydroxycyclohexyl)amino]-4-(3-isobutyl-6,6-dimethyl-4-oxo-4,5,6,7-tetrahydro-1H-indazol-1-yl)benzamide; |
| 550 | 437.2 | 4-(3-cyclopropyl-6,6-dimethyl-4-oxo-4,5,6,7-tetrahydro-1H-indazol-1-yl)-2-[(trans-4-hydroxycyclohexyl)amino]benzamide; |
| 551 | 426.2 | 4-[3-(aminomethyl)-6,6-dimethyl-4-oxo-4,5,6,7-tetrahydro-1H-indazol-1-yl]-2-[(trans-4-hydroxycyclohexyl)amino]benzamide methanesulfonate (salt); |
| 552 | 452.2 | 2-[(1-methyl-2-oxo-piperidin-1-yl)ethyl)amino]-4-(3,6,6-trimethyl-4-oxo-4,5,6,7-tetrahydro-1H-indazol-1-yl)benzamide; |
| 553 | 440.2 | 4-[3-(2-aminoethyl)-6,6-dimethyl-4-oxo-4,5,6,7-tetrahydro-1H-indazol-1-yl]-2-[(trans-4-hydroxycyclohexyl)amino]benzamide; |
| 554 | 439.2 | 2-[(trans-4-hydroxycyclohexyl)amino]-4-(3-isopropyl-6,6-dimethyl-4-oxo-4,5,6,7-tetrahydro-1H-indazol-1-yl)benzamide; |
| 555 | 437.1 | 2-[6,6-dimethyl-4-oxo-3-(trifluoromethyl)-4,5,6,7-tetrahydro-1H-indazol-1-yl]-4-(tetrahydrofuran-3-ylamino)benzamide; |
| 556 | 451.2 | 4-[3-(cyclopropylmethyl)-6,6-dimethyl-4-oxo-4,5,6,7-tetrahydro-1H-indazol-1-yl]-2-[(trans-4-hydroxycyclohexyl)amino]benzamide; |
| 557 | 424.2 | 2-[(trans-4-hydroxycyclohexyl)amino]-4-(2,3,6,6-tetramethyl-4-oxo-4,5,6,7-tetrahydro-1H-indol-1-yl)benzamide; |
| 558 | 338.1 | 4-[3-(cyclopropylmethyl)-6,6-dimethyl-4-oxo-4,5,6,7-tetrahydro-1H-indazol-1-yl]benzamide; |
| 559 | 398.2 | 2-{[2-(dimethylamino)-2-oxoethyl]amino}-4-(3,6,6-trimethyl-4-oxo-4,5,6,7-tetrahydro-1H-indazol-1-yl)benzamide; |

Example 47

Additional compounds of the invention are represented by Formula XXIII and have substituents $R_3$, $R_4$, $R_5$, $R_6$, $R_7$, $Q_1$, $Q_2$, $Q_3$, Y, $X_1$, and $X_2$ as listed in the tables below. These compounds are prepared essentially according to the procedures set forth in Schemes 1-9 above and described in the above examples.

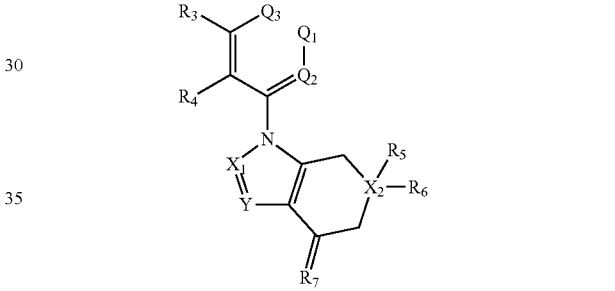

XXIII

TABLE A1

Substructures and codes for $R_3$, $R_4$

| —H | —NH$_2$ | —Cl |
|---|---|---|
| 001 | 002 | 003 |
| —Br | —F | —OH |
| 004 | 005 | 006 |
| —NO$_2$ | —CH$_3$ | —CH$_2$CH$_3$ |
| 007 | 010 | 011 |
| —CF$_3$ | —C≡C—CH$_2$OH | |
| 012 | 013 | |

TABLE A1-continued

Substructures and codes for R₃, R₄

TABLE A1-continued
Substructures and codes for R₃, R₄
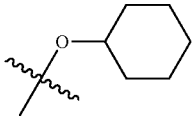
062
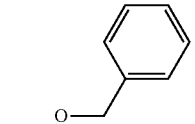
063
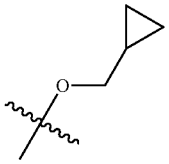
064
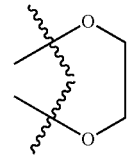
(R₃, R₄ fused)
065
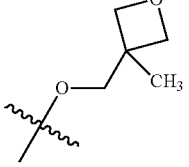
070
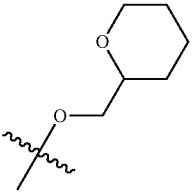
071
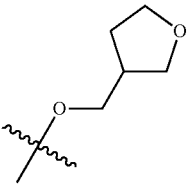
072
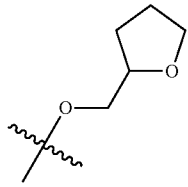
073
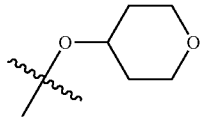
074
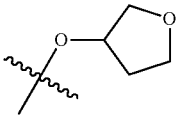
075
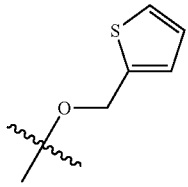
076
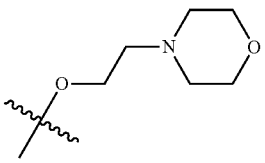
080
TABLE A1-continued
Substructures and codes for R₃, R₄
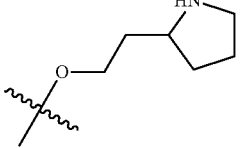
081
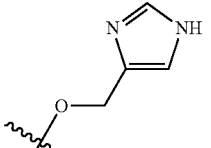
082
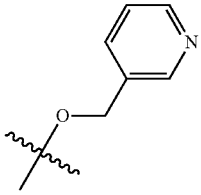
083
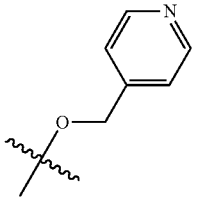
084
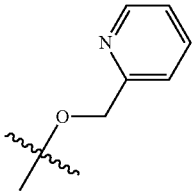
085
TABLE A2
Substructures and codes for R₃, R₄
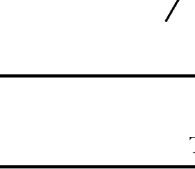
110
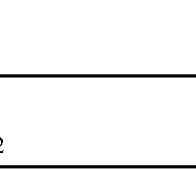
111
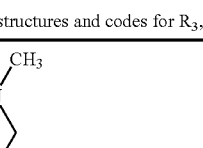
112
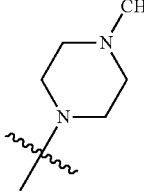
113

TABLE A2-continued
Substructures and codes for R₃, R₄
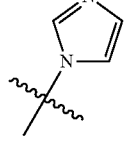
114
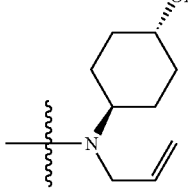
120
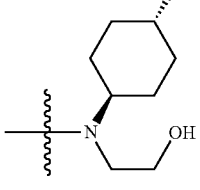
121
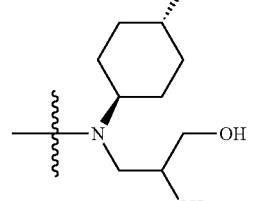
122
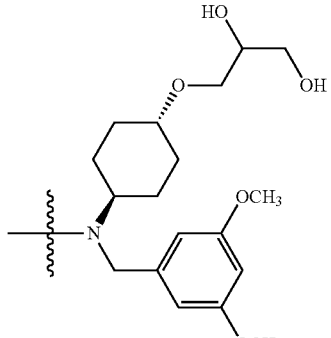
123
TABLE A3
Substructures and codes for R₃, R₄
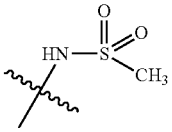
140
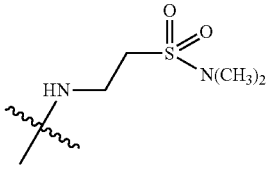
141
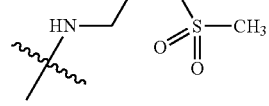
142
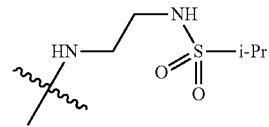
142
TABLE A3-continued
Substructures and codes for R₃, R₄
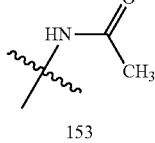
144
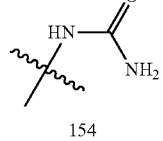
150
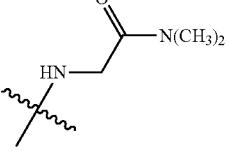
151
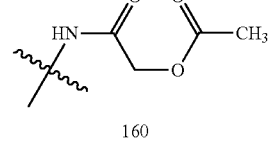
152
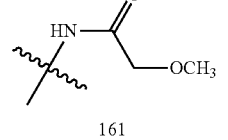
153
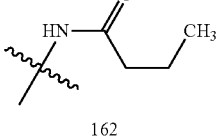
154
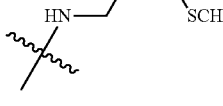
155
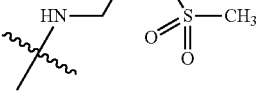
160
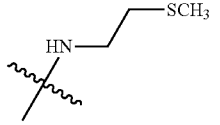
161
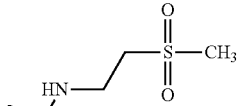
162
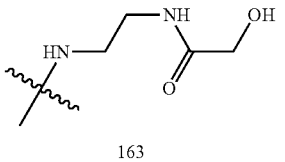
163
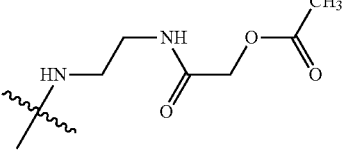
164

TABLE A3-continued
Substructures and codes for $R_3$, $R_4$
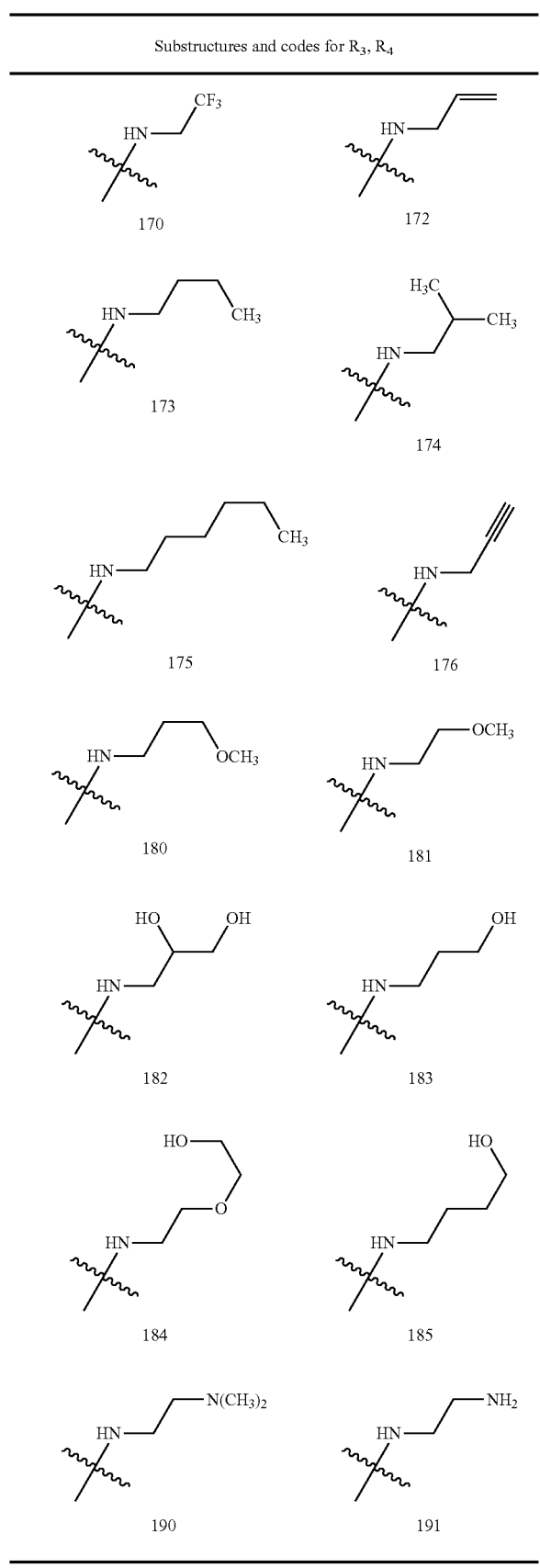
TABLE A4
Substructures and codes for $R_3$, $R_4$
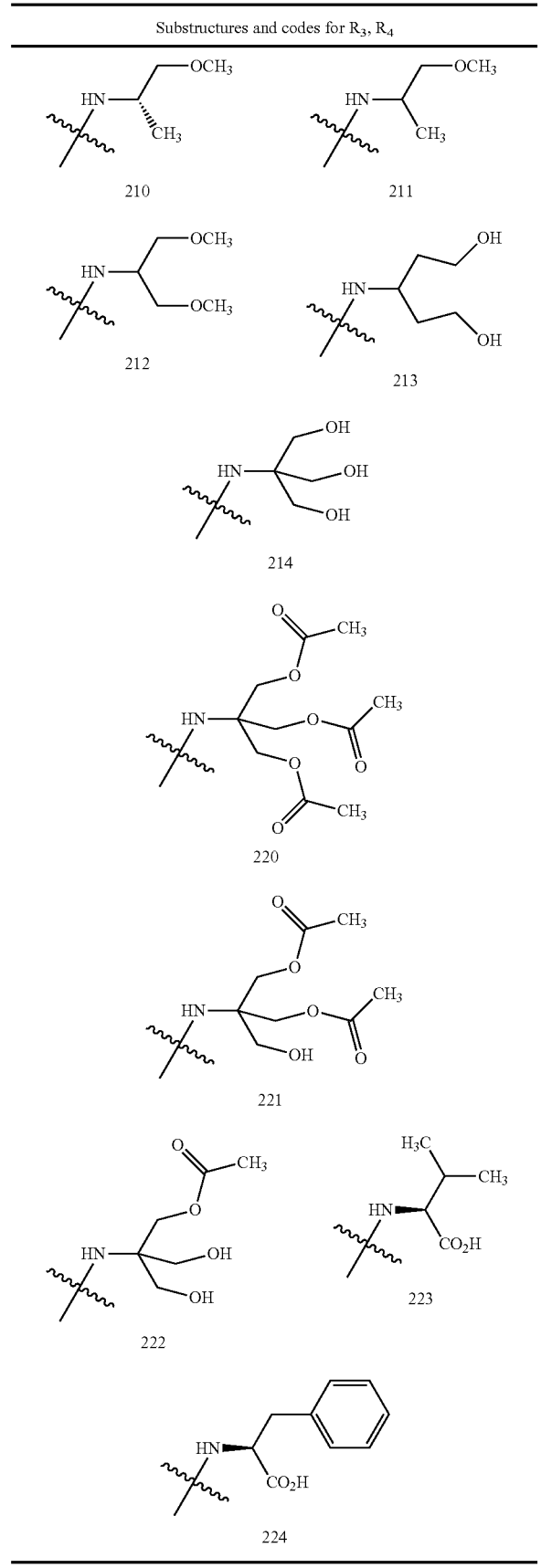

TABLE A5
Substructures and codes for R₃, R₄
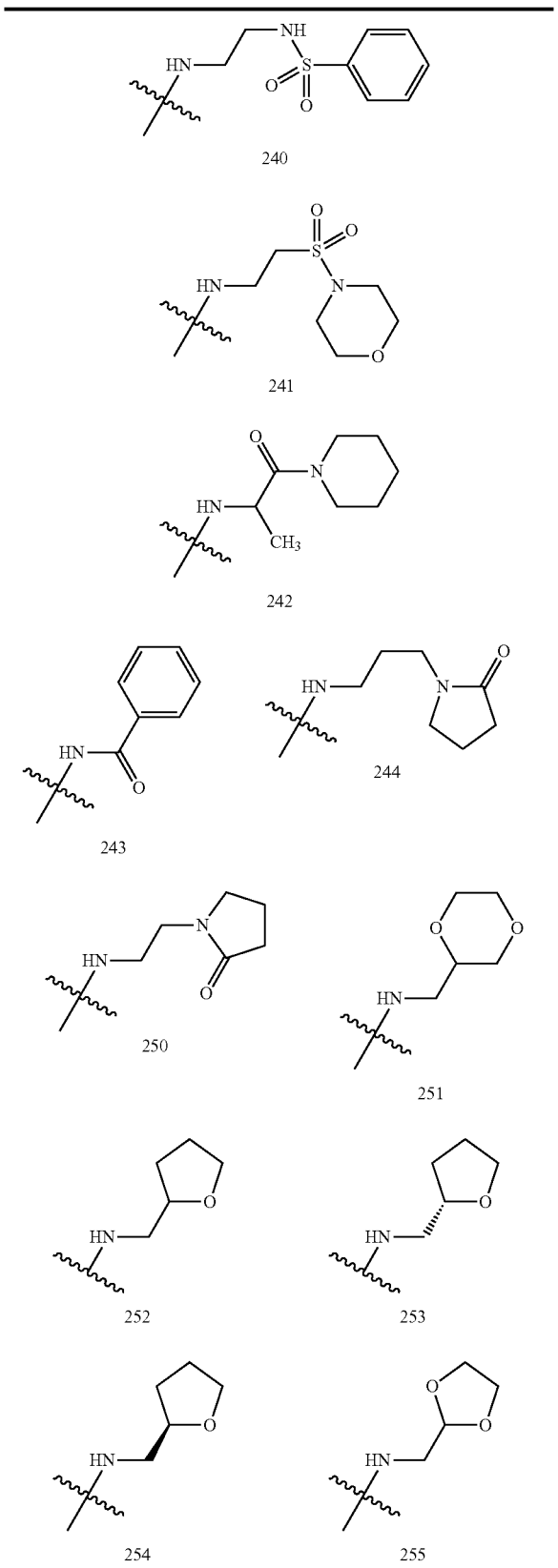
TABLE A5-continued
Substructures and codes for R₃, R₄
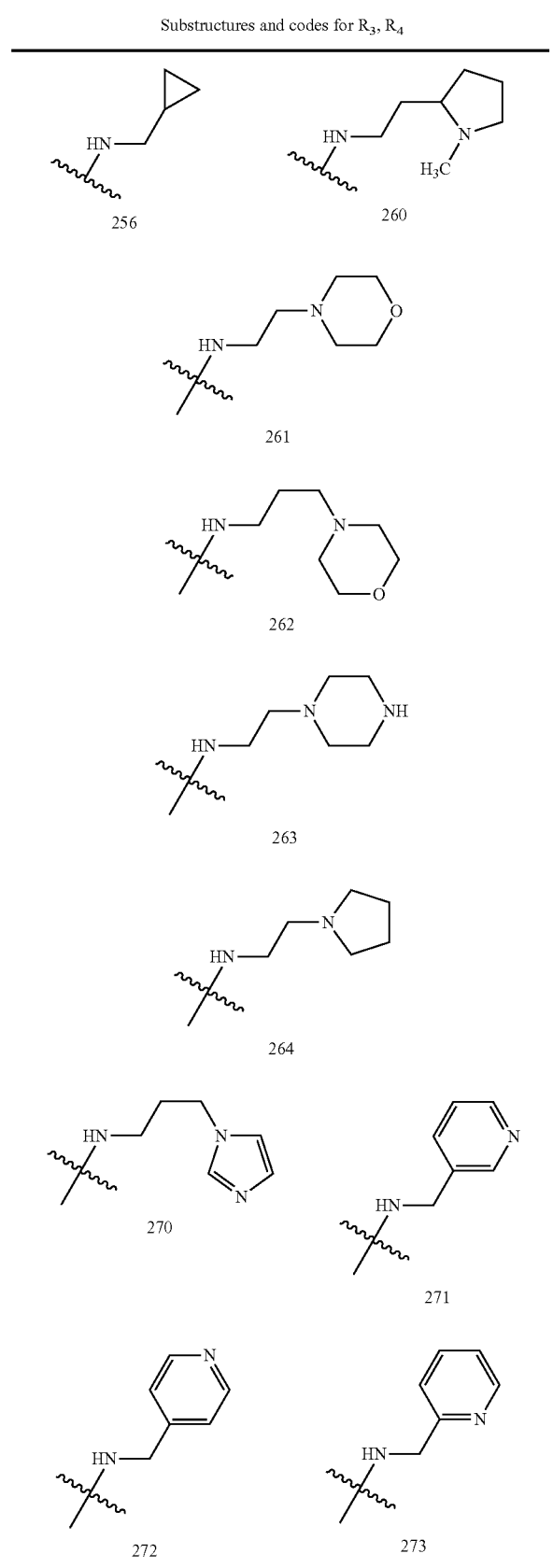

TABLE A5-continued

Substructures and codes for R₃, R₄

274, 275, 280, 281, 282, 283, 284, 285

TABLE A6

Substructures and codes for R₃, R₄

300

TABLE A6-continued

Substructures and codes for R₃, R₄

301, 302, 303, 310, 311, 312, 313, 320

TABLE A6-continued
Substructures and codes for R₃, R₄
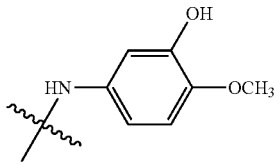
321
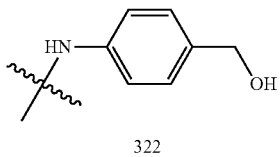
322
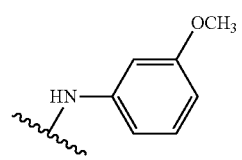
323
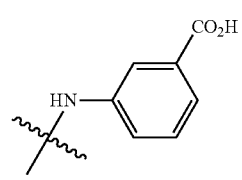
324
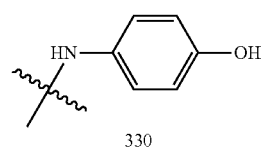
330
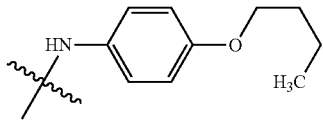
331
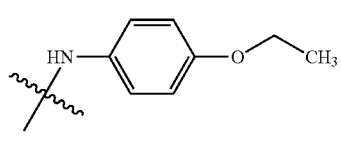
332
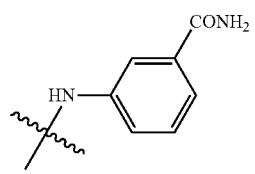
333
TABLE A6-continued
Substructures and codes for R₃, R₄
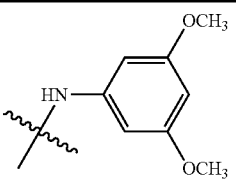
340
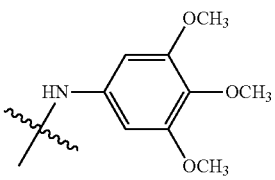
341
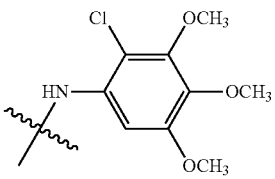
342
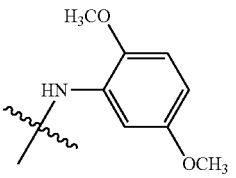
343
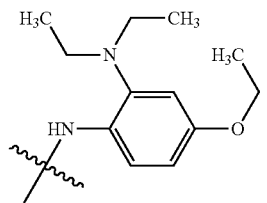
344
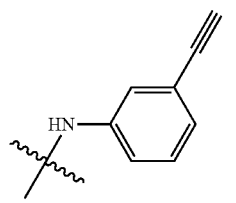
350
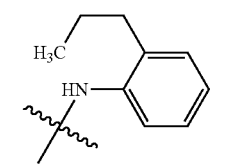
351

TABLE A6-continued
Substructures and codes for $R_3$, $R_4$
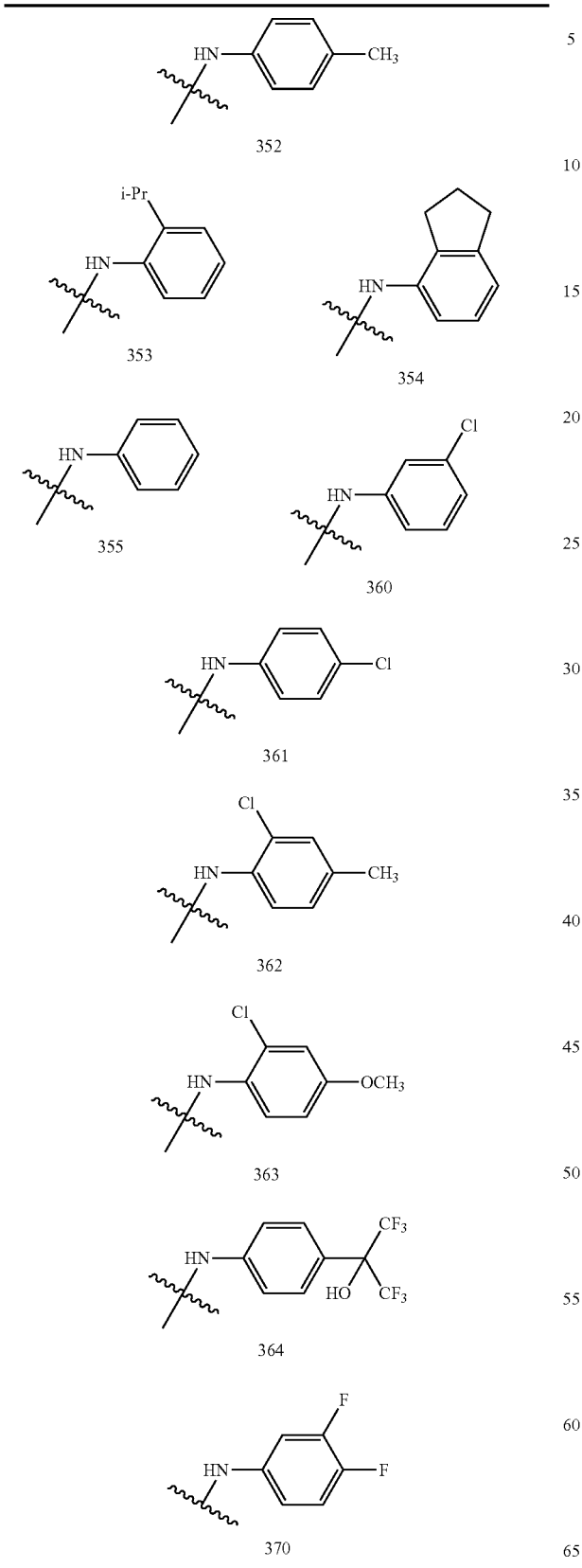
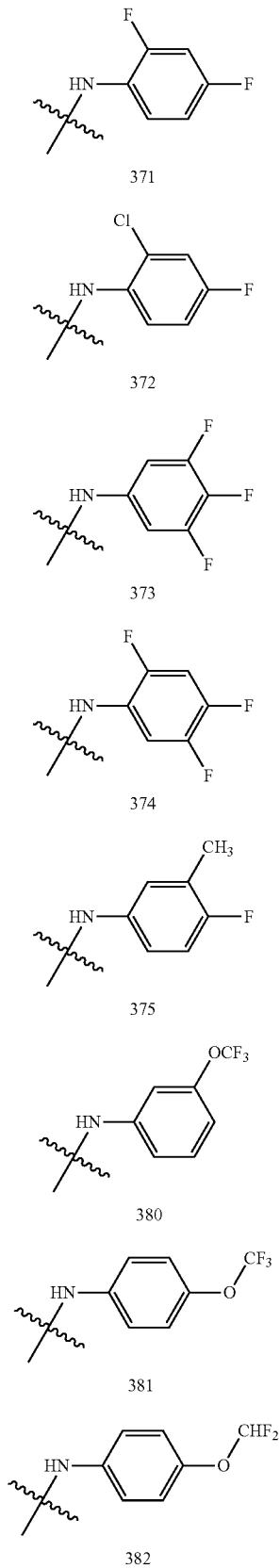

TABLE A6-continued
Substructures and codes for R₃, R₄
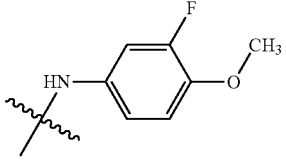
383
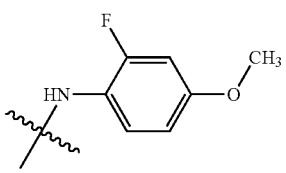
384
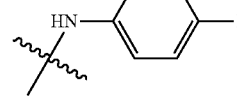
390
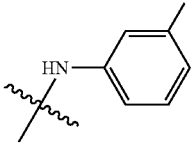
391
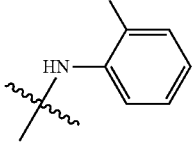
392
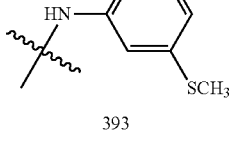
393
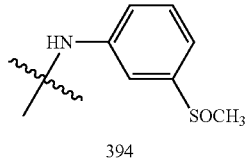
394
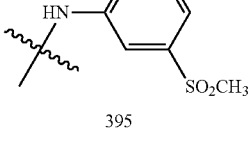
395
TABLE A7
Substructures and codes for R₃, R₄
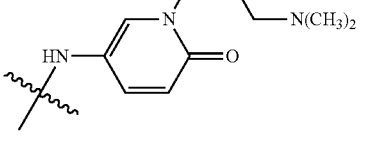
410
TABLE A7-continued
Substructures and codes for R₃, R₄
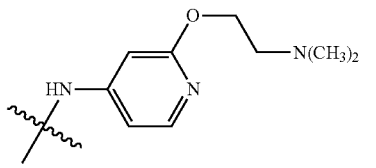
411
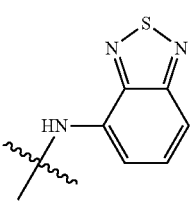
412
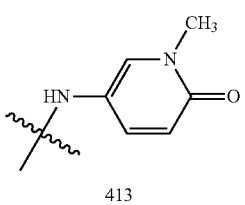
413
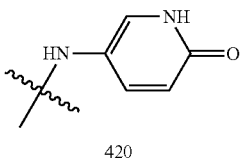
420
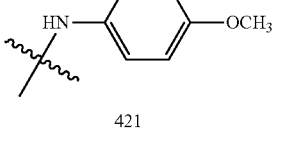
421
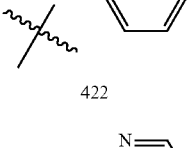
422
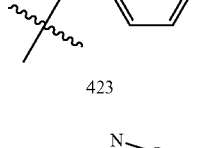
423
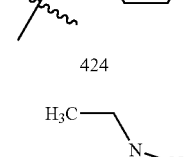
424
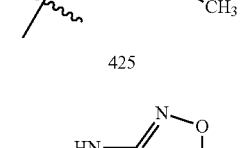
425
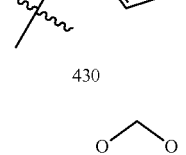
430
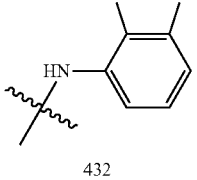
431
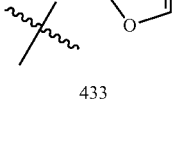
432
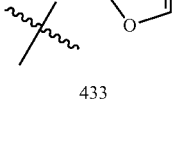
433

TABLE A7-continued
Substructures and codes for $R_3$, $R_4$
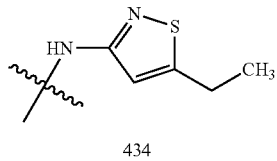
434
TABLE A8
Substructures and codes for $R_3$, $R_4$
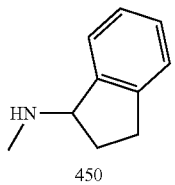
450
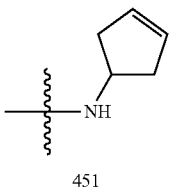
451
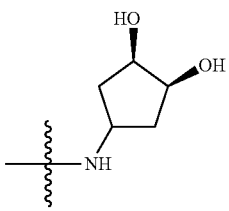
452
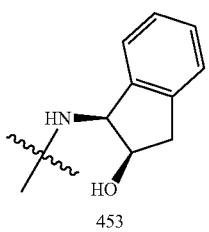
453
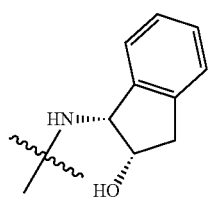
454
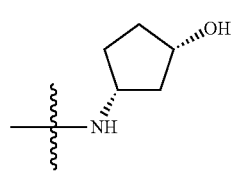
455
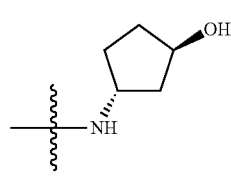
456
TABLE A8-continued
Substructures and codes for $R_3$, $R_4$
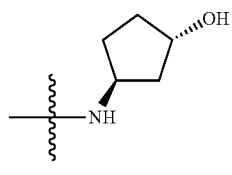
460
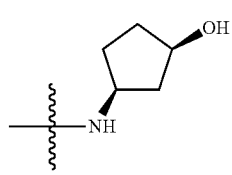
461
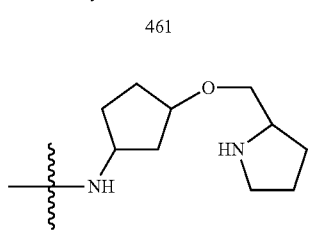
462
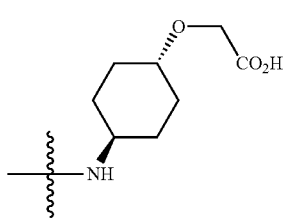
463
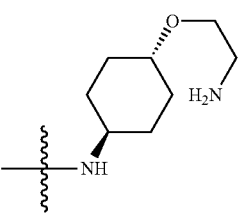
464
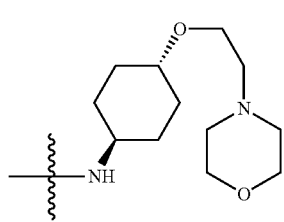
465

TABLE A8-continued
Substructures and codes for R₃, R₄
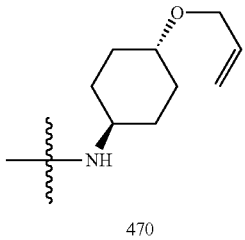
470
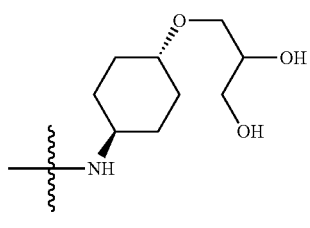
471
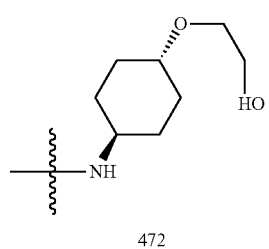
472
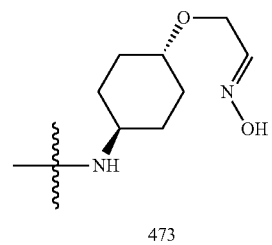
473
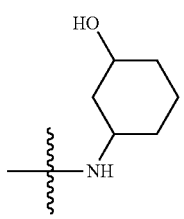
474
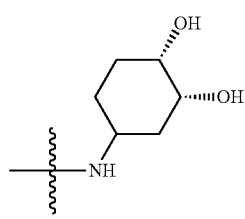
475
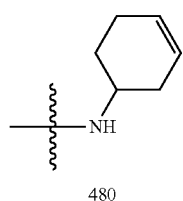
480
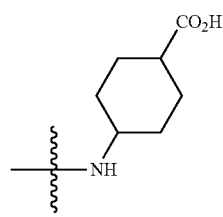
481
TABLE A8-continued
Substructures and codes for R₃, R₄
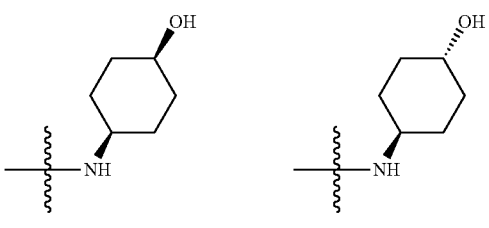
482    483
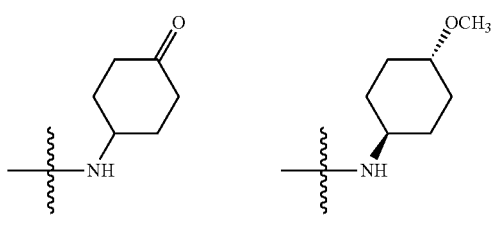
484    485
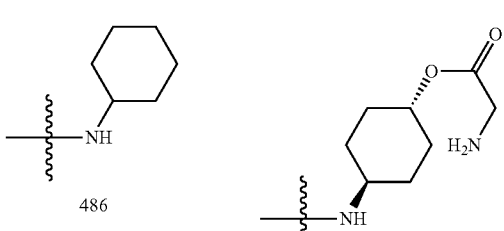
486    490
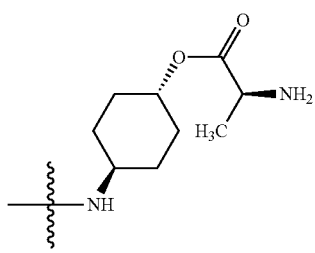
491
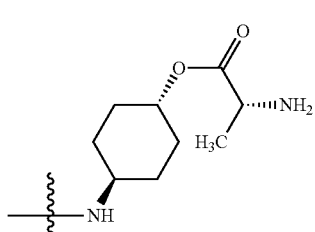
492

TABLE A8-continued
Substructures and codes for R_3, R_4
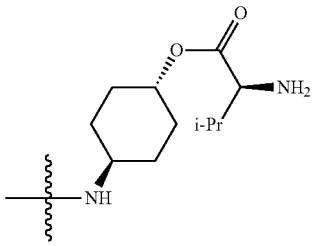
493
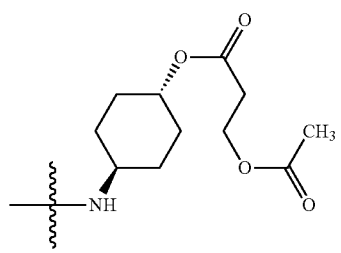
494
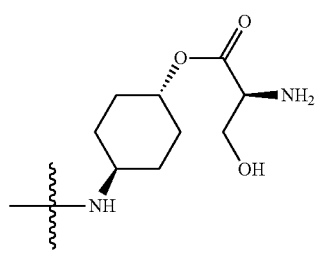
500
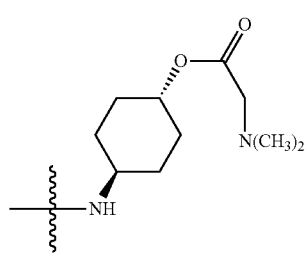
501
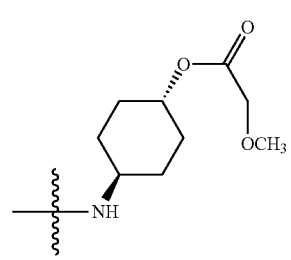
502
TABLE A8-continued
Substructures and codes for R_3, R_4
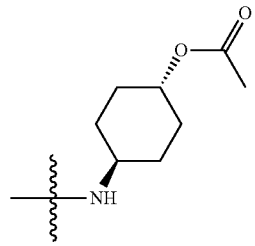
503
504          505
TABLE A9
Substructures and codes for R_3, R_4
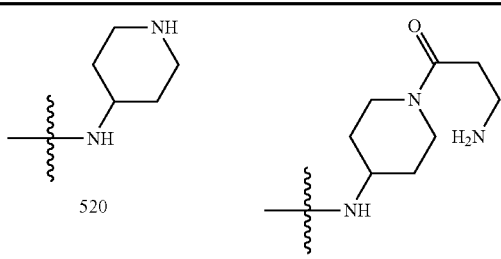
520          521
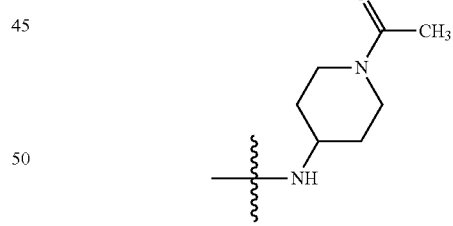
522
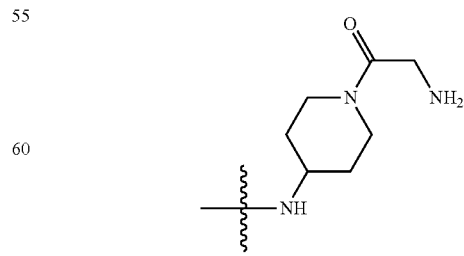
523

TABLE A9-continued
Substructures and codes for R₃, R₄
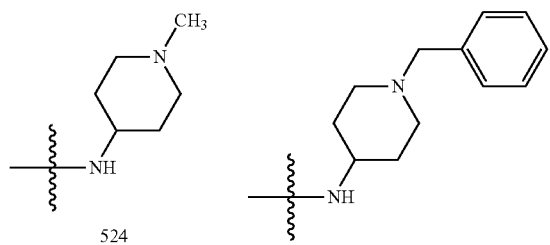
524
525
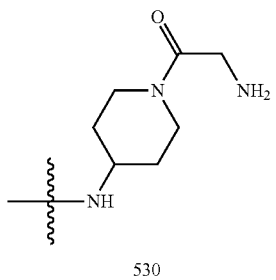
530
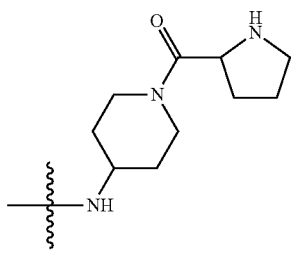
531
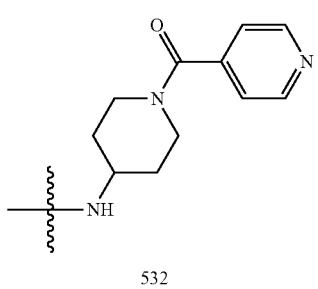
532
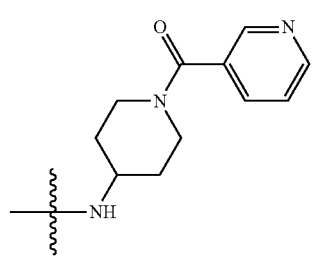
533
TABLE A9-continued
Substructures and codes for R₃, R₄
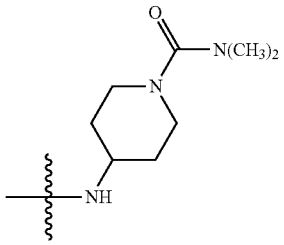
534
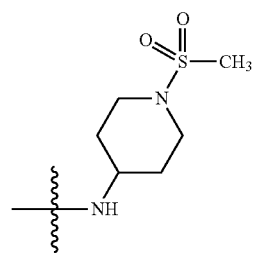
540
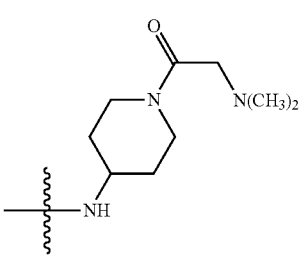
541
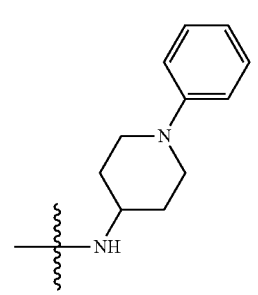
542
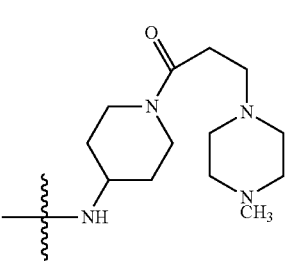
543

TABLE A9-continued
Substructures and codes for R₃, R₄
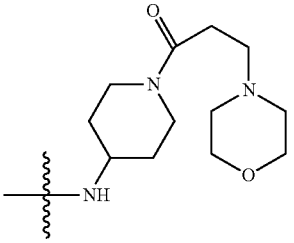
544
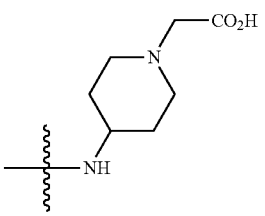
550
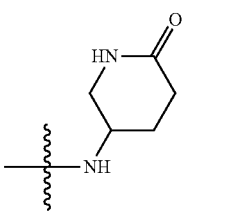
551
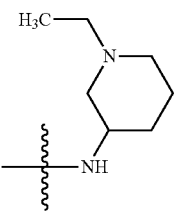
552
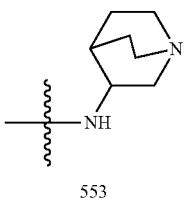
553
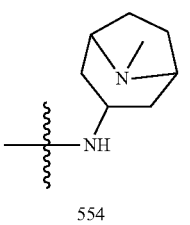
554
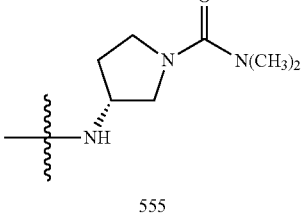
555
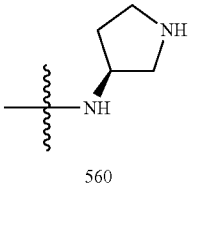
560
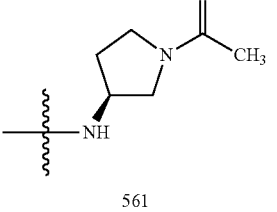
561
TABLE A9-continued
Substructures and codes for R₃, R₄
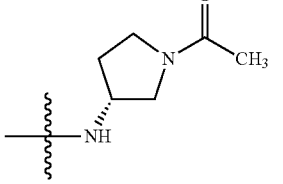
562
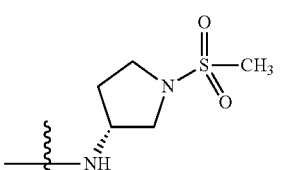
563
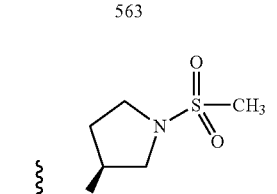
564
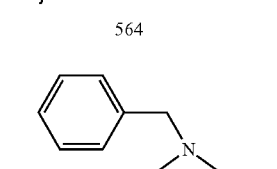
565
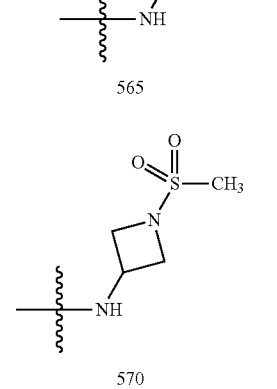
570
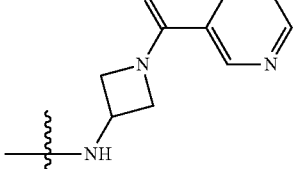
571

TABLE A9-continued
Substructures and codes for $R_3$, $R_4$
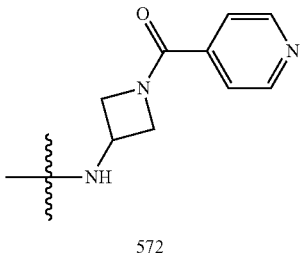
572
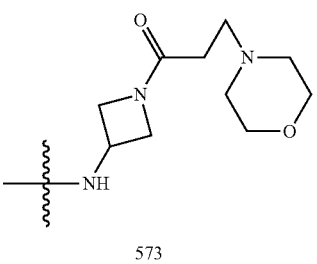
573
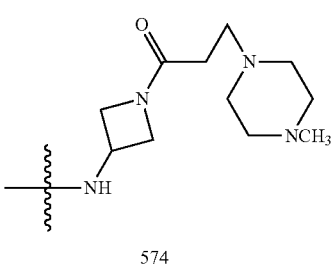
574
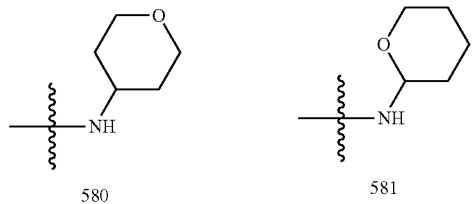
580    581
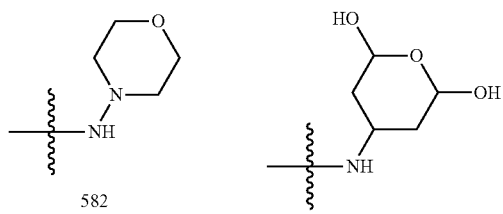
582    583
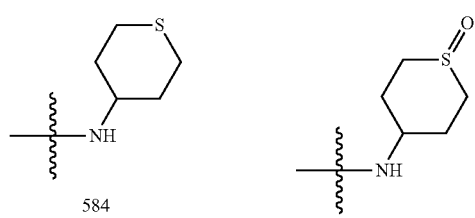
584    585
TABLE A9-continued
Substructures and codes for $R_3$, $R_4$
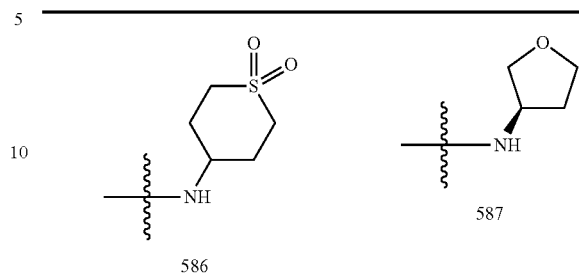
586    587
TABLE B
Substructures and codes for $Q_2$, $Q_1$, $Q_3$
| N | C—H | C—C≡N | C—CH$_3$ | C—NH$_2$ | C—CH$_2$CH$_3$ |
|---|---|---|---|---|---|
| B00 | B01 | B02 | B03 | B04 | B05 |
| C—CF$_3$ | | C—Br | | C—Cl | C—F |
| B06 | | B07 | | B08 | B09 |
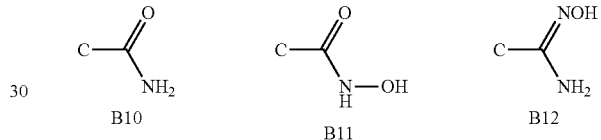
B10    B11    B12
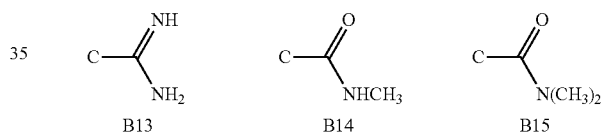
B13    B14    B15
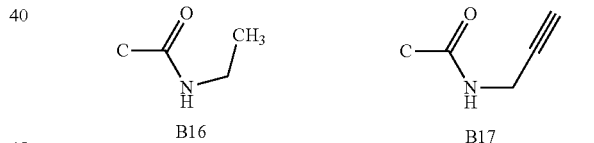
B16    B17
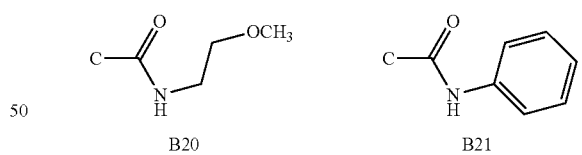
B20    B21
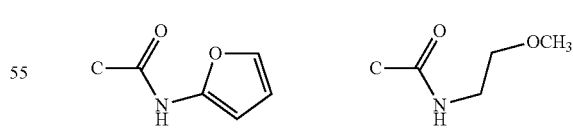
B22    B23
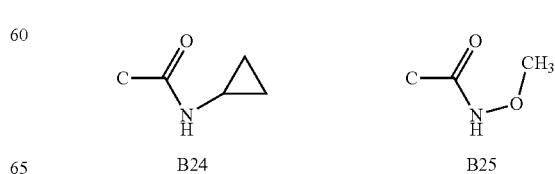
B24    B25

TABLE B-continued

Substructures and codes for $Q_2$, $Q_1$, $Q_3$

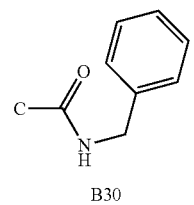
B30

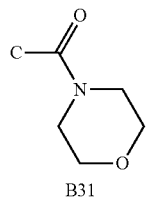
B31

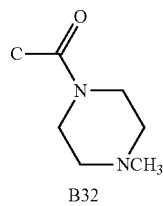
B32

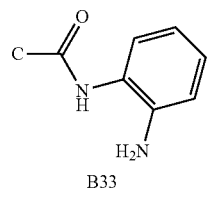
B33

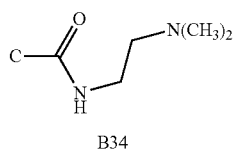
B34

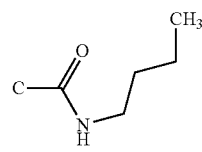
B35

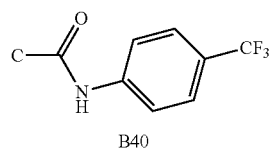
B40

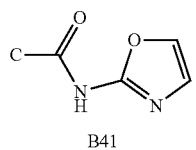
B41

C—S(=O)₂—NH₂
B42

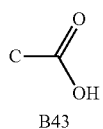
B43

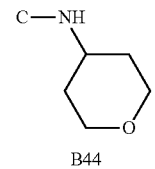
B44

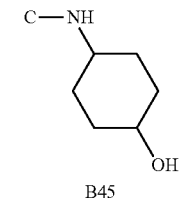
B45

TABLE C

Substructures and codes for $X_1$, Y

| N | C—H | C—CF₃ | C—CHF₂ | C—CH₂F | C—C≡N |
|---|---|---|---|---|---|
| C00 | C01 | C02 | C03 | C04 | C05 |
| C—NO₂ | | C—Cl | | C—Br | |
| C06 | | C07 | | C08 | |

C—CH₂CF₃
C09

C—C≡CH
C10

C—CH₂-cyclopropyl
C20

TABLE C-continued

Substructures and codes for $X_1$, Y

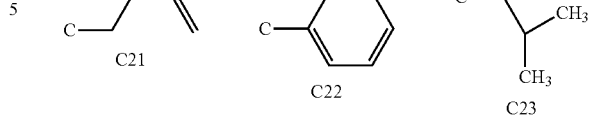

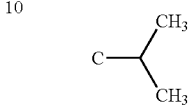 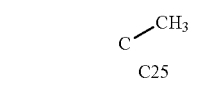 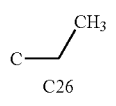
C24          C25          C26

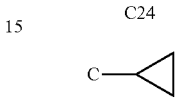 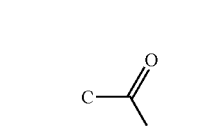 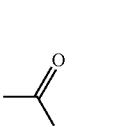
C27          C28          C29

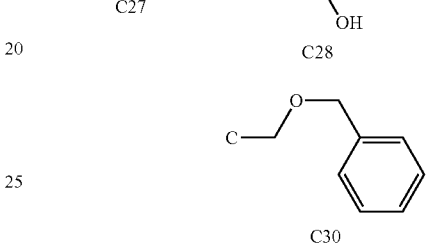
C30

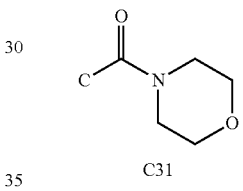
C31

C—CH₂CH₂NH₂    C—CH₂NH₂
C32              C33

C—CH₂OH
C34

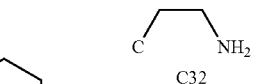
C35

C—CH₂CH₂N(CH₃)₂
C36

C—CH₂N(CH₃)₂
C37

TABLE D

Substructures and codes for $R_7$

O
D07

S
D08

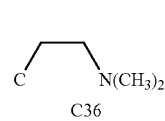
D10

TABLE D-continued

Substructures and codes for R$_7$

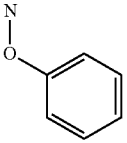

D11

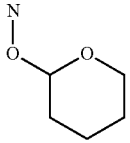

D12

TABLE E

Substructures and codes for X$_2$ (R$_5$, R$_6$)

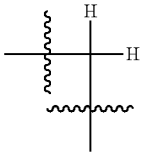

E00

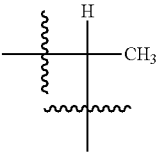

E01

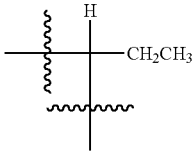

E02

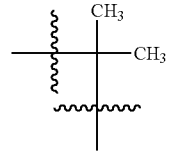

E03

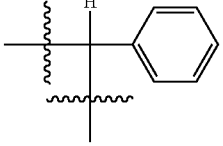

E04

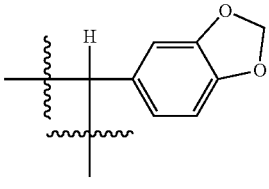

E05

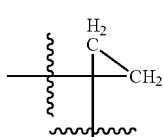

E10

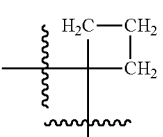

E11

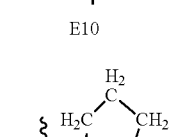

E12

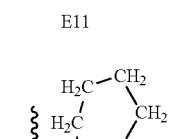

E13

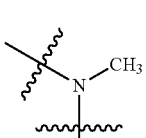

E14

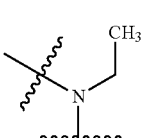

E15

Biological Evaluation

Example 48

Cell Proliferation Assays

A panel of cancer cell lines was obtained from the DCTP Tumor Repository, National Cancer Institute (Frederick, Md.) or ATCC (Rockville, Md.). Cell cultures were maintained in Hyclone RPMI 1640 medium (Logan, Utah) supplemented with 10% fetal bovine serum and 20 mM HEPES buffer, final pH 7.2, at 37° C. with a 5% $CO_2$ atmosphere. Cultures were maintained at sub-confluent densities. Human umbilical vein endothelial cells (HUVEC) were purchased from Clonetics, a division of Cambrex (Walkersville, Md.). Cultures were established from cryopreserved stocks using Clonetics EGM-2 medium supplemented with 20 mM HEPES, final pH 7.2, at 37° C. with a 5% $CO_2$ atmosphere.

For proliferation assays, cells were seeded with the appropriate medium into 96 well plates at 1,000-2,500 cells per well, depending on the cell line, and were incubated overnight. The following day, test compound, DMSO solution (negative control), or Actinomycin D (positive control) was added to the appropriate wells as 10× concentrated stocks prepared in phosphate buffered saline. The cell plates were then incubated for an additional 2-5 days, depending on the cell line, to allow proliferation to occur. To measure cell density, 50 µL of WST-1 solution (Roche Applied Science, Ind.) diluted 1:5 in phosphate buffered saline was added to each well, and the cells incubated for an additional 1-5 hrs., again depending on the cell line. Optical density was determined for each well at 450 nM using a Tecan GeniosPro plate reader (RTP, NC). The percentage of cell growth was determined by comparing the cell growth in the presence of test compounds to the cells treated with DMSO vehicle (control, 100% growth) and cells treated with Actinomycin D (10 µM, 0% growth).

Immediately after the WST-1 determination, the medium was removed from the PC-3, NCI-H460 and HUVEC cell lines, and the plates stored at −80° C. Using these assay plates, relative amounts of DNA in each well were determined using the Cyquant DNA assay kit from R&D Systems (Eugene, Oreg.) following the manufacturer's directions. Results for each compound treatment were compared to DMSO vehicle control (100%) and 10 µM Actinomycin D treated cells (0%).

Several exemplary compounds useful in the methods of the invention are listed below. The range of their inhibitory activity against PC-3 cell proliferation is demonstrated, where +++ stands for an $IC_{50}$ value that is less than 0.5 µM, ++ between 0.5 and 5 µM, + between 5 and 50 µM.

| Compound 70 | + | Compound 103 | ++ |
|---|---|---|---|
| Compound 72 | ++ | Compound 27 | +++ |
| Compound 74 | + | Compound 104 | +++ |
| Compound 76 | ++ | Compound 105 | + |
| Compound 77 | + | Compound 106 | ++ |
| Compound 81 | +++ | Compound 108 | +++ |
| Compound 82 | ++ | Compound 110 | + |
| Compound 84 | ++ | Compound 112 | + |
| Compound 93 | ++ | Compound 113 | +++ |
| Compound 94 | + | Compound 114 | +++ |
| Compound 5 | ++ | Compound 31 | +++ |
| Compound 53 | + | Compound 116 | +++ |
| Compound 55 | ++ | Compound 117 | +++ |
| Compound 97 | +++ | Compound 121 | ++ |
| Compound 98 | +++ | Compound 123 | ++ |

-continued

| Compound 99 | + | Compound 124 | +++ |
| Compound 100 | +++ | Compound 127 | +++ |
| Compound 19 | +++ | Compound 129 | ++ |
| Compound 101 | ++ | Compound 133 | + |
| Compound 102 | + | Compound 136 | ++ |

Example 49

Determination of Affinity for HSP-90

(Heat Shock Protein 90)

Affinity of test compounds for HSP-90 was determined as follows: Protein mixtures obtained from a variety of organ tissues (for example: spleen, liver and lung) were reversibly bound to a purine affinity column to capture purine-binding proteins, especially HSP-90. The purine affinity column was washed several times, and then eluted with 20 µM, 100 µM, and 500 µM of test compound. Compounds of Formula I elute HP-90 in a dose-dependent manner vs. a control elution using dimethylsulfoxide. The elution profile of Formula I compounds was determined by 1-dimensional SDS polyacrylamide gel electrophoresis. Gels were stained with a fluorescent stain such as sypro ruby (a highly sensitive fluorescent protein stain that can readily detect less than 1 fmol of total protein, i.e., less than 0.04 ng for a 40 kDa protein) or silver nitrate. The gels were imaged using a standard flat bed gel imager and the amount of protein estimated by densitometry. The percent of HSP-90 protein eluted from the column at each concentration was determined and $IC_{50}$ values were calculated from these estimates. The identity of a band containing HSP-90 was determined by protein sequencing using mass spectroscopy.

Compounds of the invention are inhibitors of HSP-90 (heat shock protein 90). Several exemplary compounds useful in the methods of the invention are listed below. The range of their relative binding affinity to HSP-90 is demonstrated, where +++ stands for very high, ++ for high and + for moderate.

| Compound 30 | ++ | Compound 55 | ++ |
| Compound 70 | + | Compound 96 | +++ |
| Compound 73 | + | Compound 98 | +++ |
| Compound 75 | +++ | Compound 99 | ++ |
| Compound 76 | +++ | Compound 102 | ++ |
| Compound 77 | ++ | Compound 103 | ++ |
| Compound 78 | + | Compound 105 | ++ |
| Compound 79 | + | Compound 34 | ++ |
| Compound 80 | + | Compound 107 | ++ |
| Compound 83 | +++ | Compound 109 | ++ |
| Compound 86 | ++ | Compound 111 | +++ |
| Compound 87 | ++ | Compound 115 | +++ |
| Compound 88 | ++ | Compound 32 | +++ |
| Compound 91 | ++ | Compound 117 | +++ |
| Compound 92 | ++ | Compound 121 | +++ |
| Compound 94 | ++ | Compound 131 | ++ |
| Compound 50 | +++ | Compound 132 | +++ |
| Compound 53 | ++ | Compound 133 | ++ |
| Compound 95 | +++ | Compound 134 | ++ |
| Compound 54 | + | Compound 135 | +++ |

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A compound of the formula,

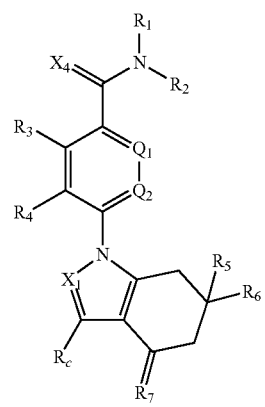

XXV or a pharmaceutically acceptable salt thereof, wherein $R_3$ and $R_4$ are independently (a) H, (b) halo, or (c) a $C_1$-$C_{15}$ alkyl group where up to six of the carbon atoms in said alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{22}$ is (i) heteroaryl, (ii) aryl, (iii) saturated or unsaturated $C_3$-$C_{10}$ cycloalkyl, or (iv) saturated or unsaturated $C_2$-$C_{10}$ heterocycloalkyl, wherein each aryl, heteroaryl, saturated or unsaturated cycloalkyl, or saturated or unsaturated heterocycloalkyl, independently, is optionally substituted with at least one group, which independently is hydroxy, halo, amino, cyano, carboxy, carboxamido, nitro, oxo, —S—($C_1$-$C_6$)alkyl, —$SO_2$—($C_1$-$C_6$)alkyl, —$SO_2$-aryl, —SO—($C_1$-$C_6$)alkyl, —SO-aryl, —$SO_2NH_2$, —$SO_2$NH—($C_1$-$C_6$)alkyl, —$SO_2$NH-aryl, ($C_1$-$C_6$)alkoxy, or mono- or di-($C_1$-$C_{10}$)alkylamino; and each $R_{22}$ is optionally fused to a $C_6$-$C_{10}$ aryl group, $C_5$-$C_8$ saturated cyclic group, or a $C_5$-$C_{10}$ heterocycloalkyl group;

wherein each (c) is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2$NH—($C_1$-$C_6$)alkyl, —$SO_2$NH-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$, wherein Z is $OR_0$ or —N($R_{30}$)$_2$, wherein each $R_{30}$ is independently —H or $C_1$-$C_6$ alkyl, or $N(R_{30})_2$ represents pyrrolidinyl, piperidinyl, piperazinyl, azepanyl, 1,3- or 1,4-diazepanyl, or morpholinyl, each of which is optionally substituted with hydroxy, amino, aminoalkyl, $C_1$-$C_6$ alkyl, mono- or di($C_1$-$C_6$)alkylamino, $C_1$-$C_6$ alkoxy, or halogen;

$R_O$ is —H, —$C_1$-$C_{10}$ alkyl, —$C_2$-$C_{10}$ alkenyl, —$C_2$-$C_{10}$ alkynyl, aryl, heteroaryl, or —$C_1$-$C_6$ acyl;

$R_{23}$ is
(1) heteroaryl,
(2) aryl,
(3) saturated or unsaturated $C_5$-$C_{10}$ cycloalkyl, or
(4) saturated or unsaturated $C_5$-$C_{10}$ heterocycloalkyl, and
the $R_{23}$ groups are optionally substituted at least one group which is independently hydroxy, oxo, halo, amino, cyano, nitro, —SH, —S—($C_1$-$C_6$)alkyl, —$SO_2$—($C_1$-$C_6$)alkyl, —$SO_2$-aryl, —SO—($C_1$-$C_6$) alkyl, —SO-aryl, —$SO_2NH_2$, —$SO_2NH$—($C_1$-$C_6$) alkyl, —$SO_2NH$-aryl, ($C_1$-$C_6$)alkoxy, or mono- or di-($C_1$-$C_{10}$)alkylamino;

or $R_3$ and $R_4$ together with the atoms to which they are attached form a 5-12 membered mono-, bi-, or tricyclic ring system fused to the ring containing $Q_1$ and $Q_2$, where the 5-12 membered ring is partially unsaturated or aromatic and optionally contains one or two of oxygen, $S(O)_m$ where m is 0, 1, or 2, nitrogen, or $NR_{33}$ where $R_{33}$ is hydrogen or $C_1$-$C_6$ alkyl;

$R_7$ is O, S, NH, N—OH, N—$NH_2$, N—$NHR_{22}$, N—NH—($C_1$-$C_6$ alkyl), N—O—($C_0$-$C_6$)alkyl-$R_{22}$, or N—($C_1$-$C_6$ alkoxy optionally substituted with carboxy);

$X_1$ is N or $CR_C$, wherein
each $R_C$ independently is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
each alkyl, aryl, cycloalkyl, heterocycloalkyl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, cyano, nitro, halo($C_1$-$C_6$)alkyl, halo($C_1$-$C_6$)alkoxy, carboxamide, heterocycloalkyl, aryl, or heteroaryl, wherein
the aryl and heteroaryl groups are optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, halo($C_1$-$C_6$)alkyl, or carboxamide;
$R_{C'}$ is —$C_1$-$C_6$ alkyl, —$OR_{C''}$, or —$N(R_1N)_2$, wherein
$R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;
each $R_{CN}$ is independently —H, $C_1$-$C_{10}$ alkyl, $C_1$-$C_{10}$ haloalkyl, $C_3$-$C_7$ cycloalkyl, heterocycloalkyl, $C_1$-$C_6$ acyl, aryl, or heteroaryl, wherein
each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$)alkoxy, or carboxamide;

$Q_1$ and $Q_2$ are independently N or $CR_Q$, wherein
each $R_Q$ is independently hydrogen, halogen, —$N(R_{CN})_2$, $C_1$-$C_6$ alkyl, $C_1$-$C_6$ haloalkyl, $C_3$-$C_7$ cycloalkyl, aryl, or heteroaryl, or $R_{21}$, wherein
each alkyl, cycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, halo($C_1$-$C_6$)alkyl, halo($C_1$-$C_6$)alkoxy, or carboxamide;

$R_1$ and $R_2$ are independently H, hydroxy, $C_1$-$C_6$ alkyl, $C_2$-$C_6$ alkenyl, $C_2$-$C_6$ alkynyl, heteroaryl, aryl, $C_3$-$C_8$ cycloalkyl, heterocycloalkyl, wherein
each alkyl, cycloalkyl, heterocycloalkyl, aryl, and heteroaryl group is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$) alkoxy, or carboxamide;
or $R_1$ and $R_2$ together with the nitrogen to which they are both attached, form a heterocycloalkyl which optionally contains one or more additional heteroatoms which are, independently, O, N, S, or $N(R_{CN})$;

$X_4$ is O, S, NH, NOH, N—$NH_2$, N—NHaryl, N—NH—($C_1$-$C_6$ alkyl), or N—($C_1$-$C_6$ alkoxy);
and
$R_5$ and $R_6$ are independently H, $C_1$-$C_6$ alkyl, or aryl, wherein the aryl is optionally substituted with from 1-4 groups that are independently $C_1$-$C_6$ alkyl, $C_1$-$C_6$ alkoxy, halogen, hydroxy, amino, mono- or di-($C_1$-$C_6$) alkylamino, nitro, halo($C_1$-$C_6$)alkyl, halo($C_1$-$C_6$) alkoxy, or carboxamide, or wherein any two adjacent substituted aryl positions, together with the carbon atoms to which they are attached, form an unsaturated cycloalkyl or heterocycloalkyl; or
$R_5$ and $R_6$ together with the carbon to which they are attached form a 3-8 membered ring.

2. A compound according to claim 1, wherein $X_1$ is N.

3. A compound according to claim 2, wherein
$R_3$ and $R_4$ are independently hydrogen, halo, or —$Z_1R_{Z1}$, wherein
$Z_1$ is —O— or —NH—;
$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —$SO_2$—($C_1$-$C_6$)alkyl, —$SO_2NH_2$, —$SO_2NH$—($C_1$-$C_6$)alkyl, —$SO_2NH$-aryl, —$SO_2$-aryl, —SO—($C_1$-$C_6$)alkyl, —$SO_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —$OC_1$-$C_{10}$ alkyl-Z, or $R_{23}$.

4. A compound according to claim 2, wherein
$R_4$ is H; and
$R_3$ hydrogen, halo, or —$Z_1R_{Z1}$, wherein
$Z_1$ is —O— or —NH—;
$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other, wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

5. A compound according to claim 2, wherein
$R_4$ is H; and
$R_3$ is —N(H)$R_{Z1}$, wherein
  $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other,
  wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

6. A compound according to claim 5, wherein
$R_C$ is methyl, ethyl, cyclopropyl, cyclopropylmethyl, fluoromethyl, difluoromethyl, or trifluoromethyl.

7. A compound according to claim 2, wherein
$R_3$ is H; and
$R_4$ is hydrogen, halo, or —$Z_1R_{Z1}$, wherein
  $Z_1$ is —O— or —NH—;
  $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other,
  wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

8. A compound according to claim 7, wherein
$R_C$ is methyl, ethyl, cyclopropyl, cyclopropylmethyl, fluoromethyl, difluoromethyl, or trifluoromethyl.

9. A compound according to claim 1, wherein
$X_1$ is $CR_{11}$, wherein
  $R_{11}$ is hydrogen, halogen, cyano, nitro, —C(O)$R_{C'}$, $C_1$-$C_{10}$ alkyl, $C_2$-$C_{10}$ alkenyl, $C_2$-$C_{10}$ alkynyl, $C_1$-$C_{10}$ haloalkyl, $C_3$-$C_7$ cycloalkyl, $C_3$-$C_7$ cycloalkyl($C_1$-$C_{10}$)alkyl, heterocycloalkyl, aryl, or heteroaryl, wherein
    $R_{C'}$ is —$C_1$-$C_6$ alkyl, —O$R_{C''}$, or —N($R_{CN}$)$_2$, wherein
      $R_{C''}$ is —H, $C_1$-$C_{10}$ alkyl, $C_1$-$C_{10}$ haloalkyl, $C_3$-$C_7$ cycloalkyl, heterocycloalkyl, aryl, or heteroaryl;
      each $R_{CN}$ is independently —H, —$C_1$-$C_{10}$ alkyl, —$C_1$-$C_{10}$-haloalkyl, —$C_3$-$C_7$ cycloalkyl, -heterocycloalkyl, —$C_1$-$C_6$ acyl, -aryl, or -heteroaryl.

10. A compound according according to claim 9, wherein
$R_{11}$ is hydrogen, halogen, $C_1$-$C_{10}$ alkyl, $C_1$-$C_{10}$ haloalkyl, $C_3$-$C_7$ cycloalkyl, $C_3$-$C_7$ cycloalkyl($C_1$-$C_{10}$)alkyl, aryl, or heteroaryl.

11. A compound according to claim 9, wherein
$R_3$ and $R_4$ are independently hydrogen, halo, or —$Z_1R_{Z1}$, wherein
  $Z_1$ is —O— or —NH—;
  $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other,
  wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

12. A compound according to claim 9, wherein
$R_4$ is H; and
$R_3$ hydrogen, halo, or —$Z_1R_{Z1}$, wherein
  $Z_1$ is —O— or —NH—;
  $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other,
  wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

13. A compound according to claim 9, wherein
$R_4$ is H; and
$R_3$ is —N(H)$R_{Z1}$, wherein
  $R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, SO$_2$, or SO, with the proviso that two O atoms, two S atoms, or an O and S atom are not immediately adjacent each other,
  wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, —SH, —S—($C_1$-$C_6$)alkyl, —SO$_2$—($C_1$-$C_6$)alkyl, —SO$_2$NH$_2$, —SO$_2$NH—($C_1$-$C_6$)alkyl, —SO$_2$NH-aryl, —SO$_2$-aryl, —SO—($C_1$-$C_6$)alkyl, —SO$_2$-aryl, $C_1$-$C_6$ alkoxy, $C_2$-$C_{10}$ alkenyloxy, $C_2$-$C_{10}$ alkynyloxy, mono- or di-($C_1$-$C_{10}$)alkylamino, —O$C_1$-$C_{10}$ alkyl-Z, or $R_{23}$.

14. A compound according to claim 13, wherein
$R_C$ is methyl, ethyl, cyclopropyl, cyclopropylmethyl, fluoromethyl, difluoromethyl, or trifluoromethyl.

15. A compound according to claim 9, wherein
$R_3$ is H; and
$R_4$ is hydrogen, halo, or $-Z_1R_{Z1}$, wherein
$Z_1$ is $-O-$ or $-NH-$;
$R_{Z1}$ is a $C_1$-$C_{14}$ alkyl group where up to five of the carbon atoms in the alkyl group are optionally replaced independently by $R_{22}$, carbonyl, ethenyl, ethynyl or a moiety selected from N, O, S, $SO_2$, or SO, with the proviso that two O atoms, two S atoms, or an O and S atom are not immediately adjacent each other,
wherein $R_{Z1}$ is optionally substituted at any available position with $C_1$-$C_{10}$ alkyl, $C_1$-$C_{10}$ haloalkyl, $C_2$-$C_{10}$ alkenyl, $C_2$-$C_{10}$ alkynyl, hydroxy, carboxy, carboxamido, oxo, halo, amino, cyano, nitro, $-SH$, $-S-(C_1$-$C_6)$alkyl, $-SO_2-(C_1$-$C_6)$alkyl, $-SO_2NH_2$, $-SO_2NH-(C_1$-$C_6)$alkyl, $-SO_2NH$-aryl, $-SO_2$-aryl, $-SO-(C_1$-$C_6)$alkyl, $-SO_2$-aryl, $C_1$-$C_6$ alkoxy, $C_2$-$C_{10}$ alkenyloxy, $C_2$-$C_{10}$ alkynyloxy, mono- or di-$(C_1$-$C_{10})$alkylamino, $-OC_1$-$C_{10}$ alkyl-Z, or $R_{23}$.

16. A compound according to claim 15, wherein
$R_C$ is methyl, ethyl, cyclopropyl, cyclopropylmethyl, fluoromethyl, difluoromethyl, or trifluoromethyl.

17. A pharmaceutical composition comprising at least one compound or salt according to claim 1 and a pharmaceutically acceptable solvent, carrier, excipient, adjuvant or a combination thereof.

18. A compound according to claim 1 which is
2-(4-Hydroxy-cyclohexylamino)-4-(3,6,6-trimethyl-4-oxo-4,5,6,7-tetrahydro-indol-1-yl)-benzamide;
2-(Tetrahydro-pyran-4-ylamino)-4-(3,6,6-trimethyl-4-oxo-4,5,6,7-tetrahydro-indol-1-yl)-benzamide ;
2-(2-Methoxy-ethylamino)-4-(3,6,6-trimethyl-4-oxo-4,5,6,7-tetrahydro-indol-1-yl)-benzamide;
2-(3,4,5-Trimethoxy-phenylamino)-4-(3,6,6-trimethyl-4-oxo-4,5,6,7-tetrahydro-indol-1-yl)-benzamide;
2-[(Pyridin-3-ylmethyl)-amino]-4-(3,6,6-trimethyl-4-α-4,5,6,7-tetrahydro-indol-1-yl)-benzamide;
2-(4-oxo-cyclohexylamino)-4-(3,6,6-trimethyl-4-oxo-4,5,6,7-tetrahydro-indol-1-yl)-benzamide;
2-[4-(2-Morpholin-4-yl-ethoxy)-cyclohexylamino]-4-(3,6,6-trimethyl-4-oxo-4,5,6,7-tetrahydro-indol-1-yl)-benzamide;
Amino-acetic acid 4-[2-carbamoyl-5-(3,6,6-trimethyl-4-oxo-4,5,6,7-tetrahydro-indol-1-yl)-phenylamino]-cyclohexyl ester; methanesulfonic acid salt;
Dimethylamino-acetic acid 4-[2-carbamoyl-5-(3,6,6-trimethyl-4-oxo-4,5,6,7-tetrahydro-indol-1-yl)-phenylamino]-cyclohexyl ester; methanesulfonic acid salt;
2-(allylamino)-4-(3-methyl-4-oxo-4,5,6,7-tetrahydroindol-1-yl)benzamide;
2-(cyclopropylamino)-4-(3-methyl-4-oxo-4,5,6,7-tetrahydroindol-1-yl)benzamide;
2-(2-methoxyethylamino)-4-(3-methyl-4-oxo-4,5,6,7-tetrahydroindol-1-yl)benzamide ; 4-(3-methyl-4-oxo-4,5,6,7-tetrahydroindol-1-yl)benzamide;
4-(3,6,6-trimethyl-4-oxo-4,5,6,7-tetrahydroindol-1-yl)benzamide;
4-(3-methyl-4-oxo-4,5,6,7-tetrahydroindol-1-yl)-2-(phenylamino)benzamide;
2-(4-hydroxycyclohexylamino)-4-(3-methyl-4-oxo-4,5,6,7-tetrahydroindol-1-yl)benzamide;
4-(3-methyl-4-oxo-4,5,6,7-tetrahydroindol-1-yl)-2-(3,4,5-trimethoxyphenylamino)benzamide;
2-(2-(dimethylamino)ethylamino)-4-(3,6,6-trimethyl-4-oxo-4,5,6,7-tetrahydroindol-1-yl)benzamide;
2-(2-(dimethylamino)ethylamino)-4-(3-methyl-4-oxo-4,5,6,7-tetrahydroindol-1-yl)benzamide;
2-(pyridin-4-ylmethylamino)-4-(3,6,6-trimethyl-4-oxo-4,5,6,7-tetrahydroindol-1-yl)benzamide;
4-(3-methyl-4-oxo-4,5,6,7-tetrahydroindol-1-yl)-2-(pyridin-3-ylmethylamino)benzamide;
tert-butyl 4-(2-carbamoyl-5-(3,6,6-trimethyl-4-oxo-4,5,6,7-tetrahydroindol-1-yl)phenylamino)piperidine-1-carboxylate;
2-amino-4-(3,6,6-trimethyl-4-oxo-4,5,6,7-tetrahydroindol-1-yl)benzamide;
2-(allylamino)-4-(3,6,6-trimethyl-4-oxo-4,5,6,7-tetrahydroindol-1-yl)benzamide;
2-(1-methylpiperidin-4-ylamino)-4-(3,6,6-trimethyl-4-oxo-4,5,6,7-tetrahydroindol-1-yl)benzamide;
2-(piperidin-4-ylamino)-4-(3,6,6-trimethyl-4-oxo-4,5,6,7-tetrahydroindol-1-yl)benzamide;
3-butoxy-4-(3,6,6-trimethyl-4-oxo-4,5,6,7-tetrahydroindol-1-yl)benzamide;
2-(2,3-dihydro-1H-inden-1-ylamino)-4-(3,6,6-trimethyl-4-oxo-4,5,6,7-tetrahydroindol-1-yl)benzamide;
1-(2-carbamoyl-5-(3,6,6-trimethyl-4-oxo-4,5,6,7-tetrahydroindol-1-yl)phenyl)urea;
3-butoxy-4-(2,6,6-trimethyl-4-oxo-4,5,6,7-tetrahydro-1H-indol-1-yl)benzamide;
2-(phenylamino)-4-(2,6,6-trimethyl-4-oxo-4,5,6,7-tetrahydro-1H-indol-1-yl)benzamide;
3-butoxy-N'-hydroxy-4-(2,6,6-trimethyl-4-oxo-4,5,6,7-tetrahydro-1H-indol-1-yl)benzimidamide;
2-Benzylamino-4-(2,6,6-trimethyl-4-oxo-4,5,6,7-tetrahydro-indol-1-yl)-benzamide;
3-Prop-2-ynyloxy-4-(2,6,6-trimethyl-4-oxo-4,5,6,7-tetrahydro-indol-1-yl)-benzamide;
2-Ethynyl-4-(2,6,6-trimethyl-4-oxo-4,5,6,7-tetrahydro-indol-1-yl)-benzamide;
2-(4-Methoxy-phenylamino)-4-(2,6,6-trimethyl-4-oxo-4,5,6,7-tetrahydro-indol-1-yl)-benzamide;
2-Cyclohexylamino-4-(2,6,6-trimethyl-4-oxo-4,5,6,7-tetrahydro-indol-1-yl)-benzamide;
2-(butylamino)-4-(2,6,6-trimethyl-4-oxo-4,5,6,7-tetrahydroindol-1-yl)benzamide;
3-(3-thienyl)-4-(2,6,6-trimethyl-4-oxo-4,5,6,7-tetrahydro-1H-indol-1-yl)benzamide;
2-methyl-4-(2,6,6-trimethyl-4-oxo-4,5,6,7-tetrahydro-1H-indol-1-yl)benzamide;
2-[(3-ethynylphenyl)amino]-4-(2,6,6-trimethyl-4-oxo-4,5,6,7-tetrahydro-1H-indol-1-yl)benzamide;
2-[(4-chlorophenyl)amino]-4-(2,6,6-trimethyl-4-oxo-4,5,6,7-tetrahydro-1H-indol-1-yl)benzamide;
2-anilino-4-(2-methyl-4-oxo-4,5,6,7-tetrahydro-1H-indol-1-yl)benzamide;
3-anilino-5-(2,6,6-trimethyl-4-oxo-4,5,6,7-tetrahydro-1H-indol-1-yl)pyridine-2-carboxamide;
2-[(3,4,5-trimethoxyphenyl)amino]-4-(2,6,6-trimethyl-4-oxo-4,5,6,7-tetrahydro-1H-indol-1-yl)benzamide;
2-pyridin-4-yl-4-(2,6,6-trimethyl-4-oxo-4,5,6,7-tetrahydro-1H-indol-1-yl)benzamide;
N-[2-(aminocarbonyl)-5-(2,6,6-trimethyl-4-oxo-4,5,6,7-tetrahydro-1H-indol-1-yl)phenyl]-L-valine;
2-morpholin-4-yl-4-(2,6,6-trimethyl-4-oxo-4,5,6,7-tetrahydro-1H-indol-1-yl)benzamide;
2-(1H-imidazol-1-yl)-4-(2,6,6-trimethyl-4-oxo-4,5,6,7-tetrahydro-1H-indol-1-yl)benzamide;

4-(3-chloro-2,6,6-trimethyl-4-oxo-4,5,6,7-tetrahydro-1H-indol-1-yl)-2-[(3,4,5-trimethoxyphenyl)amino]benzamide;
2-[(4-hydroxyphenyl)amino]-4-(2,6,6-trimethyl-4-oxo-4,5,6,7-tetrahydro-1H-indol-1-yl)benzamide;
2-[(1-ethyl-1H-pyrazol-5-yl)amino]-4-(2,6,6-trimethyl-4-oxo-4,5,6,7-tetrahydro-1H-indol-1-yl)benzamide;
2-[(5-methylisoxazol-3-yl)amino]-4-(2,6,6-trimethyl-4-oxo-4,5,6,7-tetrahydro-1H-indol-1-yl)benzamide;
2-{[4-(aminocarbonyl)phenyl]amino}-4-(2-methyl-4-oxo-4,5,6,7-tetrahydro-1H-indol-1-yl)benzamide;
4-(4-oxo-4,5,6,7-tetrahydro-1H-indol-1-yl)-2-[(3,4,5-trimethoxyphenyl)amino]benzamide;
2-[(6-methoxypyridin-3-yl)amino]-4-(2,6,6-trimethyl-4-oxo-4,5,6,7-tetrahydro-1H-indol-1-yl)benzamide;
2-(allylamino)-4-(4-oxo-4,5,6,7-tetrahydro-1H-indol-1-yl)benzamide;
4-(2,3-dimethyl-4-oxo-4,5,6,7-tetrahydro-1H-indol-1-yl)benzamide;
3-bromo-4-(2,3-dimethyl-4-oxo-4,5,6,7-tetrahydro-1H-indol-1-yl)benzamide;
2-(allylamino)-4-(2,3-dimethyl-4-oxo-4,5,6,7-tetrahydro-1H-indol-1-yl)benzamide;
4-(2,3-dimethyl-4-oxo-4,5,6,7-tetrahydro-1H-indol-1-yl)-2-[(2-methoxyethyl)amino]benzamide;
2-({3-[3-(dimethylamino)propoxy]-4-methoxyphenyl}amino)-4-(2,6,6-trimethyl-4-oxo-4,5,6,7-tetrahydro-1H-indol-1-yl)benzamide;
2-(morpholin-4-ylamino)-4-(2,6,6-trimethyl-4-oxo-4,5,6,7-tetrahydro-1H-indol-1-yl)benzamide;
2-[(2-morpholin-4-ylethyl)amino]-4-(3,6,6-trimethyl-4-oxo-4,5,6,7-tetrahydro-1H-indol-1-yl)benzamide;
2-(pyridin-4-ylamino)-4-(3,6,6-trimethyl-4-oxo-4,5,6,7-tetrahydro-1H-indol-1-yl)benzamide;
2-(acetylamino)-4-(3,6,6-trimethyl-4-oxo-4,5,6,7-tetrahydro-1H-indol-1-yl)benzamide;
2-(4-methylpiperazin-1-yl)-4-(3,6,6-trimethyl-4-oxo-4,5,6,7-tetrahydro-1H-indol-1-yl)benzamide;
2-[(methoxyacetyl)amino]-4-(3,6,6-trimethyl-4-oxo-4,5,6,7-tetrahydro-1H-indol-1-yl)benzamide;
2-({3-[2-(dimethylamino)ethoxy]-4-methoxyphenyl}amino)-4-(3,6,6-trimethyl-4-oxo-4,5,6,7-tetrahydro-1H-indol-1-yl)benzamide;
2-(pyridin-4-ylthio)-4-(3,6,6-trimethyl-4-oxo-4,5,6,7-tetrahydro-1H-indol-1-yl)benzamide;
2-({2-[2-(dimethylamino)ethoxy]pyridin-4-yl} amino)-4-(3,6,6-trimethyl-4-oxo-4,5,6,7-tetrahydro-1H-indol-1-yl)benzamide;
2-{[1-(N,N-dimethylglycyl)piperidin-4-yl]amino}-4-(3,6,6-trimethyl-4-oxo-4,5,6,7-tetrahydro-1H-indol-1-yl)benzamide;
4-(6,6-dimethyl-4-oxo-3-phenyl-4,5,6,7-tetrahydro-1H-indol-1-yl)benzamide;
2-[(2-{[2-(aminocarbonyl)-5-(3,6,6-trimethyl-4-oxo-4,5,6,7-tetrahydro-1H-indol-1-yl)phenyl]amino}ethyl)amino]-2-oxoethyl acetate;
2-{[2-(glycoloylamino)ethyl]amino}-4-(3,6,6-trimethyl-4-oxo-4,5,6,7-tetrahydro-1H-indol-1-yl)benzamide;
4-(2,6,6-trimethyl-4-oxo-4,5,6,7-tetrahydro-1H-indol-1-yl)benzamide;
4-[4-(hydroxyimino)-2,6,6-trimethyl-4,5,6,7-tetrahydro-1H-indol-1-yl]benzamide;
4-[(4-(methoxyimino)-2,6,6-trimethyl-4,5,6,7-tetrahydro-1H-indol-1-yl]benzamide;
4-{4-[(allyloxy)imino]-2,6,6-trimethyl-4,5,6,7-tetrahydro-1H-indol-1-yl} benzamide;
4-[4-(isobutoxyimino)-2,6,6-trimethyl-4 ,5,6,7-tetrahydro-1H-indol-1-yl]benzamide;
4-{4-[(benzyloxy)imino]-2,6,6-trimethyl-4,5,6,7-tetrahydro-1H-indol-1-yl}benzamide;
2-(trifluoromethyl)-4-(2,6,6-trimethyl-4-oxo-4,5,6,7-tetrahydro-1H-indol-1-yl)benzamide;
2-methoxy-4-(2,6,6-trimethyl-4-oxo-4,5,6,7-tetrahydro-1H-indol-1-yl)benzamide;
2-butoxy-4-(2,6,6-trimethyl-4-oxo-4,5,6,7-tetrahydro-1H-indol-1-yl)benzamide;
2-(butylamino)-4-(2,6,6-trimethyl-4-oxo-4,5,6,7-tetrahydro-1H-indol-1-yl)benzamide;
3-(2-ethoxyethoxy)-4-(2,6,6-trimethyl-4-oxo-4,5,6,7-tetrahydro-1H-indol-1-yl)benzamide;
3-(2-methoxyethoxy)-4-(2,6,6-trimethyl-4-oxo-4,5,6,7-tetrahydro-1H-indol-1-yl)benzamide;
2-ethoxy-4-(2,6,6-trimethyl-4-oxo-4,5,6,7-tetrahydro-1H-indol-1-yl)benzamide;
2-(2-hydroxyethoxy)-4-(2,6,6-trimethyl-4-oxo-4,5,6,7-tetrahydro-1H-indol-1-yl)benzamide;
2-[(2-methoxyethyl)amino]-4-(2,6,6-trimethyl-4-oxo-4,5,6,7-tetrahydro-1H-indol-1-yl)benzamide;
2-(2-ethoxyethoxy)-4-(2,6,6-trimethyl-4-oxo-4,5,6,7-tetrahydro-1H-indol-1-yl)benzamide;
4-(4-oxo-4,5,6,7-tetrahydro-1H-indol-1-yl)benzamide;
3-[2-(dimethylamino)ethoxy]-4-(2,6,6-trimethyl-4-oxo-4,5,6,7-tetrahydro-1H-indol-1-yl)benzamide;
3-(tetrahydrofuran-3-ylmethoxy)-4-(2,6,6-trimethyl-4-oxo-4,5,6,7-tetrahydro-1H-indol-1-yl)benzamide;
3-(4-fluorophenoxy)-4-(2,6,6-trimethyl-4-oxo-4,5,6,7-tetrahydro-1H-indol-1-yl)benzamide;
2-{[2-(dimethylamino)ethyl]amino}-4-(2,6,6-trimethyl-4-oxo-4,5,6,7-tetrahydro-1H-indol-1-yl)benzamide;
2-anilino-4-(2,6,6-trimethyl-4-oxo-4,5,6,7-tetrahydro-1H-indol-1-yl)benzamide;
3-fluoro-4-(2,6,6-trimethyl-4-oxo-4,5,6,7-tetrahydro-1H-indol-1-yl)benzamide;
4-(6,6-dimethyl-4-oxo-2-phenyl-4,5,6,7-tetrahydro-1H-indol-1-yl)benzamide;
2-chloro-4-(2,6,6-trimethyl-4-oxo-4,5,6,7-tetrahydro-1H-indol-1-yl)benzamide;
2-(benzylamino)-4-(2,6,6-trimethyl-4-oxo-4,5,6,7-tetrahydro-1H-indol-1-yl)benzamide;
2-bromo-4-(2,6,6-trimethyl-4-oxo-4,5,6,7-tetrahydro-1H-indol-1-yl)benzamide;
3-(2-hydroxyethoxy)-4-(2,6,6-trimethyl-4-oxo-4,5,6,7-tetrahydro-1H-indol-1-yl)benzamide;
2-amino-4-(2,6,6-trimethyl-4-oxo-4,5,6,7-tetrahydro-1H-indol-1-yl)benzamide;
3-(tert-butylthio)-4-(2,6,6-trimethyl-4-oxo-4,5,6,7-tetrahydro-1H-indol-1-yl)benzamide;
3-(phenylthio)-4-(2,6,6-trimethyl-4-oxo-4,5,6,7-tetrahydro-1H-indol-1-yl)benzamide;
3-(butylthio)-4-(2,6,6-trimethyl-4-oxo-4,5,6,7-tetrahydro-1H-indol-1-yl)benzamide;
2-(dimethylamino)-4-(2,6,6-trimethyl-4-oxo-4,5,6,7-tetrahydro-1H-indol-1-yl)benzamide;
3-methoxy-4-(2,6,6-trimethyl-4-oxo-4,5,6,7-tetrahydro-1H-indol-1-yl)benzamide;
3-ethoxy-4-(2,6,6-trimethyl-4-oxo-4,5,6,7-tetrahydro-1H-indol-1-yl)benzamide;
3-propoxy-4-(2,6,6-trimethyl-4-oxo-4,5,6,7-tetrahydro-1H-indol-1-yl)benzamide;
3-(benzyloxy)-4-(2,6,6-trimethyl-4-oxo-4,5,6,7-tetrahydro-1H-indol-1-yl)benzamide;
3-(2-morpholin-4-ylethoxy)-4-(2,6,6-trimethyl-4-oxo-4,5,6,7-tetrahydro-1H-indol-1-yl)benzamide;

3-(pyridin-2-ylmethoxy)-4-(2,6,6-trimethyl-4-oxo-4,5,6,7-tetrahydro-1H-indol-1-yl)benzamide;
3-(pyridin-4-ylmethoxy)-4-(2,6,6-trimethyl-4-oxo-4,5,6,7-tetrahydro-1H-indol-1-yl)benzamide;
3-(2-isopropoxyethoxy)-4-(2,6,6-trimethyl-4-oxo-4,5,6,7-tetrahydro-1H-indol-1-yl)benzamide;
3-(2-pyrrolidin-2-ylethoxy)-4-(2,6,6-trimethyl-4-oxo-4,5,6,7-tetrahydro-1H-indol-1-yl)benzamide;
3-(tetrahydro-2H-pyran-2-ylmethoxy)-4-(2,6,6-trimethyl-4-oxo-4,5,6,7-tetrahydro-1H-indol-1-yl)benzamide;
3-(tetrahydro-2H-pyran-4-yloxy)-4-(2,6,6-trimethyl-4-oxo-4,5,6,7-tetrahydro-1H-indol-1-yl)benzamide;
3-(butylamino)-4-(2,6,6-trimethyl-4-oxo-4,5,6,7-tetrahydro-1H-indol-1-yl)benzamide;
3-chloro-4-(2,6,6-trimethyl-4-oxo-4,5,6,7-tetrahydro-1H-indol-1-yl)benzamide;
3-(1H-imidazol-4-ylmethoxy)-4-(2,6,6-trimethyl-4-oxo-4,5,6,7-tetrahydro-1H-indol-1-yl)benzamide;
2-[(4-methoxyphenyl)amino]-4-(2,6,6-trimethyl-4-oxo-4,5,6,7-tetrahydro-1H-indol-1-yl)benzamide;
3-anilino-4-(2,6,6-trimethyl-4-oxo-4,5,6,7-tetrahydro-1H-indol-1-yl)benzamide;
3-(benzylamino)-4-(2,6,6-trimethyl-4-oxo-4,5,6,7-tetrahydro-1H-indol-1-yl)benzamide;
3-(3-hydroxypropoxy)-4-(2,6,6-trimethyl-4-oxo-4,5,6,7-tetrahydro-1H-indol-1-yl)benzamide;
3-(3-hydroxybutoxy)-4-(2,6,6-trimethyl-4-oxo-4,5,6,7-tetrahydro-1H-indol-1-yl)benzamide;
3-(2,3-dihydroxypropoxy)-4-(2,6,6-trimethyl-4-oxo-4,5,6,7-tetrahydro-1H-indol-1-yl)benzamide;
3-(2-methylbutoxy)-4-(2,6,6-trimethyl-4-oxo-4,5,6,7-tetrahydro-1H-indol-1-yl)benzamide;
3-(pentyloxy)-4-(2,6,6-trimethyl-4-oxo-4,5,6,7-tetrahydro-1H-indol-1-yl)benzamide;
3-(3-methylbutoxy)-4-(2,6,6-trimethyl-4-oxo-4,5,6,7-tetrahydro-1H-indol-1-yl)benzamide;
3-hydroxy-4-(2,6,6-trimethyl-4-oxo-4,5,6,7-tetrahydro-1H-indol-1-yl)benzamide;
2-(cyclohexylamino)-4-(2,6,6-trimethyl-4-oxo-4,5,6,7-tetrahydro-1H-indol-1-yl)benzamide;
3-(cyclohexyloxy)-4-(2,6,6-trimethyl-4-oxo-4,5,6,7-tetrahydro-1H-indol-1-yl)benzamide;
3-(pent-4-en-1-yloxy)-4-(2,6,6-trimethyl-4-oxo-4,5,6,7-tetrahydro-1H-indol-1-yl)benzamide;
2-(1,3-benzodioxol-5-ylamino)-4-(2,6,6-trimethyl-4-oxo-4,5,6,7-tetrahydro-1H-indol-1-yl)benzamide;
2-(hexylamino)-4-(2,6,6-trimethyl-4-oxo-4,5,6,7-tetrahydro-1H-indol-1-yl)benzamide;
3-butoxy-4-(2-methyl-4-oxo-4,5,6,7-tetrahydro-1H-indol-1-yl)benzamide;
3-(4-hydroxybutoxy)-4-(2,6,6-trimethyl-4-oxo-4,5,6,7-tetrahydro-1H-indol-1-yl)benzamide;
3-[(3-methyloxetan-3-yl)methoxy]-4-(2,6,6-trimethyl-4-oxo-4,5,6,7-tetrahydro-1H-indol-1-yl)benzamide;
3-(4-aminobutoxy)-4-(2,6,6-trimethyl-4-oxo-4,5,6,7-tetrahydro-1H-indol-1-yl)benzamide;
3-(tetrahydrofuran-3-yloxy)-4-(2,6,6-trimethyl-4-oxo-4,5,6,7-tetrahydro-1H-indol-1-yl)benzamide;
3-(tetrahydrofuran-2-ylmethoxy)-4-(2,6,6-trimethyl-4-oxo-4,5,6,7-tetrahydro-1H-indol-1-yl)benzamide;
3-[(1-ethylprop-2-en-1-yl)oxy]-4-(2,6,6-trimethyl-4-oxo-4,5,6,7-tetrahydro-1H-indol-1-yl)benzamide;
3-(2-thienylmethoxy)-4-(2,6,6-trimethyl-4-oxo-4,5,6,7-tetrahydro-1H-indol-1-yl)benzamide;
4-(6,6-dimethyl-4-oxo-4,5,6,7-tetrahydro-1H-indol-1-yl)benzamide;
2-[(methylsulfonyl)amino]-4-(2,6,6-trimethyl-4-oxo-4,5,6,7-tetrahydro-1H-indol-1-yl)benzamide;
2-(acetylamino)-4-(2,6,6-trimethyl-4-oxo-4,5,6,7-tetrahydro-1H-indol-1-yl)benzamide;
2-[(aminocarbonyl)amino]-4-(2,6,6-trimethyl-4-oxo-4,5,6,7-tetrahydro-1H-indol-1-yl)benzamide;
2-(benzoylamino)-4-(2,6,6-trimethyl-4-oxo-4,5,6,7-tetrahydro-1H-indol-1-yl)benzamide;
2-(butyrylamino)-4-(2,6,6-trimethyl-4-oxo-4,5,6,7-tetrahydro-1H-indol-1-yl)benzamide;
3-ethoxy-5-(2,6,6-trimethyl-4-oxo-4,5,6,7-tetrahydro-1H-indol-1-yl)pyridine-2-carboxamide;
2-(pyridin-3-ylamino)-4-(2,6,6-trimethyl-4-oxo-4,5,6,7-tetrahydro-1H-indol-1-yl)benzamide;
2-[(3-ethoxyphenyl)amino]-4-(2,6,6-trimethyl-4-oxo-4,5,6,7-tetrahydro-1H-indol-1-yl)benzamide;
2-[(3-methoxyphenyl)amino]-4-(2,6,6-trimethyl-4-oxo-4,5,6,7-tetrahydro-1H-indol-1-yl)benzamide;
N'-hydroxy-3-methyl-4-(2,6,6-trimethyl-4-oxo-4,5,6,7-tetrahydro-1H-indol-1-yl)benzenecarboximidamide;
3-methyl-4-(2,6,6-trimethyl-4-oxo-4,5,6,7-tetrahydro-1H-indol-1-yl)benzamide;
2-chloro-N-hydroxy-4-(2,6,6-trimethyl-4-oxo-4,5,6,7-tetrahydro-1H-indol-1-yl)benzenecarboximidamide;
2,3-difluoro-N-hydroxy-4-(2,6,6-trimethyl-4-oxo-4,5,6,7-tetrahydro-1H-indol-1-yl)benzenecarboximidamide;
8-(2,6,6-trimethyl-4-oxo-4,5,6,7-tetrahydro-1H-indol-1-yl)-2,3-dihydro-1,4-benzodioxine-5-carboxamide;
2-pentyl-4-(2,6,6-trimethyl-4-oxo-4,5,6,7-tetrahydro-1H-indol-1-yl)benzamide;
3-pentyl-4-(2,6,6-trimethyl-4-oxo-4,5,6,7-tetrahydro-1H-indol-1-yl)benzamide;
2-[(4-butoxyphenyl)amino]-4-(2,6,6-trimethyl-4-oxo-4,5,6,7-tetrahydro-1H-indol-1-yl)benzamide;
2-anilino-N'-hydroxy-4-(2,6,6-trimethyl-4-oxo-4,5,6,7-tetrahydro-1H-indol-1-yl)benzenecarboximidamide;
2-{[4-(trifluoromethoxy)phenyl]amino}-4-(2,6,6-trimethyl-4-oxo-4,5,6,7-tetrahydro-1H-indol-1-yl)benzamide;
2-[(2-chloro-4-fluorophenyl)amino]-4-(2,6,6-trimethyl-4-oxo-4,5,6,7-tetrahydro-1H-indol-1-yl)benzamide;
2-[(2-chloro-4-methylphenyl)amino]-4-(2,6,6-trimethyl-4-oxo-4,5,6,7-tetrahydro-1H-indol-1-yl)benzamide;
2-[(2-chloro-4-methoxyphenyl)amino]-4-(2,6,6-trimethyl-4-oxo-4,5,6,7-tetrahydro-1H-indol-1-yl)benzamide;
2-[(3,4-dimethoxyphenyl)amino]-4-(2,6,6-trimethyl-4-oxo-4,5,6,7-tetrahydro-1H-indol-1-yl)benzamide;
2-[(3-fluoro-4-methoxyphenyl)amino]-4-(2,6,6-trimethyl-4-oxo-4,5,6,7-tetrahydro-1H-indol-1-yl)benzamide;
2-[(3,5-dimethoxyphenyl)amino]-4-(2,6,6-trimethyl-4-oxo-4,5,6,7-tetrahydro-1H-indol-1-yl)benzamide;
2-[(2,5-dimethoxyphenyl)amino]-4-(2,6,6-trimethyl-4-oxo-4,5,6,7-tetrahydro-1H-indol-1-yl)benzamide;
2-[(4-ethoxyphenyl)amino]-4-(2,6,6-trimethyl-4-oxo-4,5,6,7-tetrahydro-1H-indol-1-yl)benzamide;
2-[(4-fluorophenyl)amino]-4-(2,6,6-trimethyl-4-oxo-4,5,6,7-tetrahydro-1H-indol-1-yl)benzamide;
2-phenoxy-4-(2,6,6-trimethyl-4-oxo-4,5,6,7-tetrahydro-1H-indol-1-yl)benzamide;
2-(phenylthio)-4-(2,6,6-trimethyl-4-oxo-4,5,6,7-tetrahydro-1H-indol-1-yl)benzamide;
2-(cyclopropylamino)-4-(2,6,6-trimethyl-4-oxo-4,5,6,7-tetrahydro-1H-indol-1-yl)benzamide;
2-(prop-2-yn-1-ylamino)-4-(2,6,6-trimethyl-4-oxo-4,5,6,7-tetrahydro-1H-indol-1-yl)benzamide;

3-(propylthio)-4-(2,6,6-trimethyl-4-oxo-4,5,6,7-tetrahydro-1H-indol-1-yl)benzamide;
N-hydroxy-3-(propylthio)-4-(2,6,6-trimethyl-4-oxo-4,5,6,7-tetrahydro-1H-indol-1-yl)benzenecarboximidamide;
N-[2-(aminocarbonyl)-5-(2,6,6-trimethyl-4-oxo-4,5,6,7-tetrahydro-1H-indol-1-yl)phenyl]-L-phenylalanine;
2-[(2-chloro-3,4,5-trimethoxyphenyl)amino]-4-(3-chloro-2,6,6-trimethyl-4-oxo-4,5,6,7-tetrahydro-1H-indol-1-yl)benzamide;
4-(6,6-dimethyl-4-oxo-4,5,6,7-tetrahydro-1H-indol-1-yl)-2-[(3,4,5-trimethoxyphenyl)amino]benzamide;
4-(2-methyl-4-oxo-4,5,6,7-tetrahydro-1H-indol-1-yl)-2-[(3,4,5-trimethoxyphenyl)amino]benzamide;
2-[(3,4,5-trifluorophenyl)amino]-4-(2,6,6-trimethyl-4-oxo-4,5,6,7-tetrahydro-1H-indol-1-yl)benzamide;
2-[(4-hydroxycyclohexyl)amino]-4-(2,6,6-trimethyl-4-oxo-4,5,6,7-tetrahydro-1H-indol-1-yl)benzamide;
2-[(4-oxocyclohexyl)amino]-4-(2,6,6-trimethyl-4-oxo-4,5,6,7-tetrahydro-1H-indol-1-yl)benzamide;
2-[(4-methylphenyl)amino]-4-(2,6,6-trimethyl-4-oxo-4,5,6,7-tetrahydro-1H-indol-1-yl)benzamide;
2-(2,3-dihydro-1H-inden-4-ylamino)-4-(2,6,6-trimethyl-4-oxo-4,5,6,7-tetrahydro-1H-indol-1-yl)benzamide;
2-[(2-propylphenyl)amino]-4-(2,6,6-trimethyl-4-oxo-4,5,6,7-tetrahydro-1H-indol-1-yl)benzamide;
2-[(2-isopropylphenyl)amino]-4-(2,6,6-trimethyl-4-oxo-4,5,6,7-tetrahydro-1H-indol-1-yl)benzamide;
2-(3-hydroxyprop-1-yn-1-yl)-4-(2,6,6-trimethyl-4-oxo-4,5,6,7-tetrahydro-1H-indol-1-yl)benzamide;
2-[(2-chloro-3,4,5-trimethoxyphenyl)amino]-4-(2,6,6-trimethyl-4-oxo-4,5,6,7-tetrahydro-1H-indol-1-yl)benzamide;
4-(4-oxo-2-phenyl-4,5,6,7-tetrahydro-1H-indol-1-yl)benzamide;
2-[(2,4,5-trifluorophenyl)amino]-4-(2,6,6-trimethyl-4-oxo-4,5,6,7-tetrahydro-1H-indol-1-yl)benzamide;
2-[(3,4,5-trimethoxybenzyl)amino]-4-(2,6,6-trimethyl-4-oxo-4,5,6,7-tetrahydro-1H-indol-1-yl)benzamide;
2-[(2-fluorophenyl)amino]-4-(2,6,6-trimethyl-4-oxo-4,5,6,7-tetrahydro-1H-indol-1-yl)benzamide;
2-[(3-fluorophenyl)amino]-4-(2,6,6-trimethyl-4-oxo-4,5,6,7-tetrahydro-1H-indol-1-yl)benzamide;
2-[(4-fluoro-3-methylphenyl)amino]-4-(2,6,6-trimethyl-4-oxo-4,5,6,7-tetrahydro-1H-indol-1-yl)benzamide;
2-[(3-hydroxy-4-methoxyphenyl)amino]-4-(2,6,6-trimethyl-4-oxo-4,5,6,7-tetrahydro-1H-indol-1-yl)benzamide;
2-[(2-fluoro-4-methoxyphenyl)amino]-4-(2,6,6-trimethyl-4-oxo-4,5,6,7-tetrahydro-1H-indol-1-yl)benzamide;
2-(tetrahydro-2H-pyran-4-ylamino)-4-(2,6,6-trimethyl-4-oxo-4,5,6,7-tetrahydro-1H-indol-1-yl)benzamide;
2-[(2,4-difluorophenyl)amino]-4-(2,6,6-trimethyl-4-oxo-4,5,6,7-tetrahydro-1H-indol-1-yl)benzamide;
2-[(3,4-difluorophenyl)amino]-4-(2,6,6-trimethyl-4-oxo-4,5,6,7-tetrahydro-1H-indol-1-yl)benzamide;
4-[4-(hydroxyimino)-2-phenyl-4,5,6,7-tetrahydro-1H-indol-1-yl]benzamide;
2-{[4-(benzyloxy)phenyl]amino}-4-(2,6,6-trimethyl-4-oxo-4,5,6,7-tetrahydro-1H-indol-1-yl)benzamide;
2-[(tetrahydrofuran-2-ylmethyl)amino]-4-(2,6,6-trimethyl-4-oxo-4,5,6,7-tetrahydro-1H-indol-1-yl)benzamide;
2-[(1,3-dioxolan-2-ylmethyl)amino]-4-(2,6,6-trimethyl-4-oxo-4,5,6,7-tetrahydro-1H-indol-1-yl)benzamide;
2-[(2-methoxy-1-methylethyl)amino]-4-(2,6,6-trimethyl-4-oxo-4,5,6,7-tetrahydro-1H-indol-1-yl)benzamide;
2-{[2-(2-hydroxyethoxy)ethyl]amino}-4-(2,6,6-trimethyl-4-oxo-4,5,6,7-tetrahydro-1H-indol-1-yl)benzamide;
2-[(4-hydroxybutyl)amino]-4-(2-methyl-4-oxo-4,5,6,7-tetrahydro-1H-indol-1-yl)benzamide;
4-(2-methyl-4-oxo-4,5,6,7-tetrahydro-1H-indol-1-yl)-2-[(3-morpholin-4-ylpropyl)amino]benzamide;
2-[(pyridin-2-ylmethyl)amino]-4-(2,6,6-trimethyl-4-oxo-4,5,6,7-tetrahydro-1H-indol-1-yl)benzamide;
2-{[2-(diethylamino)-4-ethoxyphenyl]amino}-4-(2,6,6-trimethyl-4-oxo-4,5,6,7-tetrahydro-1H-indol-1-yl)benzamide;
2-{[4-(difluoromethoxy)phenyl]amino}-4-(2,6,6-trimethyl-4-oxo-4,5,6,7-tetrahydro-1H-indol-1-yl)benzamide;
2-[(3,4-dimethoxybenzyl)amino]-4-(2,6,6-trimethyl-4-oxo-4,5,6,7-tetrahydro-1H-indol-1-yl)benzamide;
2-[(3-hydroxypropyl)amino]-4-(2,6,6-trimethyl-4-oxo-4,5,6,7-tetrahydro-1H-indol-1-yl)benzamide;
2-(allylamino)-4-(2,6,6-trimethyl-4-oxo-4,5,6,7-tetrahydro-1H-indol-1-yl)benzamide;
4-[4-(hydroxyimino)-2,6,6-trimethyl-4,5,6,7-tetrahydro-1H-indol-1-yl]-2-[(3,4,5-trimethoxyphenyl)amino]benzamide;
2-[(3-methoxypropyl)amino]-4-(2,6,6-trimethyl-4-oxo-4,5,6,7-tetrahydro-1H-indol-1-yl)benzamide;
2-(pyridin-4-ylamino)-4-(2,6,6-trimethyl-4-oxo-4,5,6,7-tetrahydro-1H-indol-1-yl)benzamide;
2-{[3-(1H-imidazol-1-yl)propyl]amino}-4-(2,6,6-trimethyl-4-oxo-4,5,6,7-tetrahydro-1H-indol-1-yl)benzamide;
2-{[2-(1H-imidazol-1-yl)ethyl]amino}-4-(2,6,6-trimethyl-4-oxo-4,5,6,7-tetrahydro-1H-indol-1-yl)benzamide;
2-(isoxazol-3-ylamino)-4-(2,6,6-trimethyl-4-oxo-4,5,6,7-tetrahydro-1H-indol-1-yl)benzamide;
2-[(pyridin-3-ylmethyl)amino]-4-(2,6,6-trimethyl-4-oxo-4,5,6,7-tetrahydro-1H-indol-1-yl)benzamide;
4-(2,6,6-trimethyl-4-oxo-4,5,6,7-tetrahydro-1H-indol-1-yl)phthalamide;
3-bromo-N'-hydroxy-4-(4-oxo-4,5,6,7-tetrahydro-1H-indol-1-yl)benzenecarboximidamide;
2-[(10-aminodecyl)amino]-4-(2,6,6-trimethyl-4-oxo-4,5,6,7-tetrahydro-1H-indol-1-yl)benzamide;
2-(allylamino)-4-(2-methyl-4-oxo-4,5,6,7-tetrahydro-1H-indol-1-yl)benzamide;
2-(2,3-dihydro-1H-inden-1-ylamino)-4-(4-oxo-4,5,6,7-tetrahydro-1H-indol-1-yl)benzamide;
2-(cyclopropylamino)-4-(2,3-dimethyl-4-oxo-4,5,6,7-tetrahydro-1H-indol-1-yl)benzamide;
2-[(2-methoxyethyl)amino]-4-(2-methyl-4-oxo-4,5,6,7-tetrahydro-1H-indol-1-yl)benzamide;
3-[(cyclopropylmethyl)amino]-4-(4-oxo-4,5,6,7-tetrahydro-1H-indol-1-yl)benzamide;
2-{[3-(3-hydroxypropoxy)-4-methoxyphenyl]amino}-4-(2,6,6-trimethyl-4-oxo-4,5,6,7-tetrahydro-1H-indol-1-yl)benzamide;
2-(allylamino)-4-(3-methyl-4-oxo-4,5,6,7-tetrahydro-1H-indol-1-yl)benzamide;
2-(cyclopropylamino)-4-(3-methyl-4-oxo-4,5,6,7-tetrahydro-1H-indol-1-yl)benzamide;
2-[(2-methoxyethyl)amino]-4-(3-methyl-4-oxo-4,5,6,7-tetrahydro-1H-indol-1-yl)benzamide;
4-(2-methyl-4-oxo-4,5,6,7-tetrahydro-1H-indol-1-yl)benzamide;

4-(3-ethyl-2-methyl-4-oxo-4,5,6,7-tetrahydro-1H-indol-1-yl)benzamide;
4-(3-methyl-4-oxo-4,5,6,7-tetrahydro-1H-indol-1-yl)benzamide;
2-[(2-{2-[2-(2-aminoethoxy)ethoxy]ethoxy}ethyl)amino]-4-(2,6,6-trimethyl-4-oxo-4,5,6,7-tetrahydro-1H-indol-1-yl)benzamide;
2-[(4-hydroxycyclohexyl)amino]-4-(2-methyl-4-oxo-4,5,6,7-tetrahydro-1H-indol-1-yl)benzamide;
4-(3,6,6-trimethyl-4-oxo-4,5,6,7-tetrahydro-1H-indol-1-yl)benzamide;
2-anilino-4-(3-methyl-4-oxo-4,5,6,7-tetrahydro-1H-indol-1-yl)benzamide;
2-[(4-hydroxycyclohexyl)amino]-4-(3-methyl-4-oxo-4,5,6,7-tetrahydro-1H-indol-1-yl)benzamide;
4-(2,3-dimethyl-4-oxo-4,5,6,7-tetrahydro-1H-indol-1-yl)-2-[(4-hydroxycyclohexyl)amino]benzamide;
2-anilino-4-(2,3-dimethyl-4-oxo-4,5,6,7-tetrahydro-1H-indol-1-yl)benzamide;
4-(3-methyl-4-oxo-4,5,6,7-tetrahydro-1H-indol-1-yl)-2-[(3,4,5-trimethoxyphenyl)amino]benzamide;
2-{[2-(dimethylamino)ethyl]amino}-4-(3,6,6-trimethyl-4-oxo-4,5,6,7-tetrahydro-1H-indol-1-yl)benzamide;
2-{[2-(dimethylamino)ethyl]amino}-4-(3-methyl-4-oxo-4,5,6,7-tetrahydro-1H-indol-1-yl)benzamide;
2-(piperidin-4-ylamino)-4-(2,6,6-trimethyl-4-oxo-4,5,6,7-tetrahydro-1H-indol-1-yl)benzamide;
2-[(4-hydroxycyclohexyl)amino]-4-(3,6,6-trimethyl-4-oxo-4,5,6,7-tetrahydro-1H-indol-1-yl)benzamide;
2-[(1-methylpiperidin-4-yl)amino]-4-(2,6,6-trimethyl-4-oxo-4,5,6,7-tetrahydro-1H-indol-1-yl)benzamide;
(4-{[2-(aminocarbonyl)-5-(2,6,6-trimethyl-4-oxo-4,5,6,7-tetrahydro-1H-indol-1-yl)phenyl]amino}piperidin-1-yl)acetic acid;
2-[(2-methoxyethyl)amino]-4-(3,6,6-trimethyl-4-oxo-4,5,6,7-tetrahydro-1H-indol-1-yl)benzamide;
2-[(pyridin-4-ylmethyl)amino]-4-(3,6,6-trimethyl-4-oxo-4,5,6,7-tetrahydro-1H-indol-1-yl)benzamide;
2-(tetrahydro-2H-pyran-4-ylamino)-4-(3,6,6-trimethyl-4-oxo-4,5,6,7-tetrahydro-1H-indol-1-yl)benzamide;
2-[(3,4,5-trimethoxyphenyl)amino]-4-(3,6,6-trimethyl-4-oxo-4,5,6,7-tetrahydro-1H-indol-1-yl)benzamide;
2-amino-4-(3,6,6-trimethyl-4-oxo-4,5,6,7-tetrahydro-1H-indol-1-yl)benzamide;
2-(allylamino)-4-(3,6,6-trimethyl-4-oxo-4,5,6,7-tetrahydro-1H-indol-1-yl)benzamide;
2-[(1-methylpiperidin-4-yl)amino]-4-(3,6,6-trimethyl-4-oxo-4,5,6,7-tetrahydro-1H-indol-1-yl)benzamide;
2-(piperidin-4-ylamino)-4-(3,6,6-trimethyl-4-oxo-4,5,6,7-tetrahydro-1H-indol-1-yl)benzamide;
3-butoxy-4-(3,6,6-trimethyl-4-oxo-4,5,6,7-tetrahydro-1H-indol-1-yl)benzamide;
2-(2,3-dihydro-1H-inden-1-ylamino)-4-(3,6,6-trimethyl-4-oxo-4,5,6,7-tetrahydro-1H-indol-1-yl)benzamide;
2-[(4-oxocyclohexyl)amino]-4-(3,6,6-trimethyl-4-oxo-4,5,6,7-tetrahydro-1H-indol-1-yl)benzamide;
2-[(aminocarbonyl)amino]-4-(3,6,6-trimethyl-4-oxo-4,5,6,7-tetrahydro-1H-indol-1-yl)benzamide;
2-{[4-(2-morpholin-4-ylethoxy)cyclohexyl]amino}-4-(3,6,6-trimethyl-4-oxo-4,5,6,7-tetrahydro-1H-indol-1-yl)benzamide;
2-[(8-methyl-8-azabicyclo[3.2.1]oct-3-yl)amino]-4-(3,6,6-trimethyl-4-oxo-4,5,6,7-tetrahydro-1H-indol-1-yl)benzamide;
2-(cyclohexylamino)-4-(3,6,6-trimethyl-4-oxo-4,5,6,7-tetrahydro-1H-indol-1-yl)benzamide;
2-(cyclopropylamino)-4-(3,6,6-trimethyl-4-oxo-4,5,6,7-tetrahydro-1H-indol-1-yl)benzamide;
2-[(cyclopropylmethyl)amino]-4-(3,6,6-trimethyl-4-oxo-4,5,6,7-tetrahydro-1H-indol-1-yl)benzamide;
2-[(3,4-dimethoxyphenyl)amino]-4-(3,6,6-trimethyl-4-oxo-4,5,6,7-tetrahydro-1H-indol-1-yl)benzamide;
2-({3-[3-(dimethylamino)propoxy]-4-methoxyphenyl}amino)-4-(3,6,6-trimethyl-4-oxo-4,5,6,7-tetrahydro-1H-indol-1-yl)benzamide;
2-{[2-(aminocarbonyl)-5-(3,6,6-trimethyl-4-oxo-4,5,6,7-tetrahydro-1H-indol-1-yl)phenyl]amino}-2-oxoethyl acetate;
4-{[2-(aminocarbonyl)-5-(3,6,6-trimethyl-4-oxo-4,5,6,7-tetrahydro-1H-indol-1-yl)phenyl]amino}cyclohexyl glycinate;
2-[(2-aminoethyl)amino]-4-(3,6,6-trimethyl-4-oxo-4,5,6,7-tetrahydro-1H-indol-1-yl)benzamide;
4-{[2-(aminocarbonyl)-5-(3,6,6-trimethyl-4-oxo-4,5,6,7-tetrahydro-1H-indol-1-yl)phenyl]amino}cyclohexyl acetate;
2-[(2-furylmethyl)amino]-4-(3,6,6-trimethyl-4-oxo-4,5,6,7-tetrahydro-1H-indol-1-yl)benzamide;
2-[(2-piperazin-1-ylethyl)amino]-4-(3,6,6-trimethyl-4-oxo-4,5,6,7-tetrahydro-1H-indol-1-yl)benzamide;
2-{[2-(1-methylpyrrolidin-2-yl)ethyl]amino}-4-(3,6,6-trimethyl-4-oxo-4,5,6,7-tetrahydro-1H-indol-1-yl)benzamide;
4-{[2-(aminocarbonyl)-5-(3,6,6-trimethyl-4-oxo-4,5,6,7-tetrahydro-1H-indol-1-yl)phenyl]amino}cyclohexyl N,N-dimethylglycinate;
2-[(1-glycylpiperidin-4-yl)amino]-4-(3,6,6-trimethyl-4-oxo-4,5,6,7-tetrahydro-1H-indol-1-yl)benzamide;
2-{[1-phenylethyl]amino}-4-(3,6,6-trimethyl-4-oxo-4,5,6,7-tetrahydro-1H-indol-1-yl)benzamide;
2-[(1-ethylpiperidin-3-yl)amino]-4-(3,6,6-trimethyl-4-oxo-4,5,6,7-tetrahydro-1H-indol-1-yl)benzamide;
2-{[1-phenylethyl]amino}-4-(3,6,6-trimethyl-4-oxo-4,5,6,7-tetrahydro-1H-indol-1-yl)benzamide;
2-[(4-methoxycyclohexyl)amino]-4-(3,6,6-trimethyl-4-oxo-4,5,6,7-tetrahydro-1H-indol-1-yl)benzamide;
N-(2-aminophenyl)-3-butoxy-4-(2,6,6-trimethyl-4-oxo-4,5,6,7-tetrahydro-1H-indol-1-yl)benzamide;
4-{[2-(aminocarbonyl)-5-(3,6,6-trimethyl-4-oxo-4,5,6,7-tetrahydro-1H-indol-1-yl)phenyl]amino}cyclohexyl L-alaninate;
4-{[2-(aminocarbonyl)-5-(3,6,6-trimethyl-4-oxo-4,5,6,7-tetrahydro-1H-indol-1-yl)phenyl]amino}cyclohexyl D-alaninate;
4-{[2-(aminocarbonyl)-5-(3,6,6-trimethyl-4-oxo-4,5,6,7-tetrahydro-1H-indol-1-yl)phenyl]amino}cyclohexyl L-valinate;
2-(tetrahydro-2H-pyran-2-ylamino)-4-(3,6,6-trimethyl-4-oxo-4,5,6,7-tetrahydro-1H-indol-1-yl)benzamide;
or 2-[(4-hydroxycyclohexyl)amino]-4-(2,3,6,6-tetramethyl-4-oxo-4,5,6,7-tetrahydro-1H-indol-1-yl)benzamide.

19. A pharmaceutical composition comprising at least one compound according to claim 18 and a pharmaceutically acceptable solvent, carrier, excipient, adjuvant or a combination thereof.

* * * * *